US007291498B2

(12) United States Patent
Roy et al.

(10) Patent No.: US 7,291,498 B2

(45) Date of Patent: Nov. 6, 2007

(54) METHODS OF GENERATING CHIMERIC ADENOVIRUSES AND USES FOR SUCH CHIMERIC ADENOVIRUSES

(75) Inventors: Soumitra Roy, Wayne, PA (US); James M. Wilson, Gladwyne, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 548 days.

(21) Appl. No.: 10/465,302

(22) Filed: Jun. 20, 2003

(65) Prior Publication Data

US 2007/0231303 A1 Oct. 4, 2007

(51) Int. Cl.

| | |
|---|---|
| ***C12N 15/861*** | (2006.01) |
| ***C12N 15/63*** | (2006.01) |
| ***C12N 15/64*** | (2006.01) |
| *A61K 48/00* | (2006.01) |

(52) U.S. Cl. .................. 435/320.1; 435/455; 435/456; 435/91.4; 435/91.41; 435/91.42; 435/235.2; 435/239

(58) Field of Classification Search .................... None
See application file for complete search history.

(56) References Cited

U.S. PATENT DOCUMENTS

| | | | |
|---|---|---|---|
| 5,712,136 | A | 1/1998 | Wickham et al. |
| 5,770,442 | A | 6/1998 | Wickham et al. |
| 5,846,782 | A | 12/1998 | Wickham et al. |
| 5,856,152 | A | 1/1999 | Wilson |
| 5,871,982 | A | 2/1999 | Wilson |
| 5,922,315 | A | 7/1999 | Roy |
| 5,965,541 | A | 10/1999 | Wickham et al. |
| 6,057,155 | A | 5/2000 | Wickham et al. |
| 6,083,716 | A | 7/2000 | Wilson et al. |
| 6,127,525 | A | 10/2000 | Crystal et al. |
| 6,153,435 | A | 11/2000 | Crystal et al. |
| 6,251,677 | B1 | 6/2001 | Wilson |
| 6,329,190 | B1 | 12/2001 | Wickham et al. |
| 6,387,368 | B1 | 5/2002 | Wilson |
| 6,465,253 | B1 | 10/2002 | Wickham et al. |
| 6,576,456 | B2 | 6/2003 | Wickham et al. |
| 6,649,407 | B2 | 11/2003 | Wickham et al. |
| 2003/0092161 | A1 | 5/2003 | Gao et al. |
| 2004/0171807 | A1 | 9/2004 | Gao et al. |

FOREIGN PATENT DOCUMENTS

| | | | |
|---|---|---|---|
| WO | WO96/13598 | A2 | 5/1996 |
| WO | WO98/10087 | A1 | 3/1998 |
| WO | WO99/41359 | A1 | 8/1999 |
| WO | WO 00/03029 | A | 1/2000 |
| WO | WO 03/000851 | A2 | 1/2003 |
| WO | WO 03/046124 | A2 | 6/2003 |

OTHER PUBLICATIONS

Wu et al, Construction and Characterization of Adenovirus Serotype 5 Packaged by Serotype 3 Hexon, Journal of Virology, vol. 76, No. 24, pp. 12775-12782 (Dec. 2002).

Roy et al, Circumvention of Immunity to the Adenovirus Major Coat Protein Hexon, Journal of Virology, vol. 72, No. 8, pp. 6875-6879, (Aug. 1998).

Gall et al, Construction and Characterization of Hexon-Chimeric Adenoviruses: Specification of Adenovirus Serotype, Journal of Virology, vol. 72, No. 12, pp. 10260-10264, (Dec. 1998).

Gall et al, Adenovirus Type 5 and 7 Capsid Chimera: Fiber Replacement Alters Receptor Tropism without Affecting Primary Immune Neutralization Epitopes, Journal of Virology, vol. 70, No. 4, pp. 2116-2123, (Apr. 1996).

Wohlfart et al, Neutralization of Adenoviruses: Kinetics, Stoichiometry, and, Mechanisms, Journal of Virology, vol. 62, No. 7, Journal of Virology, pp. 2321-2328, (Jul. 1988).

Youil et al, Hexon Gene Switch Strategy for the Generation of Chimeric Recombinant Adenovirus, Human Gene Therapy, 13, pp. 311-320, (Jan. 20, 2002).

Roy et al, Characterization of a Family of Chimpanzee Adenoviruses and Development of Molecular Clones for Gene Transfer Vectors, Human Gene Therapy, 15:519-530, (May 2004).

Roy et al, Novel Chimeric Adenovirus Vaccine Vectors, 7th Annual Meeting of the American Society of Gene Therapy [Jun. 2-6, 2004] Minneapolis, Minnesota, Abstract 1016, (e-publ. May 2, 2004).

Farina et al, Replication-defective Vector Based on a Chimpanzee Adenovirus, Journal of Virology, vol. 75, No. 23, (Dec. 2001).

Stevens et al, American Type Culture Collection Catalogue of Strains II. Viruses and Antisera, XP002301508, pp. 227, paragraph 1, (1983).

Russell, Update on Adenovirus and its Vectors, Journal of Virology, 81, pp. 2573-2604, (Nov. 2000).

Farina et al, Simian Adenovirus 25 PIII, Database EMBL, Database accession No. Q8UY83, Mar. 1, 2002, XP002313001.

Farina et al, Simian Adenovirus 25 PII, Database EMBL, Database Accession No. Q8UY79, Mar. 1, 2002, XP002313002.

Farina et al, Simian Adenovirus 25 PIV (fiber), Database EMBL, Database Accession No. Q8UY68, Mar. 1, 2002, XP002313003.

Farina et al, Simian Adenovirus 25 E2A, Database EMBL, Database Accession No. Q8UY78, Mar. 1, 2002, XP002313004.

Cuzange et al, The Penton Base of Human Adenovirus Type 3 has the RGD Motif, Gene, vol. 146, No. 2, pp. 257-259, (Apr. 1994).

(Continued)

*Primary Examiner*—David Guzo
(74) *Attorney, Agent, or Firm*—Howson & Howson LLP

(57) ABSTRACT

A method for providing an adenovirus from a serotype which does not grow efficiently in a desired cell line with the ability to grow in that cell line is described. The method involves replacing the left and right termini of the adenovirus with the corresponding termini from an adenovirus which grow efficiently in the desired cell line. At a minimum, the left terminus spans the 5' inverted terminal repeat, the left terminus spans the E4 region and the 3' inverted terminal repeat. The resulting chimeric adenovirus contains the internal regions spanning the genes encoding the penton, hexon and fiber from the serotype which does not grow efficiently in the desired cell. Also provided are vectors constructed from novel simian adenovirus sequences and proteins, host cells containing same, and uses thereof.

23 Claims, No Drawings

OTHER PUBLICATIONS

Gruber et al, Fiber Gene and Genomic Origin of Human Adenovirus Type 4, Virology, vol. 196, No. 2, pp. 603-611, (Oct. 1993).

Pring-Akerblom et al, Hexon Sequence of Adenovirus type 7 and Comparison with Other Serotypes of Subgenus B, Research in Virology, vol. 146, No. 6, pp. 383-388, (Aug. 1995).

Krasnykh et al, Generation of Recombinant Adenovirus Vectors with Modified Fibers for Altering Viral Tropism, Journal of Virology, vol. 72, No. 12, (Dec. 1998).

Wickham et al, Increased in Vitro and In Vivo Gene Transfer by Adenovirus Vectors Containing Chimeric Fiber Proteins, Journal of Virology, vol. 71, No. 11, (Nov. 1997).

STIC Sequence/Fragment search results 14, 15, .rag.

SEQUENCE LISTING

```
<160> NUMBER OF SEQ ID NOS: 15

<210> SEQ ID NO 1
<211> LENGTH: 36462
<212> TYPE: DNA
<213> ORGANISM: chimpanzee adenovirus serotype Pan5

<400> SEQUENCE: 1

catcatcaat aatatacctc aaacttttgg tgcgcgttaa tatgcaaatg aggtatttga      60

atttggggat gcggggcggt gattggctgc gggagcggcg accgttaggg gcggggcggg     120

tgacgttttg atgacgtggc cgtgaggcgg agccggtttg caagttctcg tgggaaaagt     180
```

-continued

```
gacgtcaaac gaggtgtggt ttgaacacgg aaatactcaa ttttcccgcg ctctctgaca    240
ggaaatgagg tgtttctggg cggatgcaag tgaaaacggg ccattttcgc gcgaaaactg    300
aatgaggaag tgaaaatctg agtaattccg cgtttatggc agggaggagt atttgccgag    360
ggccgagtag actttgaccg attacgtggg ggtttcgatt accgtatttt tcacctaaat    420
ttccgcgtac ggtgtcaaag tccggtgttt ttacgtaggt gtcagctgat cgccagggta    480
tttaaacctg cgctctctag tcaagaggcc actcttgagt gccagcgagt agagttttct    540
cctccgcgcc gcgagtcaga tctacacttt gaaagatgag gcacctgaga gacctgcccg    600
gtaatgtttt cctggctact gggaacgaga ttctggaact ggtggtggac gccatgatgg    660
gtgacgaccc tccggagccc cctaccccat ttgaagcgcc ttcgctgtac gatttgtatg    720
atctggaggt ggatgtgccc gagaacgacc ccaacgagga ggcggtgaat gatttgttta    780
gcgatgccgc gctgctggct gccgagcagg ctaatacgga ctctggctca gacagcgatt    840
cctctctcca taccccgaga cccggcagag gtgagaaaaa gatccccgag cttaaagggg    900
aagagctcga cctgcgctgc tatgaggaat gcttgcctcc gagcgatgat gaggaggacg    960
aggaggcgat tcgagctgca gcgaaccagg gagtgaaaac agcgagcgag ggctttagcc   1020
tggactgtcc tactctgccc ggacacggct gtaagtcttg tgaatttcat cgcatgaata   1080
ctggagataa gaatgtgatg tgtgccctgt gctatatgag agcttacaac cattgtgttt   1140
acagtaagtg tgattaactt tagctgggga ggcagagggt gactgggtgc tgactggttt   1200
atttatgtat atgtttttta tgtgtaggtc ccgtctctga cgtagatgag acccccacta   1260
cagagtgcat ttcatcaccc ccagaaattg gcgaggaacc gcccgaagat attattcata   1320
gaccagttgc agtgagagtc accgggcgta gagcagctgt ggagagtttg gatgacttgc   1380
tacagggtgg ggatgaacct ttggacttgt gtacccggaa acgccccagg cactaagtgc   1440
cacacatgtg tgtttactta aggtgatgtc agtatttata gggtgtggag tgcaataaaa   1500
tccgtgttga ctttaagtgc gtggtttatg actcaggggt ggggactgtg ggtatataag   1560
caggtgcaga cctgtgtggt cagttcagag caggactcat ggagatctgg acagtcttgg   1620
aagactttca ccagactaga cagctgctag agaactcatc ggagggagtc tcttacctgt   1680
ggagattctg cttcggtggg cctctagcta agctagtcta tagggccaag caggattata   1740
aggatcaatt tgaggatatt ttgagagagt gtcctggtat tttttgactct ctcaacttgg   1800
gccatcagtc tcactttaac cagagtattc tgagagccct tgacttttct actcctggca   1860
gaactaccgc cgcggtagcc ttttttgcct ttatccttga caaatggagt caagaaaccc   1920
atttcagcag ggattaccgt ctggactgct tagcagtagc tttgtggaga acatggaggt   1980
gccagcgcct gaatgcaatc tccggctact tgccagtaca gccggtagac acgctgagga   2040
tcctgagtct ccagtcaccc caggaacacc aacgccgcca gcagccgcag caggagcagc   2100
agcaagagga ggaccgagaa gagaacctga gagccggtct ggaccctccg gtggcggagg   2160
aggaggagta gctgacttgt ttcccgagct gcgccgggtg ctgactaggt cttccagtgg   2220
acgggagagg gggattaagc gggagaggca tgaggagact agccacagaa ctgaactgac   2280
tgtcagtctg atgagtcgca ggcgcccaga atcggtgtgg tggcatgagg tgcagtcgca   2340
ggggatagat gaggtctcag tgatgcatga gaaatattcc ctagaacaag tcaagacttg   2400
ttggttggag cccgaggatg attgggaggt agccatcagg aattatgcca agctggctct   2460
gaggccagac aagaagtaca agattaccaa actgattaat atcagaaatt cctgctacat   2520
ttcagggaat ggggccgagg tggagatcag tacccaggag agggtggcct tcagatgctg   2580
```

-continued

```
catgatgaat atgtacccgg gggtggtggg catggaggga gtcaccttta tgaacgcgag   2640
gttcaggggt gatgggtata atggggtggt ctttatggcc aacaccaagc tgacagtgca   2700
cggatgctcc ttctttggct tcaataacat gtgcattgag gcctggggca gtgtttcagt   2760
gaggggatgc agtttttcag ccaactggat gggggtcgtg ggcagaacca agagcatggt   2820
gtcagtgaag aaatgcctgt tcgagaggtg ccacctgggg gtgatgagcg agggcgaagc   2880
caaagtcaaa cactgcgcct ctaccgagac gggctgcttt gtactgatca agggcaatgc   2940
caaagtcaag cataatatga tctgtggggc ctcggatgag cgcggctacc agatgctgac   3000
ctgcgccggt gggaacagcc atatgctagc caccgtgcat gtggcctcgc acccccgcaa   3060
gacatggccc gagttcgagc acaacgtcat gacccgctgc aatgtgcacc tggggtcccg   3120
ccgaggcatg ttcatgccct accagtgcaa catgcaattt gtgaaggtgc tgctggagcc   3180
cgatgccatg tccagagtga gcctgacggg ggtgtttgac atgaatgtgg agctgtggaa   3240
aattctgaga tatgatgaat ccaagaccag gtgccgggcc tgcgaatgcg gaggcaagca   3300
cgccaggctt cagcccgtgt gtgtggaggt gacggaggac ctgcgacccg atcatttggt   3360
gttgtcctgc aacgggacgg agttcggctc cagcggggaa gaatctgact agagtgagta   3420
gtgtttggga ctgggtggga gcctgcatga tgggcagaat gactaaaatc tgtgtttttc   3480
tgcgcagcag catgagcgga agcgcctcct ttgagggagg ggtattcagc ccttatctga   3540
cggggcgtct cccctcctgg gcgggagtgc gtcagaatgt gatgggatcc acggtggacg   3600
gccggcccgt gcagcccgcg aactcttcaa ccctgaccta cgcgaccctg agctcctcgt   3660
ccgtggacgc agctgccgcc gcagctgctg cttccgccgc cagcgccgtg cgcggaatgg   3720
ccctgggcgc cggctactac agctctctgg tggccaactc gagttccacc aataatcccg   3780
ccagcctgaa cgaggagaag ctgctgctgc tgatggccca gctcgaggcc ctgacccagc   3840
gcctgggcga gctgacccag caggtggctc agctgcaggc ggagacgcgg gccgcggttg   3900
ccacggtgaa aaccaaataa aaaatgaatc aataaataaa cggagacggt tgttgatttt   3960
aacacagagt cttgaatctt tatttgattt ttcgcgcgcg gtaggccctg gaccaccggt   4020
ctcgatcatt gagcacccgg tggatctttt ccaggacccg gtagaggtgg gcttggatgt   4080
tgaggtacat gggcatgagc ccgtcccggg ggtggaggta gctccattgc agggcctcgt   4140
gctcgggggt ggtgttgtaa atcacccagt catagcaggg gcgcagggcg tggtgctgca   4200
cgatgtcctt gaggaggaga ctgatggcca cgggcagccc cttggtgtag gtgttgacga   4260
acctgttgag ctgggaggga tgcatgcggg gggagatgag atgcatcttg gcctggatct   4320
tgagattggc gatgttcccg cccagatccc gccggggggtt catgttgtgc aggaccacca   4380
gcacggtgta tccggtgcac ttggggaatt tgtcatgcaa cttggaaggg aaggcgtgaa   4440
agaatttgga gacgcccttg tgaccgccca ggttttccat gcactcatcc atgatgatgg   4500
cgatgggccc gtgggcggcg gcttgggcaa agacgtttcg ggggtcggac acatcgtagt   4560
tgtggtcctg ggtgagctcg tcataggcca ttttaatgaa tttggggcgg agggtgcccg   4620
actgggggac gaaggtgccc tcgatcccgg gggcgtagtt gccctcgcag atctgcatct   4680
cccaggcctt gagctcggag ggggggatca tgtccacctg cggggcgatg aaaaaaacgg   4740
tttccggggc gggggagatg agctgggccg aaagcaggtt ccggagcagc tgggacttgc   4800
cgcagccggt ggggccgtag atgaccccga tgaccggctg caggtggtag ttgagggaga   4860
gacagctgcc gtcctcgcgg aggagggggg ccacctcgtt catcatctcg cgcacatgca   4920
```

-continued

```
tgttctcgcg cacgagttcc gccaggaggc gctcgccccc aagcgagagg agctcttgca   4980
gcgaggcgaa gtttttcagc ggcttgagcc cgtcggccat gggcattttg gagagggtct   5040
gttgcaagag ttccagacgg tcccagagct cggtgatgtg ctctagggca tctcgatcca   5100
gcagacctcc tcgtttcgcg ggttggggcg actgcgggag tagggcacca ggcgatgggc   5160
gtccagcgag gccagggtcc ggtccttcca ggggcgcagg gtccgcgtca gcgtggtctc   5220
cgtcacggtg aaggggtgcg cgccgggctg ggcgcttgcg agggtgcgct tcaggctcat   5280
ccggctggtc gagaaccgct cccggtcggc gccctgcgcg tcggccaggt agcaattgag   5340
catgagttcg tagttgagcg cctcggccgc gtggcccttg gcgcggagct tacctttgga   5400
agtgtgtccg cagacgggac agaggaggga cttgagggcg tagagcttgg gggcgaggaa   5460
gacggactcg ggggcgtagg cgtccgcgcc gcagctggcg cagacggtct cgcactccac   5520
gagccaggtg aggtctggcc ggtcggggtc aaaaacgagg tttcctccgt gctttttgat   5580
gcgtttctta cctctggtct ccatgagctc gtgtccccgc tgggtgacaa agaggctgtc   5640
cgtgtccccg tagaccgact ttatgggccg gtcctcgagc ggggtgccgc ggtcctcgtc   5700
gtagaggaac ccgcccact  ccgagacgaa ggcccgggtc caggccagca cgaaggaggc   5760
cacgtgggag gggtagcggt cgttgtccac cagcgggtcc accttctcca gggtatgcaa   5820
gcacatgtcc ccctcgtcca catccaggaa ggtgattggc ttgtaagtgt aggccacgtg   5880
accgggggtc ccggccgggg gggtataaaa gggggcgggc ccctgctcgt cctcactgtc   5940
ttccggatcg ctgtccagga gcgccagctg ttggggtagg tattccctct cgaaggcggg   6000
catgacctcg gcactcaggt tgtcagtttc tagaaacgag gaggatttga tattgacggt   6060
gccgttggag acgcctttca tgagcccctc gtccatctgg tcagaaaaga cgatcttttt   6120
gttgtcgagc ttggtggcga aggagccgta gagggcgttg gagagcagct tggcgatgga   6180
gcgcatggtc tggttctttt ccttgtcggc gcgctccttg gcggcgatgt tgagctgcac   6240
gtactcgcgc gccacgcact tccattcggg gaagacggtg gtgagcttgt cgggcacgat   6300
tctgacccgc cagccgcggt tgtgcagggt gatgaggtcc acgctggtgg ccacctcgcc   6360
gcgcaggggc tcgttggtcc agcagaggcg cccgcccttg cgcgagcaga aggggggcag   6420
cgggtccagc atgagctcgt cggggggggtc ggcgtccacg gtgaagatgc cgggcaggag   6480
ctcggggtcg aagtagctga tgcaggtgcc cagatcgtcc agcgccgctt gccagtcgcg   6540
cacggccagc gcgcgctcgt aggggctgag gggcgtgccc cagggcatgg ggtgcgtgag   6600
cgcggaggcg tacatgccgc agatgtcgta gacgtagagg ggctcctcga ggacgccgat   6660
gtaggtgggg tagcagcgcc ccccgcggat gctggcgcgc acgtagtcgt acagctcgtg   6720
cgagggcgcg aggagcccgg tgccgaggtt ggagcgctgc ggcttttcgg cgcggtagac   6780
gatctggcgg aagatggcgt gggagttgga ggagatggtg ggcctctgga agatgttgaa   6840
gtgggcgtgg ggcagtccga ccgagtccct gatgaagtgg gcgtaggagt cctgcagctt   6900
ggcgacgagc tcggcggtga cgaggacgtc cagggcgcag tagtcgaggg tctcttggat   6960
gatgtcgtac ttgagctggc ccttctgctt ccacagctcg cggttgagaa ggaactcttc   7020
gcggtccttc cagtactctt cgagggggaa cccgtcctga tcggcacggt aagagcccac   7080
catgtagaac tggttgacgg ccttgtaggc gcagcagccc ttctccacgg ggagggcgta   7140
agcttgcgcg gccttgcgca gggaggtgtg ggtgagggcg aaggtgtcgc gcaccatgac   7200
cttgaggaac tggtgcttga agtcgaggtc gtcgcagccg ccctgctccc agagctggaa   7260
gtccgtgcgc ttcttgtagg cggggttggg caaagcgaaa gtaacatcgt tgaagaggat   7320
```

-continued

```
cttgcccgcg cggggcatga agttgcgagt gatgcggaaa ggctggggca cctcggcccg   7380
gttgttgatg acctgggcgg cgaggacgat ctcgtcgaag ccgttgatgt tgtgcccgac   7440
gatgtagagt tccacgaatc gcgggcggcc cttgacgtgg ggcagcttct tgagctcgtc   7500
gtaggtgagc tcggcggggt cgctgaggcc gtgctgctcg agggcccagt cggcgaggtg   7560
ggggttggcg ccgaggaagg aagtccagag atccacggcc agggcggtct gcaagcggtc   7620
ccggtactga cggaactgct ggcccacggc catttttttcg ggggtgacgc agtagaaggt   7680
gcgggggtcg ccgtgccagc ggtcccactt gagctggagg gcgaggtcgt gggcgagctc   7740
gacgagcggc gggtccccgg agagtttcat gaccagcatg aaggggacga gctgcttgcc   7800
gaaggacccc atccaggtgt aggtttccac gtcgtaggtg aggaagagcc tttcggtgcg   7860
aggatgcgag ccgatgggga agaactggat ctcctgccac cagttggagg aatggctgtt   7920
gatgtgatgg aagtagaaat gccgacggcg cgccgagcac tcgtgcttgt gtttatacaa   7980
gcgtccgcag tgctcgcaac gctgcacggg atgcacgtgc tgcacgagct gtacctgggt   8040
tcctttgacg aggaatttca gtgggcagtg gagcgctggc ggctgcatct ggtgctgtac   8100
tacgtcctgg ccatcggcgt ggccatcgtc tgcctcgatg gtggtcatgc tgacgaggcc   8160
gcgcgggagg caggtccaga cctcggctcg gacgggtcgg agagcgagga cgagggcgcg   8220
caggccggag ctgtccaggg tcctgagacg ctgcggagtc aggtcagtgg gcagcggcgg   8280
cgcgcggttg acttgcagga gcttttccag ggcgcgcggg aggtccagat ggtacttgat   8340
ctccacggcg ccgttggtgg cgacgtccac ggcttgcagg gtcccgtgcc cctggggcgc   8400
caccaccgtg ccccgtttct tcttgggtgc tggcggcggc ggctccatgc ttagaagcgg   8460
cggcgaggac gcgcgccggg cggcaggggc ggctcggggc ccggaggcag gggcggcagg   8520
ggcacgtcgg cgccgcgcgc gggcaggttc tggtactgcg cccggagaag actggcgtga   8580
gcgacgacgc gacggttgac gtcctggatc tgacgcctct gggtgaaggc cacgggaccc   8640
gtgagtttga acctgaaaga gagttcgaca gaatcaatct cggtatcgtt gacggcggcc   8700
tgccgcagga tctcttgcac gtcgcccgag ttgtcctggt aggcgatctc ggtcatgaac   8760
tgctcgatct cctcctcctg aaggtctccg cgaccggcgc gctcgacggt ggccgcgagg   8820
tcgttggaga tgcggcccat gagctgcgag aaggcgttca tgccggcctc gttccagacg   8880
cggctgtaga ccacggctcc gtcggggtcg cgcgcgcgca tgaccacctg ggcgaggttg   8940
agctcgacgt ggcgcgtgaa gaccgcgtag ttgcagaggc gctggtagag gtagttgagc   9000
gtggtggcga tgtgctcggt gacgaagaag tacatgatcc agcggcggag cggcatctcg   9060
ctgacgtcgc ccagggcttc caagcgctcc atggcctcgt agaagtccac ggcgaagttg   9120
aaaaactggg agttgcgcgc cgagacggtc aactcctcct ccagaagacg gatgagctcg   9180
gcgatggtgg cgcgcacctc gcgctcgaag gccccggggg gctcctcttc ttccatctcc   9240
tcctcctctt ccatctcctc cactaacatc tcttctactt cctcctcagg aggcggcggc   9300
gggggagggg ccctgcgtcg ccggcggcgc acgggcagac ggtcgatgaa gcgctcgatg   9360
gtctccccgc gccggcgacg catggtctcg gtgacggcgc gcccgtcctc gcggggccgc   9420
agcgtgaaga cgccgccgcg catctccagg tggccgccgg gggggtctcc gttgggcagg   9480
gagagggcgc tgacgatgca tcttatcaat tggcccgtag ggactccgcg caaggacctg   9540
agcgtctcga gatccacggg atccgaaaac cgctgaacga aggcttcgag ccagtcgcag   9600
tcgcaaggta ggctgagccc ggtttcttgt tcttcgggta tttggtcggg aggcgggcgg   9660
```

-continued

```
gcgatgctgc tggtgatgaa gttgaagtag gcggtcctga gacggcggat ggtggcgagg   9720
agcaccaggt ccttgggccc ggcttgctgg atgcgcagac ggtcggccat gccccaggcg   9780
tggtcctgac acctggcgag gtccttgtag tagtcctgca tgagccgctc cacgggcacc   9840
tcctcctcgc ccgcgcggcc gtgcatgcgc gtgagcccga acccgcgctg cggctggacg   9900
agcgccaggt cggcgacgac gcgctcggcg aggatggcct gctggatctg ggtgagggtg   9960
gtctggaagt cgtcgaagtc gacgaagcgg tggtaggctc cggtgttgat ggtgtaggag  10020
cagttggcca tgacggacca gttgacggtc tggtggccgg ggcgcacgag ctcgtggtac  10080
ttgaggcgcg agtaggcgcg cgtgtcgaag atgtagtcgt tgcaggtgcg cacgaggtac  10140
tggtatccga cgaggaagtg cggcggcggc tggcggtaga gcggccatcg ctcggtggcg  10200
ggggcgccgg gcgcgaggtc ctcgagcatg aggcggtggt agccgtagat gtacctggac  10260
atccaggtga tgccggcggc ggtggtggag gcgcgcggga actcgcggac gcggttccag  10320
atgttgcgca gcggcaggaa gtagttcatg gtggccgcgg tctggcccgt gaggcgcgcg  10380
cagtcgtgga tgctctagac atacgggcaa aaacgaaagc ggtcagcggc tcgactccgt  10440
ggcctggagg ctaagcgaac gggttgggct gcgcgtgtac cccggttcga gtccctgctc  10500
gaatcaggct ggagccgcag ctaacgtggt actggcactc ccgtctcgac ccaagcctgc  10560
taacgaaacc tccaggatac ggaggcgggt cgttttggcc attttcgtca ggccggaaat  10620
gaaactagta agcgcggaaa gcggccgtcc gcgatggctc gctgccgtag tctggagaaa  10680
gaatcgccag ggttgcgttg cggtgtgccc cggttcgagc ctcagcgctc ggcgccggcc  10740
ggattccgcg gctaacgtgg gcgtggctgc cccgtcgttt ccaagacccc ttagccagcc  10800
gacttctcca gttacggagc gagcccctct tttcttgtg tttttgccag atgcatcccg  10860
tactgcggca gatgcgcccc caccctccac cacaaccgcc cctaccgcag cagcagcaac  10920
agccggcgct tctgcccccg ccccagcagc agcagccagc cactaccgcg gcggccgccg  10980
tgagcggagc cggcgttcag tatgacctgg ccttggaaga gggcgagggg ctggcgcggc  11040
tgggggcgtc gtcgccggag cggcacccgc gcgtgcagat gaaaagggac gctcgcgagg  11100
cctacgtgcc caagcagaac ctgttcagag acaggagcgg cgaggagccc gaggagatgc  11160
gcgcctcccg cttccacgcg gggcgggagc tgcggcgcgg cctggaccga aagcgggtgc  11220
tgagggacga ggatttcgag gcggacgagc tgacggggat cagccccgcg cgcgcgcacg  11280
tggccgcggc caacctggtc acggcgtacg agcagaccgt gaaggaggag agcaacttcc  11340
aaaaatcctt caacaaccac gtgcgcacgc tgatcgcgcg cgaggaggtg accctgggcc  11400
tgatgcacct gtgggacctg ctggaggcca tcgtgcagaa ccccacgagc aagccgctga  11460
cggcgcagct gtttctggtg gtgcagcaca gtcgggacaa cgagacgttc agggaggcgc  11520
tgctgaatat caccgagccc gagggccgct ggctcctgga cctggtgaac attctgcaga  11580
gcatcgtggt gcaggagcgc gggctgccgc tgtccgagaa gctggcggcc atcaacttct  11640
cggtgctgag cctgggcaag tactacgcta ggaagatcta caagaccccg tacgtgccca  11700
tagacaagga ggtgaagatc gacgggtttt acatgcgcat gaccctgaaa gtgctgaccc  11760
tgagcgacga tctgggggtg taccgcaacg acaggatgca ccgcgcggtg agcgccagcc  11820
gccggcgcga gctgagcgac caggagctga tgcacagcct gcagcgggcc ctgaccgggg  11880
ccgggaccga gggggagagc tactttgaca tgggcgcgga cctgcgctgg cagcctagcc  11940
gccgggcctt ggaagctgcc ggcggttccc cctacgtgga ggaggtggac gatgaggagg  12000
aggagggcga gtacctggaa gactgatggc gcgaccgtat ttttgctaga tgcagcaaca  12060
```

-continued

```
gccaccgccg cctcctgatc ccgcgatgcg ggcggcgctg cagagccagc cgtccggcat  12120
taactcctcg gacgattgga cccaggccat gcaacgcatc atggcgctga cgacccgcaa  12180
tcccgaagcc tttagacagc agcctcaggc caaccgactc tcggccatcc tggaggccgt  12240
ggtgccctcg cgctcgaacc ccacgcacga gaaggtgctg gccatcgtga acgcgctggt  12300
ggagaacaag gccatccgcg gcgacgaggc cgggctggtg tacaacgcgc tgctggagcg  12360
cgtggcccgc tacaacagca ccaacgtgca gacgaacctg gaccgcatgg tgaccgacgt  12420
gcgcgaggcg gtgtcgcagc gcgagcggtt ccaccgcgag tcgaacctgg gctccatggt  12480
ggcgctgaac gccttcctga gcacgcagcc cgccaacgtg ccccggggcc aggaggacta  12540
caccaacttc atcagcgcgc tgcggctgat ggtggccgag gtgccccaga gcgaggtgta  12600
ccagtcgggg ccggactact tcttccagac cagtcgccag ggcttgcaga ccgtgaacct  12660
gagccaggct ttcaagaact tgcagggact gtggggcgtg caggccccgg tcggggaccg  12720
cgcgacggtg tcgagcctgc tgacgccgaa ctcgcgcctg ctgctgctgc tggtggcgcc  12780
cttcacggac agcggcagcg tgagccgcga ctcgtacctg ggctacctgc ttaacctgta  12840
ccgcgaggcc atcgggcagg cgcacgtgga cgagcagacc taccaggaga tcacccacgt  12900
gagccgcgcg ctgggccagg aggacccggg caacctggag gccaccctga acttcctgct  12960
gaccaaccgg tcgcagaaga tcccgcccca gtacgcgctg agcaccgagg aggagcgcat  13020
cctgcgctac gtgcagcaga gcgtggggct gttcctgatg caggaggggg ccacgcccag  13080
cgccgcgctc gacatgaccg cgcgcaacat ggagcccagc atgtacgccc gcaaccgccc  13140
gttcatcaat aagctgatgg actacttgca tcgggcggcc gccatgaact cggactactt  13200
taccaacgcc atcttgaacc cgcactggct cccgccgccc gggttctaca cgggcgagta  13260
cgacatgccc gaccccaacg acgggttcct gtgggacgac gtggacagca gcgtgttctc  13320
gccgcgcccc accaccacca ccgtgtggaa gaaagagggc ggggaccggc ggccgtcctc  13380
ggcgctgtcc ggtcgcgcgg gtgctgccgc ggcggtgccc gaggccgcca gccccttccc  13440
gagcctgccc ttttcgctga acagcgtgcg cagcagcgag ctgggtcggc tgacgcggcc  13500
gcgcctgctg ggcgaggagg agtacctgaa cgactccttg cttcggcccg agcgcgagaa  13560
gaacttcccc aataacggga tagagagcct ggtggacaag atgagccgct ggaagacgta  13620
cgcgcacgag cacagggacg agccccgagc tagcagcagc accggcgcca cccgtagacg  13680
ccagcggcac gacaggcagc ggggtctggt gtgggacgat gaggattccg ccgacgacag  13740
cagcgtgttg gacttgggtg ggagtggtgg tggtaacccg ttcgctcacc tgcgcccccg  13800
tatcgggcgc ctgatgtaag aatctgaaaa aataaaagac ggtactcacc aaggccatgg  13860
cgaccagcgt gcgttcttct ctgttgtttg tagtagtatg atgaggcgcg tgtacccgga  13920
gggtcctcct ccctcgtacg agagcgtgat gcagcaggcg gtggcggcgg cgatgcagcc  13980
cccgctggag gcgccttacg tgcccccgcg gtacctggcg cctacggagg ggcggaacag  14040
cattcgttac tcggagctgg cacccttgta cgataccacc cggttgtacc tggtggacaa  14100
caagtcggcg gacatcgcct cgctgaacta ccagaacgac cacagcaact tcctgaccac  14160
cgtggtgcag aacaacgatt tcacccccac ggaggccagc acccagacca tcaactttga  14220
cgagcgctcg cggtggggcg gccagctgaa aaccatcatg cacaccaaca tgcccaacgt  14280
gaacgagttc atgtacagca acaagttcaa ggcgcgggtg atggtctcgc gcaagacccc  14340
caacggggtc acagtaacag atggtagtca ggacgagctg acctacgagt gggtggagtt  14400
```

-continued

```
tgagctgccc gagggcaact tctcggtgac catgaccatc gatctgatga acaacgccat  14460
catcgacaac tacttggcgg tggggcggca gaacggggtg ctggagagcg acatcggcgt  14520
gaagttcgac acgcgcaact tccggctggg ctgggacccc gtgaccgagc tggtgatgcc  14580
gggcgtgtac accaacgagg ccttccaccc cgacatcgtc ctgctgcccg gctgcggcgt  14640
ggacttcacc gagagccgcc tcagcaacct gctgggcatc cgcaagcggc agcccttcca  14700
ggagggcttc cagatcctgt acgaggacct ggaggggggc aacatccccg cgctgctgga  14760
cgtggacgcc tacgagaaaa gcaaggagga tagcgccgcc gcggcgaccg cagccgtggc  14820
caccgcctct accgaggtgc ggggcgataa ttttgctagc gccgcgacac tggcagcggc  14880
cgaggcggct gaaaccgaaa gtaagatagt gatccagccg gtggagaagg acagcaagga  14940
gaggagctac aacgtgctcg cggacaagaa aaacaccgcc taccgcagct ggtacctggc  15000
ctacaactac ggcgaccccg agaagggcgt gcgctcctgg acgctgctca ccacctcgga  15060
cgtcacctgc ggcgtggagc aagtctactg gtcgctgccc gacatgatgc aagacccggt  15120
caccttccgc tccacgcgtc aagttagcaa ctacccggtg gtgggcgccg agctcctgcc  15180
cgtctactcc aagagcttct tcaacgagca ggccgtctac tcgcagcagc tgcgcgcctt  15240
cacctcgctc acgcacgtct tcaaccgctt ccccgagaac cagatcctcg ttcgcccgcc  15300
cgcgcccacc attaccaccg tcagtgaaaa cgttcctgct ctcacagatc acgggaccct  15360
gccgctgcgc agcagtatcc ggggagtcca gcgcgtgacc gtcactgacg ccagacgccg  15420
cacctgcccc tacgtctaca aggccctggg cgtagtcgcg ccgcgcgtcc tctcgagccg  15480
caccttctaa aaaatgtcca ttctcatctc gcccagtaat aacaccggtt ggggcctgcg  15540
cgcgcccagc aagatgtacg gaggcgctcg ccaacgctcc acgcaacacc ccgtgcgcgt  15600
gcgcgggcac ttccgcgctc cctggggcgc cctcaagggc cgcgtgcgct cgcgcaccac  15660
cgtcgacgac gtgatcgacc aggtggtggc cgacgcgcgc aactacacgc ccgccgccgc  15720
gcccgtctcc accgtggacg ccgtcatcga cagcgtggtg gccgacgcgc gccggtacgc  15780
ccgcgccaag agccggcggc ggcgcatcgc ccggcggcac cggagcaccc ccgccatgcg  15840
cgcggcgcga gccttgctgc gcagggccag gcgcacggga cgcagggcca tgctcagggc  15900
ggccagacgc gcggcctccg gcagcagcag cgccggcagg acccgcagac gcgcggccac  15960
ggcggcggcg gcggccatcg ccagcatgtc ccgcccgcgg cgcggcaacg tgtactgggt  16020
gcgcgacgcc gccaccggtg tgcgcgtgcc cgtgcgcacc cgcccccctc gcacttgaag  16080
atgctgactt cgcgatgttg atgtgtccca gcggcgagga ggatgtccaa gcgcaaattc  16140
aaggaagaga tgctccaggt catcgcgcct gagatctacg gcccggcggc ggtgaaggag  16200
gaaagaaagc cccgcaaact gaagcgggtc aaaaaggaca aaaaggagga ggaagatgtg  16260
gacggactgg tggagtttgt gcgcgagttc gccccccggc ggcgcgtgca gtggcgcggg  16320
cggaaagtga aaccggtgct gcgacccggc accacggtgg tcttcacgcc cggcgagcgt  16380
tccggctccg cctccaagcg ctcctacgac gaggtgtacg gggacgagga catcctcgag  16440
caggcggccg aacgtctggg cgagtttgct tacggcaagc gcagccgccc cgcgcccttg  16500
aaagaggagg cggtgtccat cccgctggac cacggcaacc ccacgccgag cctgaagccg  16560
gtgaccctgc agcaggtgct gcctggtgcg gcgccgcgcc ggggcttcaa gcgcgagggc  16620
ggcgaggatc tgtacccgac catgcagctg atggtgccca agcgccagaa gctggaggac  16680
gtgctggagc acatgaaggt ggaccccgag gtgcagcccg aggtcaaggt gcggcccatc  16740
aagcaggtgg ccccgggcct gggcgtgcag accgtggaca tcaagatccc cacggagccc  16800
```

-continued

```
atggaaacgc agaccgagcc cgtgaagccc agcaccagca ccatggaggt gcagacggat  16860
ccctggatgc cggcaccggc ttccaccacc cgccgaagac gcaagtacgg cgcggccagc  16920
ctgctgatgc ccaactacgc gctgcatcct tccatcatcc ccacgccggg ctaccgcggc  16980
acgcgcttct accgcggcta caccagcagc cgccgccgca agaccaccac ccgccgccgc  17040
cgtcgtcgca cccgccgcag cagcaccgcg acttccgccg ccgccctggt gcggagagtg  17100
taccgcagcg ggcgcgagcc tctgaccctg ccgcgcgcgc gctaccaccc gagcatcgcc  17160
atttaactac cgcctcctac ttgcagatat ggccctcaca tgccgcctcc gcgtccccat  17220
tacgggctac cgaggaagaa agccgcgccg tagaaggctg acggggaacg ggctgcgtcg  17280
ccatcaccac cggcggcggc gcgccatcag caagcggttg gggggaggct tcctgcccgc  17340
gctgatgccc atcatcgccg cggcgatcgg ggcgatcccc ggcatagctt ccgtggcggt  17400
gcaggcctct cagcgccact gagacacagc ttggaaaatt tgtaataaaa aatggactga  17460
cgctcctggt cctgtgatgt gtgtttttag atggaagaca tcaatttttc gtccctggca  17520
ccgcgacacg gcacgcggcc gtttatgggc acctggagcg acatcggcaa cagccaactg  17580
aacgggggcg ccttcaattg gagcagtctc tggagcgggc ttaagaattt cgggtccacg  17640
ctcaaaacct atggcaacaa ggcgtggaac agcagcacag ggcaggcgct gagggaaaag  17700
ctgaaagagc agaacttcca gcagaaggtg gtcgatggcc tggcctcggg catcaacggg  17760
gtggtggacc tggccaacca ggccgtgcag aaacagatca acagccgcct ggacgcggtc  17820
ccgcccgcgg ggtccgtgga gatgccccag gtggaggagg agctgcctcc cctggacaag  17880
cgcggcgaca agcgaccgcg tcccgacgcg gaggagacgc tgctgacgca cacggacgag  17940
ccgcccccgt acgaggaggc ggtgaaactg ggtctgccca ccacgcggcc cgtggcgcct  18000
ctggccaccg gggtgctgaa acccagcagc agcagcagcc agcccgcgac cctggacttg  18060
cctccgcctg cttcccgccc ctccacagtg gctaagcccc tgccgccggt ggccgtcgcg  18120
tcgcgcgccc cccgaggccg cccccaggcg aactggcaga gcactctgaa cagcatcgtg  18180
ggtctgggag tgcagagtgt gaagcgccgc cgctgctatt aaaagacact gtagcgctta  18240
acttgcttgt ctgtgtgtat atgtatgtcc gccgaccaga aggaggagga agaggcgcgt  18300
cgccgagttg caagatggcc accccatcga tgctgcccca gtgggcgtac atgcacatcg  18360
ccggacagga cgcttcggag tacctgagtc cgggtctggt gcagttcgcc cgcgccacag  18420
acacctactt cagtctgggg aacaagttta ggaaccccac ggtggcgccc acgcacgatg  18480
tgaccaccga ccgcagccag cggctgacgc tgcgcttcgt gcccgtggac cgcgaggaca  18540
acacctactc gtacaaagtg cgctacacgc tggccgtggg cgacaaccgc gtgctggaca  18600
tggccagcac ctactttgac atccgcggcg tgctggatcg gggccctagc ttcaaaccct  18660
actccggcac cgcttacaac agcctggctc ccaagggagc gcccaacact tgccagtgga  18720
catataaagc tgatggtgat actggtacag aaaaaaccta tacatatgga aatgcgcctg  18780
tgcaaggcat tagtattaca aaagatggta ttcaacttgg aactgacact gatgatcagc  18840
ccatttatgc agataaaact tatcaaccag agcctcaagt gggtgatgct gaatggcatg  18900
acatcactgg tactgatgaa aaatatggag gcagagctct caagcctgac accaaaatga  18960
agccctgcta tggttctttt gccaagccta ccaataaaga aggaggtcag gcaaatgtga  19020
aaaccgaaac aggcggtacc aaagaatatg acattgacat ggcattcttc gataatcgaa  19080
gtgcagctgc ggctggcctg gccccagaaa ttgttttgta tactgagaat gtggatctgg  19140
```

-continued

```
aaactccaga tactcatatt gtatacaagg cgggcacaga tgacagcagc tcttctatca  19200
atttgggtca gcagtccatg cccaacagac ccaactacat tggctttaga gacaacttta  19260
tcgggctcat gtactacaac agcactggca acatgggcgt gctggctggt caggcctccc  19320
agctgaatgc tgtggtggac ttgcaggaca gaaacactga actgtcctac cagctcttgc  19380
ttgactctct gggcgacaga accaggtatt tcagtatgtg gaatcaggcg gtggacagct  19440
atgaccccga tgtgcgcatt attgaaaatc acggtgtgga ggatgaactc cctaactatt  19500
gcttcccccct ggatgctgtg ggtagaactg atacttacca gggaattaag gccaatggtg  19560
ctgatcaaac cacctggacc aaagatgata ctgttaatga tgctaatgaa ttgggcaagg  19620
gcaatccttt cgccatggag atcaacatcc aggccaacct gtggcggaac ttcctctacg  19680
cgaacgtggc gctgtacctg cccgactcct acaagtacac gccggccaac atcacgctgc  19740
cgaccaacac caacacctac gattacatga acggccgcgt ggtggcgccc tcgctggtgg  19800
acgcctacat caacatcggg gcgcgctggt cgctggaccc catggacaac gtcaacccct  19860
tcaaccacca ccgcaacgcg ggcctgcgct accgctccat gctcctgggc aacgggcgct  19920
acgtgccctt ccacatccag gtgccccaaa agttcttcgc catcaagagc ctcctgctcc  19980
tgcccgggtc ctacacctac gagtggaact tccgcaagga cgtcaacatg atcctgcaga  20040
gctccctcgg caacgacctg cgcacggacg gggcctccat cgccttcacc agcatcaacc  20100
tctacgccac cttcttcccc atggcgcaca acaccgcctc cacgctcgag gccatgctgc  20160
gcaacgacac caacgaccag tccttcaacg actacctctc ggcggccaac atgctctacc  20220
ccatcccggc caacgccacc aacgtgccca tctccatccc ctcgcgcaac tgggccgcct  20280
tccgcggatg gtccttcacg cgcctcaaga cccgcgagac gccctcgctc ggctccgggt  20340
tcgaccccta cttcgtctac tcgggctcca tcccctacct cgacggcacc ttctacctca  20400
accacacctt caagaaggtc tccatcacct tcgactcctc cgtcagctgg cccggcaacg  20460
accgcctcct gacgcccaac gagttcgaaa tcaagcgcac cgtcgacgga gaggggtaca  20520
acgtggccca gtgcaacatg accaaggact ggttcctggt ccagatgctg gcccactaca  20580
acatcggcta ccagggcttc tacgtgcccg agggctacaa ggaccgcatg tactccttct  20640
tccgcaactt ccagcccatg agccgccagg tcgtggacga ggtcaactac aaggactacc  20700
aggccgtcac cctggcctac cagcacaaca actcgggctt cgtcggctac ctcgcgccca  20760
ccatgcgcca gggacagccc taccccgcca actaccccta cccgctcatc ggcaagagcg  20820
ccgtcgccag cgtcacccag aaaaagttcc tctgcgaccg ggtcatgtgg cgcatcccct  20880
tctccagcaa cttcatgtcc atgggcgcgc tcaccgacct cggccagaac atgctctacg  20940
ccaactccgc ccacgcgcta gacatgaatt tcgaagtcga ccccatggat gagtccaccc  21000
ttctctatgt tgtcttcgaa gtcttcgacg tcgtccgagt gcaccagccc caccgcggcg  21060
tcatcgaggc cgtctacctg cgcacgccct tctcggccgg caacgccacc acctaagccc  21120
cgctcttgct tcttgcaaga tgacggcctg tgcgggctcc ggcgagcagg agctcagggc  21180
catcctccgc gacctgggct gcgggccctg cttcctgggc accttcgaca agcgcttccc  21240
gggattcatg gccccgcaca agctggcctg cgccatcgtc aacacggccg gccgcgagac  21300
cgggggcgag cactggctgg ccttcgcctg gaacccgcgc tcccacacct gctacctctt  21360
cgacccctc gggttctcgg acgagcgcct caagcagatc taccagttcg agtacgaggg  21420
cctgctgcgc cgcagcgccc tggccaccga ggaccgctgc gtcaccctgg aaaagtccac  21480
ccagaccgtg cagggtccgc gctcggccgc ctgcgggctc ttctgctgca tgttcctgca  21540
```

-continued

```
cgccttcgtg cactggcccg accgccccat ggacaagaac cccaccatga acttgctgac  21600
gggggtgccc aacggcatgc tccagtcgcc ccaggtggaa cccaccctgc gccgcaacca  21660
ggaggcgctc taccgcttcc tcaacgccca ctccgcctac tttcgctccc accgcgcgcg  21720
catcgagaag gccaccgcct tcgaccgcat gaatcaagac atgtaaaccg tgtgtgtatg  21780
tgaatgcttt attcataata aacagcacat gtttatgcca ccttttctga ggctctgact  21840
ttatttagaa atcgaagggg ttctgccggc tctcggcgtg ccccgcgggc agggatacgt  21900
tgcggaactg gtacttgggc agccacttga actcggggat cagcagcttc ggcacgggga  21960
ggtcggggaa cgagtcgctc cacagcttgc gcgtgagttg cagggcgccc agcaggtcgg  22020
gcgcggagat cttgaaatcg cagttgggac ccgcgttctg cgcgcgggag ttgcggtaca  22080
cggggttgca gcactggaac accatcaggg ccgggtgctt cacgctcgcc agcaccgtcg  22140
cgtcggtgat gccctccacg tccagatcct cggcgttggc catcccgaag gggtcatct   22200
tgcaggtctg ccgccccatg ctgggcacgc agccgggctt gtggttgcaa tcgcagtgca  22260
gggggatcag catcatctgg gcctgctcgg agctcatgcc cgggtacatg gccttcatga  22320
aagcctccag ctggcggaag gcctgctgcg ccttgccgcc ctcggtgaag aagaccccgc  22380
aggacttgct agagaactgg ttggtggcgc agccggcgtc gtgcacgcag cagcgcgcgt  22440
cgttgttggc cagctgcacc acgctgcgcc cccagcggtt ctgggtgatc ttggcccggt  22500
cggggttctc cttcagcgcg cgctgcccgt tctcgctcgc cacatccatc tcgatcgtgt  22560
gctccttctg gatcatcacg gtcccgtgca ggcatcgcag cttgccctcg gcctcggtgc  22620
acccgtgcag ccacagcgcg cagccggtgc actcccagtt cttgtgggcg atctgggagt  22680
gcgagtgcac gaagccctgc aggaagcggc ccatcatcgt ggtcagggtc ttgttgctgg  22740
tgaaggtcag cgggatgccg cggtgctcct cgttcacata caggtggcag atgcggcggt  22800
acacctcgcc ctgctcgggc atcagctgga aggcggactt caggtcgctc tccacgcggt  22860
accggtccat cagcagcgtc atgacttcca tgcccttctc ccaggccgag acgatcggca  22920
ggctcagggg gttcttcacc gccgttgtca tcttagtcgc cgccgctgag gtcagggggt  22980
cgttctcgtc cagggtctca aacactcgct tgccgtcctt ctcggtgatg cgcacggggg  23040
gaaagctgaa gcccacggcc gccagctcct cctcggcctg cctttcgtcc tcgctgtcct  23100
ggctgatgtc ttgcaaaggc acatgcttgg tcttgcgggg tttctttttg ggcggcagag  23160
gcggcggcgg agacgtgctg ggcgagcgcg agttctcgct caccacgact atttcttctt  23220
cttggccgtc gtccgagacc acgcggcggt aggcatgcct cttctggggc agaggcggag  23280
gcgacgggct ctcgcggttc ggcgggcggc tggcagagcc ccttccgcgt tcgggggtgc  23340
gctcctggcg gcgctgctct gactgacttc ctccgcggcc ggccattgtg ttctcctagg  23400
gagcaacaag catggagact cagccatcgt cgccaacatc gccatctgcc cccgccgccg  23460
ccgacgagaa ccagcagcag aatgaaagct taaccgcccc gccgcccagc cccacctccg  23520
acgccgccgc ggccccagac atgcaagaga tggaggaatc catcgagatt gacctgggct  23580
acgtgacgcc cgcggagcac gaggaggagc tggcagcgcg cttttcagcc ccggaagaga  23640
accaccaaga gcagccagag caggaagcag agagcgagca gcagcaggct gggctcgagc  23700
atggcgacta cctgagcggg gcagaggacg tgctcatcaa gcatctggcc cgccaatgca  23760
tcatcgtcaa ggacgcgctg ctcgaccgcg ccgaggtgcc cctcagcgtg gcggagctca  23820
gccgcgccta cgagcgcaac ctcttctcgc cgcgcgtgcc ccccaagcgc cagcccaacg  23880
```

-continued

```
gcacctgcga gcccaacccg cgcctcaact tctacccggt cttcgcggtg cccgaggccc  23940
tggccaccta ccacctcttt ttcaagaacc aaaggatccc cgtctcctgc cgcgccaacc  24000
gcacccgcgc cgacgccctg ctcaacctgg gtcccggcgc ccgcctacct gatatcgcct  24060
ccttggaaga ggttcccaag atcttcgagg gtctgggcag cgacgagact cgggccgcga  24120
acgctctgca aggaagcgga gaggagcatg agcaccacag cgccctggtg gagttggaag  24180
gcgacaacgc gcgcctggcg gtgctcaagc gcacggtcga gctgacccac ttcgcctacc  24240
cggcgctcaa cctgcccccc aaggtcatga gcgccgtcat ggaccaggtg ctcatcaagc  24300
gcgcctcgcc cctctcggat gaggacatgc aggaccccga gagctcggac gagggcaagc  24360
ccgtggtcag cgacgagcag ctggcgcgct ggctgggagc gagtagcacc ccccagagct  24420
tggaagagcg gcgcaagctc atgatggccg tggtcctggt gaccgtggag ctggagtgtc  24480
tgcgccgctt cttcgccgac gcagagaccc tgcgcaaggt cgaggagaac ctgcactacc  24540
tcttcaggca cgggtttgtg cgccaggcct gcaagatctc caacgtggag ctgaccaacc  24600
tggtctccta catgggcatc ctgcacgaga accgcctggg gcagaacgtg ctgcacacca  24660
ccctgcgcgg ggaggcccgc cgcgactaca tccgcgactg cgtctacctg tacctctgcc  24720
acacctggca gacgggcatg ggcgtgtggc agcagtgcct ggaggagcag aacctgaaag  24780
agctctgcaa gctcctgcag aagaacctga aggccctgtg gaccgggttc gacgagcgca  24840
ccaccgcctc ggacctggcc gacctcatct tccccgagcg cctgcggctg acgctgcgca  24900
acggactgcc cgactttatg agtcaaagca tgttgcaaaa ctttcgctct ttcatcctcg  24960
aacgctccgg gatcctgccc gccacctgct ccgcgctgcc ctcggacttc gtgccgctga  25020
ccttccgcga gtgccccccg ccgctctgga gccactgcta cctgctgcgc ctggccaact  25080
acctggccta ccactcggac gtgatcgagg acgtcagcgg cgagggtctg ctcgagtgcc  25140
actgccgctg caacctctgc acgccgcacc gctccctggc ctgcaacccc cagctgctga  25200
gcgagaccca gatcatcggc accttcgagt tgcaaggccc cggcgagggc aagggggggtc  25260
tgaaactcac cccggggctg tggacctcgg cctacttgcg caagttcgtg cccgaggact  25320
accatccctt cgagatcagg ttctacgagg accaatccca gccgcccaag gccgaactgt  25380
cggcctgcgt catcacccag ggggccatcc tggcccaatt gcaagccatc cagaaatccc  25440
gccaagaatt tctgctgaaa aagggccacg gggtctacct ggacccccag accggagagg  25500
agctcaaccc cagcttcccc caggatgccc cgaggaagca gcaagaagct gaaagtggag  25560
ctgccgccgc cggaggattt ggaggaagac tgggagagca gtcaggcaga ggaggaggag  25620
atggaagact gggacagcac tcaggcagag gaggacagcc tgcaagacag tctggaagac  25680
gaggtggagg aggaggcaga ggaagaagca gccgccgcca gaccgtcgtc ctcggcggag  25740
aaagcaagca gcacggatac catctccgct ccgggtcggg gtcgcggcga ccgggcccac  25800
agtaggtggg acgagaccgg gcgcttcccg aaccccacca cccagaccgg taagaaggag  25860
cggcagggat acaagtcctg gcgggggcac aaaaacgcca tcgtctcctg cttgcaagcc  25920
tgcgggggca acatctcctt cacccgccgc tacctgctct tccaccgcgg ggtgaacttc  25980
ccccgcaaca tcttgcatta ctaccgtcac ctccacagcc cctactactg tttccaagaa  26040
gaggcagaaa cccagcagca gcagaaaacc agcggcagca gcagctagaa aatccacagc  26100
ggcggcaggt ggactgagga tcgcagcgaa cgagccggcg cagacccggg agctgaggaa  26160
ccggatcttt cccaccctct atgccatctt ccagcagagt cgggggcagg agcaggaact  26220
gaaagtcaag aaccgttctc tgcgctcgct cacccgcagt tgtctgtatc acaagagcga  26280
```

agaccaactt cagcgcactc tcgaggacgc cgaggctctc ttcaacaagt actgcgcgct 26340
cactcttaaa gagtagcccg cgcccgccca cacacggaaa aaggcgggaa ttacgtcacc 26400
acctgcgccc ttcgcccgac catcatcatg agcaaagaga ttcccacgcc ttacatgtgg 26460
agctaccagc cccagatggg cctggccgcc ggcgccgccc aggactactc cacccgcatg 26520
aactggctca gcgccgggcc cgcgatgatc tcacgggtga atgacatccg cgcccgccga 26580
aaccagatac tcctagaaca gtcagcgatc accgccacgc cccgccatca ccttaatccg 26640
cgtaattggc ccgccgccct ggtgtaccag gaaattcccc agcccacgac cgtactactt 26700
ccgcgagacg cccaggccga agtccagctg actaactcag gtgtccagct ggccggcggc 26760
gccgccctgt gtcgtcaccg ccccgctcag ggtataaagc ggctggtgat ccgaggcaga 26820
ggcacacagc tcaacgacga ggtggtgagc tcttcgctgg gtctgcgacc tgacggagtc 26880
ttccaactcg ccggatcggg gagatcttcc ttcacgcctc gtcaggccgt cctgactttg 26940
gagagttcgt cctcgcagcc ccgctcgggt ggcatcggca ctctccagtt cgtggaggag 27000
ttcactccct cggtctactt caaccccttc tccggctccc ccggccacta cccggacgag 27060
ttcatcccga acttcgacgc catcagcgag tcggtggacg gctacgattg aatgtcccat 27120
ggtggcgcag ctgacctagc tcggcttcga cacctggacc actgccgccg cttccgctgc 27180
ttcgctcggg atctcgccga gtttgcctac tttgagctgc ccgaggagca ccctcagggc 27240
ccggcccacg gagtgcggat catcgtcgaa gggggcctcg actcccacct gcttcggatc 27300
ttcagccagc gaccgatcct ggtcgagcgc gagcaaggac agacccttct gaccctgtac 27360
tgcatctgca accaccccgg cctgcatgaa agtctttgtt gtctgctgtg tactgagtat 27420
aataaaagct gagatcagcg actactccgg actcgattgt ggtgttcctg ctatcaaccg 27480
gtccctgttc ttcaccggga acgagaccga gctccagctt cagtgtaagc cccacaagaa 27540
gtacctcacc tggctgttcc agggctcccc gatcgccgtt gtcaaccact gcgacaacga 27600
cggagtcctg ctgagcggcc ccgccaacct tactttttcc acccgcagaa gcaagctcca 27660
gctcttccaa cccttcctcc ccgggaccta tcagtgcgtc tcgggaccct gccatcacac 27720
cttccacctg atcccgaata ccacagcgcc gctccccgct actaacaacc aaactaccca 27780
ccatcgccac cgtcgcgacc tttctgaatc taacactacc acccacaccg gaggtgagct 27840
ccgaggtcga ccaacctctg ggatttacta cggcccctgg gaggtggtgg ggttaatagc 27900
gctaggccta gttgtgggtg ggcttttggc tctctgctac ctatacctcc cttgctgttc 27960
gtacttagtg gtgctgtgtt gctggtttaa gaaatgggga agatcaccct agtgagctgc 28020
ggtgcgctgg tggcggtggt ggtgttttcg attgtgggac tgggcggcgc ggctgtagtg 28080
aaggagaagg ccgatccctg cttgcatttc aatcccgaca attgccagct gagttttcag 28140
cccgatggca atcggtgcgc ggtgctgatc aagtgcggat gggaatgcga gaacgtgaga 28200
atcgagtaca ataacaagac tcggaacaat actctcgcgt ccgtgtggca gcccggggac 28260
cccgagtggt acaccgtctc tgtccccggt gctgacggct ccccgcgcac cgtgaacaat 28320
actttcattt ttgcgcacat gtgcgacacg gtcatgtgga tgagcaagca gtacgatatg 28380
tggcccccca cgaaggagaa catcgtggtc ttctccatcg cttacagcgc gtgcacggcg 28440
ctaatcaccg ctatcgtgtg cctgagcatt cacatgctca tcgctattcg ccccagaaat 28500
aatgccgaaa aagagaaaca gccataacac gttttttcac acaccttttt cagaccatgg 28560
cctctgttaa atttttgctt ttatttgcca gtctcattac tgttataagt aatgagaaac 28620

-continued

```
tcactattta cattggcact aaccacactt tagacggaat tccaaaatcc tcatggtatt  28680
gctattttga tcaagatcca gacttaacta tagaactgtg tggtaacaag ggaaaaaata  28740
caagcattca tttaattaac tttaattgcg gagacaattt gaaattaatt aatatcacta  28800
aagagtatgg aggtatgtat tactatgttg cagaaaataa caacatgcag ttttatgaag  28860
ttactgtaac taatcccacc acacctagaa caacaacaac caccaccaca aaaactacac  28920
ctgttaccac tatgcagctc actaccaata acatttttgc catgcgtcaa atggtcaaca  28980
atagcactca acccacccca cccagtgagg aaattcccaa atccatgatt ggcattattg  29040
ttgctgtagt ggtgtgcatg ttgatcatcg ccttgtgcat ggtgtactat gccttctgct  29100
acagaaagca cagactgaac gacaagctgg aacacttact aagtgttgaa ttttaatttt  29160
ttagaaccat gaagatccta ggccttttaa ttttttctat cattacctct gctctatgca  29220
attctgacaa tgaggacgtt actgtcgttg tcggaaccaa ttatacactg aaaggtccag  29280
cgaagggtat gctttcgtgg tattgctggt ttggaactga cgagcaacag acagagctct  29340
gcaatgctca aaaaggcaaa acctcaaatt ctaaaatctc taattatcaa tgcaatggca  29400
ctgacttagt actgctcaat gtcacgaaag catatgctgg cagctacacc tgccctggag  29460
atgatactga gaacatgatt ttttacaaag tggaagtggt tgatcccact actccacctc  29520
cacccaccac aactactcac accacacaca cagaacaaac cacagcagag gaggcagcaa  29580
agttagcctt gcaggtccaa gacagttcat ttgttggcat tacccctaca cctgatcagc  29640
ggtgtccggg gctgctcgtc agcggcattg tcggtgtgct ttcgggatta gcagtcataa  29700
tcatctgcat gttcattttt gcttgctgct atagaaggct ttaccgacaa aaatcagacc  29760
cactgctgaa cctctatgtt taatttttttc cagagccatg aaggcagtta gcactctagt  29820
tttttgttct ttgattggca ctgtttttag tgttagcttt ttgaaacaaa tcaatgttac  29880
tgagggggaa aatgtgacac tggtaggcgt agagggtgct caaaatacca cctggacaaa  29940
attccatcta gatgggtgga aagaaatttg cacctggaat gtcagtactt atacatgtga  30000
aggagttaat cttaccattg tcaatgtcag ccaaattcaa aagggttgga ttaaagggca  30060
atctgttagt gttagcaata gtgggtacta tacccagcat actcttatct atgacattat  30120
agttatacca ctgcctacac ctagcccacc tagcactacc acacagacaa cccacactac  30180
acaaacaacc acatacagta catcaaatca gcctaccacc actacaacag cagaggttgc  30240
cagctcgtct ggggtccgag tggcattttt gatgttggcc ccatctagca gtcccactgc  30300
tagtaccaat gagcagacta ctgaattttt gtccactgtc gagagccaca ccacagctac  30360
ctcgagtgcc ttctctagca ccgccaatct atcctcgctt tcctctacac caatcagtcc  30420
cgctactact cctacccccg ctattctccc cactcccctg aagcaaacag acggcgacat  30480
gcaatggcag atcaccctgc tcattgtgat cgggttggtc atcctggccg tgttgctcta  30540
ctacatcttc tgccgccgca ttcccaacgc gcaccgcaag ccggcctaca agcccatcgt  30600
tgtcgggcag ccggagccgc ttcaggtgga agggggtcta aggaatcttc tcttctcttt  30660
tacagtatgg tgattgaatt atgattccta gacaaatctt gatcactatt cttatctgcc  30720
tcctccaagt ctgtgccacc ctcgctctgg tggccaacgc cagtccagac tgtattgggc  30780
ccttcgcctc ctacgtgctc tttgccttca tcacctgcat ctgctgctgt agcatagtct  30840
gcctgcttat caccttcttc cagttcattg actggatctt tgtgcgcatc gcctacctgc  30900
gccaccaccc ccagtaccgc gaccagcgag tggcgcggct gctcaggatc ctctgataag  30960
catgcgggct ctgctacttc tcgcgcttct gctgttagtg ctcccccgtc ccgtcgaccc  31020
```

```
ccggaccccc acccagtccc ccgaggaggt ccgcaaatgc aaattccaag aaccctggaa  31080
attcctcaaa tgctaccgcc aaaaatcaga catgcatccc agctggatca tgatcattgg  31140
gatcgtgaac attctggcct gcaccctcat ctcctttgtg atttacccct gctttgactt  31200
tggttggaac tcgccagagg cgctctatct cccgcctgaa cctgacacac caccacagca  31260
acctcaggca cacgcactac caccaccacc acagcctagg ccacaataca tgcccatatt  31320
agactatgag gccgagccac agcgacccat gctccccgct attagttact tcaatctaac  31380
cggcggagat gactgaccca ctggccaaca acaacgtcaa cgaccttctc ctggacatgg  31440
acggccgcgc ctcggagcag cgactcgccc aacttcgcat tcgccagcag caggagagag  31500
ccgtcaagga gctgcaggac ggcatagcca tccaccagtg caagaaaggc atcttctgcc  31560
tggtgaaaca ggccaagatc tcctacgagg tcacccagac cgaccatcgc ctctcctacg  31620
agctcctgca gcagcgccag aagttcacct gcctggtcgg agtcaacccc atcgtcatca  31680
cccagcagtc gggcgatacc aaggggtgca tccactgctc ctgcgactcc cccgactgcg  31740
tccacactct gatcaagacc ctctgcggcc tccgcgacct cctccccatg aactaatcac  31800
ccccttatcc agtgaaataa agatcatatt gatgatttga gtttaataaa aataaagaat  31860
cacttacttg aaatctgata ccaggtctct gtccatgttt tctgccaaca ccacttcact  31920
cccctcttcc cagctctggt actgcaggcc ccggcgggct gcaaacttcc tccacaccct  31980
gaaggggatg tcaaattcct cctgtccctc aatcttcatt ttatcttcta tcagatgtcc  32040
aaaaagcgcg tccgggtgga tgatgacttc gaccccgtct acccctacga tgcagacaac  32100
gcaccgaccg tgcccttcat caaccccccc ttcgtctctt cagatggatt ccaagagaag  32160
cccctggggg tgctgtccct gcgtctggcc gatcccgtca ccaccaagaa cggggaaatc  32220
accctcaagc tgggagatgg ggtggacctc gactcctcgg gaaaactcat ctccaacacg  32280
gccaccaagg ccgccgcccc tctcagtttt tccaacaaca ccatttccct taacatggat  32340
acccctttt acaacaacaa tggaaagtta ggcatgaaag tcactgctcc actgaagata  32400
ctagacacag acttgctaaa aacacttgtt gtagcttatg gacaaggttt aggaacaaac  32460
accactggtg cccttgttgc ccaactagca tccccacttg cttttgatag caatagcaaa  32520
attgccctta atttaggcaa tggaccattg aaagtggatg caaatagact gaacatcaat  32580
tgcaatagag gactctatgt tactaccaca aaagatgcac tggaagccaa tataagttgg  32640
gctaatgcta tgacatttat aggaaatgcc atgggtgtca atattgatac acaaaaaggc  32700
ttgcaatttg gcaccactag taccgtcgca gatgttaaaa acgcttaccc catacaaatc  32760
aaacttggag ctggtctcac atttgacagc acaggtgcaa ttgttgcatg gaacaaagat  32820
gatgacaagc ttacactatg gaccacagcc gacccctctc caaattgtca catatattct  32880
gaaaaggatg ctaagcttac actttgcttg acaaagtgtg gcagtcagat tctgggcact  32940
gtttccctca tagctgttga tactggcagt ttaaatccca taacaggaac agtaaccact  33000
gctcttgtct cacttaaatt cgatgcaaat ggagttttgc aaagcagctc aacactagac  33060
tcagactatt ggaatttcag acagggagat gttacacctg ctgaagccta tactaatgct  33120
ataggtttca tgcccaatct aaaagcatac cctaaaaaca caagtggagc tgcaaaaagt  33180
cacattgttg ggaaagtgta cctacatggg gatacaggca aaccactgga cctcattatt  33240
actttcaatg aaacaagtga tgaatcttgc acttactgta ttaactttca atggcagtgg  33300
ggggctgatc aatataaaaa tgaaacactt gccgtcagtt cattcacctt ttcctatatt  33360
```

-continued

```
gctaaagaat aaaccccact ctgtacccca tctctgtcta tggaaaaaac tctgaaacac  33420
aaaataaaat aaagttcaag tgttttattg attcaacagt tttacaggat tcgagcagtt  33480
atttttcctc caccctccca ggacatggaa tacaccaccc tctccccccg cacagccttg  33540
aacatctgaa tgccattggt gatggacatg cttttggtct ccacgttcca cacagtttca  33600
gagcgagcca gtctcgggtc ggtcagggag atgaaaccct ccgggcactc ccgcatctgc  33660
acctcacagc tcaacagctg aggattgtcc tcggtggtcg ggatcacggt tatctggaag  33720
aagcagaaga gcggcggtgg gaatcatagt ccgcgaacgg gatcggccgg tggtgtcgca  33780
tcaggccccg cagcagtcgc tgtcgccgcc gctccgtcaa gctgctgctc agggggtccg  33840
ggtccaggga ctccctcagc atgatgccca cggccctcag catcagtcgt ctggtgcggc  33900
gggcgcagca gcgcatgcgg atctcgctca ggtcgctgca gtacgtgcaa cacaggacca  33960
ccaggttgtt caacagtcca tagttcaaca cgctccagcc gaaactcatc gcgggaagga  34020
tgctacccac gtggccgtcg taccagatcc tcaggtaaat caagtggcgc cccctccaga  34080
acacgctgcc catgtacatg atctccttgg gcatgtggcg gttcaccacc tcccggtacc  34140
acatcaccct ctggttgaac atgcagcccc ggatgatcct gcggaaccac agggccagca  34200
ccgccccgcc cgccatgcag cgaagagacc ccgggtcccg acaatggcaa tggaggaccc  34260
accgctcgta cccgtggatc atctgggagc tgaacaagtc tatgttggca cagcacaggc  34320
atatgctcat gcatctcttc agcactctca gctcctcggg ggtcaaaacc atatcccagg  34380
gcacggggaa ctcttgcagg acagcgaacc ccgcagaaca gggcaatcct cgcacataac  34440
ttacattgtg catggacagg gtatcgcaat caggcagcac cgggtgatcc tccaccagag  34500
aagcgcgggt ctcggtctcc tcacagcgtg gtaagggggc cggccgatac gggtgatggc  34560
gggacgcggc tgatcgtgtt cgcgaccgtg ttatgatgca gttgctttcg gacattttcg  34620
tacttgctgt agcagaacct ggtccgggcg ctgcacaccg atcgccggcg gcggtcccgg  34680
cgcttggaac gctcggtgtt gaagttgtaa aacagccact ctctcagacc gtgcagcaga  34740
tctagggcct caggagtgat gaagatccca tcatgcctga tggctctaat cacatcgacc  34800
accgtggaat gggccagacc cagccagatg atgcaatttt gttgggtttc ggtgacggcg  34860
ggggagggaa gaacaggaag aaccatgatt aacttttaat ccaaacggtc tcggagcact  34920
tcaaaatgaa gatcgcggag atggcacctc tcgccccccgc tgtgttggtg gaaaataaca  34980
gccaggtcaa aggtgatacg gttctcgaga tgttccacgg tggcttccag caaagcctcc  35040
acgcgcacat ccagaaacaa gacaatagcg aaagcgggag ggttctctaa ttcctcaatc  35100
atcatgttac actcctgcac catccccaga taattttcat ttttccagcc ttgaatgatt  35160
cgaactagtt cctgaggtaa atccaagcca gccatgataa agagctcgcg cagagcgccc  35220
tccaccggca ttcttaagca caccctcata attccaagat attctgctcc tggttcacct  35280
gcagcagatt gacaagcgga atatcaaaat ctctgccgcg atccctaagc tcctccctca  35340
gcaataactg taagtactct ttcatatcct ctccgaaatt tttagccata ggaccaccag  35400
gaataagatt agggcaagcc acagtacaga taaaccgaag tcctccccag tgagcattgc  35460
caaatgcaag actgctataa gcatgctggc tagacccggt gatatcttcc agataactgg  35520
acagaaaatc gcccaggcaa tttttaagaa aatcaacaaa agaaaaatcc tccaggtgca  35580
cgtttagagc ctcgggaaca acgatggagt aaatgcaagc ggtgcgttcc agcatggtta  35640
gttagctgat ctgtagaaaa aaacaaaaat gaacattaaa ccatgctagc ctggcgaaca  35700
ggtgggtaaa tcgttctctc cagcaccagg caggccacgg ggtctccggc acgaccctcg  35760
```

```
taaaaattgt cgctatgatt gaaaaccatc acagagagac gttcccggtg gccggcgtga  35820

atgattcgac aagatgaata cacccccgga acattggcgt ccgcgagtga aaaaaagcgc  35880

ccaaggaagc aataaggcac tacaatgctc agtctcaagt ccagcaaagc gatgccatgc  35940

ggatgaagca caaaattctc aggtgcgtac aaaatgtaat tactcccctc ctgcacaggc  36000

agcaaagccc ccgatccctc caggtacaca tacaaagcct cagcgtccat agcttaccga  36060

gcagcagcac acaacaggcg caagagtcag agaaaggctg agctctaacc tgtccacccg  36120

ctctctgctc aatatatagc ccagatctac actgacgtaa aggccaaagt ctaaaaatac  36180

ccgccaaata atcacacacg cccagcacac gcccagaaac cggtgacaca ctcaaaaaaa  36240

tacgcgcact tcctcaaacg cccaaactgc cgtcatttcc gggttcccac gctacgtcat  36300

caaaattcga ctttcaaatt ccgtcgaccg ttaaaaacgt cgcccgcccc gcccctaacg  36360

gtcgccgctc ccgcagccaa tcaccgcccc gcatccccaa attcaaatac ctcatttgca  36420

tattaacgcg caccaaaagt ttgaggtata ttattgatga tg                    36462
```

```
<210> SEQ ID NO 2
<211> LENGTH: 36604
<212> TYPE: DNA
<213> ORGANISM: chimpanzee adenovirus serotype Pan6

<400> SEQUENCE: 2
```

```
catcatcaat aatatacctc aaacttttgg tgcgcgttaa tatgcaaatg agctgtttga     60

atttggggag ggaggaaggt gattggctgc gggagcggcg accgttaggg gcggggcggg    120

tgacgttttg atgacgtggc tatgaggcgg agccggtttg caagttctcg tgggaaaagt    180

gacgtcaaac gaggtgtggt ttgaacacgg aaatactcaa ttttcccgcg ctctctgaca    240

ggaaatgagg tgtttctggg cggatgcaag tgaaaacggg ccattttcgc gcgaaaactg    300

aatgaggaag tgaaaatctg agtaatttcg cgtttatggc agggaggagt atttgccgag    360

ggccgagtag actttgaccg attacgtggg ggtttcgatt accgtatttt tcacctaaat    420

ttccgcgtac ggtgtcaaag tccggtgttt ttacgtaggc gtcagctgat cgccagggta    480

tttaaacctg cgctctctag tcaagaggcc actcttgagt gccagcgagt agagttttct    540

cctccgcgcc gcgagtcaga tctacacttt gaaagatgag gcacctgaga gacctgcccg    600

gtaatgtttt cctggctact gggaacgaga ttctggaatt ggtggtggac gccatgatgg    660

gtgacgaccc tccagagccc cctaccccat ttgaggcgcc ttcgctgtac gatttgtatg    720

atctggaggt ggatgtgccc gagagcgacc ctaacgagga ggcggtgaat gatttgttta    780

gcgatgccgc gctgctggct gccgagcagg ctaatacgga ctctggctca gacagcgatt    840

cctctctcca taccccgaga cccggcagag gtgagaaaaa gatccccgag cttaaagggg    900

aagagctcga cctgcgctgc tatgaggaat gcttgcctcc gagcgatgat gaggaggacg    960

aggaggcgat tcgagctgcg gtgaaccagg gagtgaaaac tgcgggcgag agctttagcc   1020

tggactgtcc tactctgccc ggacacggct gtaagtcttg tgaatttcat cgcatgaata   1080

ctggagataa gaatgtgatg tgtgccctgt gctatatgag agcttacaac cattgtgttt   1140

acagtaagtg tgattaactt tagttgggaa ggcagagggt gactgggtgc tgactggttt   1200

atttatgtat atgttttttt atgtgtaggt cccgtctctg acgtagatga gacccccact   1260

tcagagtgca tttcatcacc cccagaaatt ggcgaggaac cgcccgaaga tattattcat   1320

agaccagttg cagtgagagt caccgggcgg agagcagctg tggagagttt ggatgacttg   1380
```

-continued

```
ctacagggtg gggatgaacc tttggacttg tgtacccgga aacgccccag gcactaagtg   1440
ccacacatgt gtgtttactt aaggtgatgt cagtatttat agggtgtgga gtgcaataaa   1500
atccgtgttg actttaagtg cgtgttttat gactcagggg tggggactgt gggtatataa   1560
gcaggtgcag acctgtgtgg tcagttcaga gcaggactca tggagatctg gactgtcttg   1620
gaagactttc accagactag acagttgcta gagaactcat cggagggagt ctcttacctg   1680
tggagattct gcttcggtgg gcctctagct aagctagtct atagggccaa acaggattat   1740
aaggaacaat ttgaggatat tttgagagag tgtcctggta tttttgactc tctcaacttg   1800
ggccatcagt ctcactttaa ccagagtatt ctgagagccc ttgacttttc tactcctggc   1860
agaactaccg ccgcggtagc ctttttttgcc tttattcttg acaaatggag tcaagaaacc   1920
catttcagca gggattaccg tctggactgc ttagcagtag ctttgtggag aacatggagg   1980
tgccagcgcc tgaatgcaat ctccggctac ttgccagtac agccggtaga cacgctgagg   2040
atcctgagtc tccagtcacc ccaggaacac caacgccgcc agcagccgca gcaggagcag   2100
cagcaagagg aggaccgaga agagaacccg agagccggtc tggaccctcc ggtggcggag   2160
gaggaggagt agctgacttg tttcccgagc tgcgccgggt gctgactagg tcttccagtg   2220
gacgggagag gggggattaag cgggagaggc atgaggagac tagccacaga actgaactga   2280
ctgtcagtct gatgagccgc aggcgcccag aatcggtgtg gtggcatgag gtgcagtcgc   2340
aggggataga tgaggtctcg gtgatgcatg agaaatattc cctagaacaa gtcaagactt   2400
gttggttgga gcccgaggat gattgggagg tagccatcag gaattatgcc aagctggctc   2460
tgaagccaga caagaagtac aagattacca aactgattaa tatcagaaat tcctgctaca   2520
tttcagggaa tggggccgag gtggagatca gtacccagga gagggtggcc ttcagatgtt   2580
gtatgatgaa tatgtacccg ggggtggtgg gcatggaggg agtcaccttt atgaacacga   2640
ggttcagggg tgatgggtat aatggggtgg tctttatggc caacaccaag ctgacagtgc   2700
acggatgctc cttctttggc ttcaataaca tgtgcatcga ggcctggggc agtgtttcag   2760
tgaggggatg cagcttttca gccaactgga tgggggtcgt gggcagaacc aagagcaagg   2820
tgtcagtgaa gaaatgcctg ttcgagaggt gccacctggg ggtgatgagc gagggcgaag   2880
ccaaagtcaa acactgcgcc tctaccgaga cgggctgctt tgtgctgatc aagggcaatg   2940
cccaagtcaa gcataacatg atctgtgggg cctcggatga gcgcggctac cagatgctga   3000
cctgcgccgg tgggaacagc catatgctgg ccaccgtgca tgtggcctcg cacccccgca   3060
agacatggcc cgagttcgag cacaacgtca tgacccgctg caatgtgcac ctgggctccc   3120
gccgaggcat gttcatgccc taccagtgca acatgcaatt tgtgaaggtg ctgctggagc   3180
ccgatgccat gtccagagtg agcctgacgg gggtgtttga catgaatgtg gagctgtgga   3240
aaattctgag atatgatgaa tccaagacca ggtgccgggc ctgcgaatgc ggaggcaagc   3300
acgccaggct tcagcccgtg tgtgtggagg tgacggagga cctgcgaccc gatcatttgg   3360
tgttgtcctg caacgggacg gagttcggct ccagcgggga agaatctgac tagagtgagt   3420
agtgtttggg gctgggtgtg agcctgcatg aggggcagaa tgactaaaat ctgtggtttt   3480
ctgtgtgttg cagcagcatg agcggaagcg cctcctttga gggaggggta ttcagccctt   3540
atctgacggg gcgtctcccc tcctgggcgg gagtgcgtca gaatgtgatg ggatccacgg   3600
tggacggccg gcccgtgcag cccgcgaact cttcaaccct gacctacgcg accctgagct   3660
cctcgtccgt ggacgcagct gccgccgcag ctgctgcttc cgccgccagc gccgtgcgcg   3720
gaatggccct gggcgccggc tactacagct ctctggtggc caactcgagt tccaccaata   3780
```

-continued

```
atcccgccag cctgaacgag gagaagctgc tgctgctgat ggcccagctc gaggccctga   3840
cccagcgcct gggcgagctg acccagcagg tggctcagct gcaggcggag acgcgggccg   3900
cggttgccac ggtgaaaacc aaataaaaaa tgaatcaata aataaacgga gacggttgtt   3960
gattttaaca cagagtcttg aatctttatt tgatttttcg cgcgcggtag gccctggacc   4020
accggtctcg atcattgagc acccggtgga tctttttccag gacccggtag aggtgggctt   4080
ggatgttgag gtacatgggc atgagcccgt cccgggggtg gaggtagctc cattgcaggg   4140
cctcgtgctc ggggatggtg ttgtaaatca cccagtcata gcaggggcgc agggcgtggt   4200
gctgcacgat gtccttgagg aggagactga tggccacggg cagccccttg gtgtaggtgt   4260
tgacgaacct gttgagctgg gagggatgca tgcgggggga gatgagatgc atcttggcct   4320
ggatcttgag attggcgatg ttcccgccca gatcccgccg gggttcatg ttgtgcagga   4380
ccaccagcac ggtgtatccg gtgcacttgg ggaatttgtc atgcaacttg gaagggaagg   4440
cgtgaaagaa tttggagacg cccttgtgac cgcccaggtt ttccatgcac tcatccatga   4500
tgatggcgat gggcccgtgg gcggcggcct gggcaaagac gtttcggggg tcggacacat   4560
cgtagttgtg gtcctgggtg agctcgtcat aggccatttt aatgaatttg gggcggaggg   4620
tgcccgactg gggacgaag gtgccctcga tcccgggggc gtagttgccc tcgcagatct   4680
gcatctccca ggccttgagc tcggaggggg ggatcatgtc cacctgcggg gcgatgaaaa   4740
aaacggtttc cggggcgggg gagatgagct gggccgaaag caggttccgg agcagctggg   4800
acttgccgca accggtgggg ccgtagatga ccccgatgac cggctgcagg tggtagttga   4860
gggagagaca gctgccgtcc tcgcggagga gggggccac ctcgttcatc atctcgcgca   4920
catgcatgtt ctcgcgcacg agttccgcca ggaggcgctc gcccccccagc gagaggagct   4980
cttgcagcga ggcgaagttt ttcagcggct tgagtccgtc ggccatgggc attttggaga   5040
gggtctgttg caagagttcc agacggtccc agagctcggt gatgtgctct agggcatctc   5100
gatccagcag acctcctcgt ttcgcgggtt ggggcgactg cgggagtagg gcaccaggcg   5160
atgggcgtcc agcgaggcca gggtccggtc cttccagggc cgcagggtcc gcgtcagcgt   5220
ggtctccgtc acggtgaagg ggtgcgcgcc gggctgggcg cttgcgaggg tgcgcttcag   5280
gctcatccgg ctggtcgaga accgctcccg gtcggcgccc tgcgcgtcgg ccaggtagca   5340
attgagcatg agttcgtagt tgagcgcctc ggccgcgtgg cccttggcgc ggagcttacc   5400
tttggaagtg tgtccgcaga cgggacagag gagggacttg agggcgtaga gcttgggggc   5460
gaggaagacg gactcggggg cgtaggcgtc cgcgccgcag ctggcgcaga cggtctcgca   5520
ctccacgagc caggtgaggt cggggcggtt ggggtcaaaa acgaggtttc ctccgtgctt   5580
tttgatgcgt ttcttacctc tggtctccat gagctcgtgt ccccgctggg tgacaaagag   5640
gctgtccgtg tccccgtaga ccgactttat gggccggtcc tcgagcgggg tgccgcggtc   5700
ctcgtcgtag aggaaccccg cccactccga gacgaaggcc cgggtccagg ccagcacgaa   5760
ggaggccacg tgggaggggt agcggtcgtt gtccaccagc gggtccacct tctccagggt   5820
atgcaagcac atgtccccct cgtccacatc caggaaggtg attggcttgt aagtgtaggc   5880
cacgtgaccg gggtcccgg ccgggggggt ataaaagggg gcgggcccct gctcgtcctc   5940
actgtcttcc ggatcgctgt ccaggagcgc cagctgttgg ggtaggtatt ccctctcgaa   6000
ggcgggcatg acctcggcac tcaggttgtc agtttctaga aacgaggagg atttgatatt   6060
gacggtgccg ttggagacgc ctttcatgag cccctcgtcc atttggtcag aaaagacgat   6120
```

-continued

```
ctttttgttg tcgagcttgg tggcgaagga gccgtagagg gcgttggaga gcagcttggc   6180
gatggagcgc atggtctggt tcttttcctt gtcggcgcgc tccttggcgg cgatgttgag   6240
ctgcacgtac tcgcgcgcca cgcacttcca ttcggggaag acggtggtga gctcgtcggg   6300
cacgattctg acccgccagc cgcggttgtg cagggtgatg aggtccacgc tggtggccac   6360
ctcgccgcgc aggggctcgt tggtccagca gaggcgcccg cccttgcgcg agcagaaggg   6420
gggcagcggg tccagcatga gctcgtcggg ggggtcggcg tccacggtga agatgccggg   6480
caggagctcg gggtcgaagt agctgatgca ggtgcccaga ttgtccagcg ccgcttgcca   6540
gtcgcgcacg gccagcgcgc gctcgtaggg gctgaggggc gtgccccagg gcatggggtg   6600
cgtgagcgcg gaggcgtaca tgccgcagat gtcgtagacg tagaggggct cctcgaggac   6660
gccgatgtag gtggggtagc agcgcccccc gcggatgctg gcgcgcacgt agtcgtacag   6720
ctcgtgcgag ggcgcgagga gccccgtgcc gaggttggag cgttgcggct tttcggcgcg   6780
gtagacgatc tggcggaaga tggcgtggga gttggaggag atggtgggcc tttggaagat   6840
gttgaagtgg gcgtggggca ggccgaccga gtccctgatg aagtgggcgt aggagtcctg   6900
cagcttggcg acgagctcgg cggtgacgag gacgtccagg gcgcagtagt cgagggtctc   6960
ttggatgatg tcatacttga gctggccctt ctgcttccac agctcgcggt tgagaaggaa   7020
ctcttcgcgg tccttccagt actcttcgag ggggaacccg tcctgatcgg cacggtaaga   7080
gcccaccatg tagaactggt tgacggcctt gtaggcgcag cagcccttct ccacggggag   7140
ggcgtaagct tgcgcggcct tgcgcaggga ggtgtgggtg agggcgaagg tgtcgcgcac   7200
catgaccttg aggaactggt gcttgaagtc gaggtcgtcg cagccgccct gctcccagag   7260
ttggaagtcc gtgcgcttct tgtaggcggg gttaggcaaa gcgaaagtaa catcgttgaa   7320
gaggatcttg cccgcgcggg gcatgaagtt gcgagtgatg cggaaaggct ggggcacctc   7380
ggcccggttg ttgatgacct gggcggcgag gacgatctcg tcgaagccgt tgatgttgtg   7440
cccgacgatg tagagttcca cgaatcgcgg gcggcccttg acgtggggca gcttcttgag   7500
ctcgtcgtag gtgagctcgg cggggtcgct gagcccgtgc tgctcgaggg cccagtcggc   7560
gacgtggggg ttggcgctga ggaaggaagt ccagagatcc acggccaggg cggtctgcaa   7620
gcggtcccgg tactgacgga actgttggcc cacggccatt ttttcggggg tgacgcagta   7680
gaaggtgcgg gggtcgccgt gccagcggtc ccacttgagc tggagggcga ggtcgtgggc   7740
gagctcgacg agcggcgggt ccccggagag tttcatgacc agcatgaagg ggacgagctg   7800
cttgccgaag gaccccatcc aggtgtaggt ttccacatcg taggtgagga agagcctttc   7860
ggtgcgagga tgcgagccga tggggaagaa ctggatctcc tgccaccagt tggaggaatg   7920
gctgttgatg tgatggaagt agaaatgccg acggcgcgcc gagcactcgt gcttgtgttt   7980
atacaagcgt ccgcagtgct cgcaacgctg cacgggatgc acgtgctgca cgagctgtac   8040
ctgggttcct ttggcgagga atttcagtgg gcagtggagc gctggcggct gcatctcgtg   8100
ctgtactacg tcttggccat cggcgtggcc atcgtctgcc tcgatggtgg tcatgctgac   8160
gagcccgcgc gggaggcagg tccagacctc ggctcggacg ggtcggagag cgaggacgag   8220
ggcgcgcagg ccggagctgt ccagggtcct gagacgctgc ggagtcaggt cagtgggcag   8280
cggcggcgcg cggttgactt gcaggagctt ttccagggcg cgcgggaggt ccagatggta   8340
cttgatctcc acggcgccgt tggtggctac gtccacggct tgcagggtgc cgtgcccctg   8400
gggcgccacc accgtgcccc gtttcttctt gggcgctgct tccatgtcgg tcagaagcgg   8460
cggcgaggac gcgcgccggg cggcaggggc ggctcggggc ccggaggcag gggcggcagg   8520
```

ggcacgtcgg cgccgcgcgc gggcaggttc tggtactgcg cccggagaag actggcgtga 8580
gcgacgacgc gacggttgac gtcctggatc tgacgcctct gggtgaaggc cacgggaccc 8640
gtgagtttga acctgaaaga gagttcgaca gaatcaatct cggtatcgtt gacggcggcc 8700
tgccgcagga tctcttgcac gtcgcccgag ttgtcctggt aggcgatctc ggtcatgaac 8760
tgctcgatct cctcctcctg aaggtctccg cggccggcgc gctcgacggt ggccgcgagg 8820
tcgttggaga tgcggcccat gagctgcgag aaggcgttca tgccggcctc gttccagacg 8880
cggctgtaga ccacggctcc gtcggggtcg cgcgcgcgca tgaccacctg ggcgaggttg 8940
agctcgacgt ggcgcgtgaa gaccgcgtag ttgcagaggc gctggtagag gtagttgagc 9000
gtggtggcga tgtgctcggt gacgaagaag tacatgatcc agcggcggag cggcatctcg 9060
ctgacgtcgc ccagggcttc caagcgttcc atggcctcgt agaagtccac ggcgaagttg 9120
aaaaactggg agttgcgcgc cgagacggtc aactcctcct ccagaagacg gatgagctcg 9180
gcgatggtgg cgcgcacctc gcgctcgaag gccccggggg gctcctcttc catctcctcc 9240
tcttcctcct ccactaacat ctcttctact tcctcctcag gaggcggtgg cgggggaggg 9300
gccctgcgtc gccggcggcg cacgggcaga cggtcgatga agcgctcgat ggtctccccg 9360
cgccggcgac gcatggtctc ggtgacggcg cgcccgtcct cgcggggccg cagcatgaag 9420
acgccgccgc gcatctccag gtggccgccg ggggggtctc cgttgggcag ggagagggcg 9480
ctgacgatgc atcttatcaa ttgacccgta gggactccgc gcaaggacct gagcgtctcg 9540
agatccacgg gatccgaaaa ccgctgaacg aaggcttcga gccagtcgca gtcgcaaggt 9600
aggctgagcc cggtttcttg ttcttcgggt atttggtcgg gaggcgggcg ggcgatgctg 9660
ctggtgatga agttgaagta ggcggtcctg agacggcgga tggtggcgag gagcaccagg 9720
tccttgggcc cggcttgctg gatgcgcaga cggtcggcca tgccccaggc gtggtcctga 9780
cacctggcga ggtccttgta gtagtcctgc atgagccgct ccacgggcac ctcctcctcg 9840
cccgcgcggc cgtgcatgcg cgtgagcccg aacccgcgct gcggctggac gagcgccagg 9900
tcggcgacga cgcgctcggt gaggatggcc tgctggatct gggtgagggt ggtctggaag 9960
tcgtcgaagt cgacgaagcg gtggtaggct ccggtgttga tggtgtagga gcagttggcc 10020
atgacggacc agttgacggt ctggtggccg ggtcgcacga gctcgtggta cttgaggcgc 10080
gagtaggcgc gcgtgtcgaa gatgtagtcg ttgcaggcgc gcacgaggta ctggtatccg 10140
acgaggaagt gcggcggcgg ctggcggtag agcggccatc gctcggtggc gggggcgccg 10200
ggcgcgaggt cctcgagcat gaggcggtgg tagccgtaga tgtacctgga catccaggtg 10260
atgccggcgg cggtggtgga ggcgcgcggg aactcgcgga cgcggttcca gatgttgcgc 10320
agcggcagga agtagttcat ggtggccgcg gtctggcccg tgaggcgcgc gcagtcgtgg 10380
atgctctaga catacgggca aaaacgaaag cggtcagcgg ctcgactccg tggcctggag 10440
gctaagcgaa cgggttgggc tgcgcgtgta ccccggttcg aatctcgaat caggctggag 10500
ccgcagctaa cgtggtactg gcactcccgt ctcgacccaa gcctgctaac gaaacctcca 10560
ggatacggag gcgggtcgtt ttttggcctt ggtcgctggt catgaaaaac tagtaagcgc 10620
ggaaagcggc cgcccgcgat ggctcgctgc cgtagtctgg agaaagaatc gccagggttg 10680
cgttgcggtg tgccccggtt cgagcctcag cgctcggcgc cggccggatt ccgcggctaa 10740
cgtgggcgtg gctgccccgt cgtttccaag acccccttagc cagccgactt ctccagttac 10800
ggagcgagcc cctctttttt tttcttgtgt ttttgccaga tgcatcccgt actgcggcag 10860

-continued

```
atgcgccccc accctccacc acaaccgccc ctaccgcagc agcagcaaca gccggcgctt  10920
ctgcccccgc cccagcagca gccagccact accgcggcgg ccgccgtgag cggagccggc  10980
gttcagtatg acctggcctt ggaagagggc gaggggctgg cgcggctggg ggcgtcgtcg  11040
ccggagcggc acccgcgcgt gcagatgaaa agggacgctc gcgaggccta cgtgcccaag  11100
cagaacctgt tcagagacag gagcggcgag gagcccgagg agatgcgcgc ctcccgcttc  11160
cacgcggggc gggagctgcg gcgcggcctg gaccgaaagc gggtgctgag ggacgaggat  11220
ttcgaggcgg acgagctgac ggggatcagc cccgcgcgcg cgcacgtggc cgcggccaac  11280
ctggtcacgg cgtacgagca gaccgtgaag gaggagagca acttccaaaa atccttcaac  11340
aaccacgtgc gcacgctgat cgcgcgcgag gaggtgaccc tgggcctgat gcacctgtgg  11400
gacctgctgg aggccatcgt gcagaacccc acgagcaagc cgctgacggc gcagctgttt  11460
ctggtggtgc agcacagtcg ggacaacgag acgttcaggg aggcgctgct gaatatcacc  11520
gagcccgagg gccgctggct cctggacctg gtgaacattt tgcagagcat cgtggtgcag  11580
gagcgcgggc tgccgctgtc cgagaagctg gcggccatca acttctcggt gctgagtctg  11640
ggcaagtact acgctaggaa gatctacaag accccgtacg tgcccataga caaggaggtg  11700
aagatcgacg ggttttacat gcgcatgacc ctgaaagtgc tgaccctgag cgacgatctg  11760
ggggtgtacc gcaacgacag gatgcaccgc gcggtgagcg ccagccgccg gcgcgagctg  11820
agcgaccagg agctgatgca cagcctgcag cgggccctga ccggggccgg gaccgagggg  11880
gagagctact ttgacatggg cgcggacctg cgctggcagc ccagccgccg ggccttggaa  11940
gctgccggcg gttcccccta cgtggaggag gtggacgatg aggaggagga gggcgagtac  12000
ctggaagact gatggcgcga ccgtattttt gctagatgca gcaacagcca ccgccgccgc  12060
ctcctgatcc cgcgatgcgg gcggcgctgc agagccagcc gtccggcatt aactcctcgg  12120
acgattggac ccaggccatg caacgcatca tggcgctgac gacccgcaat cccgaagcct  12180
ttagacagca gcctcaggcc aaccggctct cggccatcct ggaggccgtg gtgccctcgc  12240
gctcgaaccc cacgcacgag aaggtgctgg ccatcgtgaa cgcgctggtg gagaacaagg  12300
ccatccgcgg tgacgaggcc gggctggtgt acaacgcgct gctggagcgc gtggcccgct  12360
acaacagcac caacgtgcag acgaacctgg accgcatggt gaccgacgtg cgcgaggcgg  12420
tgtcgcagcg cgagcggttc caccgcgagt cgaacctggg ctccatggtg gcgctgaacg  12480
ccttcctgag cacgcagccc gccaacgtgc cccggggcca ggaggactac accaacttca  12540
tcagcgcgct gcggctgatg gtggccgagg tgccccagag cgaggtgtac cagtcggggc  12600
cggactactt cttccagacc agtcgccagg gcttgcagac cgtgaacctg agccaggctt  12660
tcaagaactt gcagggactg tggggcgtgc aggccccggt cggggaccgc gcgacggtgt  12720
cgagcctgct gacgccgaac tcgcgcctgc tgctgctgct ggtggcgccc ttcacggaca  12780
gcggcagcgt gagccgcgac tcgtacctgg gctacctgct taacctgtac cgcgaggcca  12840
tcggacaggc gcacgtggac gagcagacct accaggagat cacccacgtg agccgcgcgc  12900
tgggccagga ggacccgggc aacctggagg ccaccctgaa cttcctgctg accaaccggt  12960
cgcagaagat cccgccccag tacgcgctga gcaccgagga ggagcgcatc ctgcgctacg  13020
tgcagcagag cgtggggctg ttcctgatgc aggagggggc cacgcccagc gcggcgctcg  13080
acatgaccgc gcgcaacatg gagcccagca tgtacgcccg caaccgcccg ttcatcaata  13140
agctgatgga ctacttgcat cgggcggccg ccatgaactc ggactacttt accaacgcca  13200
tcttgaaccc gcactggctc ccgccgcccg ggttctacac gggcgagtac gacatgcccg  13260
```

-continued

```
accccaacga cgggttcctg tgggacgacg tggacagcag cgtgttctcg ccgcgtccag  13320
gaaccaatgc cgtgtggaag aaagagggcg gggaccggcg gccgtcctcg gcgctgtccg  13380
gtcgcgcggg tgctgccgcg gcggtgcccg aggccgccag cccccttcccg agcctgccct  13440
tttcgctgaa cagcgtgcgc agcagcgagc tgggtcggct gacgcgaccg cgcctgctgg  13500
gcgaggagga gtacctgaac gactccttgt tgaggcccga gcgcgagaag aacttcccca  13560
ataacgggat agagagcctg gtggacaaga tgagccgctg gaagacgtac gcgcacgagc  13620
acagggacga gccccgagct agcagcgcag gcacccgtag acgccagcgg cacgacaggc  13680
agcggggact ggtgtgggac gatgaggatt ccgccgacga cagcagcgtg ttggacttgg  13740
gtgggagtgg tggtaacccg ttcgctcacc tgcgcccccg tatcgggcgc ctgatgtaag  13800
aatctgaaaa aataaaagac ggtactcacc aaggccatgg cgaccagcgt gcgttcttct  13860
ctgttgtttg tagtagtatg atgaggcgcg tgtacccgga gggtcctcct ccctcgtacg  13920
agagcgtgat gcagcaggcg gtggcggcgg cgatgcagcc cccgctggag gcgccttacg  13980
tgcccccgcg gtacctggcg cctacggagg ggcggaacag cattcgttac tcggagctgg  14040
caccccttgta cgataccacc cggttgtacc tggtggacaa caagtcggca gacatcgcct  14100
cgctgaacta ccagaacgac cacagcaact tcctgaccac cgtggtgcag aacaacgatt  14160
tcaccccccac ggaggccagc acccagacca tcaactttga cgagcgctcg cggtggggcg  14220
gccagctgaa aaccatcatg cacaccaaca tgcccaacgt gaacgagttc atgtacagca  14280
acaagttcaa ggcgcgggtg atggtctcgc gcaagacccc caacggggtg gatgatgatt  14340
atgatggtag tcaggacgag ctgacctacg agtgggtgga gtttgagctg cccgagggca  14400
acttctcggt gaccatgacc atcgatctga tgaacaacgc catcatcgac aactacttgg  14460
cggtggggcg gcagaacggg gtgctggaga gcgacatcgg cgtgaagttc gacacgcgca  14520
acttccggct gggctgggac cccgtgaccg agctggtgat gccgggcgtg tacaccaacg  14580
aggccttcca ccccgacatc gtcctgctgc ccggctgcgg cgtggacttc accgagagcc  14640
gcctcagcaa cctgctgggc atccgcaagc ggcagccctt ccaggagggc ttccagatcc  14700
tgtacgagga cctggagggg ggcaacatcc ccgcgctctt ggatgtcgaa gcctacgaga  14760
aaagcaagga ggatagcacc gccgcggcga ccgcagccgt ggccaccgcc tctaccgagg  14820
tgcggggcga taattttgct agcgctgcgg cagcggccga ggcggctgaa accgaaagta  14880
agatagtcat ccagccggtg gagaaggaca gcaaggacag gagctacaac gtgctcgcgg  14940
acaagaaaaa caccgcctac cgcagctggt acctggccta caactacggc gaccccgaga  15000
agggcgtgcg ctcctggacg ctgctcacca cctcggacgt cacctgcggc gtggagcaag  15060
tctactggtc gctgcccgac atgatgcaag acccggtcac cttccgctcc acgcgtcaag  15120
ttagcaacta cccggtggtg ggcgccgagc tcctgcccgt ctactccaag agcttcttca  15180
acgagcaggc cgtctactcg cagcagctgc gcgccttcac ctcgctcacg cacgtcttca  15240
accgcttccc cgagaaccag atcctcgtcc gcccgcccgc gcccaccatt accaccgtca  15300
gtgaaaacgt tcctgctctc acagatcacg ggaccctgcc gctgcgcagc agtatccggg  15360
gagtccagcg cgtgaccgtc actgacgcca gacgccgcac ctgcccctac gtctacaagg  15420
ccctgggcgt agtcgcgccg cgcgtcctct cgagccgcac cttctaaaaa atgtccattc  15480
tcatctcgcc cagtaataac accggttggg gcctgcgcgc gcccagcaag atgtacggag  15540
gcgctcgcca acgctccacg caacaccccg tgcgcgtgcg cgggcacttc cgcgctccct  15600
```

-continued

```
ggggcgccct caagggccgc gtgcgctcgc gcaccaccgt cgacgacgtg atcgaccagg  15660
tggtggccga cgcgcgcaac tacacgcccg ccgccgcgcc cgtctccacc gtggacgccg  15720
tcatcgacag cgtggtggcc gacgcgcgcc ggtacgcccg caccaagagc cggcggcggc  15780
gcatcgcccg gcggcaccgg agcacccccg ccatgcgcgc ggcgcgagcc ttgctgcgca  15840
gggccaggcg cacgggacgc agggccatgc tcagggcggc cagacgcgcg gcctccggca  15900
gcagcagcgc cggcaggacc cgcagacgcg cggccacggc ggcggcggcg gccatcgcca  15960
gcatgtcccg cccgcggcgc ggcaacgtgt actgggtgcg cgacgccgcc accggtgtgc  16020
gcgtgcccgt gcgcacccgc ccccctcgca cttgaagatg ctgacttcgc gatgttgatg  16080
tgtcccagcg gcgaggagga tgtccaagcg caaatacaag gaagagatgc tccaggtcat  16140
cgcgcctgag atctacggcc ccgcggcggc ggtgaaggag gaaagaaagc cccgcaaact  16200
gaagcgggtc aaaaaggaca aaaaggagga ggaagatgac ggactggtgg agtttgtgcg  16260
cgagttcgcc ccccggcggc gcgtgcagtg gcgcgggcgg aaagtgaaac cggtgctgcg  16320
gcccggcacc acggtggtct tcacgcccgg cgagcgttcc ggctccgcct ccaagcgctc  16380
ctacgacgag gtgtacgggg acgaggacat cctcgagcag gcggtcgagc gtctgggcga  16440
gtttgcgtac ggcaagcgca gccgccccgc gcccttgaaa gaggaggcgg tgtccatccc  16500
gctggaccac ggcaacccca cgccgagcct gaagccggtg accctgcagc aggtgctacc  16560
gagcgcggcg ccgcgccggg gcttcaagcg cgagggcggc gaggatctgt acccgaccat  16620
gcagctgatg gtgcccaagc gccagaagct ggaggacgtg ctggagcaca tgaaggtgga  16680
ccccgaggtg cagcccgagg tcaaggtgcg gcccatcaag caggtggccc cgggcctggg  16740
cgtgcagacc gtggacatca agatccccac ggagcccatg gaaacgcaga ccgagcccgt  16800
gaagcccagc accagcacca tggaggtgca gacggatccc tggatgccag caccagcttc  16860
caccagcact cgccgaagac gcaagtacgg cgcggccagc ctgctgatgc ccaactacgc  16920
gctgcatcct tccatcatcc ccacgccggg ctaccgcggc acgcgcttct accgcggcta  16980
caccagcagc cgccgccgca agaccaccac ccgccgccgt cgtcgcagcc gccgcagcag  17040
caccgcgact tccgccttgg tgcggagagt gtatcgcagc gggcgcgagc ctctgaccct  17100
gccgcgcgcg cgctaccacc cgagcatcgc catttaacta ccgcctccta cttgcagata  17160
tggccctcac atgccgcctc cgcgtcccca ttacgggcta ccgaggaaga aagccgcgcc  17220
gtagaaggct gacggggaac gggctgcgtc gccatcacca ccggcggcgg cgcgccatca  17280
gcaagcggtt gggggaggc ttcctgcccg cgctgatccc catcatcgcc gcggcgatcg  17340
gggcgatccc cggcatagct tccgtggcgg tgcaggcctc tcagcgccac tgagacacaa  17400
aaaagcatgg atttgtaata aaaaaaaaaa tggactgacg ctcctggtcc tgtgatgtgt  17460
gtttttagat ggaagacatc aatttttcgt ccctggcacc gcgacacggc acgcggccgt  17520
ttatgggcac ctggagcgac atcggcaaca gccaactgaa cgggggcgcc ttcaattgga  17580
gcagtctctg gagcgggctt aagaatttcg ggtccacgct caaaacctat ggcaacaagg  17640
cgtggaacag cagcacaggg caggcgctga gggaaaagct gaaagaacag aacttccagc  17700
agaaggtggt tgatggcctg gcctcaggca tcaacggggt ggttgacctg gccaaccagg  17760
ccgtgcagaa acagatcaac agccgcctgg acgcggtccc gcccgcgggg tccgtggaga  17820
tgccccaggt ggaggaggag ctgcctcccc tggacaagcg cggcgacaag cgaccgcgtc  17880
ccgacgcgga ggagacgctg ctgacgcaca cggacgagcc gcccccgtac gaggaggcgg  17940
tgaaactggg cctgcccacc acgcggcccg tggcgcctct ggccaccgga gtgctgaaac  18000
```

-continued

```
ccagcagcag ccagcccgcg accctggact tgcctccgcc tcgcccctcc acagtggcta  18060
agcccctgcc gccggtggcc gtcgcgtcgc gcgccccccg aggccgcccc caggcgaact  18120
ggcagagcac tctgaacagc atcgtgggtc tgggagtgca gagtgtgaag cgccgccgct  18180
gctattaaaa gacactgtag cgcttaactt gcttgtctgt gtgtatatgt atgtccgccg  18240
accagaagga ggagtgtgaa gaggcgcgtc gccgagttgc aagatggcca ccccatcgat  18300
gctgccccag tgggcgtaca tgcacatcgc cggacaggac gcttcggagt acctgagtcc  18360
gggtctggtg cagttcgccc gcgccacaga cacctacttc agtctgggga acaagtttag  18420
gaaccccacg gtggcgccca cgcacgatgt gaccaccgac cgcagccagc ggctgacgct  18480
gcgcttcgtg cccgtggacc gcgaggacaa cacctactcg tacaaagtgc gctacacgct  18540
ggccgtgggc gacaaccgcg tgctggacat ggccagcacc tactttgaca tccgcggcgt  18600
gctggaccgg ggccctagct tcaaacccta ctctggcacc gcctacaaca gcctagctcc  18660
caagggagct cccaattcca gccagtggga gcaagcaaaa acaggcaatg gggaactat   18720
ggaaacacac acatatggtg tggccccaat gggcggagag aatattacaa aagatggtct  18780
tcaaattgga actgacgtta cagcgaatca gaataaacca atttatgccg acaaaacatt  18840
tcaaccagaa ccgcaagtag gagaagaaaa ttggcaagaa actgaaaact tttatggcgg  18900
tagagctctt aaaaaagaca caaacatgaa accttgctat ggctcctatg ctagacccac  18960
caatgaaaaa ggaggtcaag ctaaacttaa agttggagat gatggagttc caaccaaaga  19020
attcgacata gacctggctt tctttgatac tcccggtggc accgtgaacg gtcaagacga  19080
gtataaagca gacattgtca tgtataccga aaacacgtat ttggaaactc cagacacgca  19140
tgtggtatac aaaccaggca aggatgatgc aagttctgaa attaacctgg ttcagcagtc  19200
tatgcccaac agacccaact acattgggtt cagggacaac tttatcggtc ttatgtacta  19260
caacagcact ggcaatatgg gtgtgcttgc tggtcaggcc tcccagctga atgctgtggt  19320
tgatttgcaa gacagaaaca ccgagctgtc ctaccagctc ttgcttgact ctttgggtga  19380
cagaacccgg tatttcagta tgtggaacca ggcggtggac agttatgacc ccgatgtgcg  19440
catcatcgaa aaccatggtg tggaggatga attgccaaac tattgcttcc ccttggacgg  19500
ctctggcact aacgccgcat accaaggtgt gaaagtaaaa gatggtcaag atggtgatgt  19560
tgagagtgaa tgggaaaatg acgatactgt tgcagctcga aatcaattat gtaaaggtaa  19620
cattttcgcc atggagatta atctccaggc taacctgtgg agaagtttcc tctactcgaa  19680
cgtggccctg tacctgcccg actcctacaa gtacacgccg accaacgtca cgctgccgac  19740
caacaccaac acctacgatt acatgaatgg cagagtgaca cctccctcgc tggtagacgc  19800
ctacctcaac atcggggcgc gctggtcgct ggaccccatg gacaacgtca accccttcaa  19860
ccaccaccgc aacgcgggcc tgcgctaccg ctccatgctc ctgggcaacg ggcgctacgt  19920
gcccttccac atccaggtgc cccaaaagtt tttcgccatc aagagcctcc tgctcctgcc  19980
cgggtcctac acctacgagt ggaacttccg caaggacgtc aacatgatcc tgcagagctc  20040
cctaggcaac gacctgcgca cggacggggc ctccatcgcc ttcaccagca tcaacctcta  20100
cgccaccttc ttccccatgg cgcacaacac cgcctccacg ctcgaggcca tgctgcgcaa  20160
cgacaccaac gaccagtcct tcaacgacta cctctcggcg gccaacatgc tctaccccat  20220
cccggccaac gccaccaacg tgcccatctc catcccctcg cgcaactggg ccgccttccg  20280
cggatggtcc ttcacgcgcc tgaagacccg cgagacgccc tcgctcggct ccgggttcga  20340
```

-continued

```
ccccctacttc gtctactcgg gctccatccc ctacctagac ggcaccttct acctcaacca  20400
caccttcaag aaggtctcca tcaccttcga ctcctccgtc agctggcccg gcaacgaccg  20460
cctcctgacg cccaacgagt tcgaaatcaa gcgcaccgtc gacggagagg gatacaacgt  20520
ggcccagtgc aacatgacca aggactggtt cctggtccag atgctggccc actacaacat  20580
cggctaccag ggcttctacg tgcccgaggg ctacaaggac cgcatgtact ccttcttccg  20640
caacttccag cccatgagcc gccaggtcgt ggacgaggtc aactacaagg actaccaggc  20700
cgtcaccctg gcctaccagc acaacaactc gggcttcgtc ggctacctcg cgcccaccat  20760
gcgccagggc cagccctacc ccgccaacta cccctacccg ctcatcggca agagcgccgt  20820
cgccagcgtc acccagaaaa agttcctctg cgaccgggtc atgtggcgca tccccttctc  20880
cagcaacttc atgtccatgg gcgcgctcac cgacctcggc cagaacatgc tctacgccaa  20940
ctccgcccac gcgctagaca tgaatttcga agtcgacccc atggatgagt ccacccttct  21000
ctatgttgtc ttcgaagtct tcgacgtcgt ccgagtgcac cagccccacc gcggcgtcat  21060
cgaagccgtc tacctgcgca cgcccttctc ggccggcaac gccaccacct aagccgctct  21120
tgcttcttgc aagatgacgg cgggctccgg cgagcaggag ctcagggcca tcctccgcga  21180
cctgggctgc gggccctgct tcctgggcac cttcgacaag cgcttccctg gattcatggc  21240
cccgcacaag ctggcctgcg ccatcgtgaa cacggccggc cgcgagaccg ggggcgagca  21300
ctggctggcc ttcgcctgga acccgcgctc ccacacatgc tacctcttcg acccottcgg  21360
gttctcggac gagcgcctca agcagatcta ccagttcgag tacgagggcc tgctgcgtcg  21420
cagcgccctg gccaccgagg accgctgcgt caccctggaa aagtccaccc agaccgtgca  21480
gggtccgcgc tcggccgcct gcgggctctt ctgctgcatg ttcctgcacg ccttcgtgca  21540
ctggcccgac cgccccatgg acaagaaccc caccatgaac ttactgacgg gggtgcccaa  21600
cggcatgctc cagtcgcccc aggtggaacc caccctgcgc cgcaaccagg aagcgctcta  21660
ccgcttcctc aatgcccact ccgcctactt tcgctcccac cgcgcgcgca tcgagaaggc  21720
caccgccttc gaccgcatga atcaagacat gtaaaaaacc ggtgtgtgta tgtgaatgct  21780
ttattcataa taaacagcac atgtttatgc caccttctct gaggctctga ctttatttag  21840
aaatcgaagg ggttctgccg gctctcggca tggcccgcgg gcagggatac gttgcggaac  21900
tggtacttgg gcagccactt gaactcgggg atcagcagct tgggcacggg gaggtcgggg  21960
aacgagtcgc tccacagctt gcgcgtgagt tgcagggcgc ccagcaggtc gggcgcggag  22020
atcttgaaat cgcagttggg acccgcgttc tgcgcgcgag agttgcggta cacggggttg  22080
cagcactgga acaccatcag ggccgggtgc ttcacgcttg ccagcaccgt cgcgtcggtg  22140
atgccctcca cgtccagatc ctcggcgttg gccatcccga agggggtcat cttgcaggtc  22200
tgccgcccca tgctgggcac gcagccgggc ttgtggttgc aatcgcagtg caggggggatc  22260
agcatcatct gggcctgctc ggagctcatg cccgggtaca tggccttcat gaaagcctcc  22320
agctggcgga aggcctgctg cgccttgccg ccctcggtga agaagacccc gcaggacttg  22380
ctagagaact ggttggtggc gcagccggcg tcgtgcacgc agcagcgcgc gtcgttgttg  22440
gccagctgca ccacgctgcg cccccagcgg ttctgggtga tcttggcccg gttggggttc  22500
tccttcagcg cgcgctgccc gttctcgctc gccacatcca tctcgatagt gtgctccttc  22560
tggatcatca cggtcccgtg caggcaccgc agcttgccct cggcttcggt gcagccgtgc  22620
agccacagcg cgcagccggt gcactcccag ttcttgtggg cgatctggga gtgcgagtgc  22680
acgaagccct gcaggaagcg gcccatcatc gcggtcaggg tcttgttgct ggtgaaggtc  22740
```

-continued

```
agcgggatgc cgcggtgctc ctcgttcaca tacaggtggc agatgcggcg gtacacctcg  22800
ccctgctcgg gcatcagctg gaaggcggac ttcaggtcgc tctccacgcg gtaccggtcc  22860
atcagcagcg tcatcacttc catgcccttc tcccaggccg aaacgatcgg caggctcagg  22920
gggttcttca ccgccattgt catcttagtc gccgccgccg aggtcagggg gtcgttctcg  22980
tccagggtct caaacactcg cttgccgtcc ttctcgatga tgcgcacggg gggaaagctg  23040
aagcccacgg ccgccagctc ctcctcggcc tgcctttcgt cctcgctgtc ctggctgatg  23100
tcttgcaaag gcacatgctt ggtcttgcgg ggtttctttt tgggcggcag aggcggcggc  23160
gatgtgctgg gagagcgcga gttctcgttc accacgacta tttcttcttc ttggccgtcg  23220
tccgagacca cgcggcggta ggcatgcctc ttctggggca gaggcggagg cgacgggctc  23280
tcgcggttcg gcgggcggct ggcagagccc cttccgcgtt cgggggtgcg ctcctggcgg  23340
cgctgctctg actgacttcc tccgcggccg gccattgtgt tctcctaggg agcaacaaca  23400
agcatggaga ctcagccatc gtcgccaaca tcgccatctg cccccgccgc caccgccgac  23460
gagaaccagc agcagaatga aagcttaacc gccccgccgc ccagccccac ctccgacgcc  23520
gcggccccag acatgcaaga gatggaggaa tccatcgaga ttgacctggg ctacgtgacg  23580
cccgcggagc acgaggagga gctggcagcg cgcttttcag ccccggaaga gaaccaccaa  23640
gagcagccag agcaggaagc agagaacgag cagaaccagg ctgggcacga gcatggcgac  23700
tacctgagcg gggcagagga cgtgctcatc aagcatctgg cccgccaatg catcatcgtc  23760
aaggacgcgc tgctcgaccg cgccgaggtg cccctcagcg tggcggagct cagccgcgcc  23820
tacgagcgca acctcttctc gccgcgcgtg ccccccaagc gccagcccaa cggcacctgt  23880
gagcccaacc cgcgcctcaa cttctacccg gtcttcgcgg tgcccgaggc cctggccacc  23940
taccacctct ttttcaagaa ccaaaggatc cccgtctcct gccgcgccaa ccgcacccgc  24000
gccgacgccc tgctcaacct gggccccggc gcccgcctac ctgatatcac ctccttggaa  24060
gaggttccca agatcttcga gggtctgggc agcgacgaga ctcgggccgc gaacgctctg  24120
caaggaagcg gagaggagca tgagcaccac agcgccctgg tggagttgga aggcgacaac  24180
gcgcgcctgg cggtcctcaa gcgcacggtc gagctgaccc acttcgccta cccggcgctc  24240
aacctgcccc ccaaggtcat gagcgccgtc atggaccagg tgctcatcaa gcgcgcctcg  24300
cccctctcgg aggaggagat gcaggacccc gagagttcgg acgagggcaa gcccgtggtc  24360
agcgacgagc agctggcgcg ctggctggga gcgagtagca ccccccagag cctggaagag  24420
cggcgcaagc tcatgatggc cgtggtcctg gtgaccgtgg agctggagtg tctgcgccgc  24480
ttctttgccg acgcggagac cctgcgcaag gtcgaggaga acctgcacta cctcttcagg  24540
cacgggttcg tgcgccaggc ctgcaagatc tccaacgtgg agctgaccaa cctggtctcc  24600
tacatgggca tcctgcacga gaaccgcctg gggcaaaacg tgctgcacac caccctgcgc  24660
ggggaggccc gccgcgacta catccgcgac tgcgtctacc tgtacctctg ccacacctgg  24720
cagacgggca tgggcgtgtg gcagcagtgc ctggaggagc agaacctgaa agagctctgc  24780
aagctcctgc agaagaacct caaggccctg tggaccgggt tcgacgagcg taccaccgcc  24840
tcggacctgg ccgacctcat cttccccgag cgcctgcggc tgacgctgcg caacgggctg  24900
cccgacttta tgagccaaag catgttgcaa aactttcgct ctttcatcct cgaacgctcc  24960
gggatcctgc ccgccacctg ctccgcgctg ccctcggact tcgtgccgct gaccttccgc  25020
gagtgccccc cgccgctctg gagccactgc tacttgctgc gcctggccaa ctacctggcc  25080
```

-continued

```
taccactcgg acgtgatcga ggacgtcagc ggcgagggtc tgctggagtg ccactgccgc  25140
tgcaacctct gcacgccgca ccgctccctg gcctgcaacc cccagctgct gagcgagacc  25200
cagatcatcg gcaccttcga gttgcaaggc cccggcgacg gcgagggcaa ggggggtctg  25260
aaactcaccc cggggctgtg gacctcggcc tacttgcgca agttcgtgcc cgaggactac  25320
catcccttcg agatcaggtt ctacgaggac caatcccagc cgcccaaggc cgagctgtcg  25380
gcctgcgtca tcacccaggg ggccatcctg gcccaattgc aagccatcca gaaatcccgc  25440
caagaatttc tgctgaaaaa gggccacggg gtctacttgg acccccagac cggagaggag  25500
ctcaacccca gcttccccca ggatgccccg aggaagcagc aagaagctga aagtggagct  25560
gccgccgccg gaggatttgg aggaagactg ggagagcagt caggcagagg aggaggagat  25620
ggaagactgg gacagcactc aggcagagga ggacagcctg caagacagtc tggaggagga  25680
agacgaggtg gaggaggcag aggaagaagc agccgccgcc agaccgtcgt cctcggcgga  25740
gaaagcaagc agcacggata ccatctccgc tccgggtcgg ggtcgcggcg gccgggccca  25800
cagtaggtgg gacgagaccg ggcgcttccc gaaccccacc acccagaccg gtaagaagga  25860
gcggcaggga tacaagtcct ggcgggggca caaaaacgcc atcgtctcct gcttgcaagc  25920
ctgcgggggc aacatctcct tcacccggcg ctacctgctc ttccaccgcg gggtgaactt  25980
cccccgcaac atcttgcatt actaccgtca cctccacagc ccctactact gtttccaaga  26040
agaggcagaa acccagcagc agcagaaaac cagcggcagc agcagctaga aaatccacag  26100
cggcggcagg tggactgagg atcgcggcga acgagccggc gcagacccgg gagctgagga  26160
accggatctt tcccaccctc tatgccatct tccagcagag tcgggggcag gagcaggaac  26220
tgaaagtcaa gaaccgttct ctgcgctcgc tcacccgcag ttgtctgtat cacaagagcg  26280
aagaccaact tcagcgcact ctcgaggacg ccgaggctct cttcaacaag tactgcgcgc  26340
tcactcttaa agagtagccc gcgcccgccc acacacggaa aaaggcggga attacgtcac  26400
cacctgcgcc cttcgcccga ccatcatgag caaagagatt cccacgcctt acatgtggag  26460
ctaccagccc cagatgggcc tggccgccgg cgccgcccag gactactcca cccgcatgaa  26520
ctggctcagt gccgggcccg cgatgatctc acgggtgaat gacatccgcg cccaccgaaa  26580
ccagatactc ctagaacagt cagcgatcac cgccacgccc cgccatcacc ttaatccgcg  26640
taattggccc gccgccctgg tgtaccagga aattccccag cccacgaccg tactacttcc  26700
gcgagacgcc caggccgaag tccagctgac taactcaggt gtccagctgg ccggcggcgc  26760
cgccctgtgt cgtcaccgcc ccgctcaggg tataaagcgg ctggtgatcc gaggcagagg  26820
cacacagctc aacgacgagg tggtgagctc ttcgctgggt ctgcgacctg acggagtctt  26880
ccaactcgcc ggatcgggga gatcttcctt cacgcctcgt caggccgtcc tgactttgga  26940
gagttcgtcc tcgcagcccc gctcgggcgg catcggcact ctccagttcg tggaggagtt  27000
cactccctcg gtctacttca acccettctc cggctccccc ggccactacc cggacgagtt  27060
catcccgaac ttcgacgcca tcagcgagtc ggtggacggc tacgattgaa tgtcccatgg  27120
tggcgcagct gacctagctc ggcttcgaca cctggaccac tgccgccgct tccgctgctt  27180
cgctcgggat ctcgccgagt ttgcctactt tgagctgccc gaggagcacc ctcagggccc  27240
agcccacgga gtgcggatca tcgtcgaagg gggcctcgac tcccacctgc ttcggatctt  27300
cagccagcga ccgatcctgg tcgagcgcga acaaggacag acccttctta ctttgtactg  27360
catctgcaac caccccggcc tgcatgaaag tctttgttgt ctgctgtgta ctgagtataa  27420
taaaagctga gatcagcgac tactccggac tcgattgtgg tgttcctgct atcaaccggt  27480
```

-continued

```
ccctgttctt caccgggaac gagaccgagc tccagctcca gtgtaagccc cacaagaagt  27540
acctcacctg gctgttccag ggctccccga tcgccgttgt caaccactgc gacaacgacg  27600
gagtcctgct gagcggccct gccaacctta ctttttccac ccgcagaagc aagctccagc  27660
tcttccaacc cttcctcccc gggacctatc agtgcgtctc aggaccctgc catcacacct  27720
tccacctgat cccgaatacc acagcgccgc tccccgctac taacaaccaa actacccacc  27780
aacgccaccg tcgcgacctt tcctctgaat ctaataccac taccggaggt gagctccgag  27840
gtcgaccaac ctctgggatt tactacggcc cctgggaggt ggtggggtta atagcgctag  27900
gcctagttgc gggtgggctt ttggttctct gctacctata cctcccttgc tgttcgtact  27960
tagtggtgct gtgttgctgg tttaagaaat ggggaagatc accctagtga gctgcggtgc  28020
gctggtggcg gtgttgcttt cgattgtggg actgggcggc gcggctgtag tgaaggagaa  28080
ggccgatccc tgcttgcatt tcaatcccaa caaatgccag ctgagttttc agcccgatgg  28140
caatcggtgc gcggtactga tcaagtgcgg atgggaatgc gagaacgtga gaatcgagta  28200
caataacaag actcggaaca atactctcgc gtccgtgtgg cagcccgggg accccgagtg  28260
gtacaccgtc tctgtccccg gtgctgacgg ctccccgcgc accgtgaata atactttcat  28320
ttttgcgcac atgtgcaaca cggtcatgtg gatgagcaag cagtacgata tgtggccccc  28380
cacgaaggag aacatcgtgg tcttctccat cgcttacagc ctgtgcacgg cgctaatcac  28440
cgctatcgtg tgcctgagca ttcacatgct catcgctatt cgccccagaa ataatgccga  28500
gaaagagaaa cagccataac acgtttttc acacaccttg tttttacaga caatgcgtct  28560
gttaaatttt ttaaacattg tgctcagtat tgcttatgcc tctggttatg caaacataca  28620
gaaaaccctt tatgtaggat ctgatggtac actagagggt acccaatcac aagccaaggt  28680
tgcatggtat ttttatagaa ccaacactga tccagttaaa ctttgtaagg gtgaattgcc  28740
gcgtacacat aaaactccac ttacatttag ttgcagcaat aataatctta cacttttttc  28800
aattacaaaa caatatactg gtacttatta cagtacaaac tttcatacag gacaagataa  28860
atattatact gttaaggtag aaaatcctac cactcctaga actaccacca ccaccactac  28920
tgcaaagccc actgtgaaaa ctacaactag gaccaccaca actacagaaa ccaccaccag  28980
cacaacactt gctgcaacta cacacacaca cactaagcta accttacaga ccactaatga  29040
tttgatcgcc ctgctgcaaa agggggataa cagcaccact tccaatgagg agatacccaa  29100
atccatgatt ggcattattg ttgctgtagt ggtgtgcatg ttgatcatcg ccttgtgcat  29160
ggtgtactat gccttctgct acagaaagca cagactgaac gacaagctgg aacacttact  29220
aagtgttgaa ttttaatttt ttagaaccat gaagatccta ggccttttta gtttttctat  29280
cattacctct gctctttgtg aatcagtgga tagagatgtt actattacca ctggttctaa  29340
ttatacactg aaagggccac cctcaggtat gctttcgtgg tattgctatt ttggaactga  29400
cactgatcaa actgaattat gcaattttca aaaaggcaaa acctcaaact ctaaaatctc  29460
taattatcaa tgcaatggca ctgatctgat actactcaat gtcacgaaag catatggtgg  29520
cagttattat tgccctggac aaaacactga agaaatgatt ttttacaaag tggaagtggt  29580
tgatcccact acaccaccca ccaccacaac tattcatacc acacacacag aacaaacacc  29640
agaggcaaca gaagcagagt tggccttcca ggttcacgga gattcctttg ctgtcaatac  29700
ccctacaccc gatcagcggt gtccggggcc gctagtcagc ggcattgtcg gtgtgctttc  29760
gggattagca gtcataatca tctgcatgtt cattttttgct tgctgctata gaaggcttta  29820
```

-continued

```
ccgacaaaaa tcagacccac tgctgaacct ctatgtttaa ttttttccag agccatgaag  29880
gcagttagcg ctctagtttt ttgttctttg attggcattg tttttaatag taaaattacc  29940
agagttagct ttattaaaca tgttaatgta actgaaggag ataacatcac actagcaggt  30000
gtagaaggtg ctcaaaacac cacctggaca aaataccatc taggatggag agatatttgc  30060
acctggaatg taacttatta ttgcatagga gttaatctta ccattgttaa cgctaaccaa  30120
tctcagaatg ggttaattaa aggacagagt gttagtgtga ccagtgatgg gtactatacc  30180
cagcatagtt ttaactacaa cattactgtc ataccactgc ctacgcctag cccacctagc  30240
actaccacac agacaaccac atacagtaca tcaaatcagc ctaccaccac tacagcagca  30300
gaggttgcca gctcgtctgg ggtccgagtg gcatttttga tgttggcccc atctagcagt  30360
cccactgcta gtaccaatga gcagactact gaatttttgt ccactgtcga gagccacacc  30420
acagctacct ccagtgcctt ctctagcacc gccaatctct cctcgctttc ctctacacca  30480
atcagccccg ctactactcc tagccccgct cctcttccca ctcccctgaa gcaaacagac  30540
ggcggcatgc aatggcagat caccctgctc attgtgatcg ggttggtcat cctggccgtg  30600
ttgctctact acatcttctg ccgccgcatt cccaacgcgc accgcaagcc ggcctacaag  30660
cccatcgtta tcgggcagcc ggagccgctt caggtggaag gggtctaag gaatcttctc  30720
ttctctttta cagtatggtg attgaactat gattcctaga caattcttga tcactattct  30780
tatctgcctc ctccaagtct gtgccaccct cgctctggtg gccaacgcca gtccagactg  30840
tattgggccc ttcgcctcct acgtgctctt tgccttcgtc acctgcatct gctgctgtag  30900
catagtctgc ctgcttatca ccttcttcca gttcattgac tggatctttg tgcgcatcgc  30960
ctacctgcgc caccaccccc agtaccgcga ccagcgagtg gcgcagctgc tcaggctcct  31020
ctgataagca tgcgggctct gctacttctc gcgcttctgc tgttagtgct cccccgtccc  31080
gtcgaccccc ggtcccccac tcagtccccc gaggaggttc gcaaatgcaa attccaagaa  31140
ccctggaaat tcctcaaatg ctaccgccaa aaatcagaca tgcatcccag ctggatcatg  31200
atcattggga tcgtgaacat tctggcctgc accctcatct cctttgtgat ttacccctgc  31260
tttgactttg gttggaactc gccagaggcg ctctatctcc cgcctgaacc tgacacacca  31320
ccacagcagc aacctcaggc acacgcacta ccaccaccac agcctaggcc acaatacatg  31380
cccatattag actatgaggc cgagccacag cgacccatgc tccccgctat tagttacttc  31440
aatctaaccg gcggagatga ctgacccact ggccaataac aacgtcaacg accttctcct  31500
ggacatggac ggccgcgcct cggagcagcg actcgcccaa cttcgcattc gtcagcagca  31560
ggagagagcc gtcaaggagc tgcaggacgg catagccatc caccagtgca agagaggcat  31620
cttctgcctg gtgaaacagg ccaagatctc ctacgaggtc acccagaccg accatcgcct  31680
ctcctacgag ctcctgcagc agcgccagaa gttcacctgc ctggtcggag tcaaccccat  31740
cgtcatcacc cagcagtcgg gcgataccaa ggggtgcatc cactgctcct gcgactcccc  31800
cgactgcgtc cacactctga tcaagaccct ctgcggcctc cgcgacctcc tccccatgaa  31860
ctaatcaccc ccttatccag tgaaataaag atcatattga tgatgattta aataaaaaaa  31920
ataatcattt gatttgaaat aaagatacaa tcatattgat gatttgagtt taacaaaaat  31980
aaagaatcac ttacttgaaa tctgatacca ggtctctgtc catgttttct gccaacacca  32040
cctcactccc ctcttcccag ctctggtact gcaggccccg gcgggctgca aacttcctcc  32100
acacgctgaa ggggatgtca aattcctcct gtccctcaat cttcatttta tcttctatca  32160
gatgtccaaa aagcgcgtcc gggtggatga tgacttcgac cccgtctacc cctacgatgc  32220
```

```
agacaacgca ccgaccgtgc ccttcatcaa cccccccttc gtctcttcag atggattcca  32280
agagaagccc ctgggggtgt tgtccctgcg actggctgac cccgtcacca ccaagaacgg  32340
ggaaatcacc ctcaagctgg gagaggggt ggacctcgac tcgtcgggaa aactcatctc  32400
caacacggcc accaaggccg ccgcccctct cagtatttca aacaacacca tttcccttaa  32460
aactgctgcc cctttctaca acaacaatgg aactttaagc ctcaatgtct ccacaccatt  32520
agcagtattt cccacattta acactttagg cataagtctt ggaaacggtc ttcagacttc  32580
aaataagttg ttgactgtac aactaactca tcctcttaca ttcagctcaa atagcatcac  32640
agtaaaaaca gacaaagggc tatatattaa ctccagtgga aacagaggac ttgaggctaa  32700
tataagccta aaaagaggac tagtttttga cggtaatgct attgcaacat atattggaaa  32760
tggcttagac tatggatctt atgatagtga tggaaaaaca agacccgtaa ttaccaaaat  32820
tggagcagga ttaaattttg atgctaacaa agcaatagct gtcaaactag gcacaggttt  32880
aagttttgac tccgctggtg ccttgacagc tggaaacaaa caggatgaca agctaacact  32940
ttggactacc cctgacccaa gccctaattg tcaattactt tcagacagag atgccaaatt  33000
tactctctgt cttacaaaat gcggtagtca aatactaggc actgtggcag tggcggctgt  33060
tactgtagga tcagcactaa atccaattaa tgacacagtc aaaagcgcca tagttttcct  33120
tagatttgat tccgatggtg tactcatgtc aaactcatca atggtaggtg attactggaa  33180
ctttagggag ggacagacca ctcaaagtgt agcctataca aatgctgtgg gattcatgcc  33240
aaatataggt gcatatccaa aaacccaaag taaaacacct aaaaatagca tagtcagtca  33300
ggtatattta actggagaaa ctactatgcc aatgacacta accataactt tcaatggcac  33360
tgatgaaaaa gacacaaccc cagttagcac ctactctatg acttttacat ggcagtggac  33420
tggagactat aaggacaaaa atattacctt tgctaccaac tcattctctt tttcctacat  33480
cgcccaggaa taatcccacc cagcaagcca accccttttc ccaccacctt tgtctatatg  33540
gaaactctga aacagaaaaa taaagttcaa gtgttttatt gaatcaacag ttttacagga  33600
ctcgagcagt tatttttcct ccaccctccc aggacatgga atacaccacc ctctcccccc  33660
gcacagcctt gaacatctga atgccattgg tgatggacat gcttttggtc tccacgttcc  33720
acacagtttc agagcgagcc agtctcggat cggtcaggga gatgaaaccc tccgggcact  33780
cccgcatctg cacctcacag ctcaacagct gaggattgtc ctcggtggtc gggatcacgg  33840
ttatctggaa gaagcagaag agcggcggtg ggaatcatag tccgcgaacg ggatcggccg  33900
gtggtgtcgc atcaggcccc gcagcagtcg ctgccgccgc cgctccgtca agctgctgct  33960
caggggggttc gggtccaggg actccctcag catgatgccc acggccctca gcatcagtcg  34020
tctggtgcgg cgggcgcagc agcgcatgcg aatctcgctc aggtcactgc agtacgtgca  34080
acacaggacc accaggttgt tcaacagtcc atagttcaac acgctccagc cgaaactcat  34140
cgcgggaagg atgctaccca cgtggccgtc gtaccagatc ctcaggtaaa tcaagtggcg  34200
ctccctccag aagacgctgc ccatgtacat gatctccttg ggcatgtggc ggttcaccac  34260
ctcccggtac cacatcaccc tctggttgaa catgcagccc cggatgatcc tgcggaacca  34320
cagggccagc accgccccgc ccgccatgca gcgaagagac cccggatccc ggcaatgaca  34380
atggaggacc caccgctcgt acccgtggat catctgggag ctgaacaagt ctatgttggc  34440
acagcacagg catatgctca tgcatctctt cagcactctc agctcctcgg gggtcaaaac  34500
catatcccag ggcacgggga actcttgcag gacagcgaac cccgcagaac agggcaatcc  34560
```

-continued

```
tcgcacataa cttacattgt gcatggacag ggtatcgcaa tcaggcagca ccgggtgatc  34620
ctccaccaga gaagcgcggg tctcggtctc ctcacagcgt ggtaaggggg ccggccgata  34680
cgggtgatgg cgggacgcgg ctgatcgtgt tctcgaccgt gtcatgatgc agttgctttc  34740
ggacattttc gtacttgctg tagcagaacc tggtccgggc gctgcacacc gatcgccggc  34800
ggcggtctcg gcgcttggaa cgctcggtgt taaagttgta aaacagccac tctctcagac  34860
cgtgcagcag atctagggcc tcaggagtga tgaagatccc atcatgcctg atagctctga  34920
tcacatcgac caccgtggaa tgggccaggc ccagccagat gatgcaattt tgttgggttt  34980
cggtgacggc gggggaggga agaacaggaa gaaccatgat taacttttaa tccaaacggt  35040
ctcggagcac ttcaaaatga aggtcacgga gatggcacct ctcgcccccg ctgtgttggt  35100
ggaaaataac agccaggtca aaggtgatac ggttctcgag atgttccacg gtggcttcca  35160
gcaaagcctc cacgcgcaca tccagaaaca agacaatagc gaaagcggga gggttctcta  35220
attcctcaac catcatgtta cactcctgca ccatccccag ataattttca tttttccagc  35280
cttgaatgat tcgaactagt tcctgaggta aatccaagcc agccatgata aaaagctcgc  35340
gcagagcacc ctccaccggc attcttaagc acaccctcat aattccaaga tattctgctc  35400
ctggttcacc tgcagcagat tgacaagcgg aatatcaaaa tctctgccgc gatccctgag  35460
ctcctccctc agcaataact gtaagtactc tttcatatcg tctccgaaat ttttagccat  35520
aggaccccca ggaataagag aagggcaagc cacattacag ataaaccgaa gtcccccccca  35580
gtgagcattg ccaaatgtaa gattgaaata agcatgctgg ctagacccgg tgatatcttc  35640
cagataactg gacagaaaat cgggtaagca atttttaaga aaatcaacaa aagaaaaatc  35700
ttccaggtgc acgtttaggg cctcgggaac aacgatggag taagtgcaag gggtgcgttc  35760
cagcatggtt agttagctga tctgtaaaaa aacaaaaaat aaaacattaa accatgctag  35820
cctggcgaac aggtgggtaa atcgttctct ccagcaccag gcaggccacg gggtctccgg  35880
cgcgaccctc gtaaaaattg tcgctatgat tgaaaaccat cacagagaga cgttcccggt  35940
ggccggcgtg aatgattcga gaagaagcat acacccccgg aacattggag tccgtgagtg  36000
aaaaaaagcg gccgaggaag caatgaggca ctacaacgct cactctcaag tccagcaaag  36060
cgatgccatg cggatgaagc acaaaatttt caggtgcgta aaaaatgtaa ttactcccct  36120
cctgcacagg cagcgaagct cccgatccct ccagatacac atacaaagcc tcagcgtcca  36180
tagcttaccg agcggcagca gcagcggcac acaacaggcg caagagtcag agaaaagact  36240
gagctctaac ctgtccgccc gctctctgct caatatatag ccccagatct acactgacgt  36300
aaaggccaaa gtctaaaaat acccgccaaa taatcacaca cgcccagcac acgcccagaa  36360
accggtgaca cactcagaaa aatacgcgca cttcctcaaa cggccaaact gccgtcattt  36420
ccgggttccc acgctacgtc atcaaaacac gactttcaaa ttccgtcgac cgttaaaaac  36480
atcacccgcc ccgcccctaa cggtcgccgc tcccgcagcc aatcaccttc ctccctcccc  36540
aaattcaaac agctcatttg catattaacg cgcaccaaaa gtttgaggta tattattgat  36600
gatg                                                                36604
```

<210> SEQ ID NO 3
<211> LENGTH: 36535
<212> TYPE: DNA
<213> ORGANISM: chimpanzee adenovirus serotype Pan7

<400> SEQUENCE: 3

```
catcatcaat aatatacctc aaacttttgg tgcgcgttaa tatgcaaatg agctgtttga     60
```

-continued

```
atttggggag ggaggaaggt gattggccga gagacgggcg accgttaggg gcggggcggg    120
tgacgttttt aatacgtggc cgtgaggcgg agccggtttg caagttctcg tgggaaaagt    180
gacgtcaaac gaggtgtggt ttgaacacgg aaatactcaa ttttcccgcg ctctctgaca    240
ggaaatgagg tgtttctggg cggatgcaag tgaaaacggg ccattttcgc gcgaaaactg    300
aatgaggaag tgaaaatctg agtaatttcg cgtttatggc agggaggagt atttgccgag    360
ggccgagtag actttgaccg attacgtggg ggtttcgatt accgtatttt tcacctaaat    420
ttccgcgtac ggtgtcaaag tccggtgttt ttacgtaggc gtcagctgat cgccagggta    480
tttaaacctg cgctctctag tcaagaggcc actcttgagt gccagcgagt agagttttct    540
cctccgcgcc gcgagtcaga tctacacttt gaaagatgag gcacctgaga gacctgcccg    600
gtaatgtttt cctggctact gggaacgaga ttctggaatt ggtggtggac gccatgatgg    660
gtggcgaccc tcctgagccc cctaccccat ttgaggcgcc ttcgctgtac gatttgtatg    720
atctggaggt ggatgtgccc gagaacgacc ccaacgagga ggcggtgaat gatttgttta    780
gcgatgccgc gctgctggct gccgagcagg ctaatacgga ctctggctca gacagcgatt    840
cctctctcca taccccgaga cccggcagag gtgagaaaaa gatccccgag cttaaagggg    900
aagagctcga cctgcgctgc tatgaggaat gcttgcctcc gagcgatgat gaggaggacg    960
aggaggcgat tcgagctgca tcgaaccagg gagtgaaagc tgcgggcgaa agctttagcc   1020
tggactgtcc tactctgccc ggacacggct gtaagtcttg tgaatttcat cgcatgaata   1080
ctggagataa gaatgtgatg tgtgccctgt gctatatgag agcttacaac cattgtgttt   1140
acagtaagtg tgattaactt tagttgggaa ggcagagggt gactgggtgc tgactggttt   1200
atttatgtat atgttttttt atgtgtaggt cccgtctctg acgtagatga gacccccact   1260
tcagagtgca tttcatcacc cccagaaatt ggcgaggaac cgcccgaaga tattattcat   1320
agaccagttg cagtgagagt caccgggcgg agagcagctg tggagagttt ggatgacttg   1380
ctacagggtg gggatgaacc tttggacttg tgtacccgga aacgccccag gcactaagtg   1440
ccacacatgt gtgtttactt aaggtgatgt cagtatttat agggtgtgga gtgcaataaa   1500
atccgtgttg actttaagtg cgtggtttat gactcagggg tggggactgt gggtatataa   1560
gcaggtgcag acctgtgtgg tcagttcaga gcaggactca tggagatctg gacggtcttg   1620
gaagactttc accagactag acagctgcta gagaactcat cggagggggt ctcttacctg   1680
tggagattct gcttcggtgg gcctctagct aagctagtct atagggccaa acaggattat   1740
aaggatcaat ttgaggatat tttgagagag tgtcctggta tttttgactc tctcaacttg   1800
ggccatcagt ctcactttaa ccagagtatt ctgagagccc ttgacttttc tactcctggc   1860
agaactaccg ccgcggtagc ctttttttgcc tttatccttg acaaatggag tcaagaaacc   1920
catttcagca gggattaccg tctggactgc ttagcagtag ctttgtggag aacatggagg   1980
tgccagcgcc tgaatgcaat ctccggctac ttgccagtac agccggtaga cacgctgagg   2040
atcctgagtc tccagtcacc ccaggaacac caacgccgcc agcagccgca gcaggagcag   2100
cagcaagagg aggaggagga tcgagaagag aacccgagag ccggtctgga ccctccggtg   2160
gcggaggagg aggagtagct gacttgtttc ccgagctgcg ccgggtgctg actaggtctt   2220
ccagtggacg ggagaggggg attaagcggg agaggcatga ggagactagc cacagaactg   2280
aactgactgt cagtctgatg agccgcaggc gcccagaatc ggtgtggtgg catgaggttc   2340
agtcgcaggg gatagatgag gtctcggtga tgcatgagaa atattccctg gaacaagtca   2400
```

-continued

```
agacttgttg gttggagcct gaggatgatt gggaggtagc catcaggaat tatgccaagc   2460
tggctctgaa gccagacaag aagtacaaga ttaccaaact gattaatatc agaaattcct   2520
gctacatttc agggaatggg gccgaggtgg agatcagtac ccaggagagg gtggccttca   2580
gatgttgtat gatgaatatg tacccggggg tggtgggcat ggagggagtc acctttatga   2640
acgcgaggtt caggggtgat gggtataatg gggtggtctt tatggccaac accaagctga   2700
cagtgcacgg atgctccttc tttgggttca ataacatgtg catcgaggcc tggggcagtg   2760
tttcagtgag gggatgcagc ttttcagcca actggatggg ggtcgtgggc agaaccaaga   2820
gcaaggtgtc agtgaagaaa tgcctgttcg agaggtgcca cctgggggtg atgagcgagg   2880
gcgaagccaa agtcaaacac tgcgcctcta ctgagacggg ctgctttgtg ctgatcaagg   2940
gcaatgccca agtcaagcat aacatgatct gtggggcctc ggatgagcgc ggctaccaga   3000
tgctgacctg cgccggtggg aacagccata tgctggccac cgtgcatgtg acctcgcacc   3060
cccgcaagac atggcccgag ttcgagcaca acgtcatgac ccgatgcaat gtgcacctgg   3120
ggtcccgccg aggcatgttc atgccctacc agtgcaacat gcaatttgtg aaggtgctgc   3180
tggagcccga tgccatgtcc agagtgagcc tgacgggggt gtttgacatg aatgtggagc   3240
tgtggaaaat tctgagatat gatgaatcca agaccaggtg ccgggcctgc gaatgcggag   3300
gcaagcacgc caggcttcag cccgtgtgtg tggaggtgac ggaggacctg cgacccgatc   3360
atttggtgtt gtcctgcaac gggacggagt tcggctccag cggggaagaa tctgactaga   3420
gtgagtagtg tttgggggag gtggagggct tgtatgaggg gcagaatgac taaaatctgt   3480
gtttttctgt gtgttgcagc agcatgagcg gaagcgcctc ctttgaggga ggggtattca   3540
gcccttatct gacggggcgt ctcccctcct gggcgggagt gcgtcagaat gtgatgggat   3600
ccacggtgga cggccggccc gtgcagcccg cgaactcttc aaccctgacc tacgcgaccc   3660
tgagctcctc gtccgtggac gcagctgccg ccgcagctgc tgcttccgcc gccagcgccg   3720
tgcgcggaat ggccctgggc gccggctact acagctctct ggtggccaac tcgacttcca   3780
ccaataatcc cgccagcctg aacgaggaga agctgctgct gctgatggcc cagctcgagg   3840
ccctgaccca gcgcctgggc gagctgaccc agcaggtggc tcagctgcag gcggagacgc   3900
gggccgcggt tgccacggtg aaaaccaaat aaaaaatgaa tcaataaata aacggagacg   3960
gttgttgatt ttaacacaga gtcttgaatc tttatttgat tttcgcgcg cggtaggccc   4020
tggaccaccg gtctcgatca ttgagcaccc ggtggatttt ttccaggacc cggtagaggt   4080
gggcttggat gttgaggtac atgggcatga gcccgtcccg ggggtggagg tagctccatt   4140
gcagggcctc gtgctcgggg gtggtgttgt aaatcaccca gtcatagcag gggcgcaggg   4200
cgtggtgctg cacgatgtcc ttgaggagga gactgatggc cacgggcagc cccttggtgt   4260
aggtgttgac gaacctgttg agctgggagg gatgcatgcg gggggagatg agatgcatct   4320
tggcctggat cttgagattg gcgatgttcc cgcccagatc ccgccggggg ttcatgttgt   4380
gcaggaccac cagcacggtg tatccggtgc acttggggaa tttgtcatgc aacttggaag   4440
ggaaggcgtg aaagaatttg gagacgccct tgtgaccgcc caggttttcc atgcactcat   4500
ccatgatgat ggcgatgggc ccgtgggcgg cggcctgggc aaagacgttt cgggggtcgg   4560
acacatcgta gttgtggtcc tgggtgagct cgtcataggc cattttaatg aatttggggc   4620
ggagggtgcc cgactggggg acgaaggtgc cctcgatccc gggggcgtag ttgccctcgc   4680
agatctgcat ctcccaggcc ttgagctcgg agggggggat catgtccacc tgcggggcga   4740
tgaaaaaaac ggtttccggg gcgggggaga tgagctgggc cgaaagcagg ttccggagca   4800
```

-continued

```
gctgggactt gccgcagccg gtggggccgt agatgacccc gatgaccggc tgcaggtggt   4860
agttgaggga gagacagctg ccgtcctcgc ggaggagggg ggccacctcg ttcatcatct   4920
cgcgcacatg catgttctcg cgcacgagtt ccgccaggag gcgctcgccc cccagcgaga   4980
ggagctcttg cagcgaggcg aagtttttca gcggcttgag yccgtcggcc atgggcattt   5040
tggagagggt ctgttgcaag agttccagac ggtcccagag ctcggtgatg tgctctaggg   5100
catctcgatc cagcagacct cctcgtttcg cgggttgggg cgactgcggg agtagggcac   5160
caggcgatgg gcgtccagcg aggccagggt ccggtccttc cagggtcgca gggtccgcgt   5220
cagcgtggtc tccgtcacgg tgaaggggtg cgcgccgggc tgggcgcttg cgagggtgcg   5280
cttcaggctc atccggctgg tcgagaaccg ctcccggtcg gcgccctgcg cgtcggccag   5340
gtagcaattg agcatgagtt cgtagttgag cgcctcggcc gcgtggccct tggcgcggag   5400
cttacctttg gaagtgtgtc cgcagacggg acagaggagg gacttgaggg cgtagagctt   5460
gggggcgagg aagacggact cgggggcgta ggcgtccgcg ccgcagctgg cgcagacggt   5520
ctcgcactcc acgagccagg tgaggtcggg ccggttgggg tcaaaaacga ggtttcctcc   5580
gtgctttttg atgcgtttct tacctctggt ctccatgagc tcgtgtcccc gctgggtgac   5640
aaagaggctg tccgtgtccc cgtagaccga ctttatgggc cggtcctcga gcggggtgcc   5700
gcggtcctcg tcgtagagga accccgccca ctccgagacg aaggcccggg tccaggccag   5760
cacgaaggag gccacgtggg aggggtagcg gtcgttgtcc accagcgggt ccaccttctc   5820
cagggtatgc aagcacatgt cccccctcgtc cacatccagg aaggtgattg gcttgtaagt   5880
gtaggccacg tgaccggggg tcccggccgg gggggtataa aagggggcgg gcccctgctc   5940
gtcctcactg tcttccggat cgctgtccag gagcgccagc tgttggggta ggtattccct   6000
ctcgaaggct ggcataacct cggcactcag gttgtcagtt tctagaaacg aggaggattt   6060
gatattgacg gtgccgttgg agacgccttt catgagcccc tcgtccatct ggtcagaaaa   6120
gacgatcttt ttgttgtcga gcttggtggc gaaggagccg tagagggcgt tggagaggag   6180
cttggcgatg gagcgcatgg tctggttctt ttccttgtcg gcgcgctcct tggcggcgat   6240
gttgagctgc acgtactcgc gcgccacgca cttccattcg gggaagacgg tggtgagctc   6300
gtcgggcacg attctgaccc gccagccgcg gttgtgcagg gtgatgaggt ccacgctggt   6360
ggccacctcg ccgcgcaggg gctcgttggt ccagcagagg cgcccgccct tgcgcgagca   6420
gaagggggggc agcgggtcca gcatgagctc gtcggggggg tcggcgtcca cggtgaagat   6480
gccgggcaga agctcggggt cgaagtagct gatgcaggtg tccagatcgt ccagcgccgc   6540
ttgccagtcg cgcacggcca gcgcgcgctc gtaggggctg aggggcgtgc cccagggcat   6600
ggggtgcgtg agcgcggagg cgtacatgcc gcagatgtcg tagacgtaga ggggctcctc   6660
gaggacgccg atgtaggtgg ggtagcagcg ccccccgcgg atgctggcgc gcacgtagtc   6720
gtacagctcg tgcgagggcg cgaggagccc cgtgccgagg ttggagcgtt gcggcttttc   6780
ggcgcggtag acgatctggc ggaagatggc gtgggagttg gaggagatgg tgggcctctg   6840
gaagatgttg aagtgggcgt ggggcaggcc gaccgagtcc ctgatgaagt gggcgtagga   6900
gtcctgcagc ttggcgacga gctcggcggt gacgaggacg tccagggcgc agtagtcgag   6960
ggtctcttgg atgatgtcgt acttgagctg gcccttctgc ttccacagct cgcggttgag   7020
aaggaactct tcgcggtcct tccagtactc ttcgaggggg aacccgtcct gatcggcacg   7080
gtaagagccc accatgtaga actggttgac ggccttgtag gcgcagcagc ccttctccac   7140
```

-continued

```
ggggagggcg taagcttgtg cggccttgcg cagggaggtg tgggtgaggg cgaaggtgtc   7200
gcgcaccatg accttgagga actggtgctt gaagtcgagg tcgtcgcagc cgccctgctc   7260
ccagagctgg aagtccgtgc gcttcttgta ggcggggttg ggcaaagcga aagtaacatc   7320
gttgaagagg atcttgcccg cgcggggcat gaagttgcga gtgatgcgga aaggctgggg   7380
cacctcggcc cggttgttga tgacctgggc ggcgaggacg atctcgtcga agccgttgat   7440
gttgtgcccg acgatgtaga gttccacgaa tcgcgggcgg cccttaacgt ggggcagctt   7500
cttgagctcg tcgtaggtga gctcggcggg gtcgctgagc ccgtgctgct cgagggccca   7560
gtcggcgacg tgggggttgg cgctgaggaa ggaagtccag agatccacgg ccagggcggt   7620
ctgcaagcgg tcccggtact gacggaactg ctggcccacg gccatttttt cggggggtgac  7680
gcagtagaag gtgcgggggt cgccgtgcca gcggtcccac ttgagctgga gggcgaggtc   7740
gtgggcgagc tcgacgagcg gcgggtcccc ggagagtttc atgaccagca tgaaggggac   7800
gagctgcttg ccgaaggacc ccatccaggt gtaggtttcc acatcgtagg tgaggaagag   7860
cctttcggtg cgaggatgcg agccgatggg gaagaactgg atctcctgcc accagttgga   7920
ggaatggctg ttgatgtgat ggaagtagaa atgccgacgg cgcgccgagc actcgtgctt   7980
gtgtttatac aagcgtccgc agtgctcgca acgctgcacg ggatgcacgt gctgcacgag   8040
ctgtacctgg gttcctttga cgaggaattt cagtgggcag tggagcgctg gcggctgcat   8100
ctggtgctgt actacgtcct ggccatcggc gtggccatcg tctgcctcga tggtggtcat   8160
gctgacgagc ccgcgcggga ggcaggtcca gacttcggct cggacgggtc ggagagcgag   8220
gacgagggcg cgcaggccgg agctgtccag ggtcctgaga cgctgcggag tcaggtcagt   8280
gggcagcggc ggcgcgcggt tgacttgcag gagcttttcc agggcgcgcg ggaggtccag   8340
atggtacttg atctccacgg cgccgttggt ggcgacgtcc acggcttgca gggtcccgtg   8400
cccctggggc gccaccaccg tgccccgttt cttcttgggc gctgcttcca tgccggtcag   8460
aagcggcggc gaggacgcgc gccgggcggc aggggcggct cgggacccgg aggcaggggc   8520
ggcaggggca cgtcggcgcc gcgcgcgggc aggttctggt actgcgcccg gagaagactg   8580
gcgtgagcga cgacgcgacg gttgacgtcc tggatctgac gcctctgggt gaaggccacg   8640
ggacccgtga gtttgaacct gaaagagagt tcgacagaat caatctcggt atcgttgacg   8700
gcggcctgcc gcaggatctc ttgcacgtcg cccgagttgt cctggtaggc gatctcggtc   8760
atgaactgct cgatctcctc ctcctgaagg tctccgcggc cggcgcgctc gacggtggcc   8820
gcgaggtcgt tggagatgcg gcccatgagc tgcgagaagg cgttcatgcc ggcctcgttc   8880
cagacgcggc tgtagaccac ggctccgtcg ggtcgcgcg cgcgcatgac cacctgggcg    8940
aggttgagct cgacgtggcg cgtgaagacc gcgtagttgc agaggcgctg gtagaggtag   9000
ttgagcgtgg tggcgatgtg ctcggtgacg aagaagtaca tgatccagcg gcggagcggc   9060
atctcgctga cgtcgcccag ggcttccaag cgctccatgg cctcgtagaa gtccacggcg   9120
aagttgaaaa actgggagtt gcgcgccgag acggtcaact cctcctccag aagacggatg   9180
agctcagcga tggtggcgcg cacctcgcgc tcgaaggccc cggggggctc ctcttcttcc   9240
atctcttcct cctccactaa catctcttct acttcctcct caggaggcgg cggcggggga   9300
ggggccctgc gtcgccggcg gcgcacgggc agacggtcga tgaagcgctc gatggtctcc   9360
ccgcgccggc gacgcatggt ctcggtgacg gcgcgcccgt cctcgcgggg ccgcagcgtg   9420
aagacgccgc cgcgcatctc caggtggccg ccgggggggt ctccgttggg cagggagagg   9480
gcgctgacga tgcatcttat caattggccc gtagggactc cgcgcaagga cctgagcgtc   9540
```

-continued

```
tcgagatcca cgggatccga aaaccgctga acgaaggctt cgagccagtc gcagtcgcaa   9600
ggtaggctga gcccggtttc ttgttcttcg gggatttcgg gaggcgggcg ggcgatgctg   9660
ctggtgatga agttgaagta ggcggtcctg agacggcgga tggtggcgag gagcaccagg   9720
tccttgggcc cggcttgctg gatgcgcaga cggtcggcca tgccccaggc gtggtcctga   9780
cacctggcga ggtccttgta gtagtcctgc atgagccgct ccacgggcac ctcctcctcg   9840
cccgcgcggc cgtgcatgcg cgtgagcccg aacccgcgct ggggctggac gagcgccagg   9900
tcggcgacga cgcgctcggc gaggatggcc tgctgtatct gggtgagggt ggtctggaag   9960
tcgtcgaagt cgacgaagcg gtggtaggct ccggtgttga tggtatagga gcagttggcc  10020
atgacggacc agttgacggt ctggtggccg ggtcgcacga gctcgtggta cttgaggcgc  10080
gagtaggcgc gcgtgtcgaa gatgtagtcg ttgcaggtgc gcacgaggta ctggtatccg  10140
acgaggaagt gcggcggcgg ctggcggtag agcggccatc gctcggtggc gggggcgccg  10200
ggcgcgaggt cctcgagcat gaggcggtgg tagccgtaga tgtacctgga catccaggtg  10260
atgccggcgg cggtggtgga ggcgcgcggg aactcgcgga cgcggttcca gatgttgcgc  10320
agcggcagga agtagttcat ggtggccgcg gtctggcccg tgaggcgcgc gcagtcgtgg  10380
atgctctaga catacgggca aaaacgaaag cggtcagcgg ctcgactccg tggcctggag  10440
gctaagcgaa cgggttgggc tgcgcgtgta ccccggttcg aatctcgaat caggctggag  10500
ccgcagctaa cgtggtactg gcactcccgt ctcgacccaa gcctgctaac gaaacctcca  10560
ggatacggag gcgggtcgtt ttttggcctt ggtcgctggt catgaaaaac tagtaagcgc  10620
ggaaagcgac cgcccgcgat ggctcgctgc cgtagtctgg agaaagaatc gccagggttg  10680
cgttgcggtg tgccccggtt cgagcctcag cgctcggcgc cggccggatt ccgcggctaa  10740
cgtgggcgtg gctgccccgt cgtttccaag acccccttagc cagccgactt ctccagttac  10800
ggagcgagcc cctctttttc ttgtgttttt gccagatgca tcccgtactg cggcagatgc  10860
gcccccaccc tccacctcaa ccgcccctac cgccgcagca gcagcaacag ccggcgcttc  10920
tgcccccgcc ccagcagcag ccagccacta ccgcggcggc cgccgtgagc ggagccggcg  10980
ttcagtatga cctggccttg gaagagggcg aggggctggc gcggctgggg gcgtcgtcgc  11040
cggagcggca cccgcgcgtg cagatgaaaa gggacgctcg cgaggcctac gtgcccaagc  11100
agaacctgtt cagagacagg agcggcgagg agcccgagga gatgcgcgcc tcccgcttcc  11160
acgcggggcg ggagctgcgg cgcggcctgg accgaaagcg ggtgctgagg gacgaggatt  11220
tcgaggcgga cgagctgacg gggatcagcc ccgcgcgcgc gcacgtggcc gcggccaacc  11280
tggtcacggc gtacgagcag accgtgaagg aggagagcaa cttccaaaaa tccttcaaca  11340
accacgtgcg cacgctgatc gcgcgcgagg aggtgaccct gggcctgatg cacctgtggg  11400
acctgctgga ggccatcgtg cagaacccca cgagcaagcc gctgacggcg cagctgtttc  11460
tggtggtgca gcacagtcgg gacaacgaga cgttcaggga ggcgctgctg aatatcaccg  11520
agcccgaggg ccgctggctc ctggacctgg tgaacattct gcagagcatc gtggtgcagg  11580
agcgcgggct gccgctgtcc gagaagctgg cggctatcaa cttctcggtg ctgagcctgg  11640
gcaagtacta cgctaggaag atctacaaga ccccgtacgt gcccatagac aaggaggtga  11700
agatcgacgg gttttacatg cgcatgaccc tgaaagtgct gaccctgagc gacgatctgg  11760
gggtgtaccg caacgacagg atgcaccgcg cggtgagcgc cagccgccgg cgcgagctga  11820
gcgaccagga gctgatgcac agcctgcagc gggccctgac cggggccggg accgaggggg  11880
```

-continued

```
agagctactt tgacatgggc gcggacctgc gctggcagcc cagccgccgg gccttggaag  11940
ctgccggcgg ttccccctac gtggaggagg tggacgatga ggaggaggag ggcgagtacc  12000
tggaagactg atggcgcgac cgtatttttg ctagatgcag caacagccac cgcctcctga  12060
tcccgcgatg cgggcggcgc tgcagagcca gccgtccggc attaactcct cggacgattg  12120
gacccaggcc atgcaacgca tcatggcgct gacgacccgc aatcccgaag cctttagaca  12180
gcagcctcag gccaaccggc tctcggccat cctggaggcc gtggtgccct cgcgctcgaa  12240
ccccacgcac gagaaggtgc tggccatcgt gaacgcgctg gtggagaaca aggccatccg  12300
cggcgacgag gccgggctgg tgtacaacgc gctgctggag cgcgtggccc gctacaacag  12360
caccaacgtg cagacgaacc tggaccgcat ggtgaccgac gtgcgcgagg cggtgtcgca  12420
gcgcgagcgg ttccaccgcg agtcgaacct gggctccatg gtggcgctga acgccttcct  12480
gagcacgcag cccgccaacg tgccccgggg ccaggaggac tacaccaact tcatcagcgc  12540
gctgcggctg atggtggccg aggtgcccca gagcgaggtg taccagtcgg ggccggacta  12600
cttcttccag accagtcgcc agggcttgca gaccgtgaac ctgagccagg ctttcaagaa  12660
cttgcaggga ctgtggggcg tgcaggcccc ggtcggggac cgcgcgacgg tgtcgagcct  12720
gctgacgccg aactcgcgcc tgctgctgct gctggtggcg cccttcacgg acagcggcag  12780
cgtgagccgc gactcgtacc tgggctacct gcttaacctg taccgcgagg ccatcgggca  12840
ggcgcacgtg gacgagcaga cctaccagga gatcacccac gtgagccgcg cgctgggcca  12900
ggaggacccg ggcaacctgg aggccaccct gaacttcctg ctgaccaacc ggtcgcagaa  12960
gatcccgccc cagtacgcgc tgagcaccga ggaggagcgc atcctgcgct acgtgcagca  13020
gagcgtgggg ctgttcctga tgcaggaggg ggccacgccc agcgccgcgc tcgacatgac  13080
cgcgcgcaac atggagccca gcatgtacgc tcgcaaccgc ccgttcatca ataagctgat  13140
ggactacttg catcgggcgg ccgccatgaa ctcggactac tttaccaacg ccatcttgaa  13200
cccgcactgg ctcccgccgc ccgggttcta cacgggcgag tacgacatgc ccgaccccaa  13260
cgacgggttc ctgtgggacg acgtggacag cagcgtgttc tcgccgcgcc ccgccaccac  13320
cgtgtggaag aaagagggcg gggaccggcg gccgtcctcg gcgctgtccg gtcgcgcggg  13380
tgctgccgcg gcggtgcctg aggccgccag ccccttcccg agcctgccct tttcgctgaa  13440
cagcgtgcgc agcagcgagc tgggtcggct gacgcggccg cgcctgctgg gcgaggagga  13500
gtacctgaac gactccttgt tgaggcccga gcgcgagaag aacttcccca ataacgggat  13560
agagagcctg gtggacaaga tgagccgctg gaagacgtac gcgcacgagc acagggacga  13620
gccccgagct agcagcagcg caggcacccg tagacgccag cgacacgaca ggcagcgggg  13680
tctggtgtgg gacgatgagg attccgccga cgacagcagc gtgttggact tgggtgggag  13740
tggtggtggt aacccgttcg ctcacttgcg cccccgtatc gggcgcctga tgtaagaatc  13800
tgaaaaaata aaaaacggta ctcaccaagg ccatggcgac cagcgtgcgt tcttctctgt  13860
tgtttgtagt agtatgatga ggcgcgtgta cccggagggt cctcctccct cgtacgagag  13920
cgtgatgcag caggcggtgg cggcggcgat gcagcccccg ctggaggcgc cttacgtgcc  13980
cccgcggtac ctggcgccta cggaggggcg gaacagcatt cgttactcgg agctggcacc  14040
cttgtacgat accacccggt tgtacctggt ggacaacaag tcggcggaca tcgcctcgct  14100
gaactaccag aacgaccaca gcaacttcct gaccaccgtg gtgcagaaca acgatttcac  14160
cccacggag gccagcaccc agaccatcaa ctttgacgag cgctcgcggt ggggcggcca  14220
gctgaaaacc atcatgcaca ccaacatgcc caacgtgaac gagttcatgt acagcaacaa  14280
```

```
gttcaaggcg cgggtgatgg tctcgcgcaa gacccccaat ggggtcgcgg tggatgagaa  14340
ttatgatggt agtcaggacg agctgactta cgagtgggtg gagtttgagc tgcccgaggg  14400
caacttctcg gtgaccatga ccatcgatct gatgaacaac gccatcatcg acaactactt  14460
ggcggtgggg cgtcagaacg gggtgctgga gagcgacatc ggcgtgaagt tcgacacgcg  14520
caacttccgg ctgggctggg accccgtgac cgagctggtg atgccgggcg tgtacaccaa  14580
cgaggccttc caccccgaca tcgtcctgct gcccggctgc ggcgtggact tcaccgagag  14640
ccgcctcagc aacctgctgg gcatccgcaa gcggcagccc ttccaggagg gcttccagat  14700
cctgtacgag gacctggagg ggggcaacat ccccgcgctc ttggatgtcg aagcctatga  14760
gaaaagcaag gaggaggccg ccgcagcggc gaccgcagcc gtggccaccg cctctaccga  14820
ggtgcggggc gataattttg ctagcgccgc ggcagtggcc gaggcggctg aaaccgaaag  14880
taagatagtc atccagccgg tggagaagga cagcaaggac aggagctaca acgtgctcgc  14940
ggacaagaaa aacaccgcct accgcagctg gtacctggcc tacaactacg gcgaccccga  15000
gaagggcgtg cgctcctgga cgctgctcac cacctcggac gtcacctgcg gcgtggagca  15060
agtctactgg tcgctgcccg acatgatgca agacccggtc accttccgct ccacgcgtca  15120
agttagcaac tacccggtgg tgggcgccga gctcctgccc gtctactcca agagcttctt  15180
caacgagcag gccgtctact cgcagcagct gcgcgccttc acctcgctca cgcacgtctt  15240
caaccgcttc cccgagaacc agatcctcgt ccgcccgccc gcgcccacca ttaccaccgt  15300
cagtgaaaac gttcctgctc tcacagatca cgggaccctg ccgctgcgca gcagtatccg  15360
gggagtccag cgcgtgaccg tcactgacgc cagacgccgc acctgcccct acgtctacaa  15420
ggccctgggc gtagtcgcgc cgcgcgtcct ctcgagccgc accttctaaa aaatgtccat  15480
tctcatctcg cccagtaata acaccggttg gggcctgcgc gcgcccagca agatgtacgg  15540
aggcgctcgc caacgctcca cgcaacaccc cgtgcgcgtg cgcgggcact tccgcgctcc  15600
ctggggcgcc ctcaagggcc gcgtgcgctc gcgcaccacc gtcgacgacg tgatcgacca  15660
ggtggtggcc gacgcgcgca actacacgcc cgccgccgcg cccgcctcca ccgtggacgc  15720
cgtcatcgac agcgtggtgg ccgatgcgcg ccggtacgcc cgcgccaaga gccggcggcg  15780
gcgcatcgcc cggcggcacc ggagcacccc cgccatgcgc gcggcgcgag ccttgctgcg  15840
cagggccagg cgcacgggac gcagggccat gctcagggcg gccagacgcg cggcctccgg  15900
cagcagcagc gccggcagga cccgcagacg cgcggccacg gcggcggcgg cggccatcgc  15960
cagcatgtcc cgcccgcggc gcggcaacgt gtactgggtg cgcgacgccg ccaccggtgt  16020
gcgcgtgccc gtgcgcaccc gcccccctcg cacttgaaga tgctgacttc gcgatgttga  16080
tgtgtcccag cggcgaggag gatgtccaag cgcaaataca aggaagagat gctccaggtc  16140
atcgcgcctg agatctacgg ccccgcggtg aaggaggaaa gaaagccccg caaactgaag  16200
cgggtcaaaa aggacaaaaa ggaggaggaa gatgtggacg gactggtgga gtttgtgcgc  16260
gagttcgccc cccggcggcg cgtgcagtgg cgcgggcgga aagtgaaacc ggtgctgcgg  16320
cccggcacca cggtggtctt cacgcccggc gagcgttccg gctccgcctc caagcgctcc  16380
tacgacgagg tgtacgggga cgaggacatc ctcgagcagg cggtcgagcg tctgggcgag  16440
tttgcttacg gcaagcgcag ccgccccgcg cccttgaaag aggaggcggt gtccatcccg  16500
ctggaccacg gcaaccccac gccgagcctg aagccggtga ccctgcagca ggtgctgccg  16560
agcgcggcgc cgcgccgggg cttcaagcgc gagggcggcg aggatctgta cccgaccatg  16620
```

-continued

```
cagctgatgg tgcccaagcg ccagaagctg gaggacgtgc tggagcacat gaaggtggac  16680
cccgaggtgc agcccgaggt caaggtgcgg cccatcaagc aggtggcccc gggcctgggc  16740
gtgcagaccg tggacatcaa gatccccacg gagcccatgg aaacgcagac cgagcccgtg  16800
aagcccagca ccagcaccat ggaggtgcag acggatccct ggatgccggc gccggcttcc  16860
accactcgcc gaagacgcaa gtacggcgcg gccagcctgc tgatgcccaa ctacgcgctg  16920
catccttcca tcatccccac gccgggctac cgcggcacgc gcttctaccg cggctacacc  16980
agcagccgcc gcaagaccac cacccgccgc cgccgtcgtc gcacccgccg cagcagcacc  17040
gcgacttccg ccgccgccct ggtgcggaga gtgtaccgca gcgggcgcga gcctctgacc  17100
ctgccgcgcg cgcgctacca cccgagcatc gccatttaac tctgccgtcg cctcctactt  17160
gcagatatgg ccctcacatg ccgcctccgc gtccccatta cgggctaccg aggaagaaag  17220
ccgcgccgta gaaggctgac ggggaacggg ctgcgtcgcc atcaccaccg gcggcggcgc  17280
gccatcagca agcggttggg gggaggcttc ctgcccgcgc tgatccccat catcgccgcg  17340
gcgatcgggg cgatccccgg catagcttcc gtggcggtgc aggcctctca gcgccactga  17400
gacacagctt ggaaaatttg taataaaaaa atggactgac gctcctggtc ctgtgatgtg  17460
tgtttttaga tggaagacat caatttttcg tccctggcac cgcgacacgg cacgcggccg  17520
tttatgggca cctggagcga catcggcaac agccaactga acgggggcgc cttcaattgg  17580
agcagtctct ggagcgggct taagaatttc gggtccacgc tcaaaaccta tggcaacaag  17640
gcgtggaaca gcagcacagg gcaggcgctg agggaaaagc tgaaagagca gaacttccag  17700
cagaaggtgg tcgatggcct ggcctcgggc atcaacgggg tggtggacct ggccaaccag  17760
gccgtgcaga aacagatcaa cagccgcctg gacgcggtcc cgcccgcggg gtccgtggag  17820
atgccccagg tggaggagga gctgcctccc ctggacaagc gcggcgacaa gcgaccgcgt  17880
cccgacgcgg aggagacgct gctgacgcac acggacgagc cgcccccgta cgaggaggcg  17940
gtgaaactgg gtctgcccac cacgcggccc gtggcgcctc tggccaccgg ggtgctgaaa  18000
cccagcagca gcagccagcc cgcgaccctg gacttgcctc cgcctgcttc ccgcccctcc  18060
acagtggcta agcccctgcc gccggtggcc gtcgcgtcgc gcgcccccg aggccgcccc  18120
caggcgaact ggcagagcac tctgaacagc atcgtgggtc tgggagtgca gagtgtgaag  18180
cgccgccgct gctattaaaa gacactgtag cgcttaactt gcttgtctgt gtgtatatgt  18240
atgtccgccg accagaagga ggaagaggcg cgtcgccgag ttgcaagatg gccaccccat  18300
cgatgctgcc ccagtgggcg tacatgcaca tcgccggaca ggacgcttcg gagtacctga  18360
gtccgggtct ggtgcagttc gcccgcgcca cagacaccta cttcagtctg gggaacaagt  18420
ttaggaaccc cacggtggcg cccacgcacg atgtgaccac cgaccgcagc cagcggctga  18480
cgctgcgctt cgtgcccgtg gaccgcgagg acaacaccta ctcgtacaaa gtgcgctaca  18540
cgctggccgt gggcgacaac cgcgtgctgg acatggccag cacctacttt gacatccgcg  18600
gcgtgctgga tcgggggccc agcttcaaac cctactccgg caccgcctac aacagcctgg  18660
ctcccaaggg agcgcccaac acttgccagt ggacatataa agctggtgat actgatacag  18720
aaaaaaccta tacatatgga aatgcacctg tgcaaggcat tagcattaca aaggatggta  18780
ttcaacttgg aactgacagc gatggtcagg caatctatgc agacgaaact tatcaaccag  18840
agcctcaagt gggtgatgct gaatggcatg acatcactgg tactgatgaa aaatatggag  18900
gcagagctct taagcctgac accaaaatga agccttgcta tggttctttt gccaagccta  18960
ccaataaaga aggaggccag gcaaatgtga aaaccgaaac aggcggtacc aaagaatatg  19020
```

acattgacat ggcattcttc gataatcgaa gtgcagctgc cgccggccta gccccagaaa 19080
ttgttttgta tactgagaat gtggatctgg aaactccaga tacccatatt gtatacaagg 19140
caggtacaga tgacagtagc tcttctatca atttgggtca gcagtccatg cccaacagac 19200
ccaactacat tggcttcaga gacaacttta tcggtctgat gtactacaac agcactggca 19260
atatgggtgt actggctgga caggcctccc agctgaatgc tgtggtggac ttgcaggaca 19320
gaaacaccga actgtcctac cagctcttgc ttgactctct gggtgacaga accaggtatt 19380
tcagtatgtg gaatcaggcg gtggacagtt atgaccccga tgtgcgcatt attgaaaatc 19440
acggtgtgga ggatgaactt cctaactatt gcttccccct ggatgctgtg ggtagaactg 19500
atacttacca gggaattaag gccaatggtg ataatcaaac cacctggacc aaagatgata 19560
ctgttaatga tgctaatgaa ttgggcaagg gcaatccttt cgccatggag atcaacatcc 19620
aggccaacct gtggcggaac ttcctctacg cgaacgtggc gctgtacctg cccgactcct 19680
acaagtacac gccggccaac atcacgctgc ccaccaacac caacacctac gattacatga 19740
acggccgcgt ggtggcgccc tcgctggtgg acgcctacat caacatcggg gcgcgctggt 19800
cgctggaccc catggacaac gtcaacccct tcaaccacca ccgcaacgcg ggcctgcgat 19860
accgctccat gctcctgggc aacgggcgct acgtgccctt ccacatccag gtgccccaaa 19920
agtttttcgc catcaagagc ctcctgctcc tgcccgggtc ctacacctac gagtggaact 19980
tccgcaagga cgtcaacatg atcctgcaga gctccctcgg caacgacctg cgcacggacg 20040
gggcctccat cgccttcacc agcatcaacc tctacgccac cttcttcccc atggcgcaca 20100
acaccgcctc cacgctcgag gccatgctgc gcaacgacac caacgaccag tccttcaacg 20160
actacctctc ggcggccaac atgctctacc ccatcccggc caacgccacc aacgtgccca 20220
tctccatccc ctcgcgcaac tggcgccgcct tccgcggctg gtccttcacg cgcctcaaga 20280
cccgcgagac gccctcgctc ggctccgggt tcgaccccta cttcgtctac tcgggctcca 20340
tcccctacct cgacggcacc ttctacctca accacacctt caagaaggtc tccatcacct 20400
tcgactcctc cgtcagctgg cccggcaacg accgcctcct gacgcccaac gagttcgaaa 20460
tcaagcgcac cgtcgacgga gaggggtaca acgtggccca gtgcaacatg accaaggact 20520
ggttcctggt ccagatgctg gcccactaca acatcggcta ccagggcttc tacgtgcccg 20580
agggctacaa ggaccgcatg tactccttct tccgcaactt ccagcccatg agccgccagg 20640
tcgtggacga ggtcaactac aaggactacc aggccgtcac cctggcctac cagcacaaca 20700
actcgggctt cgtcggctac ctcgcgccca ccatgcgcca gggccagccc taccccgcca 20760
actaccccta cccgctcatc ggcaagagcg ccgtcgccag cgtcacccag aaaaagttcc 20820
tctgcgaccg ggtcatgtgg cgcatcccct tctccagcaa cttcatgtcc atgggcgcgc 20880
tcaccgacct cggccagaac atgctctacg ccaactccgc ccacgcgcta gacatgaatt 20940
tcgaagtcga ccccatggat gagtccaccc ttctctatgt tgtcttcgaa gtcttcgacg 21000
tcgtccgagt gcaccagccc caccgcggcg tcatcgaggc cgtctacctg cgcacgccct 21060
tctcggccgg caacgccacc acctaagcct cttgcttctt gcaagatgac ggcctgcgcg 21120
ggctccggcg agcaggagct cagggccatc ctccgcgacc tgggctgcgg gccctgcttc 21180
ctgggcacct tcgacaagcg cttcccggga ttcatggccc cgcacaagct ggcctgcgcc 21240
atcgtcaaca cggccggccg cgagaccggg ggcgagcact ggctggcctt cgcctggaac 21300
ccgcgctccc acacctgcta cctcttcgac cccttcgggt tctcggacga gcgcctcaag 21360

-continued

```
cagatctacc agttcgagta cgagggcctg ctgcgtcgca gcgccctggc caccgaggac  21420
cgctgcgtca ccctggaaaa gtccacccag accgtgcagg gtccgcgctc ggccgcctgc  21480
gggctcttct gctgcatgtt cctgcacgcc ttcgtgcact ggcccgaccg ccccatggac  21540
aagaacccca ccatgaactt gctgacgggg gtgcccaacg gcatgctcca gtcgccccag  21600
gtggaaccca ccctgcgccg caaccaggag gcgctctacc gcttcctcaa cgcccactcc  21660
gcctactttc gctcccaccg cgcgcgcatc gagaaggcca ccgccttcga ccgcatgaat  21720
caagacatgt aatccggtgt gtgtatgtga atgctttatt catcataata aacagcacat  21780
gtttatgcca ccttctctga ggctctgact ttatttagaa atcgaagggg ttctgccggc  21840
tctcggcatg gcccgcgggc agggatacgt tgcggaactg gtacttgggc agccacttga  21900
actcggggat cagcagcttc ggcacgggga ggtcggggaa cgagtcgctc cacagcttgc  21960
gcgtgagttg cagggcgccc agcaggtcgg gcgcggagat cttgaaatcg cagttgggac  22020
ccgcgttctg cgcgcgagag ttacggtaca cggggttgca gcactggaac accatcaggg  22080
ccgggtgctt cacgctcgcc agcaccgtcg cgtcggtgat gccctccacg tccagatcct  22140
cggcgttggc catcccgaag gggtcatct tgcaggtctg ccgccccatg ctgggcacgc  22200
agccgggctt gtggttgcaa tcgcagtgca gggggatcag catcatctgg gcctgctcgg  22260
agctcatgcc cgggtacatg gccttcatga aagcctccag ctggcggaag gcctgctgcg  22320
ccttgccgcc ctcggtgaag aagaccccgc aggacttgct agagaactgg ttggtggcgc  22380
agccagcgtc gtgcacgcag cagcgcgcgt cgttgttggc cagctgcacc acgctgcgcc  22440
cccagcggtt ctgggtgatc ttggcccggt cggggttctc cttcagcgcg cgctgcccgt  22500
tctcgctcgc cacatccatc tcgatcgtgt gctccttctg gatcatcacg gtcccgtgca  22560
ggcaccgcag cttgccctcg gcctcggtgc acccgtgcag ccacagcgcg cagccggtgc  22620
tctcccagtt cttgtgggcg atctgggagt gcgagtgcac gaagccctgc aggaagcggc  22680
ccatcatcgt ggtcagggtc ttgttgctgg tgaaggtcag cggaatgccg cggtgctcct  22740
cgttcacata caggtggcag atacggcggt acacctcgcc ctgctcgggc atcagctgga  22800
aggcggactt caggtcgctc tccacgcggt accggtccat cagcagcgtc atcacttcca  22860
tgcccttctc ccaggccgaa acgatcggca ggctcagggg gttcttcacc gttgtcatct  22920
tagtcgccgc cgccgaagtc agggggtcgt tctcgtccag ggtctcaaac actcgcttgc  22980
cgtccttctc ggtgatgcgc acgggggggaa agctgaagcc cacggccgcc agctcctcct  23040
cggcctgcct ttcgtcctcg ctgtcctggc tgatgtcttg caaaggcaca tgcttggtct  23100
tgcggggttt ctttttgggc ggcagaggcg gcggcggaga cgtgctgggc gagcgcgagt  23160
tctcgctcac cacgactatt tcttctcctt ggccgtcgtc cgagaccacg cggcggtagg  23220
catgcctctt ctggggcaga ggcggaggcg acgggctctc gcggttcggc gggcggctgg  23280
cagagcccct tccgcgttcg ggggtgcgct cctggcggcg ctgctctgac tgacttcctc  23340
cgcggccggc cattgtgttc tcctagggag caagcatgga gactcagcca tcgtcgccaa  23400
catcgccatc tgccccgcc gccgccgacg agaaccagca gcagcagaat gaaagcttaa  23460
ccgccccgcc gcccagcccc acctccgacg ccgcagcccc agacatgcaa gagatggagg  23520
aatccatcga gattgacctg ggctacgtga cgcccgcgga gcacgaggag gagctggcag  23580
cgcgcttttc agccccggaa gagaaccacc aagagcagcc agagcaggaa gcagagagcg  23640
agcagaacca ggctgggctc gagcatggcg actacctgag cggggcagag gacgtgctca  23700
tcaagcatct ggcccgccaa tgcatcatcg tcaaggacgc gctgctcgac cgcgccgagg  23760
```

-continued

```
tgcccctcag cgtggcggag ctcagccgcg cctacgagcg caacctcttc tcgccgcgcg  23820
tgccccccaa gcgccagccc aacggcacct gcgagcccaa cccgcgcctc aacttctacc  23880
cggtcttcgc ggtgcccgag gccctggcca cctaccacct ctttttcaag aaccaaagga  23940
tccccgtctc ctgccgcgcc aaccgcaccc gcgccgacgc cctgctcaac ctgggccccg  24000
gcgcccgcct acctgatatc gcctccttgg aagaggttcc caagatcttc gagggtctgg  24060
gcagcgacga gactcgggcc gcgaacgctc tgcaaggaag cggagaggag catgagcacc  24120
acagcgccct ggtggagttg gaaggcgaca acgcgcgcct ggcggtcctc aagcgcacgg  24180
tcgagctgac ccacttcgcc tacccggcgc tcaacctgcc ccccaaggtc atgagcgccg  24240
tcatggacca ggtgctcatc aagcgcgcct cgcccctctc ggaggaggag atgcaggacc  24300
ccgagagctc ggacgagggc aagcccgtgg tcagcgacga gcagctggcg cgctggctgg  24360
gagcgagtag caccccccag agcctggaag agcggcgcaa gctcatgatg gccgtggtcc  24420
tggtgaccgt ggagctggag tgtctgcgcc gcttcttcgc cgacgcggag accctgcgca  24480
aggtcgagga gaacctgcac tacctcttca gacacgggtt cgtgcgccag gcctgcaaga  24540
tctccaacgt ggagctgacc aacctggtct cctacatggg catcctgcac gagaaccgcc  24600
tggggcagaa cgtgctgcac accaccctgc gcggggaggc ccgccgcgac tacatccgcg  24660
actgcgtcta cctgtacctc tgccacacct ggcagacggg catgggcgtg tggcagcagt  24720
gcctggagga gcagaacctg aaagagctct gcaagctcct gcagaagaac ctcaaggccc  24780
tgtggaccgg gttcgacgag cgcaccaccg ccgcggacct ggccgacctc atcttccccg  24840
agcgcctgcg gctgacgctg cgcaacgggc tgcccgactt tatgagccaa agcatgttgc  24900
aaaactttcg ctctttcatc ctcgaacgct ccgggatcct gcccgccacc tgctccgcgc  24960
tgccctcgga cttcgtgccg ctgaccttcc gcgagtgccc cccgccgctc tggagccact  25020
gctacctgct gcgcctggcc aactacctgg cctaccactc ggacgtgatc gaggacgtca  25080
gcggcgaggg cctgctcgag tgccactgcc gctgcaacct ctgcacgccg caccgctccc  25140
tggcctgcaa cccccagctg ctgagcgaga cccagatcat cggcaccttc gagttgcaag  25200
gccccggcga gggcaagggg ggtctgaaac tcaccccggg gctgtggacc tcggcctact  25260
tgcgcaagtt cgtgcccgag gactaccatc ccttcgagat caggttctac gaggaccaat  25320
cccagccgcc caaggccgag ctgtcggcct gcgtcatcac ccaggggggcc atcctggccc  25380
aattgcaagc catccagaaa tcccgccaag aatttctgct gaaaaagggc cacggggtct  25440
acttggaccc ccagaccgga gaggagctca accccagctt cccccaggat gccccgagga  25500
agcagcaaga agctgaaagt ggagctgccg ccgccgccgg aggatttgga ggaagactgg  25560
gagagcagtc aggcagagga ggaggagatg gaagactggg acagcactca ggcagaggag  25620
gacagcctgc aagacagtct ggaggaggaa gacgaggtgg aggaggcaga ggaagaagca  25680
gccgccgcca gaccgtcgtc ctcggcggag gaggagaaag caagcagcac ggataccatc  25740
tccgctccgg gtcggggtcg cggcggccgg gcccacagta gatgggacga gaccgggcgc  25800
ttcccgaacc ccaccaccca gaccggtaag aaggagcggc agggatacaa gtcctggcgg  25860
gggcacaaaa acgccatcgt ctcctgcttg caagcctgcg gggcaacat ctccttcacc  25920
cggcgctacc tgctcttcca ccgcggggtg aacttccccc gcaacatctt gcattactac  25980
cgtcacctcc acagccccta ctactgtttc caagaagagg cagaaaccca gcagcagcag  26040
cagcagcaga aaaccagcgg cagcagctag aaaatccaca gcggcggcag gtggactgag  26100
```

-continued

```
gatcgcggcg aacgagccgg cgcagacccg ggagctgagg aaccggatct ttcccaccct  26160
ctatgccatc ttccagcaga gtcgggggca agagcaggaa ctgaaagtca agaaccgttc  26220
tctgcgctcg ctcacccgca gttgtctgta tcacaagagc gaagaccaac ttcagcgcac  26280
tctcgaggac gccgaggctc tcttcaacaa gtactgcgcg ctcactctta aagagtagcc  26340
cgcgcccgcc cacacacgga aaaaggcggg aattacgtca ccacctgcgc ccttcgcccg  26400
accatcatca tgagcaaaga gattcccacg ccttacatgt ggagctacca gccccagatg  26460
ggcctggccg ccggcgccgc ccaggactac tccacccgca tgaactggct cagtgccggg  26520
cccgcgatga tctcacgggt gaatgacatc cgcgcccacc gaaaccagat actcctagaa  26580
cagtcagcga tcaccgccac gccccgccat caccttaatc cgcgtaattg gcccgccgcc  26640
ctggtgtacc aggaaattcc ccagcccacg accgtactac ttccgcgaga cgcccaggcc  26700
gaagtccagc tgactaactc aggtgtccag ctggccggcg gcgccgccct gtgtcgtcac  26760
cgccccgctc agggtataaa gcggctggtg atccgaggca gaggcacaca gctcaacgac  26820
gaggtggtga gctcttcgct gggtctgcga cctgacggag tcttccaact cgccggatcg  26880
gggagatctt ccttcacgcc tcgtcaggcc gtcctgactt tggagagttc gtcctcgcag  26940
ccccgctcgg gtggcatcgg cactctccag ttcgtggagg agttcactcc ctcggtctac  27000
ttcaacccct tctccggctc cccggccac tacccggacg agttcatccc gaacttcgac  27060
gccatcagcg agtcggtgga cggctacgat tgaatgtccc atggtggcgc ggctgaccta  27120
gctcggcttc gacacctgga ccactgccgc cgcttccgct gcttcgctcg ggatctcgcc  27180
gagtttgcct actttgagct gcccgaggag caccctcagg gcccggccca cggagtgcgg  27240
atcgtcgtcg aaggggggtct cgactcccac ctgcttcgga tcttcagcca gcgtccgatc  27300
ctggccgagc gcgagcaagg acagaccctt ctgaccctgt actgcatctg caaccacccc  27360
ggcctgcatg aaagtctttg ttgtctgctg tgtactgagt ataataaaag ctgagatcag  27420
cgactactcc ggacttccgt gtgttcctgc tatcaaccag tccctgttct tcaccgggaa  27480
cgagaccgag ctccagctcc agtgtaagcc ccacaagaag tacctcacct ggctgttcca  27540
gggctctccg atcgccgttg tcaaccactg cgacaacgac ggagtcctgc tgagcggccc  27600
tgccaacctt actttttcca cccgcagaag caagctccag ctcttccaac ccttcctccc  27660
cgggacctat cagtgcgtct cgggaccctg ccatcacacc ttccacctga tcccgaatac  27720
cacagcgtcg ctccccgcta ctaacaacca aactacccac caacgccacc gtcgcgacct  27780
ttcctctggg tctaatacca ctaccggagg tgagctccga ggtcgaccaa cctctgggat  27840
ttactacggc ccctgggagg tggtagggtt aatagcgcta ggcctagttg cgggtgggct  27900
tttggctctc tgctacctat acctcccttg ctgttcgtac ttagtggtgc tgtgttgctg  27960
gtttaagaaa tggggaagat caccctagtg agctgcggtg tgctggtggc ggtggtgctt  28020
tcgattgtgg gactgggcgg cgcggctgta gtgaaggaga aggccgatcc ctgcttgcat  28080
ttcaatcccg acaaatgcca gctgagtttt cagcccgatg gcaatcggtg cgcggtgctg  28140
atcaagtgcg gatgggaatg cgagaacgtg agaatcgagt acaataacaa gactcggaac  28200
aatactctcg cgtccgtgtg gcagcccggg gaccccgagt ggtacaccgt ctctgtcccc  28260
ggtgctgacg gctccccgcg caccgtgaat aatactttca tttttgcgca catgtgcgac  28320
acggtcatgt ggatgagcaa gcagtacgat atgtggcccc ccacgaagga gaacatcgtg  28380
gtcttctcca tcgcttacag cgtgtgcacg gcgctaatca ccgctatcgt gtgcctgagc  28440
attcacatgc tcatcgctat tcgccccaga aataatgccg aaaaagaaaa acagccataa  28500
```

```
cacgtttttt cacacacctt tttcagacca tggcctctgt taaatttttg cttttatttg  28560
ccagtctcat tgccgtcatt catggaatga gtaatgagaa aattactatt tacactggca  28620
ctaatcacac attgaaaggt ccagaaaaag ccacagaagt ttcatggtat tgttatttta  28680
atgaatcaga tgtatctact gaactctgtg gaaacaataa caaaaaaaat gagagcatta  28740
ctctcatcaa gtttcaatgt ggatctgact taaccctaat taacatcact agagactatg  28800
taggtatgta ttatggaact acagcaggca tttcggacat ggaattttat caagtttctg  28860
tgtctgaacc caccacgcct agaatgacca caaccacaaa aactacacct gttaccacta  28920
tacagctcac taccaatggc tttcttgcca tgcttcaagt ggctgaaaat agcaccagca  28980
ttcaacccac cccacccagt gaggaaattc ccagatccat gattggcatt attgttgctg  29040
tagtggtgtg catgttgatc atcgccttgt gcatggtgta ctatgccttc tgctacagaa  29100
agcacagact gaacgacaag ctggaacact tactaagtgt tgaattttaa ttttttagaa  29160
ccatgaagat cctaggcctt ttagtttttt ctatcattac ctctgctcta tgcaattctg  29220
acaatgagga cgttactgtc gttgtcggat caaattatac actaaaaggt ccagcaaaag  29280
gtatgctttc gtggtattgt tggttcggaa ctgacgagca acagacagaa ctttgcaatg  29340
ctcaaaaagg caaaacctca aattctaaaa tctctaatta tcaatgcaat ggcactgact  29400
tagtattgct caatgtcacg aaagcatatg ctggcagtta cacctgccct ggagatgatg  29460
ccgacaatat gatttttac aaagtggaag tggttgatcc cactactcca ccgcccacca  29520
ccacaactac tcataccaca cacacagaac aaacaccaga ggcagcagaa gcagagttgg  29580
ccttccaggt tcacggagat tcctttgctg tcaatacccc tacacccgat cagcggtgtc  29640
cggggctgct cgtcagcggc attgtcggtg tgctttcggg attagcagtc ataatcatct  29700
gcatgttcat ttttgcttgc tgctatagaa ggctttaccg acaaaaatca gacccactgc  29760
tgaacctcta tgtttaattt tttccagagc catgaaggca gttagcgctc tagttttttg  29820
ttctttgatt ggcattgttt ttagtgctgg gtttttgaaa aatcttacca tttatgaagg  29880
tgagaatgcc actctagtgg gcatcagtgg tcaaaatgtc agctggctaa aataccatct  29940
agatgggtgg aaagacattt gcgattggaa tgtcactgtg tatacatgta atggagttaa  30000
cctcaccatt actaatgcca cccaagatca gaatggtagg tttaagggcc agagtttcac  30060
tagaaataat gggtatgaat cccataacat gtttatctat gacgtcactg tcatcagaaa  30120
tgagactgcc accaccacac agatgcccac tacacacagt tctaccacta ctaccatgca  30180
aaccacacag acaaccacta catcaactca gcatatgacc accactacag cagcaaagcc  30240
aagtagtgca gcgcctcagc cccaggcttt ggctttgaaa gctgcacaac ctagtacaac  30300
tactaggacc aatgagcaga ctactgaatt tttgtccact gtcgagagcc acaccacagc  30360
tacctccagt gccttctcta gcaccgccaa tctctcctcg ctttcctcta caccaatcag  30420
tcccgctact actcccaccc cagctcttct ccccactccc ctgaagcaaa ctgaggacag  30480
cggcatgcaa tggcagatca ccctgctcat tgtgatcggg ttggtcatcc tggccgtgtt  30540
gctctactac atcttctgcc gccgcattcc caacgcgcac cgcaaaccgg cctacaagcc  30600
catcgttatc gggcagccgg agccgcttca ggtggaaggg ggtctaagga atcttctctt  30660
ctcttttaca gtatggtgat tgaactatga ttcctagaca attcttgatc actattctta  30720
tctgcctcct ccaagtctgt gccaccctcg ctctggtggc caacgccagt ccagactgta  30780
ttgggccctt cgcctcctac gtgctctttg ccttcatcac ctgcatctgc tgctgtagca  30840
```

-continued

```
tagtctgcct gcttatcacc ttcttccagt tcattgactg gatctttgtg cgcatcgcct  30900
acctgcgcca ccacccccag taccgcgacc agcgagtggc gcggctgctc aggctcctct  30960
gataagcatg cgggctctgc tacttctcgc gcttctgctg ttagtgctcc cccgccccgt  31020
cgacccccgg tcccccactc agtcccccga agaggtccgc aaatgcaaat tccaagaacc  31080
ctggaaattc ctcaaatgct accgccaaaa atcagacatg cttcccagct ggatcatgat  31140
cattgggatc gtgaacattc tggcctgcac cctcatctcc tttgtgattt acccctgctt  31200
tgactttggt tggaactcgc cagaggcgct ctatctcccg cctgaacctg acacaccacc  31260
acagcaacct caggcacacg cactaccacc accacagcct aggccacaat acatgcccat  31320
attagactat gaggccgagc cacagcgacc catgctcccc gctattagtt acttcaatct  31380
aaccggcgga gatgactgac ccactggcca acaacaacgt caacgacctt ctcctggaca  31440
tggacggccg cgcctcggag cagcgactcg cccaacttcg cattcgccag cagcaggaga  31500
gagccgtcaa ggagctgcag gacggcatag ccatccacca gtgcaagaaa ggcatcttct  31560
gcctggtgaa acaggccaag atctcctacg aggtcacccc gaccgaccat cgcctctcct  31620
acgagctcct gcagcagcgc cagaagttca cctgcctggt cggagtcaac cccatcgtca  31680
tcacccagca gtcgggcgat accaaggggt gcatccactg ctcctgcgac tcccccgact  31740
gcgtccacac tctgatcaag accctctgcg gcctccgcga cctcctcccc atgaactaat  31800
caccccctta tccagtgaaa taaatatcat attgatgatg atttaaataa aaaataatca  31860
tttgatttga aataaagata caatcatatt gatgatttga gttttaaaaa ataaagaatc  31920
acttacttga aatctgatac caggtctctg tccatgtttt ctgccaacac cacctcactc  31980
ccctcttccc agctctggta ctgcagaccc cggcgggctg caaacttcct ccacacgctg  32040
aaggggatgt caaattcctc ctgtccctca atcttcattt tatcttctat cagatgtcca  32100
aaaagcgcgt ccgggtggat gatgacttcg accccgtcta cccctacgat gcagacaacg  32160
caccgaccgt gcccttcatc aacccccct tcgtctcttc agatggattc caagagaagc  32220
ccctgggggt gctgtccctg cgactggctg accccgtcac caccaagaac ggggaaatca  32280
ccctcaagct gggagagggg gtggacctcg actcctcggg aaaactcatc tccaacacgg  32340
ccaccaaggc cgccgcccct ctcagttttt ccaacaacac catttccctt aacatggata  32400
cccctcttta taccaaagat ggaaaattat ccttacaagt ttctccaccg ttaaacatat  32460
taaaatcaac cattctgaac acattagctg tagcttatgg atcaggttta ggactgagtg  32520
gtggcactgc tcttgcagta cagttggcct ctccactcac ttttgatgaa aaaggaaata  32580
ttaaaattaa cctagccagt ggtccattaa cagttgatgc aagtcgactt agtatcaact  32640
gcaaaagagg ggtcactgtc actacctcag gagatgcaat tgaaagcaac ataagctggc  32700
ctaaaggtat aagatttgaa ggtaatggca tagctgcaaa cattggcaga ggattggaat  32760
ttggaaccac tagtacagag actgatgtca cagatgcata cccaattcaa gttaaattgg  32820
gtactggcct tacctttgac agtacaggcg ccattgttgc ttggaacaaa gaggatgata  32880
aacttacatt atggaccaca gccgacccct cgccaaattg caaaatatac tctgaaaaag  32940
atgccaaact cacactttgc ttgacaaagt gtggaagtca aattctgggt actgtgactg  33000
tattggcagt gaataatgga agtctcaacc caatcacaaa cacagtaagc actgcactcg  33060
tctccctcaa gtttgatgca agtggagttt tgctaagcag ctccacatta gacaaagaat  33120
attggaactt cagaaaggga gatgttacac ctgctgagcc ctatactaat gctataggtt  33180
ttatgcctaa cataaaggcc tatcctaaaa acacatctgc agcttcaaaa agccatattg  33240
```

-continued

```
tcagtcaagt ttatctcaat ggggatgagg ccaaaccact gatgctgatt attactttta  33300
atgaaactga ggatgcaact tgcacctaca gtatcacttt tcaatggaaa tgggatagta  33360
ctaagtacac aggtgaaaca cttgctacca gctccttcac cttctcctac atcgcccaag  33420
aatgaacact gtatcccacc ctgcatgcca acccttccca ccccactctg tctatggaaa  33480
aaactctgaa gcacaaaata aaataaagtt caagtgtttt attgattcaa cagttttaca  33540
ggattcgagc agttattttt cctccaccct cccaggacat ggaatacacc accctctccc  33600
cccgcacagc cttgaacatc tgaatgccat tggtgatgga catgcttttg gtctccacgt  33660
tccacacagt ttcagagcga gccagtctcg ggtcggtcag ggagatgaaa ccctccgggc  33720
actcccgcat ctgcacctca cagctcaaca gctgaggatt gtcctcggtg gtcgggatca  33780
cggttatctg gaagaagcag aagagcggcg gtgggaatca tagtccgcga acgggatcgg  33840
ccggtggtgt cgcatcaggc ccgcagcag tcgctgccgc cgccgctccg tcaagctgct  33900
gctcaggggg tccgggtcca gggactccct cagcatgatg cccacggccc tcagcatcag  33960
tcgtctggtg cggcgggcgc agcagcgcat gcggatctcg ctcaggtcgc tgcagtacgt  34020
gcaacacagg accaccaggt tgttcaacag tccatagttc aacacgctcc agccgaaact  34080
catcgcggga aggatgctac ccacgtggcc gtcgtaccag atcctcaggt aaatcaagtg  34140
gcgctccctc cagaacacgc tgcccacgta catgatctcc ttgggcatgt ggcggttcac  34200
cacctcccgg taccacatca ccctctggtt gaacatgcag ccccggatga tcctgcggaa  34260
ccacagggcc agcaccgccc cgcccgccat gcagcgaaga gaccccgggt cccggcaatg  34320
gcaatggagg acccaccgct cgtacccgtg gatcatctgg gagctgaaca agtctatgtt  34380
ggcacagcac aggcatatgc tcatgcatct cttcagcact ctcagctcct cgggggtcaa  34440
aaccatatcc cagggcacgg ggaactcttg caggacagcg aaccccgcag aacagggcaa  34500
tcctcgcaca taacttacat tgtgcatgga cagggtatcg caatcaggca gcaccgggtg  34560
atcctccacc agagaagcgc gggtctcggt ctcctcacag cgtggtaagg gggccggccg  34620
atacgggtga tggcgggacg cggctgatcg tgttcgcgac cgtgtcatga tgcagttgct  34680
ttcggacatt ttcgtacttg ctgtagcaga acctggtccg ggcgctgcac accgatcgcc  34740
ggcggcggtc ccggcgcttg gaacgctcgg tgttgaaatt gtaaaacagc cactctctca  34800
gaccgtgcag cagatctagg gcctcaggag tgatgaagat cccatcatgc ctgatagctc  34860
tgatcacatc gaccaccgtg gaatgggcca gacccagcca gatgatgcaa ttttgttggg  34920
tttcggtgac ggcgggggag ggaagaacag gaagaaccat gattaacttt taatccaaac  34980
ggtctcggag cacttcaaaa tgaaggtcgc ggagatggca cctctcgccc ccgctgtgtt  35040
ggtggaaaat aacagccagg tcaaaggtga tacggttctc gagatgttcc acggtggctt  35100
ccagcaaagc ctccacgcgc acatccagaa acaagacaat agcgaaagcg ggagggttct  35160
ctaattcctc aatcatcatg ttacactcct gcaccatccc cagataattt tcatttttcc  35220
agccttgaat gattcgaact agttcctgag gtaaatccaa gccagccatg ataaagagct  35280
cgcgcagagc gccctccacc ggcattctta agcacaccct cataattcca agatattctg  35340
ctcctggttc acctgcagca gattgacaag cggaatatca aaatctctgc cgcgatccct  35400
aagctcctcc ctcagcaata actgtaagta ctctttcata tcctctccga aatttttagc  35460
cataggacca ccaggaataa gattagggca agccacagta cagataaacc gaagtcctcc  35520
ccagtgagca ttgccaaatg caagactgct ataagcatgc tggctagacc cggtgatatc  35580
```

-continued

```
ttccagataa ctggacagaa aatcacccag gcaattttta agaaaatcaa caaaagaaaa  35640

atcctccagg tgcacgttta gagcctcggg aacaacgatg aagtaaatgc aagcggtgcg  35700

ttccagcatg gttagttagc tgatctgtaa aaaacaaaaa ataaaacatt aaaccatgct  35760

agcctggcga acaggtgggt aaatcgttct ctccagcacc aggcaggcca cggggtctcc  35820

ggcgcgaccc tcgtaaaaat tgtcgctatg attgaaaacc atcacagaga gacgttcccg  35880

gtggccggcg tgaatgattc gacaagatga atacaccccc ggaacattgg cgtccgcgag  35940

tgaaaaaaag cgcccgagga agcaataagg cactacaatg ctcagtctca agtccagcaa  36000

agcgatgcca tgcggatgaa gcacaaaatc ctcaggtgcg tacaaaatgt aattactccc  36060

ctcctgcaca ggcagcgaag cccccgatcc ctccagatac acatacaaag cctcagcgtc  36120

catagcttac cgagcagcag cacacaacag gcgcaagagt cagagaaagg ctgagctcta  36180

acctgtccac ccgctctctg ctcaatatat agcccagatc tacactgacg taaaggccaa  36240

agtctaaaaa tacccgccaa ataatcacac acgcccagca cacgcccaga aaccggtgac  36300

acactcaaaa aaatacgcgc acttcctcaa acgcccaaac tgccgtcatt tccgggttcc  36360

cacgctacgt catcggaatt cgactttcaa attccgtcga ccgttaaaaa cgtcacccgc  36420

cccgccccta acggtcgccc gtctctcggc caatcacctt cctccctccc caaattcaaa  36480

cagctcattt gcatattaac gcgcaccaaa agtttgaggt atattattga tgatg       36535
```

<210> SEQ ID NO 4
<211> LENGTH: 34264
<212> TYPE: DNA
<213> ORGANISM: simian adenovirus SV-1

<400> SEQUENCE: 4

```
tccttattct ggaaacgtgc caatatgata atgagcgggg aggagcgagg cggggccggg     60

gtgacgtgcg gtgacgtggg gtgacgcggg gtggcgcgag ggcggggcgg gagtggggag    120

gcgcttagtt tttacgtatg cggaaggagg ttttataccg gaagttgggt aatttgggcg    180

tatacttgta agttttgtgt aatttggcgc gaaaaccggg taatgaggaa gttgaggtta    240

atatgtactt tttatgactg ggcggaattt ctgctgatca gcagtgaact ttgggcgctg    300

acggggaggt ttcgctacgt ggcagtacca cgagaaggct caaaggtccc atttattgta    360

ctcctcagcg ttttcgctgg gtatttaaac gctgtcagat catcaagagg ccactcttga    420

gtgccggcga gtagagtttt ctcctccgcg ctgccgcgat gaggctggtt cccgagatgt    480

acggtgtttt ctgcagcgag acggcccgga actcagatga gctgcttaat acagatctgc    540

tggatgttcc caactcgcct gtggcttcgc ctccgtcgct tcatgatctt ttcgatgtgg    600

aagtggatcc accgcaagat cccaacgagg acgcggtaaa cagtatgttc cctgaatgtc    660

tgtttgaggc ggctgaggag ggttctcaca gcagtgaaga gagcagacgg ggagaggaac    720

tggacttgaa atgctacgag gaatgtctgc cttctagcga ttctgaaacg gaacagacag    780

ggggagacgg ctgtgagtcg gcaatgaaaa atgaacttgt attagactgt ccagaacatc    840

ctggtcatgg ctgccgtgcc tgtgcttttc atagaaatgc cagcggaaat cctgagactc    900

tatgtgctct gtgttatctg cgccttacca gcgattttgt atacagtaag taaagtgttt    960

tcattggcgt acggtagggg attcgttgaa gtgctttgtg acttattatg tgtcattatt   1020

tctaggtgac gtgtccgacg tggaaggga aggagataga tcaggggctg ctaattctcc   1080

ttgcactttg ggggctgtgg ttccagttgg catttttaaa ccgagtggtg gaggagaacg   1140

agccggagga gaccgagaat ctgagagccg gcctggaccc tccagtggaa gactaggtgc   1200
```

-continued

```
tgaggatgat cctgaagagg ggactagtgg gggtgctagg aaaaagcaaa aaactgagcc   1260
tgaacctaga aactttttga atgagttgac tgtaagccta atgaatcggc agcgtcctga   1320
gacggtgttt tggactgagt tggaggatga gttcaagaag ggggaattaa acctcttgta   1380
caagtatggg tttgagcagt tgaaaactca ctggttggag ccgtgggagg atatggaaat   1440
ggctctagac acctttgcta aagtggctct gcggccggat aaagtttaca ctattcgccg   1500
cactgttaat ataaaaaaga gtgtttatgt tatcggccat ggagctctgg tgcaggtgca   1560
gaccccagac cgggtggctt tcaattgcgg catgcagagt ttgggccccg gggtgatagg   1620
tttgaatgga gttacatttc aaaatgtcag gtttactggt gatgatttta atggctctgt   1680
gtttgtgact agcacccagc taaccctcca cggtgtttac ttttttaact ttaacaatac   1740
atgtgtggag tcatggggta gggtgtctct gaggggctgc agttttcatg gttgctggaa   1800
ggcggtggtg ggaagaatta aaagtgtcat gtctgtgaag aaatgcatat ttgaacgctg   1860
tgtgatagct ctagcagtag aggggtacgg acggatcagg aataacgccg catctgagaa   1920
tggatgtttt cttttgctga aggtacggc cagcgttaag cataatatga tttgcggcag   1980
cggcctgtgc ccctcgcagc tcttaacttg cgcagatgga aactgtcaca ccttgcgcac   2040
cgtgcacata gtgtcccact cgcgccgcac ctggccaaca tttgagcaca atatgctcat   2100
gcgttgcgcc gttcacctag gtgctagacg cggcgtgttt atgccttatc aatgtaactt   2160
tagtcatact aagattttgc tggaaactga ttccttccct cgagtatgtt tcaatggggt   2220
gtttgacatg tcaatggaac tttttaaagt gataagatat gatgaaacca agtctcgttg   2280
tcgctcatgt gaatgcggag ctaatcattt gaggttgtat cctgtaaccc tgaacgttac   2340
cgaggagctg aggacggacc accacatgct gtcttgcctg cgtaccgact atgaatccag   2400
cgatgaggag tgaggtgagg ggcggagcca caaagggtat aaaggggcat gaggggtggg   2460
cgcggtgttt caaaatgagc gggacgacgg acggcaatgc gtttgagggg ggagtgttca   2520
gcccatatct gacatctcgt cttccttcct gggcaggagt tcgtcagaat gtagtgggct   2580
ccaccgtgga cggacggccg gtcgcccctg caaattccgc caccctcacc tatgccaccg   2640
tgggatcatc gttggacact gccgcggcag ctgccgcttc tgctgccgct tctactgctc   2700
gcggcatggc ggctgatttt ggactatata accaactggc cactgcagct gtggcgtctc   2760
ggtctctggt tcaagaagat gccctgaatg tgatcttgac tcgcctggag atcatgtcac   2820
gtcgcctgga cgaactggct gcgcagatat cccaagctaa ccccgatacc gcttcagaat   2880
cttaaaataa agacaaacaa atttgttgaa aagtaaaatg gctttatttg tttttttgg   2940
ctcggtaggc tcgggtccac ctgtctcggt cgttaaggac tttgtgtatg ttttccaaaa   3000
cacggtacag atgggcttgg atgttcaagt acatgggcat gaggccatct ttggggtgga   3060
gataggacca ctgaagagcg tcatgttccg gggtggtatt gtaaatcacc cagtcgtagc   3120
agggtttttg agcgtggaac tggaatatgt ccttcaggag caggctaatg gccaagggta   3180
gacccttagt gtaggtgttt acaaagcggt tgagctggga gggatgcatg cggggggaga   3240
tgatatgcat cttggcttgg attttgaggt tagctatgtt accacccagg tctctgcggg   3300
ggttcatgtt atgaaggacc accagcacgg tatagccagt gcatttgggg aacttgtcat   3360
gcagtttgga ggggaaggcg tggaagaatt tagatacccc cttgtgcccc cctaggtttt   3420
ccatgcactc atccataata atggcaatgg gacccctggc ggccgcttta gcaaacacgt   3480
tttgggggtt ggaaacatca tagttttgct ctagagtgag ctcatcatag gccatcttta   3540
```

-continued

```
caaagcgggg taggagggtg cccgactggg ggatgatagt tccatctggg cctggagcgt   3600

agttgccctc acagatctgc atctcccagg ccttaatttc cgaggggggg atcatgtcca   3660

cctgggggc gataaaaaac acggtttctg gcggggggtt aatgagctgg gtggaaagca   3720

agttacgcaa cagctgggat ttgccgcaac cggtgggacc gtagatgacc ccgatgacgg   3780

gttgcagctg gtagttcaga gaggaacagc tgccgtcggg gcgcaggagg ggagctacct   3840

cattcatcat gcttctgaca tgtttatttt cactcactaa gttttgcaag agcctctccc   3900

cacccaggga taagagttct tccaggctgt tgaagtgttt cagcggtttc aggccgtcgg   3960

ccatgggcat cttttcaagc gactgacgaa gcaagtacag tcggtcccag agctcggtga   4020

cgtgctctat ggaatctcga tccagcagac ttcttggttt cggggggttgg gccgactttc   4080

gctgtagggc accagccggt gggcgtccag ggccgcgagg gttctgtcct tccagggtct   4140

cagcgttcgg gtgagggtgg tctcggtgac ggtgaaggga tgagccccgg gctgggcgct   4200

tgcgagggtg cgcttcaggc tcatcctgct ggtgctgaag cgggcgtcgt ctccctgtga   4260

gtcggccaga tagcaacgaa gcatgaggtc gtagctgagg gactcggccg cgtgtccctt   4320

ggcgcgcagc tttcccttgg aaacgtgctg acatttggtg cagtgcagac acttgagggc   4380

gtagagtttt ggggccagga agaccgactc gggcgagtag gcgtcggctc cgcactgagc   4440

gcagacggtc tcgcactcca ccagccacgt gagctcgggt ttagcgggat caaaaaccaa   4500

gttgcctcca tttttttga tgcgtttctt accttgcgtc tccatgagtc tgtgtcccgc   4560

ttccgtgaca aaaaggctgt cggtatcccc gtagaccgac ttgaggggc gatcttccaa   4620

aggtgttccg aggtcttccg cgtacaggaa ctgggaccac tccgagacaa aggctcgggt   4680

ccaggctaac acgaaggagg cgatctgcga ggggtatctg tcgttttcaa tgagggggtc   4740

caccttttcc agggtgtgca gacacaggtc gtcctcctcc gcgtccacga aggtgattgg   4800

cttgtaagtg taggtcacgt gacccgcacc cccccaaggg gtataaaagg gggcgtgccc   4860

actctccccg tcactttctt ccgcatcgct gtggaccaga gccagctgtt cgggtgagta   4920

ggccctctca aaagccggca tgatttcggc gctcaagttg tcagtttcta caaacgaggt   4980

ggatttgata ttcacgtgcc ccgcggcgat gcttttgatg gtggaggggt ccatctgatc   5040

agaaaacacg atctttttat tgtcaagttt ggtggcgaaa gacccgtaga gggcgttgga   5100

aagcaacttg gcgatggagc gcagggtctg atttttctcc cgatcggccc tctccttggc   5160

ggcgatgttg agttgcacgt actcgcgggc cacgcaccgc cactcgggga acacggcggt   5220

gcgctcgtcg ggcaggatgc gcacgcgcca gccgcggttg tgcagggtga tgaggtccac   5280

gctggtggcc acctccccgc ggaggggctc gttggtccaa cacaatcgcc cccctttttct   5340

ggagcagaac ggaggcaggg gatctagcaa gttggcgggc ggggggtcgg cgtcgatggt   5400

aaatatgccg ggtagcagaa ttttattaaa ataatcgatt tcggtgtccg tgtcttgcaa   5460

cgcgtcttcc cacttcttca ccgccagggc cctttcgtag ggattcaggg gcggtcccca   5520

gggcatgggg tgggtcaggg ccgaggcgta catgccgcag atgtcgtaca cgtacagggg   5580

ctccctcaac accccgatgt aagtggggta acagcgcccc ccgcggatgc tggctcgcac   5640

gtagtcgtac atctcgtgag agggagccat gagcccgtct cccaagtggg tcttgtgggg   5700

tttttcggcc cggtagagga tctgcctgaa gatggcgtgg gagttggaag agatagtggg   5760

gcgttggaag acgttaaagt tggctccggg cagtcccacg gagtcttgga tgaactgggc   5820

gtaggattcc cggagcttgt ccaccagggc tgcggttacc agcacgtcga gagcgcagta   5880

gtccaacgtc tcgcggacca ggttgtaggc cgtctcttgt tttttctccc acagttcgcg   5940
```

-continued

```
attgaggagg tattcctcgc ggtctttcca gtactcttcg gcgggaaatc ctttttcgtc   6000
cgctcggtaa gaacctaaca tgtaaaattc gttcacggct ttgtatggac aacagccttt   6060
ttctaccggc agggcgtacg cttgagcggc ctttctgaga gaggtgtggg tgagggcgaa   6120
ggtgtcccgc accatcactt tcaggtactg atgtttgaag tccgtgtcgt cgcaggcgcc   6180
ctgttcccac agcgtgaagt cggtgcgctt tttctgcctg ggattgggga gggcgaatgt   6240
gacgtcgtta aagaggattt tcccggcgcg gggcatgaag ttgcgagaga tcctgaaggg   6300
tccgggcacg tccgagcggt tgttgatgac ttgcgccgcc aggacgatct cgtcgaagcc   6360
gttgatgttg tggcccacga tgtaaagttc gataaagcgc ggctgtccct tgagggccgg   6420
cgctttttc aactcctcgt aggtgagaca gtccggcgag gagagaccca gctccgcccg   6480
ggcccagtcg gagagctgag ggttagccgc gaggaaagag ctccacaggt caagggctag   6540
cagagtttgc aagcggtcgc ggaactcgcg aaactttttc cccacggcca ttttctccgg   6600
cgtcaccacg tagaaagtgc aggggcggtc gttccagacg tcccatcgga gctctagggc   6660
cagctcgcag gcttgacgaa cgagggtctc ctcgcccgag acgtgcatga ccagcatgaa   6720
gggtaccaac tgtttcccga acgagcccat ccatgtgtag gtttctacgt cgtaggtgac   6780
aaagagccgc tgggtgcgcg cgtgggagcc gatcgggaag aagctgatct cctgccacca   6840
gttggaggaa tgggtgttga tgtggtgaaa gtagaagtcc cgccggcgca cagagcattc   6900
gtgctgatgt ttgtaaaagc gaccgcagta gtcgcagcgc tgcacgctct gtatctcctg   6960
aatgagatgc gcttttcgcc cgcgcaccag aaaccggagg gggaagttga gacgggggct   7020
tggtggggcg gcatcccctt cgccttggcg gtgggagtct gcgtctgcgc cctccttctc   7080
tgggtggacg acggtgggga cgacgacgcc ccgggtgccg caagtccaga tctccgccac   7140
ggagggggcgc aggcgttgca ggagggggacg cagctgcccg ctgtccaggg agtcgagggc   7200
ggccgcgctg aggtcggcgg gaagcgtttg caagttcact ttcagaagac cggtaagagc   7260
gtgagccagg tgcacatggt acttgatttc cagggggggtg ttggaagagg cgtccacggc   7320
gtagaggagg ccgtgtccgc gcggggccac caccgtgccc cgaggaggtt ttatctcact   7380
cgtcgagggc gagcgccggg gggtagaggc ggctctgcgc cggggggcag cggaggcagt   7440
ggcacgtttt cgtgaggatt cggcagcggt tgatgacgag cccggagact gctggcgtgg   7500
gcgacgacgc ggcggttgag gtcctggatg tgccgtctct gcgtgaagac caccggcccc   7560
cgggtcctga acctgaaaga gagttccaca gaatcaatgt ctgcatcgtt aacggcggcc   7620
tgcctgagga tctcctgtac gtcgcccgag ttgtcttgat aggcgatctc ggccatgaac   7680
tgctccactt cttcctcgcg gaggtcgccg tggcccgctc gctccacggt ggcggccagg   7740
tcgttggaga tgcgacgcat gagttgagag aaggcgttga ggccgttctc gttccacacg   7800
cggctgtaca ccacgtttcc gaaggagtcg cgcgctcgca tgaccacctg ggccacgttg   7860
agttccacgt ggcgggcgaa gacggcgtag tttctgaggc gctggaagag gtagttgagc   7920
gtggtggcga tgtgctcgca gacgaagaag tacatgatcc agcgccgcag ggtcatctcg   7980
ttgatgtctc cgatggcttc gagacgctcc atggcctcgt agaagtcgac ggcgaagttg   8040
aaaaattggg agttgcgggc ggccaccgtg agttcttctt gcaggaggcg gatgagatcg   8100
gcgaccgtgt cgcgcacctc ctgctcgaaa gcgccccgag gcgcctctgc ttcttcctcc   8160
ggctcctcct cttccagggg cacgggttcc tccggcagct ctgcgacggg gacggggcgg   8220
cgacgtcgtc gtctgaccgg caggcggtcc acgaagcgct cgatcatttc gccgcgccgg   8280
```

-continued

```
cgacgcatgg tctcggtgac ggcgcgtccg ttttcgcgag gtcgcagttc gaagacgccg   8340
ccgcgcagag cgcccccgtg cagggagggt aagtggttag ggccgtcggg cagggacacg   8400
gcgctgacga tgcattttat caattgctgc gtaggcactc cgtgcaggga tctgagaacg   8460
tcgaggtcga cgggatccga gaacttctct aggaaagcgt ctatccaatc gcagtcgcaa   8520
ggtaagctga ggacggtggg ccgctggggg gcgtccgcgg gcagttggga ggtgatgctg   8580
ctgatgatgt aattaaagta ggcggtcttc aggcggcgga tggtggcgag gaggaccacg   8640
tctttgggcc cggcctgttg aatgcgcagg cgctcggcca tgccccaggc ctcgctctga   8700
cagcgacgca ggtctttgta gtagtcttgc atcagtctct ccaccggaac ctctgcttct   8760
cccctgtctg ccatgcgagt cgagccgaac cccgcagggg gctgcagcaa cgctaggtcg   8820
gccacgaccc tctcggccag cacggcctgt tggatctgcg tgagggtggt ctggaagtcg   8880
tccaggtcca cgaagcggtg ataggccccc gtgttgatgg tgtaggtgca gttggccatg   8940
acggaccagt tgacgacttg catgccgggt tgggtgatct ccgtgtactt gaggcgcgag   9000
taggcgcggg actcgaacac gtagtcgttg catgtgcgta ccagatactg gtagccaacc   9060
aggaagtggg gaggcggttc tcggtacagg ggccagccga ctgtggcggg ggcgccgggg   9120
gacaggtcgt ccagcatgag gcgatggtag tggtagatgt agcgggagag ccaggtgatg   9180
ccggccgagg tggtcgcggc cctggtgaat tcgcggacgc ggttccagat gttgcgcagg   9240
gggcgaaagc gctccatggt gggcacgctc tgccccgtga ggcgggcgca atcttgtacg   9300
ctctagatgg aaaaaagaca gggcggtcat cgactccctt ccgtagctcg gggggtaaag   9360
tcgcaagggt gcggcggcgg ggaaccccgg ttcgagaccg gccggatccg ccgctcccga   9420
tgcgcctggc cccgcatcca cgacgtccgc gtcgagaccc agccgcgacg ctccgcccca   9480
atacggaggg gagtcttttg gtgtttttc gtagatgcat ccggtgctgc ggcagatgcg   9540
acctcagacg cccaccacca ccgccgcggc ggcagtaaac ctgagcggag gcggtgacag   9600
ggaggaggag gagctggctt tagacctgga agagggagag ggctggcccc ggctgggagc   9660
gccgtcccca gagagacacc ctagggttca gctcgtgagg gacgccaggc aggcttttgt   9720
gccgaagcag aacctgttta gggaccgcag cggtcaggag gcggaggaga tgcgcgattg   9780
caggtttcgg gcgggtagag agctgagggc gggcttcgat cgggagcggc tcctgagggc   9840
ggaggatttc gagcccgacg agcgttctgg ggtgagcccg gcccgcgctc acgtctcggc   9900
ggccaacctg gtgagcgcgt acgagcagac ggtgaacgag gagcgcaact tccaaaagag   9960
ctttaacaat cacgtgagga ccctgatcgc gagggaggag gtgaccatcg ggctgatgca  10020
tctgtgggac ttcgtggagg cctacgtgca gaacccggcc agcaaacctc tgacggccca  10080
gctgttcctg atcgtgcagc acagccgcga caacgagacg ttccgcgacg ccatgttgaa  10140
catcgcggag cccgagggtc gctggctctt ggatctgatt aacatcctgc agagcatcgt  10200
ggtgcaggag aggggcctca gcttagcgga caaggtggcg gccattaact attcgatgca  10260
gagcctgggg aagttctacg ctcgcaagat ctacaagagc ccttacgtgc ccatagacaa  10320
ggaggtgaag atagacagct tttacatgcg catggcgctg aaggtgctga cgctgagcga  10380
cgacctcggc gtgtaccgta acgacaagat ccacaaggcg gtgagcgcca gccgccggcg  10440
ggagctgagc gacagggagc tgatgcacag cctgcagagg gcgctggcgg gcgccgggga  10500
cgaggagcgc gaggcttact tcgacatggg agccgatctg cagtggcgtc ccagcgcgcg  10560
cgccttggag gcggcgggct accccgacga ggaggatcgg gacgatttgg aggaggcagg  10620
cgagtacgag gacgaagcct gaccgggcag gtgttgtttt agatgcagcg gccggcggac  10680
```

-continued

```
ggggccaccg cggatcccgc acttttggca tccatgcaga gtcaaccttc gggcgtgacc  10740
gcctccgatg actgggcggc ggccatggac cgcattatgg cgctgactac ccgcaacccc  10800
gaggctttta gacagcaacc ccaggccaac cgtttttcgg ccatcttgga agcggtggtg  10860
ccctcccgca ccaaccccac acacgagaaa gtcctgacta tcgtgaacgc cctggtagac  10920
agcaaggcca tccgccgcga cgaggcgggc ttgatttaca acgctctgct ggaacgggtg  10980
gcgcgctaca acagcactaa cgttcagacc aatctggatc gcctcaccac cgacgtgaag  11040
gaggcgctgg ctcagaagga gcggtttctg agggacagca atctgggctc tctggtggca  11100
ctcaacgcct tcctgagcac gcagccggcc aacgtgcccc gcgggcagga ggactacgtg  11160
agcttcatca gcgctctgag gctgctggtg tccgaggtgc cccagagcga ggtgtatcag  11220
tctgggccgg attacttctt ccagacgtcc cgacagggct tgcaaacggt gaacctgact  11280
caggccttta aaaacttgca aggcatgtgg ggcgttaagg ccccggtggg cgatcgagcc  11340
accatctcca gtctgctgac ccccaacact cgcctgctgc tgctcttgat cgcgccgttc  11400
accaacagta gcactatcag ccgtgactcg tacctgggtc atctcatcac tttgtaccgc  11460
gaggccatcg gtcaggctca gatcgacgag cacacatatc aggagatcac taacgtgagc  11520
cgggccctgg gtcaggaaga taccggcagc ctggaagcca cgttgaactt tttgctaacc  11580
aaccggaggc aaaaaatacc ctcccagttt acgttaagcg ccgaggagga gaggattctg  11640
cgatacgtgc agcagtccgt gagtctgtac ttgatgcggg agggcgccac cgcttccacg  11700
gctttagaca tgacggctcg gaacatggaa ccgtcctttt actccgccca ccggccgttc  11760
attaaccgtc tgatggacta cttccatcgc gcggccgcca tgaacgggga gtacttcacc  11820
aatgccatcc tgaatccgca ttggatgccc ccgtccggct tctacaccgg cgagtttgac  11880
ctgcccgaag ccgacgacgg ctttctttgg gacgacgtgt ccgacagcat tttcacgccg  11940
ggcaatcgcc gattccagaa gaaggagggc ggagacgagc tcccccctctc cagcgtggag  12000
gcggcctcta ggggagagag tccctttccc agtctgtctt ccgccagcag tggtcgggta  12060
acgcgcccgc ggttgccggg ggagagcgac tacctgaacg accccttgct gcggccggct  12120
aggaagaaaa atttccccaa caacggggtg gaaagcttgg tggataaaat gaatcgttgg  12180
aagacctacg cccaggagca gcgggagtgg gaggacagtc agccgcgacc gctggttccg  12240
ccgcactggc gtcgtcagag agaagacccg gacgactccg cagacgatag tagcgtgttg  12300
gacctgggag ggagcggagc caaccccttt gctcacttgc aacccaaggg gcgttccagt  12360
cgcctctact aataaaaaag acgcggaaac ttaccagagc catggccaca gcgtgtgtcc  12420
tttcttcctc tctttcttcc tcggcgcggc agaatgagaa gagcggtgag agtcacgccg  12480
gcggcgtatg agggtccgcc cccttcttac gaaagcgtga tgggatcagc gaacgtgccg  12540
gccacgctgg aggcgcctta cgttcctccc agatacctgg gacctacgga gggcagaaac  12600
agcatccgtt actccgagct ggcacccctg tacgatacca ccaaggtgta cctggtggac  12660
aacaagtcgg cggacatcgc ctccctgaat tatcaaaacg atcacagcaa ttttctgact  12720
accgtggtgc agaacaatga cttcaccccg acggaggcgg gcacgcagac cattaacttt  12780
gacgagcgtt cccgctgggg cggtcagctg aaaaccatcc tgcacaccaa catgcccaac  12840
atcaacgagt tcatgtccac caacaagttc agggccaggc tgatggttaa aaaggctgaa  12900
aaccagcctc ccgagtacga atggtttgag ttcaccattc ccgagggcaa ctattccgag  12960
accatgacta tcgatctgat gaacaatgcg atcgtggaca attacctgca agtggggagg  13020
```

-continued

```
cagaacgggg tattggaaag cgatatcggc gtaaaatttg ataccagaaa cttccgactg  13080
gggtgggatc ccgtgaccaa gctggtgatg ccaggcgtgt acaccaacga ggcttttcac  13140
cccgacatcg tgctgctgcc ggggtgcggt gtggacttca ctcagagccg tttgagtaac  13200
ctgttaggga tcagaaagcg ccgccccttc caagagggct ttcagatcat gtatgaggac  13260
ctggaaggag gtaacattcc aggtttgcta gacgtgccgg cgtatgaaga gagtgttaaa  13320
caggcggagg cgcagggacg agagattcga ggcgacacct ttgccacgga acctcacgaa  13380
ctggtaataa aacctctgga acaagacagt aaaaaacgga gttacaacat tatatccggc  13440
actatgaata ccttgtaccg gagctggttt ctggcttaca actacgggga tcccgaaaag  13500
ggagtgagat catggaccat actcaccacc acggacgtga cctgcggctc gcagcaagtg  13560
tactggtccc tgccggatat gatgcaagac ccggtcacct tccgcccctc cacccaagtc  13620
agcaacttcc cggtggtggg caccgagctg ctgcccgtcc atgccaagag cttctacaac  13680
gaacaggccg tctactcgca actcattcgc cagtccaccg cgcttaccca cgtgttcaat  13740
cgctttcccg agaaccagat tctggtgcgc cctcccgctc ctaccattac caccgtcagt  13800
gaaaacgttc ccgccctcac agatcacgga accctgccgc tgcgcagcag tatcagtgga  13860
gttcagcgcg tgaccatcac cgacgccaga cgtcgaacct gtccctacgt ttacaaagct  13920
cttggcgtag tggctcctaa agtgctctct agtcgcacct tctaaacatg tccatcctca  13980
tctctcccga taacaacacc ggctggggac tgggctccgg caagatgtac ggcggagcca  14040
aaaggcgctc cagtcagcac ccagttcgag ttcggggcca cttccgtgct ccctggggag  14100
cttacaagcg aggactctcg ggccgaacgg cggtagacga taccatagat gccgtgattg  14160
ccgacgcccg ccggtacaac cccggaccgg tcgctagcgc cgcctccacc gtggattccg  14220
tgatcgacag cgtggtagct ggcgctcggg cctatgctcg ccgcaagagg cggctgcatc  14280
ggagacgtcg ccccaccgcc gccatgctgg cagccagggc cgtgctgagg cgggcccgga  14340
gggtaggcag aagggctatg cgccgcgctg ccgccaacgc cgccgccggg agggcccgcc  14400
gacaggctgc ccgccaggct gctgccgcca tcgctagcat ggccagaccc aggagaggga  14460
acgtgtactg ggtgcgcgat tctgtgacgg gagtccgagt gccggtgcgc agccgacctc  14520
cccgaagtta gaagatccaa gctgcgaaga cggcggtact gagtctccct gttgttatca  14580
gcccaacatg agcaagcgca agtttaaaga agaactgctg cagacgctgg tgcctgagat  14640
ctatggccct ccggacgtga agcctgacat taagccccgc gatatcaagc gtgttaaaaa  14700
gcgggaaaag aaagaggaac tcgcggtggt agacgatggc ggagtggaat ttattaggag  14760
tttcgccccg cgacgcaggg ttcaatggaa agggcggcgg gtacaacgcg ttttgaggcc  14820
gggcaccgcg gtagttttta ccccgggaga gcggtcggcc gttaggggtt tcaaaaggca  14880
gtacgacgag gtgtacggcg acgaggacat attggaacag gcggctcaac agatcggaga  14940
atttgcctac ggaaagcgtt cgcgtcgcga agacctggcc atcgctttag acagcggcaa  15000
ccccacgccc agcctcaaac ctgtgacgct gcagcaggtg ctccccgtga gcgccagcac  15060
ggacagcaag aggggaataa aaagagaaat ggaagatctg cagcccacca tccagctcat  15120
ggtccctaaa cggcagaggc tggaagaggt cctggagaaa atgaaagtgg acccaagcat  15180
agagccggac gtcaaagtca ggccgatcaa agaagtggcc cctggtctcg gggtgcagac  15240
ggtggatatc cagatccccg tcacgtcagc ttcgaccgcc gtggaagcca tggaaacgca  15300
aacggaaacc cctgccgcga tcggtaccag ggaagtggcg ttgcaaaccg acccctggta  15360
cgaatacgcc gcccctcggc gtcagaggcg acccgctcgt tacggccccg ccaacgccat  15420
```

```
catgccagaa tatgcgctgc atccgtctat cctgcccacc cccggctacc ggggagtgac  15480
gtatcgcccg tcaggaaccc gccgccgaac ccgtcgccgc cgccgctccc gtcgtgctct  15540
ggccccccgtg tcggtgcgcc gcgtaacacg ccggggaaag acagttacca ttcccaaccc  15600
gcgctaccac cctagcatcc tttaatgact ctgccgtttt gcagatggct ctgacttgcc  15660
gcgtgcgcct tcccgttccg cactatcgag gaagatctcg tcgtaggaga ggcatggcgg  15720
gtagtggtcg ccggcgggct ttgcgcaggc gcatgaaagg cggaatttta cccgctctga  15780
tacccataat cgccgccgcc atcggtgcca tacccggcgt cgcttcagtg gccttgcaag  15840
cagctcgtaa taaataaacg aaggcttttg cacttatgtc ctggtcctga ctattttatg  15900
cagaaagagc atggaagaca tcaattttac gtcgctggct ccgcggcacg gctcgcggcc  15960
gctcatgggc acctggaacg acatcggcac cagtcagctc aacgggggcg ctttcaattg  16020
ggggagcctt tggagcggca ttaaaaactt tggctccacg attaaatcct acggcagcaa  16080
agcctggaac agtagtgctg gtcagatgct ccgagataaa ctgaaggaca ccaacttcca  16140
agaaaaagtg gtcaatgggg tggtgaccgg catccacggc gcggtagatc tcgccaacca  16200
agcggtgcag aaagagattg acaggcgttt ggaaagctcg cgggtgccgc cgcagagagg  16260
ggatgaggtg gaggtcgagg aagtagaagt agaggaaaag ctgcccccgc tggagaaagt  16320
tcccggtgcg cctccgagac cgcagaagcg acccaggcca gaactagaag aaactctggt  16380
gacggagagc aaggagcctc cctcgtacga gcaagccttg aaagagggcg cctctccacc  16440
ctacccaatg acaaaaccga tcgcgcctat ggctcggccg gtgtacggga aggactacaa  16500
gcctgtcacg ctagagctcc ccccgccgcc accgccgccc cccacgcgcc cgaccgttcc  16560
cccccccctg ccggctccgt cggcgggacc cgtgtccgca cccgtcgccg tgcctctgcc  16620
agccgcccgc ccagtggccg tggccactgc cagaaacccc agaggccaga gaggagccaa  16680
ctggcaaagc acgctgaaca gcatcgtggg cctgggagtg aaaagcctga aacgccgccg  16740
ttgctattat taaaagtgta gctaaaaaat ttcccgttgt atacgcctcc tatgttaccg  16800
ccagagacgc gtgactgtcg ccgcgagcgc cgctttcaag atggccaccc catcgatgat  16860
gccgcagtgg tcttacatgc acatcgccgg gcaggacgcc tcggagtacc tgagccccgg  16920
tctcgtgcag ttcgcccgcg ccaccgacac ctacttcagc ttgggaaaca agtttagaaa  16980
ccccaccgtg gcccccaccc acgatgtaac cacggaccgc tcgcaaaggc tgaccctgcg  17040
ttttgtgccc gtagaccggg aggacaccgc gtactcttac aaagtgcgct acacgctggc  17100
cgtaggggac aaccgagtgc tggacatggc cagcacctac tttgacatcc ggggagtgct  17160
ggatcgcggt cccagtttta agccctactc gggtaccgcg tacaattccc tggctcccaa  17220
gggcgctccc aaccctgcag aatggacgaa ttcagacagc aaagttaaag tgagggcaca  17280
ggcgcctttt gttagctcgt atggtgctac agcgattaca aaagagggta ttcaggtggg  17340
agtaacctta acagactccg gatcaacacc acagtatgca gataaaacgt atcagcctga  17400
gccgcaaatt ggagaactac agtggaacag cgatgttgga accgatgaca aaatagcagg  17460
aagagtgcta aagaaaacaa cgcccatgtt cccttgttac ggctcatatg ccaggcccac  17520
taatgaaaaa ggaggacagg caacaccgtc cgctagtcaa gacgtgcaaa atcccgaatt  17580
acaatttttt gcctctacta atgtcgccaa tacaccaaaa gcagttctat atgcggagga  17640
cgtgtcaatt gaagcgccag acactcactt ggtgttcaaa ccaacagtca ctgaaggcat  17700
tacaagttca gaggctctac tgacccaaca agctgctccc aaccgtccaa actacatagc  17760
```

-continued

```
ctttagagat aattttattg gtctcatgta ctacaatagc acaggtaaca tgggagtact  17820
ggcaggccag gcttctcagc taaatgcagt tgttgacctg caagacagaa atactgagct  17880
gtcctaccaa ctcatgttgg acgccctcgg agaccgcagt cggtactttt ctatgtggaa  17940
ccaagctgtg gatagttacg atcctgatgt aagaatcata gaaaaccatg gcgtagaaga  18000
tgaattgcct aattattgct ttcctttggg aggcatggca gtaaccgaca cctactcgcc  18060
tataaaggtt aatggaggag gcaatggatg ggaagccaat aacggcgttt tcaccgaaag  18120
aggagtggaa ataggttcag ggaacatgtt tgccatggag attaacctgc aagccaacct  18180
atggcgtagc tttctgtact ccaatattgg gctgtacctg ccagactctc tcaaaatcac  18240
tcctgacaac atcacactcc cagagaacaa aaacacctat cagtatatga acggtcgcgt  18300
gacgccaccc gggctggttg acacctacgt taacgtgggc gcgcgctggt cccccgatgt  18360
catggacagt attaaccctt ttaatcacca ccgcaacgcc ggactccgct accgttccat  18420
gctcctggga aacggacgct acgtgccctt ccacatccag gtgccccaga aattctttgc  18480
aattaaaaac ctgctgctgc tccccggttc ctacacctac gagtggaact tccgcaagga  18540
cgtgaacatg atcttgcaga gctcgctggg caatgacctg cgagtggacg gggccagcat  18600
ccgcttcgac agcatcaacc tgtacgccaa ctttttcccc atggcccaca acacggcctc  18660
caccctggaa gccatgctgc gcaacgacac caacgaccaa tctttcaacg actacctgtg  18720
cgcggccaac atgctgtacc ccatccccgc caacgccacc agcgtgccca tctccattcc  18780
ctctcgcaac tgggcagcct tcaggggctg gagtttcacc cgcctcaaaa ccaaggagac  18840
cccctcgctg ggctccgggt tcgaccccta cttcgtctac tccggctcca tcccctacct  18900
ggacggcacc ttctacctca accatacttt caaaaaggtg tcaatcatgt tcgactcctc  18960
cgtcagctgg cccggcaacg accgtctgct gacgcccaac gagttcgaaa tcaagcgttc  19020
ggtggacggt gaagggtaca acgtggctca gagcaacatg accaaggact ggttcctgat  19080
tcagatgctc agccactaca acatcggcta ccagggcttc tacgtgcccg aaaattacaa  19140
ggaccgcatg tactctttct tcagaaactt ccaacccatg agccgccaaa ttgtagattc  19200
aacggcttac actaattatc aggatgtgaa actgccatac cagcataaca actcagggtt  19260
cgtgggctac atgggaccca ccatgcgaga ggggcaggcc tacccggcca actatcccta  19320
tcccctgatt ggggccaccg ccgtgcccag cctcacgcag aaaaagttcc tctgcgaccg  19380
ggtgatgtgg aggatcccct tctctagcaa cttcatgtct atgggctccc tcaccgacct  19440
ggggcagaac atgctgtacg ccaactccgc tcacgccttg gatatgacct ttgaggtgga  19500
tcccatggat gagcccacgc ttctctatgt tctgtttgaa gtcttcgacg tggtgcgcat  19560
ccaccagccg caccgcggcg tcatcgaggc cgtctacctg cgcacacctt tctctgccgg  19620
taacgccacc acctaaagaa gccgatgggc tccagcgaac aggagctgca ggccattgtt  19680
cgcgacctgg gctgcgggcc ctactttttg ggcaccttcg acaagcgttt tcccggcttc  19740
atgtccccc acaagccggc ctgtgccatc gttaacacgg ccggacggga gaccgggggg  19800
gtccactggc tcgccttcgc ctggaacccg cgtaaccgca cctgctacct gttcgaccct  19860
tttggtttct ccgacgaaag gctgaagcag atctaccagt tcgagtacga ggggctcctc  19920
aagcgcagcg ctctggcctc cacgcccgac cactgcgtca ccctggaaaa gtccacccaa  19980
acggtccagg ggcccctctc ggccgcctgc gggctcttct gttgcatgtt tttgcacgcc  20040
ttcgtgcact ggcctcacac cccatggat cacaacccca ccatggatct gctcaccgga  20100
gtgcccaaca gcatgcttca cagcccccag gtcgccccca ccctgcgccg taaccaggaa  20160
```

-continued

```
cacctgtatc gctttctggg gaaacactct gcctattttc gccgccaccg gcagcgcatc  20220
gaacgggcca cggccttcga aagcatgagc caaagagtgt aatcaataaa aaacattttt  20280
atttgacatg atacgcgctt ctggcgtttt attaaaaatc gaagggttcg agggaggggt  20340
cctcgtgccc gctggggagg gacacgttgc gatactggaa acgggcgctc caacgaaact  20400
cggggatcac cagccgcggc aggggcacgt cttctaggtt ctgcttccaa aactgccgca  20460
ccagctgcag ggctcccatg acgtcgggcg ccgatatctt gaagtcgcag ttagggccgg  20520
agctcccgcg gctgttgcgg aacacggggt tggcacactg gaacaccagc acgccggggt  20580
tgtggatact ggccagggcc gtcgggtcgg tcacctccga cgcatccaga tcctcggcgt  20640
tgctcagggc aaacggggtc agcttgcaca tctgccgccc aatctggggt actaggtcgc  20700
gcttgttgag gcagtcgcag cgcagaggga tcaggatgcg tcgctgcccg cgttgcatga  20760
tagggtaact cgccgccagg aactcctcca tttgacggaa ggccatctgg gctttgccgc  20820
cctcggtgta gaatagcccg caggacttgc tagagaatac gttatgaccg cagttgacgt  20880
cctccgcgca gcagcgggcg tcttcgttct tcagctgaac cacgttgcgg ccccaacggt  20940
tctggaccac cttggctcta gtggggtgct ccttcagcgc ccgctgtccg ttctcgctgg  21000
ttacatccat ttccaacacg tgctccttgc agaccatctc cactccgtgg aagcaaaaca  21060
ggacgccctc ctgctgggta ctgcgatgct cccatacggc gcatccggtg ggctcccagc  21120
tcttgtgttt tacccccgcg taggcttcca tgtaagccat aaggaatctg cccatcagct  21180
cggtgaaggt cttctggttg gtgaaggtta gcggcaggcc gcggtgctcc tcgttcaacc  21240
aagtttgaca gatcttgcgg tacaccgctc cctggtcggg cagaaactta aaagccgctc  21300
tgctgtcgtt gtctacgtgg aacttctcca ttaacatcat catggtttcc ataccctctt  21360
cccacgctgt caccagtggt ttgctgtcgg ggttcttcac caacacggcg gtagaggggc  21420
cctcgccggc cccgacgtcc ttcatggtca ttctttgaaa ctccacggag ccgtccgcgc  21480
gacgtactct gcgcaccgga gggtagctga agcccacctc caccacggtg ccttcgccct  21540
cgctgtcgga gacaatctcc ggggatggcg gcggcgcggg tgtcgccttg cgagccttct  21600
tcttgggagg gagctgaggc gcctcctgct cgcgctcggg gctcatctcc cgcaagtagg  21660
gggtaatgga gctgcctgct tggttctgac ggttggccat tgtatcctag gcagaaagac  21720
atggagctta tgcgcgagga aactttaacc gccccgtccc ccgtcagcga cgaagatgtc  21780
atcgtcgaac aggacccggg ctacgttacg ccgcccgagg atctggaggg gcctgaccgg  21840
cgcgacgcta gtgagcggca ggaaaatgag aaagaggagg cctgctacct cctggaaggc  21900
gacgttttgc taaagcattt cgccaggcag agcaccatag ttaaggaggc cttgcaagac  21960
cgctccgagg tgcccttgga cgtcgccgcg ctctcccagg cctacgaggc gaaccttttc  22020
tcgcctcgag tgcctccgaa gagacagccc aacggcacct gcgagcccaa cccgcgactc  22080
aacttctacc ccgtgttcgc cgtaccagag gcgctggcca cctatcacat tttttttcaaa  22140
aaccaacgca tccccctatc gtgccgggcc aaccgcaccg cggccgatag gaatctcagg  22200
cttaaaaacg gagccaacat acctgatatc acgtcgctgg aggaagtgcc caagattttc  22260
gagggtctgg gtcgagatga gaagcgggcg gcgaacgctc tgcagaaaga acagaaagag  22320
agtcagaacg tgctggtgga gctggagggg gacaacgcgc gtctggccgt cctcaaacgc  22380
tgcatagaag tctcccactt cgcctacccc gccctcaact tgccacccaa agttatgaaa  22440
tcggtcatgg atcagctgct catcaagaga gctgagcccc tggatcccga ccaccccgag  22500
```

-continued

```
gcggaaaact cagaggacgg aaagcccgtc gtcagcgacg aggagctcga gcggtggctg  22560
gaaaccaggg acccccaaca gttgcaagag aggcgcaaga tgatgatggc ggccgtgctg  22620
gtcaccgtgg agctggaatg cctgcaacgg tttttcagcg acgtggagac gctacgcaaa  22680
atcggggaat ccctgcacta caccttccgc cagggctacg tccgccaggc ctgcaagatc  22740
tccaacgtgg agctcagcaa cctggtctcc tacatgggca tcctccacga gaaccggctg  22800
gggcagagcg tgctgcactg caccttgcaa ggcgaggcgc ggcgggacta cgtgcgagac  22860
tgcatctacc tcttcctcac cctcacctgg cagaccgcca tgggcgtctg gcagcagtgc  22920
ttggaagaga gaaacctcaa agagctagac aaactcctct gccgccagcg gcgcgccctg  22980
tggtccggtt tcagcgagcg cacggtcgcc agcgctctgg cggacatcat cttcccggag  23040
cgcctgatga aaaccttgca aaacggcctg ccggatttca tcagtcaaag cattttgcaa  23100
aacttccgct cttttgtcct ggaacgctcc gggatcttgc ccgccatgag ctgcgcgcta  23160
ccttctgact ttgtccccct ctcctaccgc gagtgccctc ccccactgtg gagccactgc  23220
tacctcttcc aactggccaa ctttctggcc taccactccg acctcatgga agacgtaagc  23280
ggagagggtt tactggagtg ccactgccgc tgcaacctgt gcacccccca cagatcgctg  23340
gcctgcaaca ccgagctact cagcgaaacc caggtcatag gtaccttcga gatccagggg  23400
ccccagcagc aagagggtgc ttccggcttg aagctcactc cggcgctgtg gacctcggct  23460
tacttacgca aatttgtagc cgaggactac cacgcccaca aaattcagtt ttacgaagac  23520
caatctcgac caccgaaagc cccccctcacg gcctgcgtca tcacccagag caagatcctg  23580
gcccaattgc aatccatcaa ccaagcgcgc cgcgatttcc ttttgaaaaa gggtcggggg  23640
gtgtacctgg acccccagac cggcgaggaa ctcaacccgt ccacactctc cgtcgaagca  23700
gcccccccga gacatgccgc ccaagggaac cgccaagcag ctgatcgctc ggcagagagc  23760
gaagaagcaa gagctgctcc agcagcaggt ggaggacgag gaagagatgt gggacagcca  23820
ggcagaggag gtgtcagagg acgaggagga gatggaaagc tgggacagcc tagacgagga  23880
ggaggacgag ctttcagagg aagaggcgac cgaagaaaaa ccacctgcat ccagcgcgcc  23940
ttctctgagc cgacagccga agccccggcc cccgacgccc ccggccggct cactcaaagc  24000
cagccgtagg tgggacgcca ccgaatctcc agcggcagcg gcaacggcag cgggtaaggc  24060
caaacgcgag cggcgggggt attgctcctg gcgggcccac aaaagcagta ttgtgaactg  24120
cttgcaacac tgcgggggaa acatctcctt tgcccgacgc tacctcctct tccatcacgg  24180
tgtggccttc cctcgcaacg ttctctatta ttaccgtcat ctctacagcc cctacgaaac  24240
gctcggagaa aaaagctaag gcctcctccg ccgcgaggaa aaactccgcc gccgctgccg  24300
ccgccaagga tccaccggcc accgaagagc tgagaaagcg catctttccc actctgtatg  24360
ctatctttca gcaaagccgc gggcagcacc ctcagcgcga actgaaaata aaaaaccgct  24420
ccttccgctc gctcacccgc agctgtctgt accacaagag agaagaccag ctgcagcgca  24480
ccctggacga cgccgaagca ctgttcagca aatactgctc agcgtctctt aaagactaaa  24540
agacccgcgc tttttccccc tcggccgcca aaacccacgt catcgccagc atgagcaagg  24600
agattcccac cccctacatg tggagctatc agccccagat gggcctggcc gcgggggccg  24660
cccaggacta ctccagcaag atgaactggc tcagcgccgg cccccacatg atctcacgag  24720
ttaacggcat ccgagcccac cgaaaccaga ttctcttaga acaggcggca atcaccgcca  24780
caccccggcg ccaactcaac ccgcctagtt ggcccgccgc ccaggtgtat caggaaaatc  24840
cccgcccgac cacagtcctc ctgccacgcg acgcggaggc cgaagtcctc atgactaact  24900
```

-continued

```
ctggggtaca attagcgggc gggtccaggt acgccaggta cagaggtcgg gccgctcctt  24960
actctcccgg gagtataaag agggtgatca ttcgaggccg aggtatccag ctcaacgacg  25020
agacggtgag ctcctcaacc ggtctcagac ctgacggagt cttccagctc ggaggagcgg  25080
gccgctcttc cttcaccact cgccaggcct acctgaccct gcagagctct tcctcgcagc  25140
cgcgctccgg gggaatcggc actctccagt tcgtggaaga gttcgttccc tccgtctact  25200
tcaacccctt ctccggctcg cctggacgct acccggacgc cttcattccc aactttgacg  25260
cagtgagtga atccgtggac ggctacgact gatgacagat ggtgcggccg tgagagctcg  25320
gctgcgacat ctgcatcact gccgtcagcc tcgctgctac gctcgggagg cgatcgtctt  25380
cagctacttt gagctgccgg acgagcaccc tcagggtccg gctcacgggt tgaaactcga  25440
gatcgagaac gcgctcgagt ctcgcctcat cgacaccttc accgcccgac ctctcctggt  25500
agaaatccaa cgggggatca ctaccatcac cctgttctgc atctgcccca cgcccggatt  25560
acatgaagat ctgtgttgtc atctttgcgc tcagtttaat aaaaactgaa ctttttgccg  25620
caccttcaac gccatctgtg atttctacaa caaaaagttc ttctggcaaa ggtacacaaa  25680
ctgtatttta ttctaattct acctcatcta tcgtgctgaa ctgcgcctgc actaacgaac  25740
ttatccagtg gattgcaaac ggtagtgtgt gcaagtactt ttgggggaac gatatagtta  25800
gtagaaataa cagcctttgc gagcactgca actcctccac actaatcctt tatcccccat  25860
ttgttactgg atggtatatg tgcgttggct ccggtttaaa tcctagttgc tttcataagt  25920
ggtttctaca aaaagagacc cttcccaaca attctgtttc ttttttcgcc ctatcctact  25980
gctgttctcc ctctggttac tctttcaaac ctctaattgg tattttagct ttgatactca  26040
taatctttat taactttata ataattaaca acttacagta aacatgcttg ttctactgct  26100
cgccacatct ttcgctctct ctcacgccag aacaagtatt gttggcgcag gttacaatgc  26160
aactcttcaa tctgcttaca tgccagattc cgaccagata ccccatatta cgtggtactt  26220
acaaacctcc aaacctaatt cttcatttta tgaaggaaac aaactctgcg atgactccga  26280
caacagaacg cacacatttc cccacccttc actacaattc gaatgcgtaa acaaaagctt  26340
gaagctttac aacttaaagc cttcagattc tggcttgtac catgctgtag ttgaaaaaag  26400
taatttagaa gtccacagtg attacattga attgacggtt gtggacctgc cacctccaaa  26460
atgtgaggtt tcctcctctt accttgaagt tcaaggcgtg gatgcctact gcctcataca  26520
cattaactgc agcaactcta aatatccagc tagaatttac tataatggac aggaaagtaa  26580
tcttttttat tatttaacaa caagcgctgg taacggtaaa cagttacctg actattttac  26640
tgctgttgtt gaattttcca cctacagaga aacgtatgcc aagcggcctt acaatttctc  26700
atacccgttt aacgaccttt gcaatgaaat acaagcgctc gaaactggaa ctgattttac  26760
tccaatttc attgctgcca ttgttgtaag cttaattacc attattgtca gcctagcatt  26820
ttactgcttt tacaagccca aaaaccctaa gtttgaaaaa cttaaactaa aacctgtcat  26880
tcaacaagtg tgattttgtt ttccagcatg gtagctgcat ttctacttct cctctgtcta  26940
cccatcattt tcgtctcttc aactttcgcc gcagtttccc acctggaacc agagtgccta  27000
ccgcctttttg acgtgtatct gattctcacc tttgtttgtt gtatatccat ttgcagtata  27060
gcctgctttt ttataacaat ctttcaagcc gccgactatt tttacgtgcg aattgcttac  27120
tttagacacc atcctgaata cagaaatcaa aacgttgcct ccttactttg tttggcatga  27180
ttaagttatt gctgatactt aattatttac ccctaatcaa ctgtaattgt ccattcacca  27240
```

-continued

```
aaccctggtc attctacacc tgttatgata aaatccccga cactcctgtt gcttggcttt  27300
acgcagccac cgccgctttg gtatttatat ctacttgcct tggagtaaaa ttgtatttta  27360
ttttacacac tgggtggcta catcccagag aagatttacc tagatatcct cttgtaaacg  27420
cttttcaatt acagcctctg cctcctcctg atcttcttcc tcgagctccc tctattgtga  27480
gctactttca actcaccggt ggagatgact gactctcagg acattaatat tagtgtggaa  27540
agaatagctg ctcagcgtca gcgagaaacg cgagtgttgg aatacctgga actacagcaa  27600
cttaaagagt cccactggtg tgagaaagga gtgctgtgcc atgttaagca ggcagccctt  27660
tcctacgatg tcagcgttca gggacatgaa ctgtcttaca ctttgccttt gcagaaacaa  27720
accttctgca ccatgatggg ctctacctcc atcacaatca cccaacaagc cgggcctgta  27780
gagggggcta tcctctgtca ctgtcacgca cctgattgca tgtccaaact aatcaaaact  27840
ctctgtgctt taggtgatat ttttaaggtg taaatcaata ataaacttac cttaaatttg  27900
acaacaaatt tctggtgaca tcattcagca gcaccacttt accctcttcc cagctctcgt  27960
atgggatgcg atagtgggtg gcaaacttcc tccaaaccct aaaagaaata ttggtatcca  28020
cttccttgtc ctcacccaca attttcatct tttcatagat gaaaagaacc agagttgatg  28080
aagacttcaa ccccgtctac ccctatgaca ccacaaccac tcctgcagtt ccctttatat  28140
caccccccctt tgtaaacagc gatggtcttc aggaaaaccc cccaggtgtt ttaagtctgc  28200
gaatagctaa accccctatat ttcgacatgg agagaaaact agccctttca cttggaagag  28260
ggttgacaat taccgccgcc ggacaattag aaagtacgca gagcgtacaa accaacccac  28320
cgttgataat taccaacaac aacacactga ccctacgtca ttctcccccc ttaaacctaa  28380
ctgacaatag cttagtgcta ggctactcga gtcctctccg cgtcacagac aacaaactta  28440
catttaactt cacatcacca ctccgttatg aaaatgaaaa ccttactttt aactatacag  28500
agcctcttaa acttataaat aacagccttg ccattgacat caattcctca aaaggcctta  28560
gtagcgtcgg aggctcacta gctgtaaacc tgagttcaga cttaaagttt gacagcaacg  28620
gatccatagc ttttggcata caaaccctgt ggaccgctcc gacctcgact ggcaactgca  28680
ccgtctacag cgagggcgat tccctactta gtctctgttt aaccaaatgc ggagctcacg  28740
tcttaggaag tgtaagttta accggtttaa caggaaccat aacccaaatg actgatattt  28800
ctgtcaccat tcaatttaca tttgacaaca atggtaagct actaagctct ccacttataa  28860
acaacgcctt tagtattcga cagaatgaca gtacggcctc aaaccctacc tacaacgccc  28920
tggcgtttat gcctaacagt accatatatg caagaggggg aggtggtgaa ccacgaaaca  28980
actactacgt ccaaacgtat cttaggggaa atgttcaaaa accaatcatt cttactgtaa  29040
cctacaactc agtcgccaca ggatattcct tatcttttaa gtggactgct cttgcacgtg  29100
aaaagtttgc aaccccaaca acctcgtttt gctacattac agaacaataa aaccgtgtac  29160
cccaccgttt cgtttttttc agatgaaacg ggcgagagtt gatgaagact tcaacccagt  29220
gtacccttat gacccccccac atgctcctgt tatgcccttc attactccac cttttacctc  29280
ctcggatggg ttgcaggaaa aaccacttgg agtgttaagt ttaaactaca gagatcccat  29340
tactacgcaa aatgagtctc ttacaattaa actaggaaac ggcctcactc tagacaacca  29400
gggacaacta acatcaaccg ctggcgaagt agaacctcca ctcactaacg ctaacaacaa  29460
acttgcactg gtctatagcg atcctttagc agtaaagcgc aacagcctaa ccttatcgca  29520
caccgctccc cttgttattg ctgataactc tttagcattg caagtttcag agcctatttt  29580
tataaatgac aaggacaaac tagccctgca aacagccgcg ccccttgtaa ctaacgctgg  29640
```

```
caccccttcgc ttacaaagcg ccgccccttt aggcattgca gaccaaaccc taaaactcct  29700
gtttaccaac cctttgtact tgcagaataa ctttctcacg ttagccattg aacgacccct  29760
tgccattacc aatactggaa agctggctct acagctctcc ccaccgctac aaacagcaga  29820
cacaggcttg actttgcaaa ccaacgtgcc attaactgta agcaacggga ccctaggctt  29880
agccataaag cgcccactta ttattcagga caacaacttg tttttggact tcagagctcc  29940
cctgcgtctt ttcaacagcg acccagtact agggcttaac ttttacaccc ctcttgcggt  30000
acgcgatgag gcgctcactg ttaacacagg ccgcggcctc acagtgagtt acgatggttt  30060
aattttaaat cttggtaagg atcttcgctt tgacaacaac accgtttctg tcgctcttag  30120
tgctgctttg cctttacaat acactgatca gcttcgcctt aacgtgggcg ctgggctgcg  30180
ttacaatcca gtgagtaaga aattggacgt gaaccccaat caaaacaagg gtttaacctg  30240
ggaaaatgac tacctcattg taaagctagg aaatggatta ggttttgatg gcgatggaaa  30300
catagctgtt tctcctcaag ttacatcgcc tgacacctta tggaccactg ccgacccatc  30360
cccaattgt tccatctaca ctgatttaga tgccaaaatg tggctctcgt tggtaaaaca  30420
agggggtgtg gttcacggtt ctgttgcttt aaaagcattg aaaggaaccc tattgagtcc  30480
tacggaaagc gccattgtta ttatactaca ttttgacaat tatggagtgc gaattctcaa  30540
ttatcccact ttgggcactc aaggcacgtt gggaaataat gcaacttggg gttataggca  30600
gggagaatct gcagacacta atgtactcaa tgcactagca tttatgccca gttcaaaaag  30660
gtacccaaga gggcgtggaa gcgaagttca gaatcaaact gtgggctaca cttgtataca  30720
gggtgacttt tctatgcccg taccgtacca aatacagtac aactatggac caactggcta  30780
ctcctttaaa tttatttgga gaactgtttc aagacaacca tttgacatcc catgctgttt  30840
tttctcttac attacggaag aataaaacaa ctttttcttt ttattttctt tttattttac  30900
acgcacagta aggcttcctc caccccttcca tctcacagca tacaccagcc tctccccctt  30960
catggcagta aactgttgtg agtcagtccg gtatttggga gttaagatcc aaacagtctc  31020
tttggtgatg aaacatggat ccgtgatgga cacaaatccc tgggacaggt tctccaacgt  31080
ttcggtaaaa aactgcatgc cgccctacaa aacaaacagg ttcaggctct ccacgggtta  31140
tctccccgat caaactcaga cagagtaaag gtgcgatgat gttccactaa accacgcagg  31200
tggcgctgtc tgaacctctc ggtgcgactc ctgtgaggct ggtaagaagt tagattgtcc  31260
agcagcctca cagcatggat catcagtcta cgagtgcgtc tggcgcagca gcgcatctga  31320
atctcactga gattccggca agaatcgcac accatcacaa tcaggttgtt catgatccca  31380
tagctgaaca cgctccagcc aaagctcatt cgctccaaca gcgccaccgc gtgtccgtcc  31440
aaccttactt taacataaat caggtgtctg ccgcgtacaa acatgctacc cgcatacaga  31500
acctcccggg gcaaacccct gttcaccacc tgcctgtacc agggaaacct cacatttatc  31560
agggagccat agatagccat tttaaaccaa ttagctaaca ccgcccccacc agctctacac  31620
tgaagagaac cgggagagtt acaatgacag tgaataatcc atctctcata acccctaatg  31680
gtctgatgga aatccagatc taacgtggca cagcagatac acactttcat atacattttc  31740
atcacatgtt tttcccaggc cgttaaaata caatcccaat acacgggcca ctcctgcagt  31800
acaataaagc taatacaaga tggtatactc ctcacctcac taacattgtg catgttcata  31860
ttttcacatt ctaagtaccg agagttctcc tctacaacag cactgccgcg gtcctcacaa  31920
ggtggtagct ggtgacgatt gtaaggagcc agtctgcagc gataccgtct gtcgcgttgc  31980
```

-continued

```
atcgtagacc agggaccgac gcacttcctc gtacttgtag tagcagaacc acgtccgctg  32040
ccagcacgtc tccaagtaac gccggtccct gcgtcgctca cgctccctcc tcaacgcaaa  32100
gtgcaaccac tcttgtaatc cacacagatc cctctcggcc tccggggcga tgcacacctc  32160
aaacctacag atgtctcggt acagttccaa acacgtagtg agggcgagtt ccaaccaaga  32220
cagacagcct gatctatccc gacacactgg aggtggagga agacacggaa gaggcatgtt  32280
attccaagcg attcaccaac gggtcgaaat gaagatcccg aagatgacaa cggtcgcctc  32340
cggagccctg atggaattta acagccagat caaacattat gcgattttcc aggctatcaa  32400
tcgcggcctc caaaagagcc tggacccgca cttccacaaa caccagcaaa gcaaaagcgt  32460
tattatcaaa ctcttcgatc atcaagctgc aggactgtac aatgcccaag taattttcat  32520
ttctccactc gcgaatgatg tcgcggcaaa tagtctgaag gttcatgccg tgcatattaa  32580
aaagctccga aagggcgccc tctatagcca tgcgtagaca caccatcatg actgcaagat  32640
atcgggctcc tgagacacct gcagcagatt taacagaccc aggtcaggtt gctctccgcg  32700
atcgcgaatc tccatccgca aagtcatttg caaataatta aatagatctg cgccgactaa  32760
atctgttaac tccgcgctag gaactaaatc aggtgtggct acgcagcaca aaagttccag  32820
ggatggcgcc aaactcacta gaaccgctcc cgagtagcaa aactgatgaa tgggagtaac  32880
acagtgtaaa atgttcagcc aaaaatcact aagctgctcc tttaaaaagt ccagtacttc  32940
tatattcagt tcgtgcaagt actgaagcaa ctgtgcggga atatgcacag caaaaaaaat  33000
agggcggctc agatacatgt tgacctaaaa taaaaagaat cattaaacta aagaagcctg  33060
gcgaacggtg ggatatatga cacgctccag cagcaggcaa gcaaccggct gtccccggga  33120
accgcggtaa aattcatccg aatgattaaa aagaacaaca gagacttccc accatgtact  33180
cggttggatc tcctgagcac agagcaatac ccccctcaca ttcatatccg ctacagaaaa  33240
aaaacgtccc agatacccag cgggaatatc caacgacagc tgcaaagaca gcaaaacaat  33300
ccctctggga gcaatcacaa aatcctccgg tgaaaaaagc acatacatat tagaataacc  33360
ctgttgctgg ggcaaaaagg cccgtcgtcc cagcaaatgc acataaatat gttcatcagc  33420
cattgccccg tcttaccgcg taaacagcca cgaaaaaatc gagctaaaat ccacccaaca  33480
gcctatagct atatatacac tccacccaat gacgctaata ccgcaccacc cacgaccaaa  33540
gttcacccac acccacaaaa cccgcgaaaa tccagcgccg tcagcacttc cgcaatttca  33600
gtctcacaac gtcacttccg cgcgcctttt cactttccca cacacgccct tcgcccgccc  33660
gccctcgcgc caccccgcgt caccccacgt caccgcacgt caccccggcc ccgcctcgct  33720
cctccccgct cattatcata ttggcacgtt tccagaataa ggtatattat tgatgcagca  33780
aaacaatccc tctgggagca atcacaaaat cctccggtga aaaaagcaca tacatattag  33840
aataaccctg ttgctggggc aaaaaggccc gtcgtcccag caaatgcaca taaatatgtt  33900
catcagccat tgccccgtct taccgcgtaa acagccacga aaaaatcgag ctaaaatcca  33960
cccaacagcc tatagctata tatacactcc acccaatgac gctaataccg caccacccac  34020
gaccaaagtt cacccacacc cacaaaaccc gcgaaaatcc agcgccgtca gcacttccgc  34080
aatttcagtc tcacaacgtc acttccgcgc gccttttcac tttcccacac acgcccttcg  34140
cccgcccgcc ctcgcgccac cccgcgtcac cccacgtcac cgcacgtcac cccggccccg  34200
cctcgctcct ccccgctcat tatcatattg gcacgtttcc agaataaggt atattattga  34260
tgca                                                               34264
```

-continued

<210> SEQ ID NO 5
<211> LENGTH: 31044
<212> TYPE: DNA
<213> ORGANISM: simian adenovirus SV-25

<400> SEQUENCE: 5
catcatcaat aatatacctt attctggaaa cgtgccaata tgataatgag cggggaggag 60
cgaggcgggg ccggggtgac gtgcggtgac gcggggtggc gcgagggcgg ggcgaagggc 120
gcgggtgtgt gtgtgggagg cgcttagttt ttacgtatgc ggaaggaggt tttataccgg 180
aagatgggta atttgggcgt atacttgtaa gttttgtgta atttggcgcg aaaactgggt 240
aatgaggaag ttgaggttaa tatgtacttt ttatgactgg gcggaatttc tgctgatcag 300
cagtgaactt tgggcgctga cggggaggtt tcgctacgtg acagtaccac gagaaggctc 360
aaaggtccca tttattgtac tcttcagcgt tttcgctggg tatttaaacg ctgtcagatc 420
atcaagaggc cactcttgag tgctggcgag aagagttttc tcctccgtgc tgccacgatg 480
aggctggtcc ccgagatgta cggtgttttt agcgacgaga cggtgcgtaa ctcagatgac 540
ctgctgaatt cagacgcgct ggaaatttcc aattcgcctg tgctttcgcc gccgtcactt 600
cacgacctgt ttgtgttttg gctcaacgct tagcaacgtg ttatataggg tcaagaagga 660
gcaggagacg cagtttgcta ggctgttggc cgatactcct ggagtttttg tggctctgga 720
tctaggccat cactctcttt tccaagagaa aattatcaaa aacttaactt ttacgtctcc 780
tggtcgcacg gttgcttccg ctgcctttat tacctatatt ttggatcaat ggagcaacag 840
cgacagccac ctgtcgtggg agtacatgct ggattacatg tcgatggcgc tgtggagggc 900
catgctgcgg aggagggttt gcatttactt gcgggcgcag cctccgcggc tggaccgagt 960
ggaggaggag gacgagccgg gggagaccga gaacctgagg gccgggctgg accctccaac 1020
ggaggactag gtgctgagga tgatcccgaa gaggggacta gtggggctag gaagaagcaa 1080
aagactgagt ctgaacctcg aaactttttg aatgagttga ctgtgagttt gatgaatcgt 1140
cagcgtccgg agacaatttt ctggtctgaa ttggaggagg aattcaggag gggggaactg 1200
aacctgctat acaagtatgg gtttgaacag ttaaaaactc actggttgga gccgtgggag 1260
gattttgaaa ccgccttgga cacttttgct aaagtggctc tgcggccgga taaggtttac 1320
actatccgcc gcactgttaa cataaagaag agtgtttatg ttataggcca tggagctctg 1380
gtgcaggtgc aaaccgtcga ccgggtggcc tttagttgcg gtatgcaaaa tctgggcccc 1440
ggggtgatag gcttaaatgg tgtaacattt cacaatgtaa ggtttactgg tgaaagtttt 1500
aacggctctg tgtttgcaaa taacacacag ctgacgctcc acggcgttta ctttttttaac 1560 tttaataaca catgtgtgga gtcgtggggc agggtgtctt tgaggggctg ctgttttcac 1620
ggctgctgga aggcggtggt gggaagactt aaaagtgtaa catctgtaaa aaaatgcgtg 1680
tttgagcggt gtgtgttggc tttaactgtg gagggctgtg gacgcattag gaataatgcg 1740
gcgtctgaga atggatgttt tcttttgcta aaaggcacgg ctagtattaa gcataacatg 1800
atatgcggca gcggtctgta cccttcacag ctgttaactt gcgcggatgg aaactgtcag 1860
accttgcgca ccgtgcacat agcgtcccac cagcgccgcg cctggccaac attcgagcac 1920
aatatgctta tgcgttgtgc cgtccacttg ggccctaggc gaggcgtgtt tgtgccttac 1980
cagtgtaact ttagccatac caagatttta ctagaacctg ataccttctc tcgagtgtgt 2040
ttcaatgggg tgtttgacat gtcaatggaa ctgtttaaag tgataagata tgatgaatcc 2100
aagtctcgtt gtcgcccatg tgaatgcgga gctaatcatc tgaggttgta tcctgtaacc 2160

-continued

```
ctaaacgtta ccgaggagct gaggacggat caccacatgt tgtcctgcct gcgcaccgac   2220
tatgaatcca gcgacgagga gtgaggtgag gggcggagcc acaaagggta taaaggggcg   2280
tgaggggtgg gtgtgatgat tcaaaatgag cgggacgacg gacggcaacg cgtttgaggg   2340
tggagtgttc agcccttatc tgacatctcg tcttccttcc tgggcaggag tgcgtcagaa   2400
tgtagtgggc tccaccgtgg acggacgacc ggtcgcccct gcaaattccg ccaccctcac   2460
ctatgccacc gtgggatcat cgttggacac tgccgcggca gctgccgctt ctgctgccgc   2520
ttctactgct cgcggcatgg cggctgattt tggactgtat aaccaactgg ccactgcagc   2580
tgtggcgtct cggtctctgg ttcaagaaga tgccctgaat gtgatcctga ctcgcctgga   2640
gatcatgtca cgtcgcttgg acgaactggc tgcgcagata tcccaagcta accccgatac   2700
cacttcagaa tcctaaaata aagacaaaca aatatgttga aagtaaaat ggctttattt   2760
gtttttttg gctcggtagg ctcgggtcca cctgtctcgg tcgttaagaa ctttgtgtat   2820
gttttccaaa acacggtaca gatgggcttg gatgttcaag tacatgggca tgaggccatc   2880
tttggggtga agataggacc attgaagagc gtcatgctcc ggggtggtgt tgtaaattac   2940
ccagtcgtag cagggtttct gggcgtggaa ctggaagatg tcctttagga gtaggctgat   3000
ggccaagggc aggcccttag tgtaggtgtt tacaaagcgg ttaagctggg agggatgcat   3060
gcggggggag atgatatgca tcttggcttg gatcttgagg ttagctatgt taccacccag   3120
gtctctgcgg gggttcatgt tatgaaggac caccagcacg gtgtagccgg tgcatttggg   3180
gaacttgtca tgcagtttgg aggggaaggc gtggaagaat ttagagaccc ccttgtggcc   3240
ccctaggttt tccatgcact catccataat gatggcaatg ggacccctgg cggccgcttt   3300
ggcaaacacg ttttgggggt tggaaacatc atagttttgc tctagagtga gctcatcata   3360
ggccatctta acaaagcggg gtaggagggt gcccgactgg gggatgatag ttccatctgg   3420
gcctggggcg tagttaccct cacagatctg catctcccag gccttaattt ccgagggggg   3480
tatcatgtcc acctgggggg caataaagaa cacggtttct ggcgggggat tgatgagctg   3540
ggtggaaagc aagttacgca gcagttgaga tttgccacag ccggtggggc cgtagatgac   3600
cccgatgacg ggttgcagct ggtagttgag agaggaacag ctgccgtcgg ggcgcaggag   3660
gggggctacc tcattcatca tgcttctaac atgtttattt tcactcacta agttttgcaa   3720
gagcctctcc ccacccaggg ataagagttc ttccaggctg ttgaagtgtt tcagcggttt   3780
taggccgtcg gccatgggca tcttttcgag cgactgacga agcaagtaca gtcggtccca   3840
gagctcggtg acgtgctcta tggaatctcg atccagcaga cttcttggtt gcgggggttg   3900
ggtcgacttt cgctgtaggg caccagccgg tgggcgtcca gggccgcgag ggttctgtcc   3960
ttccagggtc tcagcgtccg ggtgagggtg gtctcggtga cggtgaaggg atgagccccg   4020
ggctgggcgc ttgcgagggt gcgcttcagg ctcatcctgc tggtgctgaa gcggacgtcg   4080
tctccctgtg agtcggccag atagcaacga agcatgaggt cgtagctgag ggactcggcc   4140
gcgtgtccct tggcgcgcag ctttcccttg gaaacgtgct gacatttggt gcagtgcaga   4200
cattggaggg cgtagagttt gggggccagg aagaccgact cgggcgagta ggcgtcggct   4260
ccgcactgag cgcagacggt ctcgcactcc actagccacg tgagctcggg tttagcggga   4320
tcaaaaacca agttgcctcc atttttttg atgcgtttct taccttgcgt ttccatgagt   4380
ttgtggcccg cttccgtgac aaaaaggctg tcggtgtctc cgtagacaga cttgaggggg   4440
cgatcttcca aaggtgttcc gaggtcttcc gcgtacagga actgggacca ctccgagacg   4500
aaggctctgg tccaggctaa cacgaaggag gcaatctgcg aggggtatct gtcgttttca   4560
```

```
atgaggggt ccacctttc cagggtgtgc agacacaggt cgtcctcctc cgcgtccacg   4620
aaggtgattg gcttgtaagt gtaggtcacg tgatctgcac cccccaaagg ggtataaaag   4680
ggggcgtgcc caccctctcc gtcactttct tccgcatcgc tgtggaccag agccagctgt   4740
tcgggtgagt aggccctctc aaaagccggc atgatctcgg cgctcaagtt gtcagtttct   4800
acaaacgagg tggatttgat attcacgtgc cccgcggcga tgcttttgat ggtggagggg   4860
tccatctgat cagaaaacac gatctttttg ttgtcaagtt tggtggcgaa agacccgtag   4920
agggcgttgg aaagcaactt ggcgatggag cgcagggtct gatttttctc ccgatcggcc   4980
ctctccttgg cggcgatgtt gagttgcacg tactcccggg ccgcgcaccg ccactcgggg   5040
aacacggcgg tgcgctcgtc gggcaggatg cgcacgcgcc agccgcgatt gtgcagggtg   5100
atgaggtcca cgctggtagc cacctccccg cggaggggct cgttggtcca acacaatcgc   5160
ccccctttc tggagcagaa cggaggcagg ggatctagca agttggcggg cggggggtcg   5220
gcgtcgatgg tgaagatacc gggtagcagg atcttattaa aataatcgat ttcggtgtcc   5280
gtgtcttgca acgcgtcttc ccacttcttc accgccaggg ccctttcgta gggattcagg   5340
ggcggtcccc agggcatggg gtgggtcagg gccgaggcgt acatgccgca gatgtcatac   5400
acgtacaggg gttccctcaa caccccgatg taagtggggt aacagcgccc cccgcggatg   5460
ctggctcgca cgtagtcgta catctcgcgc gagggagcca tgaggccgtc tcccaagtgg   5520
gtcttgtggg gtttttcggc ccggtagagg atctgtctga agatggcgtg ggagttggaa   5580
gagatggtgg ggcgttggaa gacgttaaag ttggccccgg gtagtcccac ggagtcttgg   5640
atgaactggg cgtaggattc ccggagtttg tccaccaggg cggcggtcac cagcacgtcg   5700
agagcgcagt agtccaacgt ctcgcggacc aggttgtagg ccgtctcttg tttttctcc   5760
cacagttcgc ggttgaggag gtattcctcg cggtctttcc agtactcttc ggcgggaaat   5820
cctttttcgt ccgctcggta agaacctaac atgtaaaatt cgttcaccgc tttgtatgga   5880
caacagcctt tttctaccgg cagggcgtac gcttgagcgg cctttctgag agaggtgtgg   5940
gtgagggcga aggtgtcccg caccatcact ttcaggtact gatgtttgaa gtccgtgtcg   6000
tcgcaggcgc cctgttccca cagcgtgaag tcggtgcgct tttctgcct gggattgggg   6060
agggcgaagg tgacatcgtt aaagagtatt ttcccggcgc ggggcatgaa gttgcgagag   6120
atcctgaagg gcccgggcac gtccgagcgg ttgttgatga cctgcgccgc caggacgatc   6180
tcgtcgaagc cgttgatgtt gtgacccacg atgtaaagtt cgatgaagcg cggctgtccc   6240
ttgagggccg gcgctttttt caactcctcg taggtgagac agtccggcga ggagagaccc   6300
agctcagccc gggcccagtc ggagagttga ggattagccg caaggaagga gctccataga   6360
tccaaggcca ggagagtttg caagcggtcg cggaactcgc ggaacttttt ccccacggcc   6420
attttctccg gtgtcactac gtaaaaggtg ttggggcggt tgttccacac gtcccatcgg   6480
agctctaggg ccagctcgca ggcttggcga acgagggtct cctcgccaga gacgtgcatg   6540
accagcataa agggtaccaa ctgtttcccg aacgagccca tccatgtgta ggtttctacg   6600
tcgtaggtga caaagagccg ctgggtgcgc gcgtgggagc cgatcggaaa gaagctgatc   6660
tcctgccacc agctggagga atgggtgtta atgtggtgga agtagaagtc ccgccggcgc   6720
acagagcatt cgtgctgatg tttgtaaaag cgaccgcagt agtcgcagcg ctgcacgctc   6780
tgtatctcct gaacgagatg cgcttttcgc ccgcgcacca gaaaccggag ggggaagttg   6840
agacgggggg ctggtggggc gacatcccct tcgccttggc ggtgggagtc tgcgtctgcg   6900
```

-continued

```
tcctccttct ctgggtggac gacggtgggg acgacgacgc cccgggtgcc gcaagtccag   6960
atctccgcca cggaggggtg caggcgctgc aggaggggac gcagctgccc gctgtccagg   7020
gagtcgaggg aagtcgcgct gaggtcggcg ggaagcgttt gcaagttcac tttcagaaga   7080
ccggtaagag cgtgagccag gtgcagatgg tacttgattt ccaggggggt gttggatgaa   7140
gcgtccacgg cgtagaggag tccgtgtccg cgcggggcca ccaccgtgcc ccgaggaggt   7200
tttatctcac tcgtcgaggg cgagcgccgg ggggtagagg cggctctgcg ccggggggca   7260
gcggaggcag aggcacgttt tcgtgaggat tcggcagcgg ttgatgacga gcccggagac   7320
tgctggcgtg ggcgacgacg cggcggttga ggtcctggat gtgccgtctc tgcgtgaaga   7380
ccaccggccc ccgggtcctg aacctaaaga gagttccaca gaatcaatgt ctgcatcgtt   7440
aacggcggcc tgcctgagga tctcctgcac gtcgcccgag ttgtcctgat aggcgatctc   7500
ggccatgaac tgttccactt cttcctcgcg gaggtcaccg tggcccgctc gctccacggt   7560
ggcggccagg tcgttggaga tgcggcgcat gagttgagag aaggcgttga ggccgttctc   7620
gttccacacg cggctgtaca ccacgtttcc gaaggagtcg cgcgctcgca tgaccacctg   7680
ggccacgttg agttccacgt ggcgggcgaa gacggcgtag tttctgaggc gctggaagag   7740
gtagttgagc gtggtggcga tgtgctcgca gacgaagaag tacataatcc agcgccgcag   7800
ggtcatctcg ttgatgtctc cgatggcttc gagacgctcc atggcctcgt agaagtcgac   7860
ggcgaagttg aaaaattggg agttgcgggc ggccaccgtg agttcttctt gcaggaggcg   7920
gatgagatcg gcgaccgtgt cgcgcacctc ctgttcgaaa gcgccccgag gcgcctctgc   7980
ttcttcctcc ggctcctcct cttccagggg ctcgggttcc tccggcagct ctgcgacggg   8040
gacggggcgg cgacgtcgtc gtctgaccgg caggcggtcc acgaagcgct cgatcatttc   8100
gccgcgccgg cgacgcatgg tctcggtgac ggcgcgtccg ttttcgcgag gtcgcagttc   8160
gaagacgccg ccgcgcagag cgccccccgtg cagggagggt aagtggttag ggccgtcggg   8220
cagggacacg gcgctgacga tgcattttat caattgctgc gtaggcactc cgtgcaggga   8280
tctgagaacg tcgaggtcga cgggatccga gaacttctct aggaaagcgt ctatccaatc   8340
gcaatcgcaa ggtaagctga gaacggtggg tcgctggggg gcgttcgcgg gcagttggga   8400
ggtgatgctg ctgatgatgt aattaaagta ggcggtcttc aggcggcgga tggtggcgag   8460
gaggaccacg tctttgggcc cggcctgttg aatgcgcagg cgctcggcca tgccccaggc   8520
ctcgctctga cagcgacgca ggtctttgta gaagtcttgc atcagtctct ccaccggaac   8580
ctctgcttct cccctgtctg ccatgcgagt cgagccgaac cccgcagggg gctgcagcaa   8640
cgctaggtcg gccacgaccc tttcggccag cacggcctgt tgaatctgcg tgagggtggc   8700
ctggaagtcg tccaggtcca cgaagcggtg ataggccccc gtgttgatgg tgtaggtgca   8760
gttggccatg acggaccagt tgacgacttg catgccgggt tgggtgatct ccgtgtactt   8820
gaggcgcgag taggccctgg actcgaacac gtagtcgttg catgtgcgca ccagatactg   8880
gtagccgacc aggaagtgag gaggcggctc tcggtacagg ggccagccaa cggtggcggg   8940
ggcgccgggg gacaggtcgt ccagcatgag gcggtggtag tggtagatgt agcgggagag   9000
ccaggtgatg ccggccgagg tggttgcggc cctggtgaat tcgcggacgc ggttccagat   9060
gttgcgcagg ggaccaaagc gctccatggt gggcacgctc tgccccgtga ggcgggcgca   9120
atcttgtacg ctctagatgg aaaaaagaca gggcggtcat cgactccttt ccgtagcttg   9180
gggggtaaag tcgcaagggt gcggcggcgg ggaaccccgg ttcgagaccg gccggatccg   9240
ccgctcccga tgcgcctggc cccgcatcca cgacgtccgc gccgagaccc agccgcgacg   9300
```

```
ctccgcccca atacggaggg gagtcttttg gtgttttttc gtagatgcat ccggtgctgc   9360
ggcagatgcg accccagacg cccactacca ccgccgtggc ggcagtaaac ctgagcggag   9420
gcggtgacag ggaggaggaa gagctggctt tagacctgga agagggagag ggctggccc    9480
ggctgggagc gccatcccca gagagacacc ctagggttca gctcgtgagg gacgccaggc   9540
aggcttttgt gccgaagcag aacctgttta gggaccgcag cggtcaggag gcggaggaga   9600
tgcgcgattg caggtttcgg gcgggcagag agctcagggc gggcttcgat cgggagcggc   9660
tcctgagggc ggaggatttc gagcccgacg agcgttctgg ggtgagcccg gcccgcgctc   9720
acgtatcggc ggccaacctg gtgagcgcgt acgagcagac ggtgaacgag gagcgcaact   9780
tccaaaagag ctttaacaat cacgtgagga ccctgatcgc gagggaggag gtgaccatcg   9840
ggctgatgca tctgtgggac ttcgtggagg cctacgtgca gaacccggct agcaaacccc   9900
tgacggccca gctgttcctg atcgtgcagc acagccgcga caacgagacg ttccgcgacg   9960
ccatgttgaa catcgcggag cccgagggtc gctggctctt ggatctgatt aacatcctgc  10020
agagcatcgt ggtgcaggag aggggcctga gtttagcgga caaggtggcg gccattaact  10080
attcgatgca gagcctgggg aagttctacg ctcgcaagat ctacaagagc ccttacgtgc  10140
ccatagacaa ggaggtgaag atagacagct tttacatgcg catggcgctg aaggtgctga  10200
cgctgagcga cgacctcggc gtgtaccgta acgacaagat ccacaaggcg gtgagcgcca  10260
gccgccggcg ggagctgagc gacagggagc tgatgcacag cctgcagagg gcgctggcgg  10320
gcgccgggga cgaggagcgc gaggcttact tcgacatggg agccgatctg cagtggcgtc  10380
ccagcgcgcg cgccttggag gcggcgggtt atcccgacga ggaggatcgg gacgatttgg  10440
aggaggcagg cgagtacgag gacgaagcct gaccgggcag gtgttgtttt agatgcagcg  10500
gccggcggac gggaccaccg cggatcccgc acttttggca tccatgcaga gtcaaccttc  10560
gggcgtgacc gcctccgatg actgggcggc ggccatggac cgcatcatgg cgctgaccac  10620
ccgcaacccc gaggctttta ggcagcaacc ccaggccaac cgtttttcgg ccatcttgga  10680
agcggtggtg ccgtcgcgca ccaacccgac gcacgagaaa gtcctgacta tcgtgaacgc  10740
cctggtagac agcaaggcca tccgccgtga cgaggcgggc ttgatttaca acgctctttt  10800
ggaacgcgtg gcgcgctaca acagcactaa cgtgcagacc aatctggacc gcctcaccac  10860
cgacgtgaag gaggcgctgg cgcagaagga gcggtttctg agggacagta atctgggctc  10920
tctggtggca ctgaacgcct tcctgagctc acagccggcc aacgtgcccc gcgggcagga  10980
ggattacgtg agcttcatca gcgctctgag actgctggtg tccgaggtgc cccagagcga  11040
ggtgtaccag tctgggccgg attacttttt ccagacgtcc cgacagggct tgcaaacggt  11100
gaacctgact caggccttta aaaacttgca aggcatgtgg ggggtcaagg ccccggtggg  11160
cgatcgcgcc actatctcca gtctgctgac ccccaacact cgcctgctgc tgctcttgat  11220
cgcaccgttt accaacagta gcactatcag ccgtgactcg tacctgggtc atctcatcac  11280
tctgtaccgc gaggccatcg gccaggctca gatcgacgag catacgtatc aggagattac  11340
taacgtgagc cgtgccctgg gtcaggaaga taccggcagc ctggaagcca cgttgaactt  11400
tttgctaacc aaccggaggc aaaaaatacc ctcccagttc acgttaagcg ccgaggagga  11460
gaggattctg cgatacgtgc agcagtccgt gagcctgtac ttgatgcgcg agggcgccac  11520
cgcttccacg gctttagaca tgacggctcg gaacatggaa ccgtcctttt actccgccca  11580
ccggccgttc attaaccgtc tgatggacta cttccatcgc gcggccgcca tgaacggga   11640
```

-continued

```
gtacttcacc aatgccatcc tgaatccgca ttggatgccc ccgtccggct tctacaccgg  11700
ggagtttgac ctgcccgaag ccgacgacgg ctttctgtgg gacgacgtgt ccgatagcat  11760
tttcacgccg gctaatcgcc gattccagaa gaaggagggc ggagacgagc tcccccctctc  11820
cagcgtggaa gcggcctcaa ggggagagag tccctttcca agtctgtctt ccgccagtag  11880
cggtcgggta acgcgtccac ggttgccggg ggagagcgac tacctgaacg accccttgct  11940
gcgaccggct agaaagaaaa attttcccaa taacggggtg gaaagcttgg tggataaaat  12000
gaatcgttgg aagacgtacg cccaggagca gcgggagtgg gaggacagtc agccgcggcc  12060
gctggtaccg ccgcattggc gtcgccagag agaagacccg gacgactccg cagacgatag  12120
tagcgtgttg gacctgggag ggagcggagc caacccctttt gctcacttgc aacccaaggg  12180
gcgctcgagt cgcctgtatt aataaaaaag acgcggaaac ttaccagagc catggccaca  12240
gcgtgtgtgc tttcttcctc tctttcttcc tcggcgcggc agaatgagaa gagcggtgag  12300
agtcacgccg gcggcgtatg agggcccgcc cccttcttac gaaagcgtga tgggatcagc  12360
gaacgtgccg gccacgctgg aggcgcctta cgttcctccc agatacctgg gacctacgga  12420
gggcagaaac agcatccgtt actccgagct ggcgcccctg tacgatacca cccaaggtgta  12480
cctggtggac aacaagtcgg cggacatcgc ctccctgaat taccaaaacg atcacagtaa  12540
ctttctgact accgtggtgc agaacaatga cttcaccccg acggaggcgg gcacgcagac  12600
cattaacttt gacgagcgtt cccgctgggg cggtcagctg aaaaccatcc tgcacaccaa  12660
catgcccaac atcaacgagt tcatgtccac caacaagttc agggctaagc tgatggtaga  12720
aaaaagtaat gcggaaactc ggcagccccg atacgagtgg ttcgagttta ccattccaga  12780
gggcaactat tccgaaacta tgactatcga tctcatgaat aacgcgatcg tggacaatta  12840
cctgcaagtg gggagacaga acggggtgct ggaaagcgat atcggcgtga aattcgatac  12900
cagaaacttc cgactggggt gggatcccgt gaccaagctg gtgatgccag gcgtgtacac  12960
caacgaggct tttcacccgg acatcgtgct gctgccgggg tgcggtgtgg acttcactca  13020
gagccgtttg agtaacctgt taggaattag aaagcgccgc cccttccaag agggctttca  13080
aatcatgtat gaggacctgg agggaggtaa tatacccgcc ttactggacg tgtcgaagta  13140
cgaagctagc atacaacgcg ccaaagcgga gggtagagag attcggggag acacctttgc  13200
ggtagctccc caggacctgg aaatagtgcc tttaactaaa gacagcaaag acagaagcta  13260
caatattata aacaacacga cggacaccct gtatcggagc tggtttctgg cttacaacta  13320
cggagacccc gagaaaggag tgagatcatg gaccatactc accaccacgg acgtgacctg  13380
tggctcgcag caagtgtact ggtccctgcc ggatatgatg caagacccgg tcaccttccg  13440
cccctccacc caagtcagca acttcccggt ggtgggcacc gagctgctgc ccgtccatgc  13500
caagagcttc tacaacgagc aggccgtcta ctcgcaactt attcgccagt ccaccgcgct  13560
tacccacgtg ttcaatcgct ttcccgagaa ccagattctg gtgcgccctc ccgctcctac  13620
cattaccacc gtcagtgaaa acgttcccgc cctcacagat cacggaaccc tgccgctgcg  13680
cagcagtatc agtggagttc agcgcgtgac catcaccgac gccagacgtc gaacctgccc  13740
ctacgtttac aaagcgcttg gcgtggtggc tcctaaagtt ctttctagtc gcaccttcta  13800
aaaacatgtc catcctcatc tctcccgata acaacaccgg ctggggactg ggctccggca  13860
agatgtacgg cggagccaaa aggcgctcca gtcagcaccc agttcgagtt cggggccact  13920
tccgcgctcc ttggggagct tacaagcgag gactctcggg tcgaacggct gtagacgata  13980
ccatagatgc cgtgattgcc gacgcccgcc ggtacaaccc cggaccggtc gctagcgccg  14040
```

-continued

```
cctccaccgt ggattccgtg atcgacagcg tggtagccgg cgctcgggcc tatgctcgcc  14100
gcaagaggcg gctgcatcgg agacgtcgcc ccaccgccgc catgctggca gccagggccg  14160
tgctgaggcg ggcccggagg gcaggcagaa gggctatgcg ccgcgctgcc gccaacgccg  14220
ccgccgggag ggcccgccga caggctgccc gccaggctgc cgctgccatc gctagcatgg  14280
ccagacccag gagagggaac gtgtactggg tgcgtgattc tgtgacggga gtccgagtgc  14340
cggtgcgcag ccgacctccc cgaagttaga agatccaagc tgcgaagacg gcggtactga  14400
gtctccctgt tgttatcagc ccaacatgag caagcgcaag tttaaagaag aactgctgca  14460
gacgctggtg cctgagatct atggccctcc ggacgtgaag ccagacatta agccccgcga  14520
tatcaagcgt gttaaaaagc gggaaaagaa agaggaactc gcggtggtag acgatggcgg  14580
agtggaattt attaggagtt tcgccccgcg acgcagggtt caatggaaag ggcggcgggt  14640
acaacgcgtt ttgaggccgg gcaccgcggt agtttttacc ccgggagagc ggtcggccgt  14700
taggggtttc aaaaggcagt acgacgaggt gtacggcgac gaggacatat tggaacaggc  14760
ggctcaacag atcggagaat ttgcctacgg aaagcgttcg cgtcgcgaag acctggccat  14820
cgccttagac agcggcaacc ccacgcccag cctcaaaccc gtgacgctgc agcaggtgct  14880
tcccgtgagc gccagcacgg acagcaagag ggggattaag agagaaatgg aagatctgca  14940
tcccaccatc caactcatgg tccctaaacg gcagaggctg gaagaggtcc tggagaagat  15000
gaaagtggac cccagcatag agccggatgt aaaagtcaga cctattaagg aagtggcccc  15060
cggtcttggg gtgcaaacgg tggacattca aatccccgtc accaccgctt caaccgccgt  15120
ggaagctatg gaaacgcaaa cggagacccc tgccgcgatc ggtaccaggg aagtggcgtt  15180
gcaaacggag ccttggtacg aatacgcagc ccctcggcgt cagaggcgtt ccgctcgtta  15240
cggccccgcc aacgccatca tgccagaata tgcgctgcat ccgtctattc tgcccactcc  15300
cggataccgg ggtgtgacgt atcgcccgtc tggaacccgc cgccgaaccc gtcgccgccg  15360
ccgctcccgt cgcgctctgg cccccgtgtc ggtgcggcgt gtgacccgcc ggggaaagac  15420
agtcgtcatt cccaacccgc gttaccaccc tagcatcctt taataactct gccgttttgc  15480
agatggctct gacttgccgc gtgcgccttc ccgttccgca ctatcgagga agatctcgtc  15540
gtaggagagg catgacgggc agtggtcgcc ggcgggcttt gcgcaggcgc atgaaaggcg  15600
gaattttacc cgccctgata cccataattg ccgccgccat cggtgccata cccggcgttg  15660
cttcagtggc gttgcaagca gctcgtaata aataaacaaa ggcttttgca cttatgacct  15720
ggtcctgact attttatgca gaaagagcat ggaagacatc aattttacgt cgctggctcc  15780
gcggcacggc tcgcggccgc tcatgggcac ctggaacgac atcggcacca gtcagctcaa  15840
cgggggcgct ttcaattggg ggagcctttg gagcggcatt aaaaactttg gctccacgat  15900
taaatcctac ggcagcaaag cctggaacag tagtgctggt cagatgctcc gagataaact  15960
gaaggacacc aacttccaag aaaaagtggt caatggggtg gtgaccggca tccacggcgc  16020
ggtagatctc gccaaccaag cggtgcagaa agagattgac aggcgtttgg aaagctcgcg  16080
ggtgccgccg cagagagggg atgaggtgga ggtcgaggaa gtagaagtag aggaaaagct  16140
gcccccgctg gagaaagttc ccggtgcgcc tccgagaccg cagaagcggc ccaggccaga  16200
actagaagag actctggtga cggagagcaa ggagcctccc tcgtacgagc aagccttgaa  16260
agagggcgcc tctccaccct cctacccgat gactaagccg atcgcaccca tggctcgacc  16320
ggtgtacggc aaggattaca agcccgtcac gctagagctg cccccaccgc cccccacgcg  16380
```

-continued

```
cccgaccgtc cccccccctgc cgactccgtc ggcggccgcg gcgggacccg tgtccgcacc 16440
atccgctgtg cctctgccag ccgcccgtcc agtggccgtg gccactgcca gaaaccccag 16500
aggccagaga ggagccaact ggcaaagcac gctgaacagc atcgtgggcc tgggagtgaa 16560
aagcctgaaa cgccgccgtt gctattatta aaaaagtgta gctaaaaagt ctcccgttgt 16620
atacgcctcc tatgttaccg ccagagacga gtgactgtcg ccgcgagcgc cgctttcaag 16680
atggccaccc catcgatgat gccgcagtgg tcttacatgc acatcgccgg ccaggacgcc 16740
tcggagtacc tgagtcccgg cctcgtgcag tttgcccgcg ccaccgacac ctacttcagc 16800
ttgggaaaca agtttagaaa ccccaccgtg gcccccaccc acgatgtgac cacggaccgc 16860
tcgcagaggc tgaccctgcg ctttgtgccc gtagaccggg aggacaccgc gtactcttac 16920
aaagtgcgct acacgttggc cgtaggggac aaccgagtgc tggacatggc cagcacctac 16980
tttgacatcc ggggggtgct ggatcggggt cccagcttca agccctattc cggcaccgct 17040
tacaactccc tggcccccaa gggagctccc aacccctcgg aatggacgga cacttccgac 17100
aacaaactta aagcatatgc tcaggctccc taccagagtc aaggacttac aaaggatggt 17160
attcaggttg ggctagttgt gacagagtca ggacaaacac cccaatatgc aaacaaagtg 17220
taccaacccg agccacaaat tggggaaaac caatggaatt tagaacaaga agataaagcg 17280
gcgggaagag tcctaaagaa agataccccct atgtttccct gctatgggtc atatgccagg 17340
cccacaaacg aacaaggagg gcaggcaaaa aaccaagaag tagatttaca gttttttgcc 17400
actccgggcg acacccagaa cacggctaaa gtggtacttt atgctgaaaa tgtcaacctg 17460
gaaactccag atactcactt agtgtttaaa cccgatgacg acagcaccag ttcaaaactt 17520
cttcttgggc agcaggctgc acctaacaga cccaactaca taggttttag agataatttt 17580
attggtttaa tgtactacaa tagcactgga aacatgggcg tgctggccgg acaggcttct 17640
caattgaatg ccgtagtcga cttgcaggac agaaacaccg agttgtccta ccagctgatg 17700
ctggacgcac tgggggatcg cagccgatat ttttcaatgt ggaatcaggc agtagacagc 17760
tatgacccag acgttagaat tatagaaaac cacggagtgg aagacgaact gccaaactat 17820
tgttttcctc tgggaggaat ggtggtgact gacaattaca actctgtgac gcctcaaaat 17880
ggaggcagtg gaaatacatg gcaggcagac aatactacat ttagtcaaag aggagcgcag 17940
attggctccg gaaacatgtt tgccctggaa attaacctac aggccaacct ctggcgcggc 18000
ttcttgtatt ccaatattgg gttgtatctt ccagactctc tgaaaatcac cccgacaac 18060
atcacgctgc cagaaaacaa aaacacttat cagtacatga acggtcgcgt aacgccaccc 18120
gggctcatag acacctatgt aaacgtgggc gcgcgctggt cccccgatgt catggacagc 18180
attaaccccct tcaaccacca ccgtaacgcg ggcttgcgct accgctccat gctcttgggc 18240
aacggccgtt atgtgccttt tcacattcag gtgccccaaa aattctttgc cattaaaaac 18300
ctgctgcttc tccccggttc ctatacctat gagtggaact tccgcaagga tgtcaacatg 18360
atcctgcaga gctcgctggg taatgacctg cgagtggacg gggccagcat acgctttgac 18420
agcattaacc tgtatgccaa cttttttccc atggcccaca acacggcctc taccctggaa 18480
gccatgctgc gcaacgacac caatgaccag tccttcaacg actacctgtg cgcggctaac 18540
atgctgtacc ccatccccgc caacgccacc agcgtgccca tttctattcc ttctcggaac 18600
tgggctgcct tcaggggctg gagttttact cgcctcaaaa ccaaggagac tccctcgctg 18660
ggctccggtt ttgaccccta ctttgtttac tccggctcca ttccctacct agatggcacc 18720
ttttacctca accacacttt caaaaaggtg tctattatgt ttgactcctc ggttagctgg 18780
```

-continued

```
cccggcaacg accgcctgct aacgcccaac gagttcgaaa ttaagcgttc cgtggacggt  18840
gaagggtaca acgtggccca gagcaacatg accaaggact ggtttctaat tcaaatgctc  18900
agtcactata atataggtta ccagggcttc tatgtgcccg agaactacaa ggaccgcatg  18960
tactccttct tccgcaactt ccaaccaatg agccggcagg tggtagatac cgtgacttat  19020
acagactaca aagatgtcaa gctcccctac caacacaaca actcagggtt cgtgggctac  19080
atgggaccca ccatgcgaga gggacaggcc tacccggcca actatcccta ccccctgatc  19140
ggagagactg ccgtacccag cctcacgcag aaaaagttcc tctgcgaccg ggtgatgtgg  19200
aggataccct tctctagcaa ctttatgtcg atgggctccc tcaccgacct ggggcagaac  19260
atgctgtacg ccaactccgc tcacgccttg gacatgactt ttgaggtgga tcccatggat  19320
gagcccacgc ttctctatgt tctgtttgaa gtcttcgacg tggtgcgcat ccaccagccg  19380
caccgcggcg tcatcgaggc cgtctacctg cgcacacctt tctctgccgg taacgccacc  19440
acctaaagaa gctgatgggt tccagcgaac aggagttgca ggccattgtt cgcgacctgg  19500
gctgcgggcc ctgctttttg ggcaccttcg acaagcgttt tcccggattc atgtcccccc  19560
acaagccggc ctgcgccatc gttaacacgg ccggacggga gacagggggg gtgcactggc  19620
tcgccttcgc ctggaacccg cgcaaccgca cctgctacct gttcgaccct tttggtttct  19680
ccgacgaaag gctgaagcag atctaccaat tcgagtacga ggggctcctc aagcgcagcg  19740
ctctggcctc cacgcccgac cactgcgtca ccctggaaaa gtccacccag acggtccagg  19800
ggcccctctc ggccgcctgc gggcttttct gttgcatgtt tttgcacgcc ttcgtgcact  19860
ggcctcacac ccccatggag cgcaacccca ccatggatct gctcaccgga gtgcccaaca  19920
gcatgcttca cagtccccag gtcgccccca ccctgcgtcg caatcaggac cacctgtatc  19980
gctttctggg gaaacactct gcctatttcc gccgccaccg gcagcgcatc gaacaggcca  20040
cggccttcga aagcatgagc caaagagtgt aatcaataaa aaccgttttt atttgacatg  20100
atacgcgctt ctggcgtttt tattaaaaat cgaagggttc gagggagggg tcctcgtgcc  20160
cgctggggag ggacacgttg cggtactgga atcgggcgct ccaacgaaac tcggggatca  20220
ccagccgcgg cagggccacg tcttccatgt tctgcttcca aaactgtcgc accagctgca  20280
gggctcccat cacgtcgggc gctgagatct tgaagtcgca gttagggccg gagcccccgc  20340
ggctgttgcg gaacacgggg ttggcacact ggaacaccaa cacgctgggg ttgtggatac  20400
tagccagggc cgtcgggtcg gtcacctccg atgcatccag atcctcggca ttgctcaggg  20460
cgaacggggt cagcttgcac atctgccgcc cgatctgggg taccaggtcg cgcttgttga  20520
ggcagtcgca gcgcagaggg atgaggatgc gacgctgccc gcgttgcatg atggggtaac  20580
tcgccgccag gaactcctct atctgacgga aggccatctg ggccttgacg ccctcggtga  20640
aaaatagccc acaggacttg ctggaaaaca cgttattgcc acagttgatg tcttccgcgc  20700
agcagcgcgc atcttcgttc ttcagctgaa ccacgttgcg accccagcgg ttctgaacca  20760
ccttggcttt cgtgggatgc tccttcagcg cccgctgtcc gttctcgctg gtcacatcca  20820
tttccaccac gtgctccttg cagaccatct ccactccgtg gaaacagaac agaatgccct  20880
cctgttgggt attgcgatgc tcccacacgg cgcacccggt ggactcccag ctcttgtgtt  20940
tcacccccgc gtaggcttcc atgtaagcca ttagaaatct gcccatcagc tcagtgaagg  21000
tcttctggtt ggtgaaggtt agcggcaggc cgcggtgttc ctcgttcaac caagtttgac  21060
agatcttgcg gtacacggct ccctggtcgg gcagaaactt aaaagtcgtt ctgctctcgt  21120
```

-continued

```
tgtccacgtg gaacttctcc atcaacatcg tcatgacttc catgcccttc tcccaggcag  21180
tcaccagcgg cgcgctctcg gggttcttca ccaacacggc ggtggagggg ccctcgccgg  21240
ccccgacgtc cttcatggac attttttgaa actccacggt gccgtccgcg cggcgtactc  21300
tgcgcatcgg agggtagctg aagcccacct ccatgacggt gctttcgccc tcgctgtcgg  21360
agacgatctc cggggagggc ggcggaacgg gggcagactt gcgagccttc ttcttgggag  21420
ggagcggagg cacctcctgc tcgcgctcgg gactcatctc ccgcaagtag gggtgatgg  21480
agcttcctgg ttggttctga cggttggcca ttgtatccta ggcagaaaga catggagctt  21540
atgcgcgagg aaactttaac cgccccgtcc cccgtcagcg acgaagaggt catcgtcgaa  21600
caggacccgg gctacgttac gccgcccgag gatctggagg ggcccttaga cgaccggcgc  21660
gacgctagtg agcggcagga aaatgagaaa gaggaggagg agggctgcta cctcctggaa  21720
ggcgacgttt tgctaaagca tttcgccagg cagagcacca tactcaagga ggccttgcaa  21780
gaccgctccg aggtgccctt ggacgtcgcc gcgctctccc aggcctacga ggcgaacctt  21840
ttctcgcccc gagtgcctcc gaagagacag cccaacggca cctgcgagcc caacccgcga  21900
ctcaacttct accccgtgtt cgccgtgccc gaggcgctgg ccacctacca catctttttc  21960
aaaaaccagc gcattcccct ttcctgccgg gccaaccgca ccgcggccga taggaagcta  22020
acactcagaa acggagtcag catacctgat atcacgtcac tggaggaagt gcctaagatc  22080
ttcgagggtc tgggtcgaga tgagaagcgg gcggcgaacg ctctgcagaa agaacagaaa  22140
gagagtcaga acgtgctggt ggagctggag gggggacaacg cgcgtctgac cgtcctcaaa  22200
cgttgcatag aagtttccca cttcgcctac ccggccctca acctgccgcc caaagttatg  22260
aaatcggtca tggaccagct actcatcaag agagctgagc ccctgaatcc cgaccaccct  22320
gaggcggaaa actcagagga cggaaagccc gtcgtcagcg acgaggagct cgagcggtgg  22380
ctggaaacca gggaccccca gcagttgcaa gagaggcgca agatgatgat ggcggccgtg  22440
ctggtcacgg tggagctaga atgcctgcaa cggtttttca gcgacgtgga gacgctacgc  22500
aaaatcgggg agtccctgca ctacaccttc cgccagggct acgttcgcca ggcctgcaaa  22560
atctccaacg tagagctcag caacctggtt tcctacatgg gcatcctcca cgagaaccgg  22620
ctggggcaga gcgtgctgca ctgcaccttg caaggcgagg cgcgaaggga ctacgtccga  22680
gactgcgtct acctcttcct caccctcacc tggcagaccg ccatgggcgt gtggcagcag  22740
tgcttggaag agagaaacct caaagagctg gacaaactcc tctgccgcca gcggcgggcc  22800
ctctggaccg gcttcagcga gcgcacggtc gcctgcgccc tggcagacat catttcccca  22860
gaacgcctga tgaaaacctt gcagaacggc ctgccggatt tcatcagtca gagcatcttg  22920
caaaacttcc gctccttcgt cctggagcgc tccgggatct tgcccgccat gagctgcgcg  22980
ctgccttctg actttgtccc cctttcctac cgcgagtgcc ctcccccact gtggagccac  23040
tgctacctct tccaactggc caactttctg gcctaccact ccgacctcat ggaagacgtg  23100
agcggagagg ggctgctcga gtgccactgc cgctgcaacc tctgcacccc ccacagatcg  23160
ctggcctgca acaccgagct gctcagcgaa acccaggtca taggtacctt cgagatccag  23220
gggccccagc agcaagaggg tgcttccggc ttgaagctca ctccggcgct gtggacctcg  23280
gcttacttac gcaaatttgt agccgaggac taccacgccc acaaaattca gttttacgaa  23340
gaccaatctc gaccaccgaa agccccccctc acggcctgcg tcatcaccca gagcaaaatc  23400
ctggcccaat tgcaatccat caaccaagcg cgccgagatt tccttttgaa aaagggtcgg  23460
ggggtgtacc tggaccccca gaccggcgag gaactcaacc cgtccacact ttccgtcgaa  23520
```

```
gcagcccccc cgagacatgc cacccaaggg aaccgccaag cagctgatcg ctcggcagag  23580
agcgaagaag caagagctgc tccagcagca ggtggaggac gaggaagagc tgtgggacag  23640
ccaggcagag gaggtgtcag aggacgagga ggagatggaa agctgggaca gcctagacga  23700
ggaggacgag ctttcagagg aagaggcgac cgaagaaaaa ccacctgcat ccagcgcgcc  23760
ttctctgagc cgacagccga agccccggcc cccgacgccc ccggccggct cactcaaagc  23820
cagccgtagg tgggacgcca ccggatctcc agcggcagcg gcaacggcag cgggtaaggc  23880
caaacgcgag cggcgggggt attgctcctg gcggacccac aaaagcagta tcgtgaactg  23940
cttgcaacac tgcgggggaa acatctcctt tgcccgacgc tacctcctct tccatcacgg  24000
tgtggccttc cctcgcaacg ttctctatta ttaccgtcat ctctacagcc cctacgaaac  24060
gctcggagaa aaaagctaag gcctcctctg ccgcgaggaa aaactccgcc gccgctgccg  24120
ccaaggatcc gccggccacc gaggagctga gaaagcgcat ctttcccact ctgtatgcta  24180
tctttcagca aagccgcggg cagcaccctc agcgcgaact gaaaataaaa aaccgctcct  24240
tccgctcact cacccgcagc tgtctgtacc acaagagaga agaccagctg cagcgcaccc  24300
tggacgacgc cgaagcactg ttcagcaaat actgctcagc gtctcttaaa gactaaaaga  24360
cccgcgcttt ttcccccctcg ggcgccaaaa cccacgtcat cgccagcatg agcaaggaga  24420
ttcccacccc ttacatgtgg agctatcagc cccagatggg cctggccgcg gggccgcccc  24480
aggactactc cagcaaaatg aactggctca gcgccggccc ccacatgatc tcacgagtta  24540
acggcatccg agcccaccga aaccagatcc tcttagaaca ggcggcaatc accgccacac  24600
cccggcgcca actcaacccg cccagttggc ccgccgccca ggtgtatcag gaaactcccc  24660
gcccgaccac agtcctcctg ccacgcgacg cggaggccga agtcctcatg actaactctg  24720
gggtacaatt agcgggcggg tccaggtacg ccaggtacag aggtcgggcc gctccttact  24780
ctcccgggag tataaagagg gtgatcattc gaggccgagg tatccagctc aacgacgagg  24840
cggtgagctc ctcaaccggt ctcagacctg acggagtctt ccagctcgga ggagcgggcc  24900
gctcttcctt caccactcgc caggcctacc tgaccctgca gagctcttcc tcgcagccgc  24960
gctccggggg aatcggcact ctccagttcg tggaagagtt cgtcccctcc gtctacttca  25020
acccgttttc cggctcacct ggacgctacc cggacgcctt cattcccaac tttgacgcag  25080
tgagtgaatc cgtggacggc tacgactgat gacagatggt gcggccgtga gagctcggct  25140
gcgacatctg catcactgcc gccagcctcg ctgctacgct cgggaggcga tcgtgttcag  25200
ctactttgag ctgccggacg agcaccctca gggaccggct cacgggttga aactcgagat  25260
tgagaacgcg cttgagtctc acctcatcga cgccttcacc gcccggcctc tcctggtaga  25320
aaccgaacgc gggatcacta ccatcaccct gttctgcatc tgccccacgc ccggattaca  25380
tgaagatctg tgttgtcatc tttgcgctca gtttaataaa aactgaactt tttgccgtac  25440
cttcaacgcc acgcgttgtt tctccttgtg aaaaaacccc aggagtcctt aacttacaca  25500
tagcaaaacc cttgtatttt accatagaaa aacaactagc cctttcaatt ggaaaagggt  25560
taacaatttc tgctacagga cagttggaaa gcacagcaag cgtacaggac agcgctacac  25620
cacccctacg tggtatttcc cctttaaagc tgacagacaa cggtttaaca ttaagctatt  25680
cagatcccct gcgtgtggta ggtgaccaac ttacgtttaa ttttacttct ccactacgtt  25740
acgaaaatgg cagtcttaca ttcaactaca cttctcccat gacactaata aacaacagtc  25800
ttgctattaa cgtcaatacc tccaaaggcc tcagtagtga caacggcaca ctcgctgtaa  25860
```

-continued

```
atgttactcc agattttaga tttaacagct ctggtgcctt aacttttggc atacaaagtc  25920
tatggacttt tccaaccaaa actcctaact gtaccgtgtt taccgaaagt gactccctgc  25980
tgagtctttg cttgactaaa tgcggagctc acgtacttgg aagcgtgagt ttaagcggag  26040
tggcaggaac catgctaaaa atgacccaca cttctgttac cgttcagttt tcgtttgatg  26100
acagtggtaa actaatattc tctccacttg cgaacaacac ttggggtgtt cgacaaagcg  26160
agagtccgtt gcccaaccca tccttcaacg ctctcacgtt tatgccaaac agtaccattt  26220
attctagagg agcaagtaac gaacctcaaa acaattatta tgtccagacg tatcttagag  26280
gcaacgtgcg aaagccaatt ctactaactg ttacctacaa ctcagttaat tcaggatatt  26340
ccttaacttt taaatgggat gctgtcgcca atgaaaaatt tgccactcct acatcttcgt  26400
tttgctatgt tgcagagcaa taaaaccctg ttaccccacc gtctcgtttt tttcagatga  26460
aacgagcgag agttgatgaa gacttcaacc cagtgtaccc ttatgacccc ccatacgctc  26520
ccgtcatgcc cttcattact ccgcctttta cctcctcgga tgggttgcag gaaaaaccac  26580
ttggagtgtt aagtttaaac tacagggatc ccattactac acaaaatggg tctctcacgt  26640
taaaactagg aaacggcctc actctaaaca accagggaca gttaacatca actgctggcg  26700
aagtggagcc tccgctcact aatgctaaca acaaacttgc actagcctat agcgaaccat  26760
tagcagtaaa aagcaaccgc ctaactctat cacacaccgc tccccttgtc atcgctaata  26820
attctttagc gttgcaagtt tcagagccta tttttgtaaa tgacgatgac aagctagccc  26880
tgcagacagc cgcccccctt gtaaccaacg ctggcaccct tcgcttacag agcgctgccc  26940
ctttaggatt ggttgaaaat actcttaaac tgctgttttc taaacccttg tatttgcaaa  27000
atgattttct tgcattagcc attgaacgcc ccctggctgt agcagccgca ggtactctga  27060
ccctacaact tactcctcca ttaaagacta acgatgacgg gctaacacta tccacagtcg  27120
agccattaac tgtaaaaaac ggaaacctag gcttgcaaat atcgcgccct ttagttgttc  27180
aaaacaacgg cctttcgctt gctattaccc ccccgctgcg tttgtttaac agcgaccccg  27240
ttcttggttt gggcttcact tttcccctag ctgtcacaaa caacctcctc tccttaaaca  27300
tgggagacgg agttaaactt acctataata aactaacagc caatttgggt agggatttac  27360
aatttgaaaa cggtgcgatt gccgtaacgc ttactgccga attacctttg caatacacta  27420
acaaacttca actgaatatt ggagctggcc ttcgttacaa tggagccagc agaaaactag  27480
atgtaaacat taaccaaaat aaaggcttaa cttgggacaa cgatgcagtt attcccaaac  27540
taggatcggg cttacaattt gaccctaatg gcaacatcgc tgttatccct gaaaccgtga  27600
agccgcaaac gttatggacg actgcagatc cctcgcctaa ctgctcagtg taccaggact  27660
tggatgccag gctgtggctc gctcttgtta aaagtggcga catggtgcat ggaagcattg  27720
ccctaaaagc cctaaaaggg acgttgctaa atcctacagc cagctacatt tccattgtga  27780
tatattttta cagcaacgga gtcaggcgta ccaactatcc aacgtttgac aacgaaggca  27840
ccttagctaa cagcgccact tggggatacc gacaggggca atctgctaac actaatgtga  27900
ccaatgccac tgaatttatg cccagctcaa gcaggtaccc cgtgaataaa ggagacaaca  27960
ttcaaaatca atctttttca tacacctgta ttaaaggaga ttttgctatg cctgtcccgt  28020
tccgtgtaac atataatcac gccctggaag ggtattccct taagttcacc tggcgcgttg  28080
tagccaatca ggcctttgat attccttgct gttcattttc atacatcaca gaataaaaaa  28140
ccactttttc attttaattt ctttttattt tacacgaaca gtgagacttc ctccaccctt  28200
ccatttgaca gcatacacca gcctctcccc cttcatagca gtaaactgtt gtgaatcagt  28260
```

-continued

```
ccggtatttg ggagttaaaa tccaaacagt ctctttggtg atgaaacgtc gatcagtaat  28320
ggacacaaat ccctgggaca ggttttccaa cgtttcggtg aaaaactgca caccgcccta  28380
caaaacaaac aggttcaggc tctccacggg ttatctcccc gatcaaactc agacagggta  28440
aaggtgcggt ggtgttccac taaaccacgc aggtggcgct gtctgaacct ctcggtgcga  28500
ctcctgtgag gctggtaaga agttagattg tccagtagcc tcacagcatg tatcatcagt  28560
ctacgagtgc gtctggcgca gcagcgcatc tgaatctcac tgagattccg gcaagaatcg  28620
cacaccatca caatcaggtt gttcatgatc ccatagctga acacgctcca gccaaagctc  28680
attcgctcca acagcgccac cgcgtgtccg tccaacctta ctttaacata aatcaggtgt  28740
ctgccgcgta caaacatgct acccacatac agaacttccc ggggcaggcc cctgttcacc  28800
acctgtctgt accagggaaa cctcacattt atcagggagc catagatggc cattttaaac  28860
caattagcta ataccgcccc accagctcta cactgaagag aaccgggaga gttacaatga  28920
cagtgaataa tccatctctc ataacccctg atggtctgat gaaaatctag atctaacgtg  28980
gcacaacaaa tacacacttt catatacatt ttcataacat gtttttccca ggccgttaaa  29040
atacaatccc aatacacggg ccactcctgc agtacaataa agctaataca agatggtata  29100
ctcctcacct cactgacact gtgcatgttc atattttcac attctaagta ccgagagttc  29160
tcctctacag cagcactgct gcggtcctca caaggtggta gctggtgatg attgtagggg  29220
gccagtctgc agcgataccg tctgtcgcgt tgcatcgtag accaggaacc gacgcacctc  29280
ctcgtacttg tggtagcaga accacgtccg ctgccagcac gtctccacgt aacgccggtc  29340
cctgcgtcgc tcacgctccc tcctcaatgc aaagtgcaac cactcttgta atccacacag  29400
atccctctcg gcctccgggg tgatgcacac ctcaaaccta cagatgtctc ggtacagttc  29460
caaacacgta gtgagggcga gttccaacca agacagacag cctgatctat cccgacacac  29520
tggaggtgga ggaagacacg gaagaggcat gttattccaa gcgattcacc aacgggtcga  29580
aatgaagatc ccgaagatga caacggtcgc ctccggagcc ctgatggaat ttaacagcca  29640
gatcaaacgt tatgcgattc tccaagctat cgatcgccgc ttccaaaaga gcctggaccc  29700
gcacttccac aaacaccagc aaagcaaaag cactattatc aaactcttca atcatcaagc  29760
tgcaggactg tacaatgcct aagtaatttt cgtttctcca ctcgcgaatg atgtcgcggc  29820
agatagtctg aaggttcatc ccgtgcaggg taaaaagctc cgaaagggcg ccctctacag  29880
ccatgcgtag acacaccatc atgactgcaa gatatcgggc tcctgagaca cctgcagcag  29940
atttaacaga tcaaggtcag gttgctctcc gcgatcacga atctccatcc gcaaggtcat  30000
ttgcaaaaaa ttaaataaat ctatgccgac tagatctgtc aactccgcat taggaaccaa  30060
atcaggtgtg gctacgcagc acaaaagttc cagggatggt gccaaactca ctagaaccgc  30120
tcccgagtaa caaaactgat gaatgggagt aacacagtgt aaaatgtgca accaaaaatc  30180
actaaggtgc tcctttaaaa agtccagtac ttctatattc agtccgtgca agtactgaag  30240
caactgtgcg ggaatatgca caacaaaaaa aatagggcgg ctcagataca tgttgaccta  30300
aaataaaaag aatcattaaa ctaaagaagc ttggcgaacg gtgggataaa tgacacgctc  30360
cagcagcaga caggcaaccg gctgtccccg ggaaccgcgg taaaattcat ccgaatgatt  30420
aaaaagaaca acagaaactt cccaccatgt actcggttgg atctcctgag cacacagcaa  30480
taccccccctc acattcatgt ccgccacaga aaaaaaacgt cccagatacc cagcggggat  30540
atccaacgac agctgcaaag acagcaaaac aatccctctg ggagcgatca caaaatcctc  30600
```

-continued

```
cggtgaaaaa agcacataca tattagaata accctgttgc tggggcaaaa aggcccggcg  30660

tcccagcaaa tgcacataaa tatgttcatc agccattgcc ccgtcttacc gcgtaatcag  30720

ccacgaaaaa atcgagctaa aattcaccca acagcctata gctatatata cactccgccc  30780

aatgacgcta ataccgcacc acccacgacc aaagttcacc cacacccaca aaacccgcga  30840

aaatccagcg ccgtcagcac ttccgcaatt tcagtctcac aacgtcactt ccgcgcgcct  30900

tttcacattc ccacacacac ccgcgccctt cgccccgccc tcgcgccacc ccgcgtcacc  30960

gcacgtcacc ccggccccgc ctcgctcctc cccgctcatt atcatattgg cacgtttcca  31020

gaataaggta tattattgat gatg                                         31044
```

<210> SEQ ID NO 6
<211> LENGTH: 34115
<212> TYPE: DNA
<213> ORGANISM: simian adenovirus SV-39

<400> SEQUENCE: 6

```
catcatcaat ataacaccgc aagatggcga ccgagttaac atgcaaatga ggtgggcgga     60

gttacgcgac ctttgtcttg ggaacgcgga agtgggcgcg gcgggtttcg gggaggagcg    120

cggggcgggg cgggcgtgtc gcgcggcggt gacgcgccgg ggacccggaa attgagtagt    180

ttttattcat tttgcaagtt tttctgtaca ttttggcgcg aaaactgaaa cgaggaagtg    240

aaaagtgaaa aatgccgagg tagtcaccgg gtggagatct gacctttgcc gtgtggagtt    300

tacccgctga cgtgtgggtt tcggtctcta ttttttcact gtggttttcc gggtacggtc    360

aaaggtcccc attttatgac tccacgtcag ctgatcgcta gggtatttaa tgcgcctcag    420

accgtcaaga ggccactctt gagtgccggc gagaagagtt ttctcctccg cgttccgcca    480

actgtgaaaa aatgaggaac ttcttgctat ctccggggct gccagcgacc gtagccgccg    540

agctgttgga ggacattgtt accggagctc tgggagacga tcctcaggtg atttctcact    600

tttgtgaaga ttttagtctt catgatctct atgatattga tccgggtgtt gaggggcaag    660

aggatgaatg gctggagtct gtggatgggt tttttccgga cgctatgctg ctagaggctg    720

atttgccacc acctcacaac tctcacactg agcccgagtc agctgctatt cctgaattgt    780

catcaggtga acttgacttg gcttgttacg agactatgcc tccggagtcg gatgaggagg    840

acagcgggat cagcgatccc acggctttta tggtctctaa ggcgattgct atactaaaag    900

aagatgatga tggcgatgat ggatttcgac tggacgctcc ggcggtgccg gggagagact    960

gtaagtcctg tgaataccac cgggatcgta ccggagaccc gtctatgttg tgttctctgt   1020

gttatctccg tcttaacgct gcttttgtct acagtaagtg ttttgtgctt ttttaccctg   1080

tggctttgtt gagtttattt ttttctgtgt ctcatagggt gttgtttatt ataggtcctg   1140

tttcagatgt ggaggaacct gatagtacta ctggaaatga ggaggaaaag ccctccccgc   1200

cgaaactaac tcagcgctgc agacctaata ttttgagacc ctcggcccag cgtgtgtcat   1260

cccggaaacg tgctgctgtt aattgcatag aagatttatt ggaagagccc actgaacctt   1320

tggacttgtc cttaaagcga ccccgcccgc agtagggcgc ggtgccagtt ttttctctct   1380

agcttccggg tgactcagtg caataaaaat ttcttggca acaggtgtat gtgtttactt   1440

tacgggcggg aagggattag gggagtataa agctggaggg gaaaaatctg aggctgtcag   1500

atcgagtgag aagttccatg gacttgtacg agagcctaga gaatctaagt tctttgcgac   1560

gtttgctgga ggaggcctcc gacagaacct cttacatttg gaggtttctg ttcggttccc   1620

ctctgagtcg ctttttgcac cgggtgaagc gagagcacct gacggaattt gatgggcttt   1680
```

```
tagagcagct gcctggactg tttgattctt tgaatctcgg ccaccggacg ctgctagagg   1740
agaggctttt tccacaattg gacttttcct ctccaggccg tctgtgttca gcgcttgctt   1800
ttgctgtaca tctgttggac agatggaacg agcagacgca gctcagcccg ggttacactc   1860
tggacttcct gacgctatgc ctatggaagt tcggaatcag gagggggagg aagctgtacg   1920
ggcgcttggt ggagaggcat ccgtctctgc gccagcagcg tctgcaagct caagtgctgc   1980
tgaggcggga ggatctggaa gccatttcgg aggaggagag cggcatggaa gagaagaatc   2040
cgagagcggg gctggaccct ccggcggagg agtagggggg ataccggacc cttttcctga   2100
gttggctttg gggcggtgg gggcgcttc tgtggtacgt gaggatgaag aggggcgcca   2160
acgcggtcag aagagggagc attttgagtc ctcgactttc ttggctgatg taaccgtggc   2220
cctgatggcg aaaaacaggc tggaggtggt gtggtacccg gaagtatggg aggactttga   2280
gaagggggac ttgcacctgc tggaaaaata taactttgag caggtgaaaa catactggat   2340
gaacccggat gaggactggg aggtggtttt gaaccgatac ggcaaggtag ctctgcgtcc   2400
cgactgtcgc taccaggttc gcgacaaggt ggtcctgcga cgcaacgtgt acctgttggg   2460
caacggcgcc accgtggaga tggtggaccc cagaaggggt ggttttgtgg ccaatatgca   2520
agaaatgtgc cctggggtgg tgggcttgtc tggggtgact tttcatagtg tgaggtttag   2580
cggtagcaat tttggggggtg tggttattac cgcgaacact cctgtggtcc tgcataattg   2640
ctactttttt ggcttcagca acacctgtgt ggaaatgagg gtgggaggca aagtgcgcgg   2700
gtgttccttt tacgcttgct ggaaggggggt ggtgagccag ggtaaggcta aagtgtctgt   2760
tcacaagtgt atgttggaga gatgcacctt gggcatttcc agtgagggct tcctccacgc   2820
cagcgacaac gtggcttctg acaacggctg cgcctttctt atcaagggag ggggtcgcat   2880
ctgtcacaac atgatatgcg gccctgggga tgtcccccca aagccttacc agatggttac   2940
ctgcacagat ggcaaggtgc gcatgctcaa gcctgtgcac attgtgggcc accggcgcca   3000
ccgctggcca gagtttgaac acaatgtgat gacccgctgt agcttgtacc tgggaggcag   3060
gcgaggagtt ttcttgccca gacagtgtaa cctggcccac tgcaacgtga tcatggaaca   3120
atccgccgct acccaggttt gctttggagg aatatttgat ataagcatgg tggtgtataa   3180
gatcctgcgc tacgacgact gtcgggctcg tactcgaacc tgcgactgcg gagcctctca   3240
cctgtgtaac ctgactgtga tggggatggt gactgaggag gtgcgactgg accactgtca   3300
gcactcttgc ctgcgggagg agttttcttc ctcggacgag gaggactagg taggtggttg   3360
gggcgtggcc agcgagaggg tgggctataa aggggaggtg tcggctgacg ctgtcttctg   3420
tttttcaggt accatgagcg gatcaagcag ccagaccgcg ctgagcttcg acggggccgt   3480
gtacagcccc tttctgacgg ggcgcttgcc tgcctgggcc ggagtgcgtc agaatgttac   3540
cggttcgacc gtggacggac gtcccgtgga tccatctaac gctgcttcta tgcgctacgc   3600
tactatcagc acatctactc tggacagcgc cgctgccgcc gcagccgcca cctcagccgc   3660
tctctccgcc gccaagatca tggctattaa cccaagcctt tacagccctg tatccgtgga   3720
cacctcagcc ctggagcttt accggcgaga tctagctcaa gtggtggacc aactcgcagc   3780
cgtgagccaa cagttgcagc tggtgtcgac ccgagtggag caactttccc gccctcccca   3840
gtaaccgcaa aaattcaata aacagaattt aataaacagc acttgagaaa agtttaaact   3900
tgtggttgac tttattcctg gatagctggg gggagggaac ggcgggaacg gtaagacctg   3960
gtccatcgtt cccggtcgtt gagaacacgg tggatttttt ccaagacccg atagaggtgg   4020
```

-continued

```
gtctgaacgt tgagatacat gggcatgagc ccgtctcggg ggtggaggta ggcccactgc   4080
agggcctcgt tttcaggggt ggtgttgtaa atgatccagt cgtaggcccc ccgctgggcg   4140
tggtgctgga agatgtcctt cagcagcaag ctgatggcaa cgggaagacc cttggtgtag   4200
gtgttgacaa agcggttgag ttgggagggg tgcatgcggg gactgatgag gtgcattttg   4260
gcctggatct tgaggttggc tatgttgccg cccagatcgc gcctgggatt catgttatgc   4320
aagaccacca gcaccgagta accggtgcag cgggggaatt tgtcgtgcag cttggaaggg   4380
aaagcgtgga agaatttgga gacccctcgg tgcccgccta ggttttccat gcactcatcc   4440
atgatgatgg cgatgggccc ccgggaggca gcctgggcaa aaacgttgcg gggtccgtg    4500
acatcgtagt tgtggtcctg ggtgagttca tcataggaca ttttgacaaa gcgcgggcag   4560
agggtcccag actggggaat gatggttcca tccggtccgg gggcgtagtt gccctcgcag   4620
atttgcattt cccaggcttt gatttcagag ggagggatca tgtcaacctg gggggcgatg   4680
aaaaaaatgg tctctggggc gggggtgatg agctgggtgg aaagcaggtt gcgcaagagc   4740
tgtgacttgc cgcagccggt gggcccgtag atgacagcta tgacgggttg cagggtgtag   4800
tttagagagc tacaactgcc atcatccttc aaaagcgggg ccacactgtt taaaagttct   4860
ctaacatgta agttttcccg cactaagtcc tgcaggagac gtgaccctcc tagggagaga   4920
agttcaggaa gcgaagcaaa gtttttaagt ggcttgaggc catcggccaa gggcaagttc   4980
ctgagagttt gactgagcag ttccagccgg tcccagagct cggttacgtg ctctacggca   5040
tctcgatcca gcagacctcc tcgtttcggg ggttggggcg gctctggctg tagggaatga   5100
ggcggtgggc gtccagctgg gccatggtgc ggtccctcca tgggcgcagg gttctcttca   5160
gggtggtctc ggtcacggtg aatgggtggg ccccgggctg ggcgctggcc agggtgcgct   5220
tgaggctgag gcggctggtg gcgaaccgtt gcttttcgtc tccctgcaag tcagccaaat   5280
agcaacggac catgagctca tagtccaggc tctctgcggc atgtcctttg gcgcgaagct   5340
tgcctttgga aacgtgcccg cagtttgagc agagcaagca ttttagcgcg tagagttttg   5400
gcgccaagaa cacggattcc ggggaataag catccccacc gcagttggag caaacggttt   5460
cgcattccac cagccaggtc agctgaggat cttttgggtc aaaaaccaag cgcccgccgt   5520
tttttttgat gcgcttccta cctcgggtct ccatgaggcg gtgcccgcgt tcggtgacga   5580
agaggctgtc ggtgtctccg tagacggagg tcagggcgcg ctcctccagg ggggtcccgc   5640
ggtcctcggc gtagagaaac tcgcaccact ctgacataaa cgcccgggtc caggctagga   5700
cgaatgaggc gatgtgggaa gggtaccggt cgttatcgat gagggggtcg gtttttttcca  5760
aggtgtgcag gcacatgtcc ccctcgtccg cttccaaaaa tgtgattggc ttgtaggtgt   5820
aagtcacgtg atcctgtcct tccgcggggg tataaaaggg ggcgtttccc ccctcctcgt   5880
cactctcttc cggttcgctg tcgccaaagg ccagctgttg gggtacgtaa acgcgggtga   5940
aggcgggcat gacctgtgcg ctgaggttgt cagtttctat atacgaggaa gatttgatgg   6000
cgagcgcccc cgtggagatg cccttgaggt gctcggggcc catttggtca gaaaacacaa   6060
tctgtcggtt atcaagcttg gtggcaaaag acccgtagag ggcgttggag agcaacttgg   6120
cgatggagcg ctgggtttgg tttttttccc ggtcggcttt ttccttggcc gcgatgttga   6180
gctggacgta ctccctggcc acgcacttcc agccgggaaa aacggccgtg cgctcgtccg   6240
gcaccagcct cacgctccat ccgcggttgt gcagggtgat gacgtcgatg ctggtggcca   6300
cctctccgcg caggggctcg ttggtccagc agaggcgacc gcccttgcga gagcagaagg   6360
ggggcagggg gtcaagcagg cgctcgtccg gggggtcggc gtcgatggta aagatggcgg   6420
```

-continued

```
gcagcaggtg tttgtcaaag taatcgatct gatgcccggg gcaacgcagg gcggtttccc   6480
agtcccgcac cgccaaggcg cgctcgtatg gactgagggg ggcgccccag ggcatgggat   6540
gcgtcagggc cgaggcgtac atgccgcaga tgtcatagac gtaaaggggc tcctccagga   6600
cgccgaggta ggtggggtag cagcgccccc cgcggatgct ggcccgtacg tagtcgtaga   6660
gctcgtgcga gggggccaga aggtggcggc tgaggtgagc gcgctggggc ttttcatctc   6720
ggaagaggat ctgcctgaag atggcgtggg agttggagga gatggtgggc cgctgaaaaa   6780
tgttgaagcg ggcgtcgggc agacccacgg cctcgccgat aaagtgggcg taggactctt   6840
gcagcttttc caccagggag gcggtgacca gcacgtccag agcgcagtag tccagggttt   6900
cccgcacgat gtcataatgc tcttcctttt tttccttcca gaggtctcgg ttgaagagat   6960
actcttcgcg gtctttccag tactcttgga gaggaaaccc gttttcgtct ccacggtaag   7020
agcccaacat gtaaaactgg ttgacggcct gatagggaca gcatcccttc tccacgggca   7080
gcgagtaggc cagggcggcc ttgcgcaggg aggtgtgagt cagggcaaag gtgtcgcgga   7140
ccataacttt tacaaactgg tacttaaagt cccggtcgtc gcacatgcct cgctcccagt   7200
ctgagtagtc tgtgcgcttt ttgtgcttgg ggttaggcag ggagtaggtg acgtcgttaa   7260
agaggatttt gccacatctg ggcataaagt tgcgagagat tctgaagggg ccgggcacct   7320
ccgagcggtt gttgatgact tggcagcca ggagaatttc gtcgaagccg ttgatgttgt   7380
gccccacgac gtagaactct atgaaacgcg gagcgccgcg cagcaggggg cacttttcaa   7440
gttgctggaa agtaagttcc cgcggctcga cgccgtgttc cgtgcggctc cagtcctcca   7500
ccgggtttcg ctccacaaaa tcctgccaga tgtggtcgac tagcaagagc tgcagtcggt   7560
cgcgaaattc gcggaatttt ctgccgatgg cttgcttctg gggggttcaag caaaaaaagg  7620
tgtctgcgtg gtcgcgccag gcgtcccagc cgagctcgcg agccagattc agggccagca   7680
gcaccagagc cggctcaccg gtgattttca tgacgaggag aaagggcacc agctgttttc   7740
cgaacgcgcc catccaggtg taggtctcca cgtcgtaggt gagaaacaga cgttcggtcc   7800
gcgggtgcga tcccaggggg aaaaacttga tgggctgcca ccattgggag ctctgggcgt   7860
ggatgtgatg gaagtaaaag tcccggcggc gcgtggaaca ttcgtgctgg tttttgtaaa   7920
agcggccgca gtggtcgcag cgcgagacgg agtgaaggct gtgaatcagg tgaatcttgc   7980
gtcgctgagg gggccccaga gccaaaaagc ggagcgggaa cgaccgcgcg gccacttcgg   8040
cgtccgcagg caagatggat gagggttcca ccgttccccg cccgcggacc gaccagactt   8100
ccgccagctg cggcttcagt tcttgcacca gctctcgcag cgtttcgtcg ctgggcgaat   8160
cgtgaatacg gaagttgtcg ggtagaggcg ggaggcggtg gacttccagg aggtgtgtga   8220
gggccggcag gagatgcagg tggtacttga tttcccacgg atgacggtcg cgggcgtcca   8280
aggcgaagag atgaccgtgg ggccgcggcg ccaccagcgt tccgcggggg gtctttatcg   8340
gcggcgggga cgggctcccg gcggcagcgg cggctcggga cccgcgggca agtcgggcag   8400
cggcacgtcg gcgtggagct cgggcagggg ctggtgctgc gcgcggagct gactggcaaa   8460
ggctatcacc cggcgattga cgtcctggat ccggcggcgc tgcgtgaaga ccaccggacc   8520
cgtggtcttg aacctgaaag agagttcgac agaatcaatc tcggcatcgt taaccgcggc   8580
ctggcgcagg atttcggcca cgtccccgga gttgtcttga tacgcgattt ctgccatgaa   8640
ctggtcgatt tcctcttcct gcaagtctcc gtgaccggcg cgttcgacgg tggccgcgag   8700
atcgttggag atgcggccca tgagctggga aaaggcattg atgccgacct cgttccacac   8760
```

-continued

```
tcggctgtac accacctctc cgtgaacgtc gcgggcgcgc atcaccacct gggcgagatt   8820
gagttccacg tggcgggcga aaaccggata gtttcggagg cgctgataca gatagttgag   8880
ggtggtggcg gcgtgctcgg ccacaaaaaa atacatgatc cagcggcgga gggtcagctc   8940
gttgatgtcg cccagcgcct ccaggcgttc catggcctcg taaaagtcca cggcaaagtt   9000
gaaaaattgg ctgttcctgg ccgagaccgt gagctcttct tccaagagcc gaatgagatc   9060
cgccacggtg gccctgactt cgcgttcgaa agccccgggt gcctcctcca cctcttcctc   9120
ctcgacttct tcgaccgctt cggcacctc ctcttcctcg accaccacct caggcggggc   9180
tcggcggcgc cggcggcgga cgggcaggcg gtcgacgaaa cgctcgatca tttccccccct   9240
ccgtcgacgc atggtctcgg tgacggcgcg accctgttcg cgaggacgca gggtgaaggc   9300
gccgccgccg agcggaggta acagggagat cgggggggcgg tcgtggggga gactgacggc   9360
gctaactatg catctgatca atgtttgcgt agtgacctcg ggtcggagcg agctcagcgc   9420
ttgaaaatcc acgggatcgg aaaaccgttc caggaacgcg tctagccaat cacagtcgca   9480
aggtaagctg aggaccgtct cggggggcttg tctgttctgt cttcccgcgg tggtgctgct   9540
gatgaggtag ttgaagtagg cgctcttgag gcggcggatg gtggacagga gaaccacgtc   9600
tttgcgccca gcttgctgta tccgcaggcg gtcggccatg ccccacactt ctccttgaca   9660
gcggcggagg tccttgtagt attcttgcat cagcctttcc acgggcacct cgtcttcttc   9720
ttccgctcgg ccggacgaga gccgcgtcag gccgtacccg cgctgcccct gtggttggag   9780
cagggccagg tcggccacga cgcgctcggc cagcacggcc tgctggatgc gggtgagggt   9840
gtcctgaaag tcgtcgagat ccacaaagcg gtggtacgcg ccagtgttga tggtgtaggt   9900
gcagttgctc atgacggacc agtttacggt ctgggtgcca tggcccacgg tttccaggta   9960
gcggagacgc gagtaggccc gcgtctcgaa gatgtagtcg ttgcaggtcc gcagcaggta  10020
ctggtagccc accagcagat gcggcggcgg ctggcggtag aggggccacc gctgggtggc  10080
gggggcgttg gggcgagat cttccaacat gaggcggtga tagccgtaga tgtagcgcga  10140
catccaagtg atgccgctgg ccgtggtgct ggcgcgggcg tagtcgcgaa cgcggttcca  10200
gatgtttcgc agcggctgga agtactcgat ggtggggcga ctctgccccg tgaggcgggc  10260
gcagtcggcg atgctctacg gggaaaaaga agggccagtg aacaaccgcc ttccgtagcc  10320
ggaggagaac gcaagggggt caaagaccac cgaggctcgg gttcgaaacc cgggtggcgg  10380
cccgaatacg gagggcggtt ttttgctttt ttctcagatg catcccgtgc tgcggcagat  10440
gcgtccgaac gcggggtccc agtccccggc ggtgcctgcg gccgtgacgg cggcttctac  10500
ggccacgtcg cgctccaccc cgcctaccac ggcccaggcg gcggtggctc tgcgcggcgc  10560
aggggaaccc gaagcagagg cggtgttgga cgtggaggag ggccaggggt tggctcggct  10620
gggggccctg agtcccgagc ggcacccgcg cgtggctctg aagcgcgacg cggcggaggc  10680
gtacgtgccg cggagcaatc tgtttcgcga ccgcagcggc gaggaggccg aggagatgcg  10740
agacttgcgt tttcgggcgg ggagggagtt gcgtcacggg ctggaccggc agagggttct  10800
gagagaggag gactttgagg cggacgagcg cacgggggtg agtcccgcgc gggctcacgt  10860
ggcggccgcc aacctggtga gcgcgtacga gcagacggtc aaggaggaga tgaacttcca  10920
gaagagcttc aatcatcacg tgcgcacgct gattgcgcgc gaagaggtgg ccatcggcct  10980
catgcatctg tgggattttg tggaggcgta cgttcagaac cccagcagca agccgctgac  11040
ggctcagctg ttcctcatcg tgcaacatag tcgagacaac gaaacgttca gggaggccat  11100
gctgaacatt gcagagcctg aggggcgctg gctcttggat ctcattaaca tcttgcagag  11160
```

-continued

```
tatcgtagtg caggagcgct cgctgagcct ggccgacaag gtggctgcca tcaactacag  11220
catgctgtcg ctgggcaaat tttacgcccg caagatctac aagtctccgt tcgtccccat  11280
agacaaggag gtgaagatag acagctttta catgcgcatg gcgctcaagg tgctgactct  11340
aagcgacgac ctgggggtgt accgcaacga ccgcatacac aaggcggtga gcgccagccg  11400
ccggcgcgag ctgagcgacc gcgagctttt gcacagcctg catcgggcgt tgactggtgc  11460
cggcagcgcc gaggcggccg agtactttga cgccggagcg gacttgcgct ggcagccatc  11520
ccgacgcgcg ctggaggcgg ctggcgtcgg ggagtacggg gtcgaggacg acgatgaagc  11580
ggacgacgag ttgggcattg acttgtagcc gtttttcgtt agatatgtcg gcgaacgagc  11640
cgtctgcggc cgccatggtg acggcggcgg gcgcgcccca ggacccggcc acgcgcgcgg  11700
cgctgcagag tcagccttcc ggagtgacgc ccgcggacga ctggtccgag gccatgcgtc  11760
gcatcctggc gctgacggcg cgcaaccccg aggcttttcg gcagcagccg caggcaaacc  11820
ggtttgcggc cattttggaa gcggtggtgc cctccagacc caaccccacc cacgaaaagg  11880
tgctggccat cgtcaacgcc ctggcggaga ccaaggccat ccgcccagac gaggccgggc  11940
aggtttacaa cgcgctgcta gaaagggtgg gacgctacaa cagctccaac gtgcagacca  12000
atctggaccg cttggtgacg gacgtgaagg aggccgtagc ccagcgagag cggtttttca  12060
aggaagccaa tctgggctcg ctggtggccc tcaacgcctt cctgagcacg ctgccggcga  12120
acgtgccccg cggtcaggag gactacgtga actttctgag cgccctccgc ctgatggtgg  12180
ccgaggtgcc gcagagcgag gtgtaccagt ctggccccaa ctactacttc cagacctccc  12240
ggcagggcct gcagacggta aacctgacgc aggcctttca gaacctgcag ggcctttggg  12300
gggtgcgcgc tccgctgggc gaccgcagca cggtgtccag cctgctgacc cccaatgccc  12360
ggctgctctt gcttctcatt gctccgttca ccgacagcgg ttccatcagc cgcgactctt  12420
acctgggaca cctgctcacc ctgtaccggg aggccatcgg gcaggcgcgg gtggacgagc  12480
agacgtacca ggaaatcacc agcgtgagcc gcgcgctggg gcaggaggac acgggcagct  12540
tggaggcgac tctgaacttc ctgctgacca accggcggca gcgcctacct ccccagtacg  12600
cgctgaacgc ggaggaggag cgcatcctgc gtttcgtgca gcagagcacc gcgctgtact  12660
tgatgcggga aggcgcctct cccagcgctt cgctggacat gacggcggcc aacatggagc  12720
catcgttcta cgccgccaac cgtcccttcg tcaaccggct aatggactat ttgcatcggg  12780
cggcggccct gaacccggaa tactttacta acgtcatcct gaacgaccgt tggctgccac  12840
ctcccggctt ctacacgggg gagttcgacc tcccggaggc caacgacggt ttcatgtggg  12900
acgacgtgga cagcgtgttc ctgcccggca agaaggaggc gggtgactct cagagccacc  12960
gcgcgagcct cgcagacctg gggcgaccg ggcccgcgtc tccgctgcct cgcctgccga  13020
gcgccagcag cgccagcgtg ggcgggtga gccgtccgcg cctcagcggt gaggaggact  13080
ggtggaacga tccgctgctc cgtccggccc gcaacaaaaa cttccccaac aacgggatag  13140
aggatttggt agacaaaatg aaccgttgga agacgtatgc ccaggagcat cgggagtggc  13200
aggcgaggca acccatgggc cctgttctgc cgccctctcg gcgcccgcgc agggacgaag  13260
acgccgacga ttcagccgat gacagcagcg tgttggatct gggcgggagc gggaacccct  13320
ttgcccacct gcaacctcgc ggcgtgggtc ggcggtggcg ctaggaaaaa aaattattaa  13380
aagcacttac cagagccatg gtaagaagag caacaaaggt gtgtcctgct ttcttcccgg  13440
tagcaaaatg cgtcgggcgg tggcagttcc ctccgcggca atggcgttag gcccgccccc  13500
```

-continued

```
ttcttacgaa agcgtgatgg cagcggccac cctgcaagcg ccgttggaga atccttacgt  13560
gccgccgcga tacctggagc ctacgggcgg gagaaacagc attcgttact cggagctgac  13620
gcccctgtac gacaccaccc gcctgtacct ggtggacaac aagtcagcag atatcgccac  13680
cttgaactac cagaacgacc acagcaactt tctcacgtcc gtggtgcaga acagcgacta  13740
cacgcccgcc gaagcgagca cgcagaccat taacttggac gaccgctcgc gctggggcgg  13800
ggacttgaaa accattctgc acactaacat gcccaacgtg aacgagttca tgtttaccaa  13860
ctcgttcagg gctaaactta tggtggcgca cgaggccgac aaggacccgg tttatgagtg  13920
ggtgcagctg acgctgccgg aggggaactt ttcagagatt atgaccatag acctgatgaa  13980
caacgccatt atcgaccact acctggcggt agccagacag caggggggtga aagaaagcga  14040
gatcggcgtc aagtttgaca cgcgcaactt tcgtctgggc tgggacccgg agacggggct  14100
tgtgatgccg ggggtgtaca cgaacgaagc tttccatccc gacgtggtcc tcttgccggg  14160
ctgcggggtg gactttacct acagccggtt aaacaacctg ctaggcatac gcaagagaat  14220
gccctttcag gaagggtttc agatcctgta cgaggacctg gagggcggta acatcccggc  14280
cctgctggac gtgccggcgt acgaggagag catcgccaac gcaagggagg cggcgatcag  14340
gggcgataat ttcgcggcgc agccccaggc ggctccaacc ataaaacccg ttttggaaga  14400
ctccaaaggg cggagctaca acgtaatagc caacaccaac aacacggctt acaggagctg  14460
gtatctggct tataactacg gcgacccgga gaagggggtt agggcctgga ccctgctcac  14520
cactccggac gtgacgtgcg gttcagagca ggtctactgg tcgctgcctg acatgtacgt  14580
ggaccctgtg acgtttcgct ccacgcagca agttagcaac tacccagtgg tgggagcgga  14640
gcttatgccg attcacagca agagctttta caacgagcag gccgtctact cacagctcat  14700
tcgtcagacc accgccctaa cgcacgtttt caaccgcttc cccgagaacc aaatcctagt  14760
gcgacctcca gcgcccacca tcaccaccgt cagcgagaac gtgcccgctc taaccgatca  14820
cgggacgctg cctttgcaga acagcatccg cggagttcag cgagttacca tcacggacgc  14880
ccgtcgtcgg acctgtccct acgtctacaa agccttggga atcgtggccc cgcgcgtcct  14940
gtcgagtcgc actttctaga tgtccatcct catctctccc agcaacaata ccggttgggg  15000
tctgggcgtg accaaaatgt acggaggcgc caaacgacgg tccccacaac atcccgtgcg  15060
agtgcgcggg cactttagag ccccatgggg gtcgcacacg cgcgggcgca ccggccgaac  15120
caccgtcgac gacgtgatcg atagcgtggt ggccgacgcc cgcaactacc agcccgctcg  15180
atccacggtg gacgaagtca tcgacggcgt ggtggccgac gccagggcct acgcccgcag  15240
aaagtctcgt ctgcgccgcc gccgttcgct aaagcgcccc acggccgcca tgaaagccgc  15300
tcgctctctg ctgcgtcgcg cacgtatcgt gggtcgccgc gccgccagac gcgcagccgc  15360
caacgccgcc gccggccgag tgcgccgccg ggccgcccag caggccgccg ccgccatctc  15420
cagtctatcc gccccccgac gcgggaatgt gtactgggtc agggactcgg ccaccggcgt  15480
gcgagttccc gtgagaaccc gtcctcctcg tccctgaata aaaagttcta agcccaatcg  15540
gtgttccgtt gtgtgttcag ctcgtcatga ccaaacgcaa gtttaaagag gagctgctgc  15600
aagcgctggt ccccgaaatc tatgcgccgg cgccggacgt gaaaccgcgt cgcgtgaaac  15660
gcgtgaagaa gcaggaaaag ctagagacaa aagaggaggc ggtggcgttg ggagacgggg  15720
aggtggagtt tgtgcgctcg ttcgcgccgc gtcggcgagt gaattggaag ggcgcaaggg  15780
tgcaacgggt gctgcgtccc ggcacggtgg tgtctttcac ccgggtgaa aaatccgcct  15840
ggaagggcat aaagcgcgtg tacgatgagg tgtacgggga cgaagacatt ctggagcagg  15900
```

-continued

```
cgctggatag aagcggggag tttgcttacg gcaagagggc gaggacgggc gagatcgcca  15960
tcccgctgga cacttccaac cccaccccca gtctgaaacc cgtgacgctg caacaggtgt  16020
tgccggtgag cgccccctcg cgacgcggca taaaacgcga gggcggcgag ctgcagccca  16080
ccatgcagct cctggttccc aagaggcaga aactagagga cgtactggac atgataaaaa  16140
tggagcccga cgtgcagccc gatattaaaa tccgtcccat caaagaagtg gcgccgggaa  16200
tgggcgtgca gaccgtggac atccagattc ccatgaccag cgccgcacag gcggtagagg  16260
ccatgcagac cgacgtgggg atgatgacgg acctgcccgc agctgctgcc gccgtggcca  16320
gcgccgcgac gcaaacggaa gccggcatgc agaccgaccc gtggacggag gcgcccgtgc  16380
agccggccag aagacgcgtc agacggacgt acggccccgt ttctggcata atgccggagt  16440
acgcgctgca tccttccatc atccccaccc ccggctaccg gggcgcacc taccgtccgc  16500
gacgcagcac cactcgccgc cgtcgccgca cggcacgagt cgccaccgcc agagtgagac  16560
gcgtaacgac acgtcgcggc cgccgcttga ccctgcccgt ggtgcgctac catcccagca  16620
ttctttaaaa aaccgctcct acgttgcaga tgggcaagct tacttgtcga ctccgtatgg  16680
ccgtgcccgg ctaccgagga agatcccgcc gacgacggac tttgggaggc agcggtttgc  16740
gccgccgtcg ggcggttcac cggcgcctca agggaggcat tctgccggcc ctgatcccca  16800
taatcgccgc agccatcggg gccattcccg gaatcgccag cgtagcggtg caggctagcc  16860
agcgccactg attttactaa ccctgtcggt cgcgccgtct ctttcggcag actcaacgcc  16920
cagcatggaa gacatcaatt tctcctctct ggccccgcgg cacggcacgc ggccgtatat  16980
ggggacgtgg agcgagatcg gcacgaacca gatgaacggg ggcgctttca attggagcgg  17040
tgtgtggagc ggcttgaaaa atttcggttc cactctgaaa acttacggca accgggtgtg  17100
gaactccagc acggggcaga tgctgaggga caagctaaag gacacgcagt ttcagcaaaa  17160
ggtggtggac ggcatcgctt cgggcctcaa cggcgccgtc gacctggcca accaggccat  17220
tcaaaaggaa attaacagcc gcctggagcc gcggccgcag gtggaggaga acctgccccc  17280
tctggaggcg ctgcccccca agggagagaa gcgcccgcgg cccgacatgg aggagacgct  17340
agttactaag agcgaggagc cgccatcata cgaggaggcg gtgggtagct cgcagctgcc  17400
gtccctcacg ctgaagccca ccacctatcc catgaccaag cccatcgcct ccatggcgcg  17460
ccccgtggga gtcgacccgc ccatcgacgc ggtggccact ttggacctgc cgcgccccga  17520
acccggcaac cgcgtgcctc ccgtccccat cgctccgccg gtttctcgcc ccgccatccg  17580
ccccgtcgcc gtggccactc cccgctatcc gagccgcaac gccaactggc agaccaccct  17640
caacagtatt gtcggactgg gggtgaagtc tctgaagcgc cgtcgctgtt tttaaagcac  17700
aatttattaa acgagtagcc ctgtcttaat ccatcgttgt atgtgtgcct atatcacgcg  17760
ttcagagcct gaccgtccgt caagatggcc actccgtcga tgatgccgca gtggtcgtac  17820
atgcacatcg ccgggcagga cgcctcggag tacctgagcc cgggtctggt gcagtttgcc  17880
cgtgcgacgg aaacctactt ctcactgggc aacaagttca ggaaccccac cgtggcgccc  17940
acccacgacg tcaccaccga tcggtcccag cgactgacaa tccgcttcgt ccccgtggac  18000
aaggaagaca ccgcttactc ctacaaaacc cgcttcacgc tggccgtggg cgacaaccgg  18060
gtgctagaca tggccagtac ctactttgac atccgcggcg tgatcgaccg cggacctagc  18120
ttcaagcctt actccggcac ggcttacaac tcactggctc ccaaaggggc gcccaacaac  18180
agccaatgga acgccacaga taacgggaac aagccagtgt gttttgctca ggcagctttt  18240
```

-continued

```
ataggtcaaa gcattacaaa agacggagtg caaatacaga actcagaaaa tcaacaggct  18300
gctgccgaca aaacttacca accagagcct caaattggag tttccacctg ggataccaac  18360
gttaccagta acgctgccgg acgagtgtta aaagccacca ctcccatgct gccatgttac  18420
ggttcatatg ccaatcccac taatccaaac gggggtcagg caaaaacaga aggagacatt  18480
tcgctaaact ttttcacaac aactgcggca gcagacaata atcccaaagt ggttctttac  18540
agcgaagatg taaaccttca agcccccgat actcacttag tatataagcc aacggtggga  18600
gaaaacgtta tcgccgcaga agccctgcta acgcagcagg cgtgtcccaa cagagcaaac  18660
tacataggtt tccgagataa ctttatcggt ttaatgtatt ataacagcac agggaacatg  18720
ggagttctgg caggtcaggc ctcgcagtta aacgcagttg tagacctgca agatcgaaac  18780
acggaactgt cctatcagct aatgctagat gctctgggtg acagaactcg atatttctca  18840
atgtggaatc aggccgtgga cagctacgat ccagacgtta ggattatcga gaaccatggg  18900
gtggaagacg agctgcccaa ttactgtttt ccactcccag gcatgggtat ttttaactcc  18960
tacaaggggg taaaaccaca aaatggcggt aatggtaact gggaagcaaa cggggaccta  19020
tcaaatgcca atgagatcgc tttaggaaac atttttgcca tggaaattaa cctccacgca  19080
aacctgtggc gcagcttctt gtacagcaat gtggcgctgt acctgccaga cagctataaa  19140
ttcactcccg ctaacatcac tctgcccgcc aaccaaaaca cctacgagta tatcaacggg  19200
cgcgtcactt ctccaaccct ggtggacacc tttgttaaca ttggagcccg atggtcgccg  19260
gatcccatgg acaacgtcaa ccccttttaac catcaccgga acgcgggcct ccgttaccgc  19320
tccatgctgc tgggaaatgg acgcgtggtg cctttccaca tacaagtgcc gcaaaaattt  19380
ttcgcgatta agaacctcct gcttttgccc ggctcctaca cttacgagtg gagcttcaga  19440
aaagacgtga acatgattct gcagagcacc ctgggcaatg atcttcgagt ggacggggcc  19500
agcgtccgca ttgacagcgt caacttgtac gccaactttt tccccatggc gcacaacacc  19560
gcttctacct tggaagccat gctgcgaaac gacaccaacg accagtcgtt taacgactac  19620
ctcagcgcgg ccaacatgct ttatcccatt ccggccaacg ccaccaacgt tcccatttcc  19680
attccctccc gcaactgggc ggccttccgg ggatggagct tcacccgcct taaagccaag  19740
gaaacgcctt ccttgggctc cggctttgac ccctactttg tgtactcagg caccattcct  19800
tacctggacg gcagctttta cctcaaccac actttcaaac gtctgtccat catgttcgat  19860
tcttccgtaa gttggccggg caacgaccgc ctcctgacgc cgaacgagtt cgaaattaag  19920
cgcattgtgg acggggaagg ctacaacgtg gctcaaagta acatgaccaa agactggttt  19980
ttaattcaaa tgctcagcca ctacaacatc ggctaccaag gcttctatgt tcccgagggc  20040
tacaaggatc ggatgtattc tttcttccga aactttcagc ccatgagccg ccaggtgccg  20100
gatcccaccg ctgccggcta tcaagccgtt cccctgccca gacaacacaa caactcgggc  20160
tttgtggggt acatgggccc gaccatgcgc gaaggacagc catacccggc caactacccc  20220
tatcccctga tcggcgctac cgccgtcccc gccattaccc agaaaaagtt tttgtgcgac  20280
cgcgtcatgt ggcgcatacc tttttccagc aactttatgt caatgggggc cctgaccgac  20340
ctcggacaga acatgcttta cgctaactcc gcccatgccc tggatatgac ttttgaggtg  20400
gaccccatga acgagcccac gttgctgtac atgctttttg aggtgttcga cgtggtcaga  20460
gtgcaccagc cgcaccgcgg tattatcgag gccgtgtacc tgcgcacccc cttctctgcg  20520
ggcaatgcca ccacataagc cgctgaacta gctggttttt accccagatc ccatgggctc  20580
cacggaagac gaactgcggg ccattgtgcg agacctgggc tgcggaccct acttcctggg  20640
```

-continued cacctttgac aagcggtttc ccgggttcgt gtctcctcgc aaactcgcgt gcgcgatcgt 20700
gaataccgcc ggccgagaga ccggaggaga gcattggcta gctctgggct ggaacccccg 20760
ctcgtccacg tttttcctgt tcgacccctt tggcttttca gaccaacgct tgaagcagat 20820
ctatgcattt gaatatgagg gtctactcaa gcgaagcgcg ctggcctcct ccgccgatca 20880
ctgtctaacc ctggtaaaga gcactcagac ggttcagggc cctcacagcg ccgcctgtgg 20940
cctttttgt tgcatgtttt tgcacgcctt tgtgaactgg ccggacaccc ccatggaaaa 21000
caaccccacc atggacctcc tgactggcgt tcccaactcc atgctccaaa gccccagcgt 21060
gcagaccacc ctcctccaaa accagaaaaa tctgtacgcc tttctgcaca agcactctcc 21120
ctactttcgc cgccatcggg aacaaataga aaatgcaacc gcgtttaaca aaactctgta 21180
acgtttaata aatgaacttt ttattgaact ggaaaacggg tttgtgattt ttaaaaatca 21240
aaggggttga gctggacatc catgtgggag gccggaaggg tggtgttctt gtactggtac 21300
ttgggcagcc acttaaactc tggaatcaca aacttgggca gcggtatttc tgggaagttg 21360
tcgtgccaca gctggcgggt cagctgaagt gcctgcagaa catcgggggc ggagatcttg 21420
aagtcgcagt ttatctggtt cacggcacgc gcgttgcggt acatgggatt ggcacactga 21480
aacaccagca ggctgggatt cttgatgcta gccagggcca cggcgtcggt cacgtcaccg 21540
gtgtcttcta tgttggacag cgaaaaaggc gtgactttgc aaagctggcg tcccgcgcga 21600
ggcacgcaat ctcccaggta gttgcactca cagcggatgg gcagaagaag atgcttgtgg 21660
ccgcgggtca tgtagggata ggccgctgcc ataaaagctt cgatctgcct gaaagcctgc 21720
ttggccttgt gcccttcggt ataaaaaaca ccgcaggact tgttggaaaa ggtattactg 21780
gcgcaagcgg catcgtgaaa gcaagcgcgt gcgtcttcgt ttcgtaactg caccacgctg 21840
cggccccacc ggttctgaat caccttggcc ctgccggggt tttccttgag agcgcgctgg 21900
ccggcttcgc tgcccacatc catttccacg acatgctcct tgttaatcat ggccagaccg 21960
tggaggcagc gcagctcctc gtcatcgtcg gtgcagtgat gctcccacac gacgcagcca 22020
gtgggctccc acttgggctt ggaggcctcg gcaatgccag aatacaggag aacgtagtgg 22080
tgcagaaaac gtcccatcat ggtgccaaag gttttctggc tgctgaaggt catcgggcag 22140
tacctccagt cctcgttaag ccaagtgttg cagatcttcc tgaagaccgt gtactgatcg 22200
ggcataaagt ggaactcatt gcgctcggtc ttgtcgatct tatacttttc catcagacta 22260
tgcataatct ccatgccctt ttcccaggcg caaacaatct tggtgctaca cgggttaggt 22320
atggccaaag tggttggcct ctgaggcggc gcttgttctt cctcttgagc cctctcccga 22380
ctgacggggg ttgaaagagg gtgcccttg gggaacggct tgaacacggt ctggcccgag 22440
gcgtcccgaa gaatctgcat cggggattg ctggccgtca tggcgatgat ctgaccccgg 22500
ggctcctcca cttcgtcctc ctcgggactt tcctcgtgct tttcggggga cggtacggga 22560
gtaggggaa gagcgcggcg cgccttcttc ttgggcggca gttccggagc ctgctcttga 22620
cgactggcca ttgtcttctc ctaggcaaga aaaacaagat ggaagactct ttctcctcct 22680
cctcgtcaac gtcagaaagc gagtcttcca ccttaagcgc cgagaactcc cagcgcatag 22740
aatccgatgt gggctacgag actcccccg cgaacttttc gccgcccccc ataaacacta 22800
acgggtggac ggactacctg gccctaggag acgtactgct gaagcacatc aggcggcaga 22860
gcgttatcgt gcaagatgct ctcaccgagc gactcgcggt tccgctggaa gtggcggaac 22920
ttagcgccgc ctacgagcga accctcttct ccccaaagac tccccccaag aggcaggcta 22980

-continued

```
acggcacctg cgagcctaac cctcgactca acttctaccc tgcctttgcc gtgccagagg  23040
tactggctac gtaccacatt tttttccaaa accacaaaat ccctctctcg tgccgcgcca  23100
accgcaccaa agccgatcgc gtgctgcgac tggaggaagg ggctcgcata cctgagattg  23160
cgtgtctgga ggaagtccca aaaatctttg aaggtctggg ccgcgacgaa aagcgagcag  23220
caaacgctct ggaagagaac gcagagagtc acaacagcgc cttggtagaa ctcgagggcg  23280
acaacgccag actggccgtc ctcaaacggt ccatagaagt cacgcacttc gcctaccccg  23340
ccgttaacct ccctccaaaa gttatgacag cggtcatgga ctcgctgctc ataaagcgcg  23400
ctcagccctt agacccagag cacgaaaaca acagtgacga aggaaaaccg gtggtttctg  23460
atgaggagtt gagcaagtgg ctgtcctcca acgaccccgc cacgttggag gaacgaagaa  23520
aaaccatgat ggccgtggtg ctagttaccg tgcaattaga atgtctgcag aggttctttt  23580
cccacccaga gaccctgaga aaagtggagg aaacgctgca ctacacattt aggcacggct  23640
acgtgaagca agcctgcaag atttccaacg tagaacttag caacctcatc tcctacctgg  23700
ggatcttgca cgaaaaccgc ctcggacaaa acgtgctgca cagcacactg aaaggagaag  23760
cccgccgaga ctatgtgcga gactgcgtgt tcctagcgct agtgtacacc tggcagagcg  23820
gaatgggagt ctggcagcag tgcctggagg acgaaaacct caaagagctt gaaaagctgc  23880
tggtgcgctc cagaagggca ctgtggacca gttttgacga gcgcaccgcc gcgcgagacc  23940
tagctgatat tatttttcct cccaagctgg tgcagactct ccgggaagga ctgccagatt  24000
ttatgagtca aagcatcttg caaaacttcc gctctttcat cttggaacgc tcgggaatct  24060
tgcccgccac tagctgcgcc ctacccacag attttgtgcc tctccactac cgcgaatgcc  24120
caccgccgct gtggccgtac acttacttgc ttaaactggc caactttcta atgttccact  24180
ctgacctggc agaagacgtt agcggcgagg ggctgctaga atgccactgc cgctgcaacc  24240
tgtgcacccc ccaccgctct ctagtatgca acactcccct gctcaatgag acccagatca  24300
tcggtacctt tgaaatccag ggaccctccg acgcggaaaa cggcaagcag gggtctgggc  24360
taaaactcac agccggactg tggacctccg cctacttgcg caaatttgta ccagaagact  24420
atcacgccca ccaaattaaa ttttacgaaa accaatcaaa accacccaaa agcgagttaa  24480
cggcttgcgt cattacgcag agcagcatag ttgggcagtt gcaagccatt aacaaagcgc  24540
ggcaagagtt tctcctaaaa aaaggaaaag gggtctactt ggacccccag accggcgagg  24600
aactcaacgg accctcctca gtcgcaggtt gtgtgcccca tgccgcccaa aaagaacacc  24660
tcgcagtgga acatgccaga gacggaggaa gaggagtgga gcagtgtgag caacagcgaa  24720
acggaggaag agccgtggcc cgaggggtgc aacggggaag aggacacgga gggacggcga  24780
agtcttcgcc gaagaactct cgccgctgcc cccgaagtcc cagccggccg cctcggccca  24840
agatcccgca cacacccgta gatgggatag caagaccaaa aagccgggta agagaaacgc  24900
tcgcccccgc cagggctacc gctcgtggag aaagcacaaa aactgcatct tatcgtgctt  24960
gctccagtgc ggcggagacg tttcgttcac ccgtagatac ttgcttttta acaaaggggt  25020
ggccgtcccc cgtaacgtcc tccactacta ccgtcactct tacagctccg aagcggacgg  25080
ctaagaaaac gcagcagttg ccggcgggag gactgcgtct cagcgcccga gaacccccag  25140
ccaccaggga gctccgaaac cgcatatttc ccaccctcta cgctatcttt cagcaaagcc  25200
gggggcagca gcaagaactg aaaataaaaa accgcacgct gaggtcgctt acccgaagct  25260
gcctctatca caagagcgaa gagcagctgc agcgaaccct ggaggacgca gaagcgctgt  25320
tccagaagta ctgcgcgacc accctaaata actaaaaaag cccgcgcgcg ggacttcaaa  25380
```

-continued

```
ccgtctgacg tcaccagccg cgcgccaaaa tgagcaaaga gattcccacg ccttacatgt  25440
ggagttacca gccgcagatg ggattagccg ccggcgccgc ccaggattac tccacgaaaa  25500
tgaactggct cagcgccggg ccccacatga tttcccgcgt aaacgacatt cgcgcccacc  25560
gcaatcagct attgttagaa caggctgctc tgaccgccac gccccgtaat aacctgaacc  25620
ctcccagctg gccagctgcc ctggtgtacc aggaaacgcc tccacccacc agcgtacttt  25680
tgccccgtga cgcccaggcg gaagtccaga tgactaacgc gggcgcgcaa ttagcgggcg  25740
gatcccggtt tcggtacaga gttcacggcg ccgcacccta tagcccaggt ataaagaggc  25800
tgatcattcg aggcagaggt gtccagctca acgacgagac agtgagctct tcgcttggtc  25860
tacgaccaga cggagtgttc cagctcgcgg gctcgggccg ctcttcgttc acgcctcgcc  25920
aggcatacct gactctgcag agctctgcct ctcagcctcg ctcgggagga atcggacccc  25980
ttcagtttgt ggaggagttt gtgccctcgg tctactttca gcctttctcc ggatcgcccg  26040
gccagtaccc ggacgagttc atccccaact tcgacgcggt gagtgactct gtggacggtt  26100
atgactgatg tcgagcccgc ttcagtgcta gtggaacaag cgcggctcaa tcacctggtt  26160
cgttgccgcc gccgctgctg cgtggctcgc gacttgagct tagctctcaa gtttgtaaaa  26220
aacccgtccg aaaccgggag cgctgtgcac gggttggagc tagtgggtcc tgagaaggcc  26280
accatccacg ttctcagaaa ctttgtggaa aaacccattt tggttaaacg agatcagggg  26340
ccttttgtaa tcagcttact ctgcacctgt aaccatgttg accttcacga ctattttatg  26400
gatcatttgt gcgctgaatt caataagtaa agcgaattct taccaagatt atgatgtcca  26460
tgactgttcc tcgccactat acgatgttgt gccagtaaac tctcttgtcg acatctatct  26520
gaactgttcc ttttggtccg cacagcttac ttggtactac ggtgacaccg tcctttctgg  26580
ctcactgggc agctcacacg gaataacact tcacctcttt tcgccgtttc gatacggaaa  26640
ctacagctgt cgtgccggta cctgcctcca cgttttcaat cttcagccct gtccaccgac  26700
caaacttgta tttgtcgact ctaagcactt acagctcaac tgcagcattc taggccccag  26760
tatcttgtgg acatacaata aaatcaggtt ggtggaattt gtctactacc cacccagcgc  26820
ccgcggtttt ggggaaattc ctttccagat ctactacaac tatcttgcca cacattatgc  26880
aagtcaacag caactaaact tgcaagcacc cttcacgcca ggagagtact cctgtcacgt  26940
aggctcctgc acagaaactt ttattctctt caacagatct tctgccattg aacgcttcac  27000
tactaactac tttagaaacc aagttgtgct tttcactgac gaaaccccta acgtcaccct  27060
ggactgtgca tgtttttctc atgacaccgt aacttggact cttaacaata ctctctggct  27120
cgcgttcgat aaccaaagct tgattgttaa aaattttgat ttaaccttta ctaaaccctc  27180
tcctcgcgaa atagttatct ttgctccttt taatccaaaa actaccttag cctgtcaggt  27240
tttgtttaag ccttgccaaa caaactttaa gtttgtttat ttgcctccgc aatctgtcaa  27300
actcatagaa aaatacaaca aagcgcccgt cttggctcct aaaaccttct accactggct  27360
aacctacacg gggctgtttg cactaattgt ttttttccta attaacattt ttatatgttt  27420
cttgccttcc tccttctttt cgcgaacacc gttgccgcag aaagacctct ccttattact  27480
gtagcgcttg ctatacaaaa ccaagagtgg tcaaccgtgc tctcaatcta ttttcaattt  27540
ttcattttgt ccttaatact ttctcttatt gtcgttaaca atgatctgga gcattggtct  27600
cgcctttttt tggctgctta gtgcaaaagc cactattttt cacaggtatg tggaagaagg  27660
aactagcacc ctctttacga tacctgaaac aattaaggcg gctgatgaag tttcttggta  27720
```

-continued

```
caaaggctcg ctctcagacg gcaaccactc attctcagga cagacccttt gcatccaaga  27780
aacttatttt aaatcagaac tacaatacag ctgcataaaa aactttttcc atctctacaa  27840
catctcaaaa ccctatgagg gtatttacaa tgccaaggtt tcagacaact ccagcacacg  27900
gaacttttac tttaatctga cagttattaa agcaatttcc attcctatct gtgagtttag  27960
ctcccagttt ctttctgaaa cctactgttt aattactata aactgcacta aaaatcgcct  28020
tcacaccacc ataatctaca atcacacaca atcaccttgg gttttaaacc taaaattttc  28080
tccacacatg ccttcgcaat ttctcacgca agttaccgtc tctaacataa gcaagcagtt  28140
tggcttttac tatcctttcc acgaactgtg cgaaataatt gaagccgaat atgaaccaga  28200
ctactttact tacattgcca ttggtgtaat cgttgtttgc ctttgctttg ttattggggg  28260
gtgtgtttat ttgtacattc agagaaaaat attgctctcg ctgtgctcct gcggttacaa  28320
agcagaagaa agaattaaaa tctctacact ttattaatgt tttccagaaa tggcaaaact  28380
aacgctccta cttttgcttc tcacgccggt gacgcttttt accatcactt tttctgccgc  28440
cgccacactc gaacctcaat gtttgccacc ggttgaagtc tactttgtct acgtgttgct  28500
gtgctgcgtt agcgtttgca gtataacatg ttttaccttt gtttttcttc agtgcattga  28560
ctacttctgg gtcagactct actaccgcag acacgcgcct cagtatcaaa atcaacaaat  28620
tgccagacta ctcggtctgc catgattgtc ttgtatttta ccctgatttt ttttcacctt  28680
acttgcgctt gtgattttca cttcactcaa ttttggaaaa cgcaatgctt cgacccgcgc  28740
ctctccaacg actggatgat ggctcttgca attgccacgc ttggggcgtt tggacttttt  28800
agtggttttg ctttgcatta caaatttaag actccatgga cacatggctt tctttcagat  28860
tttccagtta cacctactcc gccgcctccc ccggccatcg acgtgcctca ggttccctca  28920
ccttctccat ctgtctgcag ctactttcat ctgtaatggc cgacctagaa tttgacggag  28980
tgcaatctga gcaaagggct atacacttcc aacgccagtc ggaccgcgaa cgcaaaaaca  29040
gagagctgca aaccatacaa aacacccacc aatgtaaacg cgggatattt tgtattgtaa  29100
aacaagctaa gctccactac gagcttctat ctggcaacga ccacgagctc caatacgtgg  29160
tcgatcagca gcgtcaaacc tgtgtattct taattggagt ttcccccatt aaagttactc  29220
aaaccaaggg tgaaaccaag ggaaccataa ggtgctcatg tcacctgtca gaatgccttt  29280
acactctagt taaaacccta tgtggcttac atgattctat cccctttaat taaataaact  29340
tactttaaat ctgcaatcac ttcttcgtcc ttgtttttgt cgccatccag cagcaccacc  29400
ttcccctctt cccaactttc atagcatatt ttccgaaaag aggcgtactt tcgccacacc  29460
ttaaagggaa cgtttacttc gctttcaagc tctcccacga ttttcattgc agatatgaaa  29520
cgcgccaaag tggaagaagg atttaacccc gtttatccct atggatattc tactccgact  29580
gacgtggctc ctccctttgt agcctctgac ggtcttcaag aaaacccacc tggggtcttg  29640
tccctaaaaa tatccaaacc tttaactttt aatgcctcca aggctctaag cctggctatt  29700
ggtccaggat taaaaattca agatggtaaa ctagtggggg agggacaagc aattcttgca  29760
aacctgccgc ttcaaatcac caacaacaca atttcactac gttttgggaa cacacttgcc  29820
ttgaatgaca ataatgaact ccaaaccaca ctaaaatctt catcgcccct taaaatcaca  29880
gaccagactc tgtcccttaa catagggac agccttgcaa ttaaagatga caaactagaa  29940
agcgctcttc aagcgaccct cccactctcc attagcaaca acaccatcag cctcaacgtg  30000
ggcaccggac tcaccataaa tggaaacgtt ttacaagctg ttcccttaaa tgctctaagt  30060
cccctaacta tttccaacaa taacatcagc ctgcgctatg gcagttccct gacggtgctt  30120
```

aacaatgaac tgcaaagcaa cctcacagtt cactcccctt taaaactcaa ctccaacaac 30180
tcaatttctc tcaacactct atctccgttt agaatcgaga atggtttcct cacgctctat 30240
ttgggaacaa aatctggctt gctagttcaa aacagtggct taaaagttca agcgggctac 30300
ggcctgcaag taacagacac caatgctctc acattaagat atctcgctcc actgaccatt 30360
ccagactcgg gctcagaaca aggcattctt aaagtaaaca ctggacaggg cctaagtgtg 30420
aaccaagctg gagcgcttga aacatcccta ggaggtggat taaaatatgc tgataacaaa 30480
ataacctttg atacaggaaa cggactgaca ttatctgaaa ataaacttgc agtagctgca 30540
ggtagtggtc taacttttag agatggtgcc ttggtagcca cgggaaccgc atttacgcaa 30600
acactgtgga ctacggctga tccgtctccc aactgcacaa ttatacagga ccgcgacaca 30660
aaatttactt tggcgcttac cattagtggg agccaagtgc tggggacggt ttccattatt 30720
ggagtaaaag gcccccttc aagtagcata ccgtcagcta ccgttacagt acaacttaac 30780
tttgattcca acggagccct attgagctcc tcttcactta aaggttactg gggtatcgc 30840 caaggtccct caattgaccc ttaccccata attaatgcct taaactttat gccaaactca 30900
ctggcttatc cccgggaca agaaatccaa gcaaaatgta acatgtacgt ttctactttt 30960
ttacgaggaa atccacaaag accaatagtt ttaaacatca cttttaataa tcaaaccagc 31020 gggtttcca ttagatttac atggacaaat ttaaccacag gagaagcatt tgcaatgccc 31080
ccatgcactt tttcctacat tgctgaacaa caataaacta tgtaaccctc accgttaacc 31140
cgcctccgcc cttccatttt attttataaa ccacccgatc caccttttca gcagtaaaca 31200
attgcatgtc agtaggggca gtaaaacttt tgggagttaa aatccacaca ggttcttcac 31260
aagctaagcg aaaatcagtt acacttataa aaccatcgct aacatcggac aaagacaagc 31320
atgagtccaa agcttccggt tctggatcag atttttgttc attaacagcg ggagaaacag 31380
cttctggagg attttccatc tccatctcct tcatcagttc caccatgtcc accgtggtca 31440
tctgggacga gaacgacagt tgtcatacac ctcataagtc accggtcgat gacgaacgta 31500
cagatctcga agaatgtcct gtcgccgcct ttcggcagca ctgggccgaa ggcgaaagcg 31560
cccatgttta acaatggcca gcaccgcccg cttcatcagg cgcctagttc ttttagcgca 31620
acagcgcatg cgcagctcgc taagactggc gcaagaaaca cagcacagaa ccaccagatt 31680
gttcatgatc ccataagcgt gctgacacca gcccatacta acaaattgtt tcactattct 31740
agcatgaatg tcatatctga tgttcaagta aattaaatgg cgccccctta tgtaaacact 31800
tcccacgtac aacacctcct ttggcatctg ataattaacc acctcccgat accaaataca 31860
tctctgatta atagtcgccc cgtacactac ccgattaaac caagttgcca acataatccc 31920
ccctgccata cactgcaaag aacctggacg gctacaatga cagtgcaaag tccacacctc 31980
gttgccatgg ataactgagg aacgccttaa gtcaatagtg gcacaactaa tacaaacatg 32040
taaatagtgt ttcaacaagt gccactcgta tgaggtgagt atcatgtccc agggaacggg 32100
ccactccata aacactgcaa aaccaacaca tcctaccatc ccccgcacgg cactcacatc 32160
gtgcatggtg ttcatatcac agtccggaag ctgaggacaa ggaaaagtct cgggagcatt 32220
ttcatagggc ggtagtgggt actccttgta ggggttcagt cggcaccggt atctcctcac 32280
cttctgggcc ataacacaca agttgagatc tgatttcaag gtactttctg aatgaaaacc 32340
aagtgctttc ccaacaatgt atccgatgtc ttcggtcccc gcgtcggtag cgctccttgc 32400
agtacacacg gaacaaccac tcacgcaggc ccagaagaca gttttccgcg gacggtgaca 32460

-continued

```
agttaatccc cctcagtctc agagccaata tagtttcttc cacagtagca taggccaaac  32520

ccaaccagga aacacaagct ggcacgtccc gttcaacggg aggacaagga agcagaggca  32580

gaggcatagg caaagcaaca gaatttttat tccaactggt cacgtagcac ttcaaacacc  32640

aggtcacgta aatggcagcg atcttgggtt tcctgatgga acataacagc aagatcaaac  32700

atgagacgat tctcaaggtg attaaccaca gctggaatta aatcctccac gcgcacattt  32760

agaaacacca gcaatacaaa agcccggttt tctccgggat ctatcatagc agcacagtca  32820

tcaattagtc ccaagtaatt ttcccgtttc caatctgtta taatttgcag aataatgccc  32880

tgtaaatcca agccggccat ggcgaaaagc tcagataatg cactttccac gtgcattcgt  32940

aaacacaccc tcatcttgtc aatccaaaaa gtcttcttct tgagaaacct gtagtaaatt  33000

aagaatcgcc aggttaggct cgatgcctac atcccggagc ttcattctca gcatgcactg  33060

caaatgatcc agcagatcag aacagcaatt agcagccagc tcatccccgg tttccagttc  33120

cggagttccc acggcaatta tcactcgaaa cgtgggacaa atcgaaataa catgagctcc  33180

cacgtgagca aaagccgtag ggccagtgca ataatcacag aaccagcgga aaaaagattg  33240

cagctcatgt ttcaaaaagc tctgcagatc aaaattcagc tcatgcaaat aacacagtaa  33300

agtttgcggt atagtaaccg aaaaccacac gggtcgacgt tcaaacatct cggcttacct  33360

aaaaaagaag cacattttta aaccacagtc gcttcctgaa caggaggaaa tatggtgcgg  33420

cgtaaaacca gacgcgccac cggatctccg gcagagccct gataatacag ccagctgtgg  33480

ttaaacagca aaacctttaa ttcggcaacg gttgaggtct ccacataatc agcgcccaca  33540

aaaatcccat ctcgaacttg ctcgcgtagg gagctaaaat ggccagtata gccccatggc  33600

acccgaacgc taatctgcaa gtatatgaga gccaccccat tcggcgggat cacaaaatca  33660

gtcggagaaa acaacgtata caccccggac tgcaaaagct gttcaggcaa acgcccctgc  33720

ggtccctctc ggtacaccag caaagcctcg ggtaaagcag ccatgccaag cgcttaccgt  33780

gccaagagcg actcagacga aaaagtgtac tgaggcgctc agagcagcgg ctatatactc  33840

tacctgtgac gtcaagaacc gaaagtcaaa agttcacccg gcgcgcccga aaaaacccgc  33900

gaaaatccac ccaaaaagcc cgcgaaaaac acttccgtat aaaatttccg ggttaccggc  33960

gcgtcaccgc cgcgcgacac gcccgccccg ccccgcgctc ctccccgaaa cccgccgcgc  34020

ccacttccgc gttcccaaga caaaggtcgc gtaactccgc ccacctcatt tgcatgttaa  34080

ctcggtcgcc atcttgcggt gttatattga tgatg                             34115
```

<210> SEQ ID NO 7
<211> LENGTH: 44
<212> TYPE: DNA
<213> ORGANISM: Artificial
<220> FEATURE:
<223> OTHER INFORMATION: primer P5L

<400> SEQUENCE: 7

```
gcgcacgcgt ctctatcgat gaattccatt ggtgatggac atgc                    44
```

<210> SEQ ID NO 8
<211> LENGTH: 36
<212> TYPE: DNA
<213> ORGANISM: Artificial
<220> FEATURE:
<223> OTHER INFORMATION: primer P5ITR

<400> SEQUENCE: 8

```
gcgcatttaa atcatcatca ataatatacc tcaaac                             36
```

<210> SEQ ID NO 9
<211> LENGTH: 31
<212> TYPE: DNA
<213> ORGANISM: Artificial
<220> FEATURE:
<223> OTHER INFORMATION: primer P5XTOP

<400> SEQUENCE: 9
gatacctagg aacgaggagg atttgatatt g 31

<210> SEQ ID NO 10
<211> LENGTH: 20
<212> TYPE: DNA
<213> ORGANISM: Artificial
<220> FEATURE:
<223> OTHER INFORMATION: primer P5XBOT

<400> SEQUENCE: 10
atgtacgcct ccgcgctcac 20

<210> SEQ ID NO 11
<211> LENGTH: 31
<212> TYPE: DNA
<213> ORGANISM: Artificial
<220> FEATURE:
<223> OTHER INFORMATION: primer P5E4

<400> SEQUENCE: 11
gatcgaattc ccactctgta ccccatctct g 31

<210> SEQ ID NO 12
<211> LENGTH: 31967
<212> TYPE: DNA
<213> ORGANISM: Simian adenovirus
<220> FEATURE:
<221> NAME/KEY: CDS
<222> LOCATION: (13796)..(15322)
<220> FEATURE:
<221> NAME/KEY: CDS
<222> LOCATION: (18257)..(21010)
<220> FEATURE:
<221> NAME/KEY: CDS
<222> LOCATION: (27192)..(29015)

<400> SEQUENCE: 12
catcatcata atatacctta tttgggaacg gtgccaatat gataatgagg aggcggggtt 60
aggggtggag tgagggtggg gtgcggatga cgcgggcgcg gggcggggtg ggagtctgac 120
gtggggcgcg gggtggagcg cgagggtgag ggcggggcga gggcggcggg cgcggcggaa 180
ttgacgtaca cggtagtaag tttgagcgga aattaagtga attgggcgtg ttttttgtaa 240
ctttttgacg tacacggtag taagtttgag cggaaattaa gtgaattggg cgtgtttttt 300
gtaacttttt gacgtacacg gtagtaagtt tgagcggaaa ttaagtgaat tgggcgtgtt 360
ttttgtaact ttttgacgta cacggtagta agtttgagcg gaaattaagt gaattgggcg 420 tgtttttttgt aactttttga cgtacacggt agtaagtttg agcggaaatt aagtgaattg 480
ggcgtgtttt ttgtaacttt ttgacgtaca cggtagtaag tttgagcgga aattaagtga 540
attgggcgtg ttttttgtaa ctttttgacg tacacggtag taagtttgag cggaaattaa 600
gtgaattggg cgtgtttttt gtaacttttt ggtcattttg gcgcgaaaac tgagtaatga 660
ggaagtgaga cggactctgc cctttttttac ggttgggagg gaaaactgct gatcagcgct 720
gaactttggg ctctgacgcg gtggtttccc tacgtggcag tgccacgaga aggctcaaag 780

-continued

```
tcctcgtttt attgtgtgct cagccttttt gagggtattt aaacaccgtc agaccgtcaa    840
gaggccactc ttgagtgcga gcgagtagag ttttctcctc cgtcgctgcc gcggctgctc    900
agtcttaccg ccaggatgcg aatgctgccg gagatcttca ccgggtcctg ggaagatgtt    960
ttccagggac ttttagaatc tgaagacaac tttccccaac ctcctgagcc ggaggagcta   1020
cctgaggttt cgcttcacga tctgtttgac gtggaggtgg agagccccga cggagatccg   1080
aacgaggaag ctgttgatgg tatgttcccc gactggatga tatctcagag cgagagtgct   1140
gaaggcagtg cggactcggg cgtttctggg gttggaaacc tggtggaggt ggatctggac   1200
ttgaagtgtt acgaggaagg ttttcctcct agcgactcag agactgatga agcctcagaa   1260
gcggaaggtc aagaggagtc tgtgtgtggt tatgtgaaga ttaatgaggg ggagaacctg   1320
ctggtgttgg actgtccgga ccaacctgga catggctgtc gagcctgtga ctttcaccgg   1380
gggaccagcg gaaacccgga agctatctgt gctttgtgct acatgcgtct gaacgagcac   1440
tgcatataca gtgagtgtta ttcatgggtt atttatgggg aaagttgggg gaaagtcttg   1500
agaaggggaa aagtttaaca tgtcattttt gtacttgata ggtccagttt cggacgctga   1560
gggggattct gagtcccctg ctggtccttc ccagccctca ccctgctctt tgaccgccac   1620
gcccgcacct gacctagtta gaccaacgcc ctgccgagtg tcctgtagac gacgtgcagc   1680
tgttaattgc atagaagatt tattggcccc tgatgacgag aacgcacctt tgaacctgtg   1740
cctgaaacgc cctaagacat cttgagtgtt tatgctgtta ataaaagtgt tgacccttag   1800
atcctgtgtt tattccttgg gcgtgtgcgc gggtatataa agcagctgcg ggctggagtg   1860
ttagtttatt ctgatggagt actggagtga gctgcagaat taccagagcc tccggcgcct   1920
gctggagttg gcctctgcca gaacatccac ctgctggagg ttctgttttg gctcgactct   1980
cagtaacgtg gtgtatcggg tgaagcaaga gtacagctcg cgcttttctg agctgttggc   2040
ccgctacccg gctgtttttg tttctctgga tctaggccat cacgtttatt tccaagaagc   2100
tgtagtcaga tatttggatt tttctactcc cgggcgtgcg gtttctgcga ttgccttcat   2160
ctgctttgtg ctagatcgat ggagcgccca aacccgcctg agcccggggt acaccctgga   2220
ctacctgacc atgtccctgt ggagggccat gctgcggaag aggagggtct caggcttctc   2280
gccggcgcgg cctccgcacg gactggatcc ggtgctggag gagtcggagc tggaggagga   2340
ggagaacccg agggccggcc tggaccctcc ggcggaatag tgacggaacc ggaggatccc   2400
caagagggta ctagtcaggg gggagggggg ccgaagagaa agcgggatga agaggaggcg   2460
atggaccccg acaggtttct aaaagaactg actttaagct taatgtctaa gagaagaccc   2520
gagacggtgt ggtggtctga tttggagaag gagttccacc agggggagat gaatctgttg   2580
tacaagtatg ggtttgagca ggtgaagact cactggctgg aagcctggga ggactgggag   2640
atggctttta acatgtttgc caaggtggcg ctgcgcccgg acactattta caccgtgact   2700
aagacggtgg aaatccgcaa gcctgtgtat gtgattggca acggggccgt ggttcggttc   2760
cagaccaccg accgggtggc ctttaattgc tgtatgcaga acctgggccc gggggtgatt   2820
aatcttaatg gagtgacctt ttgcaatgtc agattcgcgg gggatggatt caacgggacg   2880
gtgtttgccg ccaccaccca gataacccta cacggggtgt tcttccagca tgtaggcggg   2940
gcttgtgtag atacctgggc gagggcctct gtgaggggct gcacctttgt gggctgttgg   3000
aaagcggtgg tgggtcgacc caagagtgtg ctgtctgtga agaaatgtgt gtttgagaga   3060
tgtctgatgg ccatggtggt ggagggccag ggtaggatcc gccataacgc gggctccgag   3120
```

-continued

```
aatacctgtt ttgccctgct gaagggtacg gcgaccgtga agcataacat gatctgcggg   3180
gtgggtcact cgcagctgct gacctgtgcg gatggcaact gccaggccct gcgcacggtg   3240
catgtggtgt cccaccggcg ccgcccctgg ccggtgtttg aacataacat gctgatgcgc   3300
tgtaccatgc acctgggcta ccgccgcggc gtgtttgtgc cccatcagtg taacctgacc   3360
cacaccaagg tgttgctgga gacggatgct tttcgcgag tgaatctgaa tggggtgttc    3420
gatctgacta tggagatgta caagatagtg agatttgatg aatcaaagac ccgttgtcgc   3480
ccctgcgagt gcggtgccaa tcacctgagg atgtatcccg tgaccctgaa cgtgacggag   3540
gagctgcgcc cggaccacca gatgctgtcc tgtctgcgca ccgattacga aagcagcgat   3600
gaggattaag aggtgagggg cggggcttgc atggggtata aaggtggggg aggaggtggg   3660
gagggggaaa acccaaaatg agcggatcga tggaagggag cgctgtgagt tttgagggcg   3720
gggtgttcag cccatatctg acaacccgtc tccccgcctg gcaggagtg cgtcagaatg    3780
tggtgggctc caacgtggac ggacgtccgg tggcccctgc caactccgcc actctcacct   3840
acgccaccgt cggatcgtcg ctggacaccg ccgctgccgc cgccgcttca gccgccgctt   3900
ctactgctcg cggtatggca gctgatttcg gactgtatca gcaactggct gcgcctcgct   3960
cgtcgctgag agaagatgat gccctgtccg tggtgctgac ccgcctggag gagctgtccc   4020
agcagctgca agagctgtct gccaaagtgg atgcacagaa cgtccccgct acccaatgaa   4080
taaataaacg agacaccgag tgtgtttgga aatcaaaatg tgtttttatt tgtttttttct   4140
ggcgcggtag gcccttgacc acctgtcgcg gtcgttaagg accttgtgga tgttttccag   4200
cacccggtag aggtgggctt ggatgttgag gtacatgggc atgagcccgt ctcgggggtg   4260
gaggtagcac cactggaggg cgtcgtgctc gggggtggtg ttgtagataa tccagtcgta   4320
gcagggtttt tgggcatgga agcggaagat gtctttgaga agcaggctga tggccagggg   4380
gaggcccttg gtgtaggtgt tcacaaagcg gttgagctgg gagggatgca tgcgggggga   4440
gatgagatgc atcttggcct gaatcttgag gttggcgatg ttgccgccca gatcccgccg   4500
ggggctcatg ttgtgcagga ccaccaggac ggtgtagccg gtgcacttgg ggaatttgtc   4560
atgcaacttg gaagggaagg cgtggaagaa cttggagacc cccttgtggc cgccgaggtt   4620
ctccatgcat tcgtccatga tgatggcgat gggacccctg gcggccgccc tggcgaagac   4680
gttgtcgggg tgggagacgt cgtagttctg ttccagggtg agctcgtcgt aggccatttt   4740
gacgaagcgg gggagcaggg tgcccgactg gggacgatg gtaccttcgg gacccggggc     4800
gtagttgccc tcgcagattt gcatctccca ggccttgatc tccgaggggg ggatcatgtc   4860
cacctggggc gcgatgaaga agacggtctc cggggcgggg ttgatgagct gggaggagag   4920
gaggttgcgg agcagctgcg acttgccgca cccggtgggc ccgtagatga ccccgatgac   4980
gggttgcagc tggtagttta aggagctgca gctgccgtcc tcgcgcagga acggggcgac   5040
ctcgttcatc atgcttctga cgtgatggtt ttccctgacg aggtcttgca agagccgctc   5100
gccgcccagg gagagaagct cttccaggct gcggaaatgc ttgaggggtt tgaggccgtc   5160
ggccatggtc atcttttcca gggactggcg gagcaggtac aggcggtccc agagctcggt   5220
gacgtgttct acggcatctc gatccagcag acttcttggt tgcgggggtt ggggcggctt   5280
tggctgtagg ggaccagccg gtgcgcgtcc agggaggcga gggtgacgtc tttccagggc   5340
cgcagcgttc gcgtgagggt ggtctcggtg acggtgaagg gatgcgctcc cggttgggcg   5400
ctggccaggg tcctcttgag actcatcctg ctggtgtgga agcgggcgtc ttctccctgg   5460
gagtcggcca ggtagcattt gagcatgagg tcgtagctga gggcctcggc cgcgtggccc   5520
```

ttggcgcgca gcttgccttt ggagacgtgt ccgcaggcgg gacagtgcag gcacttgagg 5580
gcgtagagct tgggggccag gaagacggac tcgggggagt aggcgtcggc gccgcactga 5640
gcgcacgtgg tctcgcactc gacgagccag gtgagctccg ggtgttgggg atcaaaaacc 5700
agctggcccc cgtgtttttt gatgcgcttc ttacctcggg tctccatgag gcggcgtccg 5760
gcttcggtga cgaagaggct gtcggtgtcg ccgtagacgg atttgagcgc gcgctgctcc 5820
aggggaatcc cgcgatcctc cgcgtgcagg aactcggacc actctgagac gaaggcccgg 5880
gtccacgcga ggacaaagga ggcgatctgg gacgggtagc ggtcgttctc caccagggga 5940
tccaccttct ccagggtgtg caggcagagg tcgtcctcct ccgcgtccat gaaggtgatt 6000
ggcttgtaag tgtatgtcac gtgaccgtcg ggtcgcgcgg tgggcttata aaagggggcg 6060
tgcccggcct ccccgtcact ttcttccgca tcgctgtgga cgagatccag ctgctcgggt 6120
gagtaggcgc gctggaaggc gggcatgacc tcggcgctga gggtgtcagt ttccacgaac 6180
gaggtggatt tgatattgac ctgtccggcg gcgatgcttt tgacggtggc ggggtccatc 6240
tggtcagaaa agacgatctt tttgttgtcc agcttggtgg cgaacgaccc gtagagggcg 6300
ttggagagca gcttggcgat ggagcgcagg gtctggttct tctcgcggtc ggcgcgctcc 6360
ttggcggcga tgttgagctg gacgtactcg cgggccacgc agcgccattc ggggaagacg 6420
gtggcgcgct cgtccggcag gaggcgcacg cgccagccgc ggttgtgcag ggtgatgagg 6480
tccacgctgg tggccacctc gccgcgcagt ggctcgttgg tccagcagag gcgcccgccc 6540
ttgcgcgagc agaagggggg caggacgtcg agctggtcct ccgcgggggg gtcggcgtcg 6600
atggtgaaga tgcccggtag caggtggcgg tcgaagtagt cgatggcgac cgcggggtcg 6660
gcgagggcgc gttcccagtc cctgaccgcc agggcgcgct cgtaggggtt gaggggcgcc 6720
ccccagggca tgggatgggt gagggccgag gcgtacatgc cgcagatgtc gtagacgtag 6780
aggggctcgc ggagcacgcc gaggtaggtg ggatagcagc gtccgccgcg gatgctggcg 6840
cgcacgtagt cgtacatctc gtgcgagggg gcgaggaggc cgcctccgag gtcgccgcgc 6900
tgcggtctga cggcccggta ggtgacctgg cggaagatgg cgtgcgagtt ggaggagatg 6960
gtgggccgct ggaagatgtt gaagctggcc tcggggagtc cgacggcgtc gtggacgaac 7020
tgggcgtagg agtcgcgcag cttctgcacg agcgcggcgg tgacgagcac gtccagggcg 7080
cagtagtcga gggtctcgcg gacgaggtcg taacggggct cttgcttctt ttcccagagt 7140
tcgcggttga ggaggtactc ctcgcgatcc ttccagtact cttcggccgg aaagccgcgt 7200
tcgtccgcca ggtaagaacc cagcatgtag aagcggttga cggctcggta gggacagcag 7260
cccttctcga cgggcaggga gtaggcctgc gcggccttcc tgagcgaggt gtgggtgagg 7320
gcgaaggtgt cgcgcaccat gaccttgagg aactggaacc tgaagtcggt gtcgtcgcag 7380
gcgccccgct cccagagccc gtagtcggtg cgtttctggc tgcgggggtt gggcagggcg 7440
aaggtgacgt cgttgaagag gatcttgccg gcgcgcggca tgaagttgcg ggtgatcctg 7500
aagggccccg gcacgtccga gcggttgtta atgacctggg ccgcgaggac gatctcgtcg 7560
aagccgttga tgttgtggcc gacgatgtag agctcgacga agcgcgggcg cccctgcagc 7620
ttgggggcct tcttgagctc ctcgtaggtg aggcagtcgg gcgagtagag gcccagctcc 7680
tgtcgggccc attcggccac ctgggggttg gcttgcaaga agccccgcca gagctgcagg 7740
gcgagctggg tctggaggcg gtcgcggtag tcgcggaact tttgcccac cgccatcttc 7800 tcgggggtga ccacgtagaa ggtgcggccg tcctggcccc aggcgtccca gttctgctcg 7860

-continued

```
cgggcgagac ggcaggcctc ctcgacgagg gcctcctccc cggagagatg catgactagc   7920
atgaagggga cgagttgctt gccgaaggca cccatccacg tgtaggtctc tacgtcgtag   7980
gtgacgaaga gacgttcggt gcgaggatgc gagccgagag gaaagaagtt gatctcctgc   8040
caccagccgg aggagtgggc gttgacgtgg tggaagtaga agtcacgccg gcggaccgtg   8100
cattcgtgct gatatttgta aaagcgggcg cagtactcgc agcgctgcac gctctgcact   8160
tcctgaacga gatgcacccg gcgcccgcgc accaggaggc ggagggggca gtccagtgga   8220
gcttcggcgc gctgtccttc agcctcgtca tgctcttctg cacctgcacg ctcctgctgt   8280
gggtggagga cggagggagt gacgacgccg cgcgagccgc aggtccagat gtcgacgcgc   8340
ggcggcctga ggctcagcgc cagggtgcgg atctgagcgg cgtccaggga gtcgaggaag   8400
gcctcgctga ggtcgacggg cagcgtccgc cggtggactt gcaggagacg ggtaagggcc   8460
ggcgccaggc gctgatggta cttgatctcg agcggttcgt tggtggaggt gtcgatggcg   8520
tagagcaggg cctgaccgcg ggcggcgacg atggtgccgc ggtgccggcg gtaggtggcg   8580
tattcggggg ggctcgttac atcacccgcc tgggcctggc gccgggcggc agcgggggtt   8640
ctggtcccgc cggcatgggc ggcagcggca cgtcggcgcg gggctccggc agcggctggt   8700
gctgagctcg cagctgactg gcgtgcgcga cgacgcggcg gttgaggtcc tggatgtgcc   8760
tccgctgcgt gaagaccacc ggtccccgga ctcggaacct gaaagagagt tcgacagaat   8820
caatctcggc atcgttgacg gccgcctgac gcaggatctc ctgcacgtcg cccgagttgt   8880
cctggtaggc gatctcggac atgaactggt cgatctcttc ctcctggagt tcgccgcgtc   8940
cggcgcgttc gacggtggcc gcgaggtcgt tggagatgcg agccatgagc tgggagaagg   9000
cgttgaggcc gttctcgttc cacacgcgac tgtagacgac gttgccgacg gcgtcccggg   9060
cgcgcatgac cacctgcgcg acgttgagct ccacgtgtcg cgcgaagacg gcgtagttgc   9120
gcaggcgctg gaagaggtag ttgagggtgg tggcgatgtg ctcgcagacg aagaagtaca   9180
tgacccagcg gcgcagcgtc atctcgttga tgtctccgag ggcttccaag cgctccatgg   9240
cctcgtagaa gtcgacggcg aagttgaaga actgggagtt gcgcgccgcg accgtcagct   9300
cgtcttgcaa gagccggatc agctgggcca cggtctcccg cacctcgcgt tcgaaggccc   9360
ccggcgcttc ttcctcctct ggttcctcgg cggcctcttc ttccatgacg gcttcctctt   9420
cctccggttc ctcgggcacg ggcctccggc ggcgacggcg cctgatgggc aggcggtcca   9480
cgaagcgttc gatgatctct ccgcggcggc ggcgcatggt ttcggtgacg gcgcggccgt   9540
tctctcgggg ccgcagttcg aagacgcccc cgcgcaggcc gccggcgccg ccgagagggg   9600
gcaggaggtg ggggccttcg ggcagcgaga gggcgctgac gatgcaccgt atcatctgtt   9660
gcgtaggtac agctctccag gagtcgttga gcgagtccag ttggacggga tccgagaact   9720
tttcgaggaa agcttcgatc caatcgcagt cgcaaggtaa gctgaggacg gtgggatgag   9780
gggcttggcg ggaggcggag gcggcagaag aggaggagga gggcaggctg gaggtgatgc   9840
tgctgatgat gtaattgaag taggcggttt tcaaacggcg gatggtggcg aggaggacga   9900
cgtctttggg cccggcctgc tggatgcgca ggcggtcggc catgccccag gcgtggctct   9960
ggcatcggcg caggtccttg tagtagtctt gcatgagtct ctcgacgggg acgtcgtctt  10020
cgtcggcccg gtcggccatg cgggtggagc cgaacccgcg caggggctgc agcagggcca  10080
ggtcggcgac cacgcgttcg gccagcacgg cctgctggat ctgggtgagc gtggtctgga  10140
agtcgtccag gtccacgaag cggtggtagg agcccgtgtt gatggtgtag gtgcagttgg  10200
ccatgacgga ccagttgacg acttgcatgc cgggctgggt gatctcggtg tagcggaggc  10260
```

```
gcgagtaggc ccgcgactcg aagacgtagt cgttgcaggt gcgcacgagg tactggtagc  10320
cgacgaggaa gtgcggcggc ggctcgcggt agaggggcca gcgcacggtg gcgggggcgc  10380
cgggggccag gtcctccagc atgaggcggt ggtagtggta gacgtagcgc gagagccagg  10440
tgatgccggc ggcggaggtg gcggcgcggg cgaagtcgcg gacgcggttc cagatgttgc  10500
gcaaggggc gaagcgctcc atggtgggca cgctctggcc ggtgaggcgg gcgcagtcct  10560
gcacgctcta gacgggacag agagcgggag gttagcggct ccgctccgtg gcctggggga  10620
cagaccgcca gggtgcgacg gcggggaacc ccggttcgag accggctgga tccgtccgtc  10680
cccgacgcgc cggccccgcg tccacgaccc caccagaggc cgagacccag ccgcggtgcc  10740
cggaccccag atacggaggg gagccttttt gtggtttttt cccgtagatg catccggtgt  10800
tgcgacagat gcgtccgtcg ccagcgccgc cgacgcagcc gccgctcccg ccccccacta  10860
gcgccgcgga ggctctgtcc ggcggccgcg gcgacccgga ggaggaggcc atcctcgact  10920
tggaagaagg cgagggcctg gcccggctgg gagcgccctc cccgagcgc catccccgcg  10980
tgcagctggc gagagactcg cgccaggcct acgtgccgcc gcagaatctg ttcagggacc  11040
gcagcggcca ggagcccgag gagatgaggg accgcaggtt tcacgcgggg cgggagctgc  11100
gcgcgggctt cgaccgtcgg cgggtgttgc gcgccgaaga cttcgagccc gacgagcgca  11160
gcggagtaag tccggcacgg gcgcacgtgt cggcggccaa cctggtgacc gcgtacgagc  11220
agacggtgaa cgaggagcgg agctttcaga aaagcttcaa caaccacgtg cgcaccctga  11280
tcgcgcgcga ggaggtggcc atcggcctga tgcatctgtg ggactttgtg gaggcgtacg  11340
tgcagaaccc gtcgagcaag ccgctgacgg cgcagttgtt cctgatcgtg cagcacagtc  11400
gggacaacga gacgttccgc gaggcgatgc tgaacatcgc ggagcccgag ggccgctggc  11460
tcttggacct gattaacatc ctgcagagca tcgtggtgca ggagcgcagc ctgagcctgg  11520
ccgacaaggt ggcggccatc aactacagca tgttgagcct gggcaagttt tacgcccgca  11580
agatctacaa gagcccctac gtgcccatag acaaggaggt gaagatcgac agcttttaca  11640
tgcggatggc gctgaaagtg ctgacgctga gcgacgatct gggggtgtac cgcaacgacc  11700
gcatccacaa ggccgtgagc gccagccgcc ggcgcgagct gagcgaccgc gagctgatgc  11760
acagcctgcg gagggcgctg gcgggcgccg gcggcggcga ggaggccgag tcctacttcg  11820
acatggggc ggacttgcag tggcagccca gcgcgcgggc cctggaggcg gcgggctacc  11880
gcggcggcgg cggcgtggtc gaggcggagg acgaggacga ggtggagtac gaggaggagg  11940
actgatcggc gaggtgtttt cgtagatgca gcgcgcgacg gcggcggcga gcgggccgca  12000
gggggacccc gccgtgctgg cggccctgca gagccaacct tcgggcgtga acgcctccga  12060
tgactgggcg gcggccatgg accgcatttt ggccttgacc acccgcaacc ccgaggcctt  12120
tagacagcag ccgcaggcca accgcttttc ggccatcttg gaagccgtgg tgccctcgcg  12180
caccaacccc acgcacgaga aggtcctggc ggtggtgaac gcgctgctgg agagcaaggc  12240
gatccgcaag gacgaggcgg ggctgattta caacgccctg ctggagcggg tggcgcgcta  12300
caacagcacc aacgtgcagg ccaacctgga ccgtctgacg acggacgtgc gggaggcggt  12360
ggcgcagcgg gagcgcttca tgcgcgacac gaacctgggc tcgcaggtgg ccctgaacgc  12420
cttcctgagc acgcagccgg ccaacgtgcc gcgcgggcag gaggactacg tcagtttcat  12480
cagcgcgctg cgcctcctgg tggccgaggt gccgcagagc gaggtgtacc agtcgggtcc  12540
ggactacttc ttccagacct cgcggcaggg cctgcagacg gtgaacctga cgcaggcctt  12600
```

-continued

```
caagaacctg gaaggcatgt ggggcgtgcg ggcccccgtg ggcgaccggg cgacgatctc  12660

cagcttgctg acgccgaaca cgcggctgct gctgctgctg atcgcgccct tcaccaatag  12720

cagtaccatc agccgcgact cgtacctggg ccacctgatc acgctgtacc gcgaggccat  12780

cgggcaggcg caggtggacg agcagacctt ccaggagatt acgagcgtga gccgggccct  12840

ggggcagcag gacacgggta gcctggaggc gacgctgaat tttctgctga ccaaccggcg  12900

gcagaagatc cctcccagt acacgctgag cacggaggag gagcgcatct tgcgctacgt  12960

gcagcagtcc gtgagcctgt atctgatgcg cgagggggcg agcccctcgt cggcgctgga  13020

catgacggcc cgtaacatgg agccgtcgct gtacgcggcc caccggccgt tcgtgaaccg  13080

cctgatggac tacctgcacc gcgccgccgc catgaacggc gagtacttta cgaacgccat  13140

cctgaacccg cactggatgc cgccgtccgg tttctacacg gggactttg acatgcccga  13200

gggcgacgac gggttcctgt gggacgacgt gtcggacagc gtgttcgcgc cggtgcgtcc  13260

gggcaagaag gagggcggcg acgagctgcc gctgtccgtg gtggaggcgg cgtcgcgcgg  13320

ccagagcccg ttccccagcc tcccgtcgtt gtcggcgagc agcagcagcg gccgggtctc  13380

gcgcccgcgg ctggagggcg actacctgaa cgacccgctg ctgcgccccg cccggcccaa  13440

gaactttccc aacaacgggg tggagagcct agtggataag atgaatcgct ggaagaccta  13500

cgcccaggag cagcgggagt gggaggagag tcagccccgc cccctgcctc cgccgcgctc  13560

caggtggcgc cggcgggaag aagacccgga agactcggcg gacgatagca gcgtgttgga  13620

cttgggggg accggtgccg cctcgacaaa cccgttcgcc cacctgcgcc cgcagggccg  13680

gctgggtcgg ctgtattgag gaaagaaact aataaaagaa aaaagagctt gcttaccaga  13740

gccatggtcg cagcgtcggt ccctttgtgt gtgttttctc ctccccggta gcgaa atg   13798
                                                              Met
                                                              1

agg cgc gcg gtg gga gtg ccg ccg gtg atg gcg tac gcc gag ggt cct    13846
Arg Arg Ala Val Gly Val Pro Pro Val Met Ala Tyr Ala Glu Gly Pro
            5                   10                  15

cct cct tct tac gaa acg gtg atg ggc gcc gcg gat tcg ccg gcc acg    13894
Pro Pro Ser Tyr Glu Thr Val Met Gly Ala Ala Asp Ser Pro Ala Thr
        20                  25                  30

ctg gag gcg ctc tac gtc cct ccc cgc tac ctg ggg cct acg gag ggg    13942
Leu Glu Ala Leu Tyr Val Pro Pro Arg Tyr Leu Gly Pro Thr Glu Gly
    35                  40                  45

agg aac agc atc cgt tac tca gag ctg gcg ccg ctg tac gac acc acc    13990
Arg Asn Ser Ile Arg Tyr Ser Glu Leu Ala Pro Leu Tyr Asp Thr Thr
50                  55                  60                  65

cgc gtg tac ctg gtg gat aac aag tcg gcg gac atc gcg tcg ctg aac    14038
Arg Val Tyr Leu Val Asp Asn Lys Ser Ala Asp Ile Ala Ser Leu Asn
                70                  75                  80

tac cag aac gac cat agc aac ttt ctg acc acg gtg gtg cag aac aat    14086
Tyr Gln Asn Asp His Ser Asn Phe Leu Thr Thr Val Val Gln Asn Asn
            85                  90                  95

gac ttt acc ccg gtg gag gcg ggc acg cag acc ata aat ttc gac gag    14134
Asp Phe Thr Pro Val Glu Ala Gly Thr Gln Thr Ile Asn Phe Asp Glu
        100                 105                 110

cgc tcg cgg tgg ggc ggc gac ctg aaa acc atc ctg cgc acc aac atg    14182
Arg Ser Arg Trp Gly Gly Asp Leu Lys Thr Ile Leu Arg Thr Asn Met
    115                 120                 125

ccc aac atc aac gag ttc atg tcc acc aac aag ttc agg gcc cgg ttg    14230
Pro Asn Ile Asn Glu Phe Met Ser Thr Asn Lys Phe Arg Ala Arg Leu
130                 135                 140                 145

atg gta gag aaa gtg aac aag gaa acc aat gcc cct cga tac gag tgg    14278
```

-continued

```
Met Val Glu Lys Val Asn Lys Glu Thr Asn Ala Pro Arg Tyr Glu Trp
                150                 155                 160

ttt gag ttc acc ctg ccc gag ggc aac tac tcg gag acc atg acc ata    14326
Phe Glu Phe Thr Leu Pro Glu Gly Asn Tyr Ser Glu Thr Met Thr Ile
            165                 170                 175

gac ctg atg aat aac gcg atc gtg gac aac tac ttg gaa gtg ggg cgg    14374
Asp Leu Met Asn Asn Ala Ile Val Asp Asn Tyr Leu Glu Val Gly Arg
        180                 185                 190

cag aac ggg gtg ctg gag agc gac atc ggg gtg aag ttt gac acg cgc    14422
Gln Asn Gly Val Leu Glu Ser Asp Ile Gly Val Lys Phe Asp Thr Arg
    195                 200                 205

aac ttc cgg ctg ggc tgg gac ccg gtc acc aag ctg gtc atg ccc ggc    14470
Asn Phe Arg Leu Gly Trp Asp Pro Val Thr Lys Leu Val Met Pro Gly
210                 215                 220                 225

gtg tac acc aac gag gcc ttc cac ccc gac atc gtc ctg ctg ccc ggc    14518
Val Tyr Thr Asn Glu Ala Phe His Pro Asp Ile Val Leu Leu Pro Gly
                230                 235                 240

tgc ggc gtg gac ttc acg cag agc cgg ctg agc aac ctg ctg ggg atc    14566
Cys Gly Val Asp Phe Thr Gln Ser Arg Leu Ser Asn Leu Leu Gly Ile
            245                 250                 255

cgc aag cgg atg ccc ttc cag gcg ggt ttt cag atc atg tac gag gac    14614
Arg Lys Arg Met Pro Phe Gln Ala Gly Phe Gln Ile Met Tyr Glu Asp
        260                 265                 270

ctg gag ggc ggc aac atc ccc gcc ttg cta gac gtg gcg aaa tac gag    14662
Leu Glu Gly Gly Asn Ile Pro Ala Leu Leu Asp Val Ala Lys Tyr Glu
    275                 280                 285

gcc agc att cag aag gcg cgg gag cag ggc cag gag atc cgc ggc gac    14710
Ala Ser Ile Gln Lys Ala Arg Glu Gln Gly Gln Glu Ile Arg Gly Asp
290                 295                 300                 305

aac ttt acc gtc atc ccc cgg gac gtg gag atc gtg ccc gtg gag aag    14758
Asn Phe Thr Val Ile Pro Arg Asp Val Glu Ile Val Pro Val Glu Lys
                310                 315                 320

gat agc aag gac cgc agt tac aac cta ctc ccc ggc gac cag acc aac    14806
Asp Ser Lys Asp Arg Ser Tyr Asn Leu Leu Pro Gly Asp Gln Thr Asn
            325                 330                 335

acg gcc tac cgc agc tgg ttc ctg gcc tac aac tac ggc gac ccc gag    14854
Thr Ala Tyr Arg Ser Trp Phe Leu Ala Tyr Asn Tyr Gly Asp Pro Glu
        340                 345                 350

aag ggc gtc agg tcc tgg acg ctg ctg acc acc acg gac gtc acc tgc    14902
Lys Gly Val Arg Ser Trp Thr Leu Leu Thr Thr Thr Asp Val Thr Cys
    355                 360                 365

ggc tcg cag cag gtg tac tgg tcg ctc ccg gac atg atg caa gac ccc    14950
Gly Ser Gln Gln Val Tyr Trp Ser Leu Pro Asp Met Met Gln Asp Pro
370                 375                 380                 385

gtg acc ttc cgg ccc tcc agc caa gtc agc aac tac ccc gtg gtg gga    14998
Val Thr Phe Arg Pro Ser Ser Gln Val Ser Asn Tyr Pro Val Val Gly
                390                 395                 400

gtc gag ctc ctg ccg gtg cac gcc aag agc ttt tac aac gag cag gcc    15046
Val Glu Leu Leu Pro Val His Ala Lys Ser Phe Tyr Asn Glu Gln Ala
            405                 410                 415

gtc tac tcg cag ctc atc cgc cag tcc acc gcg ctc acg cac gtc ttc    15094
Val Tyr Ser Gln Leu Ile Arg Gln Ser Thr Ala Leu Thr His Val Phe
        420                 425                 430

aac cgc ttc ccc gag aac cag atc ctg gtg cgc ccg ccc gct ccg acc    15142
Asn Arg Phe Pro Glu Asn Gln Ile Leu Val Arg Pro Pro Ala Pro Thr
    435                 440                 445

att acc acc gtc agt gaa aac gtt ccc gcc ctc aca gat cac gga acc    15190
Ile Thr Thr Val Ser Glu Asn Val Pro Ala Leu Thr Asp His Gly Thr
450                 455                 460                 465
```

-continued

```
ctg ccg ctg cgc agc agt atc agt gga gtc cag cgc gtg acc atc act    15238
Leu Pro Leu Arg Ser Ser Ile Ser Gly Val Gln Arg Val Thr Ile Thr
                470                 475                 480

gac gcc cgg cga agg acc tgc ccc tac gtg cac aag gcc ctg ggc ata    15286
Asp Ala Arg Arg Arg Thr Cys Pro Tyr Val His Lys Ala Leu Gly Ile
            485                 490                 495

gtc gct ccc aaa gtg ctc tct agc cgc acc ttt taa caagcatgtc        15332
Val Ala Pro Lys Val Leu Ser Ser Arg Thr Phe
        500                 505

cattctcatc tcgcccgaca acaacaccgg ctggggcctg cgctcggccg gcatgtacgg  15392

cggcgccaag cggcgctcca gcgagcaccc cgtccgcgtc cgcggccact accgggcccc  15452

ctggggcgcc cacaagcgcg gcgtctccac gcgcaccacc gtcgacgacg ccatcgacgc  15512

cgtcgtggcc caggccagac gctaccgccg gcccaagtcg acggtggacg ccgtcatcga  15572

cagcgtggtg gccgacgcgc ggcgatacgc tcgacgcaag cggcgtctgc accgccgtcg  15632

ccgtcccacc gccgccatgc tggccgccag agcggtcctg agacgcgcgc gccgcgtggg  15692

ccgccgagcc atgcgccgag ccgcggccaa cgccagcgcg ggtcgcgccc gtcgtcaggc  15752

cgcccggcag gccgccgccg ccatcgccaa cctggcccaa ccccgccggg gaaacgtgta  15812

ctgggtgcga gacgcgtcgg gcgtgcgcgt gccggtgcgc acccgccccc ctcggagtta  15872

gaagacaaaa agacggacga agactgagtt tccctgtcgt tgccagcatg agcaagcgca  15932

agttcaaaga agagctgctg gaggccctcg tgcccgagat ctacggcccg gccgccgctg  15992

ccgccgcggt ggcggacgtc aagcccgaag ttaagccccg cgcgctgaag cgggttaaaa  16052

agcgggaaaa gaaagaggag aagcaggaag cagggttgct agacgtcgac gacggcgtgg  16112

agttcgtgcg gtccttcgcg ccccgtcgcc gggtgcagtg gcggggtcgc cgcgtcaagc  16172

tcgtcccgcg gccgggcacc gtggtgtctt tcaccccgg cctgcgttcg gccacgcgcg   16232

gcctgaagcg cgagtacgac gaggtctatg gcgacgaaga catcctggag caggccgccc  16292

agcagctcgg ggagtttgct tacggcaagc gcggccgcta cggggaggtg gcgctggcgc  16352

tggaccaggg caatcccacg cccagcctca agcccgtcac gctgcagcag gtgctgcccg  16412

tgagcgcgtc gaccgagagc aagcggggca tcaagaggga gatgggcgac ctgcagccca  16472

ccatgcaact catggtgccc aaacggcaga agctggagga cgtgctggag aacatgaaag  16532

tggatcccag catcgagccc gaagtgaaag tgcgacccat caaggaagtg ggcccgggcc  16592

taggcgtgca gacggtggac attcagatcc ccgtgcgcgc ctcccccgtt tctgccacca  16652

ctacgacggc cgtggaggcc atggaaacgc agacggagct gcccgcggcc ttggcggcag  16712

ccgccaccgc cgccgcggct acccgagaga tgggcatgca gaccgacccc tggtacgagt  16772

tcgccggccc cgcccgtcgt ccacgagccc gtcggtacgc ggcgaccacc tcccggctcc  16832

ctgactacgt cttgcatcct tccatcacgc cgacgcccgg ctaccgcgga acgaccttcc  16892

gccccggtcg cgcgcgcacc accacccgcc gtcgtcgcac cacccgccgc cgtcgcagcc  16952

gtcgcgcact ggctcccatc gcggttcgcc gcgtcgtccg ccggggtcgc acgctgaccc  17012

tgcccaccgc gcgttaccac cccagcatcg tcatttaacc tgcgctgccg ttttgcagat  17072

ggctctgacg tgccgctttc gcttccccgt tcggcactac cgaggaagat ctcgccgtag  17132

gactggtcta gcgggcagcg gtctccgacg ccgccgccgc gcggtgcacc ggcgcatgaa  17192

gggcggcatt ctgcccgcgc tgatccccat tatcgccgcc gccatcgggg cgatccccgg  17252

cgtggcctcg gtggccttgc aagcagctcg caaaaattaa ataaagaagg cttgacactc  17312

actgcctggt cctgactgtt tcatgcagac aagacatgga agacatcaat tttgcgtcgt  17372
```

```
tggccccgcg gcacggctcg cggccgttca tgggcacctg gaacgagatc ggcaccagcc  17432

agctcaacgg gggcgctttc agttggagca gcctgtggag cggcattaaa aactttgggt  17492

ccacgattaa gacctatggc aacaaggcgt ggaacagtag cactggtcag atgctccgcg  17552

ataagctgaa ggaccagaac ttccagcaga aagtggtaga cggtctggcc tcgggcatca  17612

acggggtggt ggacctggcc aaccaggcgg tgcagaacca gatcaaccag cgtctggaga  17672

acagccgcca gccgcccgcg gccctgcagc agcgtccgca ggtggaggag gtggaagtgg  17732

aggagaagct gccgcccctg gagacggtgt cgccggtggg cgtgcctagc aaggggggaga  17792

agcggccgcg gcccgagctc gaggagaccc tagtgaccga gaccctggag ccgccctcgt  17852

acgagcaggc cttgaaagag ggggccacgc ccctgcccat gacccggccc atcggaccca  17912

tggcccgacc ggtctacggc aaggaacaca aagccgtgac gctagagctg cctccgccgg  17972

cgcccaccgt acccccgatg cccggtccca ccctgggcac cgccgtgcct cgtcccgccg  18032

ccccgccggt cgccgtggcc acgcccgcgc gcccgagtcg cggagccaac tggcagagca  18092

ctctgaacag catcgtgggc ctgggagtga aaagcctgaa acgccgccgg tgttactatt  18152

aaagccagct aaataccat gtgttgtatg cgcctcctgt gtcacgccag aaaaagccag  18212

ccgagtgacg ggtcaccgcc gccgccaaga gcgccgcttt caag atg gcc acc ccc   18268
                                                 Met Ala Thr Pro
                                                     510

tcg atg atg ccg cag tgg tct tac atg cac atc gcc ggg cag gac gcc    18316
Ser Met Met Pro Gln Trp Ser Tyr Met His Ile Ala Gly Gln Asp Ala
        515                 520                 525

tcg gag tac ctg agc ccg ggc ctg gtg cag ttc gcc cgc gcc acc gac    18364
Ser Glu Tyr Leu Ser Pro Gly Leu Val Gln Phe Ala Arg Ala Thr Asp
    530                 535                 540

acg tac ttc agc ctg ggc aac aag ttt agg aac ccc acg gtg gcc ccc    18412
Thr Tyr Phe Ser Leu Gly Asn Lys Phe Arg Asn Pro Thr Val Ala Pro
545                 550                 555                 560

acc cac gac gtg acg acg gac cgg tcc cag cgg ctg acg ctg cgg ttc    18460
Thr His Asp Val Thr Thr Asp Arg Ser Gln Arg Leu Thr Leu Arg Phe
                565                 570                 575

gtg ccc gtc gac cgc gag gac acc gcg tac tcg tac aaa gtg cgc ttc    18508
Val Pro Val Asp Arg Glu Asp Thr Ala Tyr Ser Tyr Lys Val Arg Phe
            580                 585                 590

acg ctg gcc gtg ggc gac aac cgc gtg ctg gac atg gcc agc acg tac    18556
Thr Leu Ala Val Gly Asp Asn Arg Val Leu Asp Met Ala Ser Thr Tyr
        595                 600                 605

ttt gac atc cgc ggc gtg ttg gac cgc ggt ccc agc ttc aaa ccc tac    18604
Phe Asp Ile Arg Gly Val Leu Asp Arg Gly Pro Ser Phe Lys Pro Tyr
    610                 615                 620

tcc ggc acc gcc tac aac tcc ctg gcc ccc aag ggc gcc ccc aac ccg    18652
Ser Gly Thr Ala Tyr Asn Ser Leu Ala Pro Lys Gly Ala Pro Asn Pro
625                 630                 635                 640

tca gaa tgg aag ggc tca gac aac aaa att agt gta aga ggt cag gct    18700
Ser Glu Trp Lys Gly Ser Asp Asn Lys Ile Ser Val Arg Gly Gln Ala
                645                 650                 655

ccg ttt ttt agt aca tcc att aca aag gat ggt att caa gtg gcc act    18748
Pro Phe Phe Ser Thr Ser Ile Thr Lys Asp Gly Ile Gln Val Ala Thr
            660                 665                 670

gat act tct agc gga gct gtg tat gct aaa aag gaa tat cag cct gaa    18796
Asp Thr Ser Ser Gly Ala Val Tyr Ala Lys Lys Glu Tyr Gln Pro Glu
        675                 680                 685

cca caa gta ggg caa gaa caa tgg aac agc gaa gcc agt gat agt gat    18844
Pro Gln Val Gly Gln Glu Gln Trp Asn Ser Glu Ala Ser Asp Ser Asp
```

-continued

```
    690                 695                 700

aaa gta gct ggt agg att cta aaa gac aca aca ccc atg ttc cct tgt    18892
Lys Val Ala Gly Arg Ile Leu Lys Asp Thr Thr Pro Met Phe Pro Cys
705                 710                 715                 720

tac ggt tcc tac gcc aag ccc aca aat gaa cag ggg ggg caa ggc act    18940
Tyr Gly Ser Tyr Ala Lys Pro Thr Asn Glu Gln Gly Gly Gln Gly Thr
                725                 730                 735

aat act gta gat ctg cag ttc ttt gcc tct tca tcg gct acc tct acg    18988
Asn Thr Val Asp Leu Gln Phe Phe Ala Ser Ser Ser Ala Thr Ser Thr
            740                 745                 750

cct aaa gcc gta ctc tat gcc gag gac gtg gca ata gaa gca cca gac    19036
Pro Lys Ala Val Leu Tyr Ala Glu Asp Val Ala Ile Glu Ala Pro Asp
        755                 760                 765

acc cat ttg gtg tac aaa ccg gca gtt aca acc acg acc act agt tcc    19084
Thr His Leu Val Tyr Lys Pro Ala Val Thr Thr Thr Thr Thr Ser Ser
    770                 775                 780

caa gac ctg cta act cag cag gct gct ccc aac cga ccc aac tac att    19132
Gln Asp Leu Leu Thr Gln Gln Ala Ala Pro Asn Arg Pro Asn Tyr Ile
785                 790                 795                 800

ggc ttc agg gat aat ttt atc ggt ctc atg tat tac aac tcc act ggc    19180
Gly Phe Arg Asp Asn Phe Ile Gly Leu Met Tyr Tyr Asn Ser Thr Gly
                805                 810                 815

aat atg ggt gtt ttg gca ggg caa gct tct cag cta aac gcg gtg gtt    19228
Asn Met Gly Val Leu Ala Gly Gln Ala Ser Gln Leu Asn Ala Val Val
            820                 825                 830

gac ttg caa gac aga aac acc gag ctg tcc tac cag ctc atg ctt gat    19276
Asp Leu Gln Asp Arg Asn Thr Glu Leu Ser Tyr Gln Leu Met Leu Asp
        835                 840                 845

gct ttg ggc gac cgc agt cgt tac ttc tcc atg tgg aac cag gcc gta    19324
Ala Leu Gly Asp Arg Ser Arg Tyr Phe Ser Met Trp Asn Gln Ala Val
    850                 855                 860

gac agc tat gac cct gat gtc aga att att gaa aat cat ggt gtg gag    19372
Asp Ser Tyr Asp Pro Asp Val Arg Ile Ile Glu Asn His Gly Val Glu
865                 870                 875                 880

gat gag ctg cca aac tac tgt ttc ccg cta gga ggg tcg cta gta act    19420
Asp Glu Leu Pro Asn Tyr Cys Phe Pro Leu Gly Gly Ser Leu Val Thr
                885                 890                 895

gaa act tat aca ggc cta tca ccc caa aac gga agt aac acg tgg aca    19468
Glu Thr Tyr Thr Gly Leu Ser Pro Gln Asn Gly Ser Asn Thr Trp Thr
            900                 905                 910

acc gac agc acc acc tat gca act aga ggg gtg gaa atc ggc tct ggc    19516
Thr Asp Ser Thr Thr Tyr Ala Thr Arg Gly Val Glu Ile Gly Ser Gly
        915                 920                 925

aac atg ttc gcc atg gaa att aat ttg gcg gcc aat cta tgg agg agt    19564
Asn Met Phe Ala Met Glu Ile Asn Leu Ala Ala Asn Leu Trp Arg Ser
    930                 935                 940

ttc ctg tac tcc aac gtg gcc ctg tac ctg ccc gac gag tac aag ctc    19612
Phe Leu Tyr Ser Asn Val Ala Leu Tyr Leu Pro Asp Glu Tyr Lys Leu
945                 950                 955                 960

acc ccc gac aac atc acc ctc ccc gac aac aaa aac act tac gac tac    19660
Thr Pro Asp Asn Ile Thr Leu Pro Asp Asn Lys Asn Thr Tyr Asp Tyr
                965                 970                 975

atg aac ggc cgc gtg gcc gcc ccc agc tcc ctc gac acc tac gtc aac    19708
Met Asn Gly Arg Val Ala Ala Pro Ser Ser Leu Asp Thr Tyr Val Asn
            980                 985                 990

atc ggg gcg cgc tgg tcc ccc gac  ccc atg gac aac gtc  aac ccc ttc  19756
Ile Gly Ala Arg Trp Ser Pro Asp  Pro Met Asp Asn Val  Asn Pro Phe
        995                 1000                1005

aac cac  cac cgc aac gcg gga  ctg cgc tac cgc tcc  atg ctg ctg     19801
```

-continued

```
Asn His  His Arg Asn Ala Gly  Leu Arg Tyr Arg Ser  Met Leu Leu
    1010                 1015                 1020

ggc aac  ggc cgc tac gta ccc  ttc cac atc caa gtg  ccc cag aaa     19846
Gly Asn  Gly Arg Tyr Val Pro  Phe His Ile Gln Val  Pro Gln Lys
    1025                 1030                 1035

ttc ttc  gcc atc aaa aac ctc  ctg ctc ctc ccc ggg  tcc tac acc     19891
Phe Phe  Ala Ile Lys Asn Leu  Leu Leu Leu Pro Gly  Ser Tyr Thr
    1040                 1045                 1050

tac gag  tgg aac ttc cgc aag  gac gtc aac atg atc  ctc cag agc     19936
Tyr Glu  Trp Asn Phe Arg Lys  Asp Val Asn Met Ile  Leu Gln Ser
    1055                 1060                 1065

agc ctg  ggt aac gac ctc cgc  gtc gac ggg gcc agc  gtc agg ttc     19981
Ser Leu  Gly Asn Asp Leu Arg  Val Asp Gly Ala Ser  Val Arg Phe
    1070                 1075                 1080

gac agc  atc aac ctg tac gcc  aac ttc ttc ccc atg  gcc cac aac     20026
Asp Ser  Ile Asn Leu Tyr Ala  Asn Phe Phe Pro Met  Ala His Asn
    1085                 1090                 1095

acc gcc  tcc acg ctc gag gcc  atg ctg cgc aac gac  acc aac gac     20071
Thr Ala  Ser Thr Leu Glu Ala  Met Leu Arg Asn Asp  Thr Asn Asp
    1100                 1105                 1110

cag tcg  ttc aac gac tac ctc  tgc gct gcc aac atg  ctc tac ccc     20116
Gln Ser  Phe Asn Asp Tyr Leu  Cys Ala Ala Asn Met  Leu Tyr Pro
    1115                 1120                 1125

atc ccc  gcc aac gcc acc agc  gtg ccc atc tcc att  ccc tcg cgg     20161
Ile Pro  Ala Asn Ala Thr Ser  Val Pro Ile Ser Ile  Pro Ser Arg
    1130                 1135                 1140

aac tgg  gcc gcc ttc cgg ggc  tgg agc ttc acc cgg  ctc aag acc     20206
Asn Trp  Ala Ala Phe Arg Gly  Trp Ser Phe Thr Arg  Leu Lys Thr
    1145                 1150                 1155

aag gag  acc ccc tct ctg ggc  tcc ggc ttc gat ccc  tac ttc acc     20251
Lys Glu  Thr Pro Ser Leu Gly  Ser Gly Phe Asp Pro  Tyr Phe Thr
    1160                 1165                 1170

tac tcg  ggc tcc atc ccc tac  ctg gac ggc acc ttc  tac ctc aac     20296
Tyr Ser  Gly Ser Ile Pro Tyr  Leu Asp Gly Thr Phe  Tyr Leu Asn
    1175                 1180                 1185

cac act  ttc aag aag gtc tcc  atc atg ttc gac tcc  tcc gtc agc     20341
His Thr  Phe Lys Lys Val Ser  Ile Met Phe Asp Ser  Ser Val Ser
    1190                 1195                 1200

tgg ccc  ggc aac gac cgc ctg  ctg acc ccc aac gag  ttc gag atc     20386
Trp Pro  Gly Asn Asp Arg Leu  Leu Thr Pro Asn Glu  Phe Glu Ile
    1205                 1210                 1215

aag cgc  acc gtg gac ggg gaa  ggg tac aac gtg gcc  cag tgc aac     20431
Lys Arg  Thr Val Asp Gly Glu  Gly Tyr Asn Val Ala  Gln Cys Asn
    1220                 1225                 1230

atg acc  aag gac tgg ttc ctc  atc cag atg ctc agc  cac tac aac     20476
Met Thr  Lys Asp Trp Phe Leu  Ile Gln Met Leu Ser  His Tyr Asn
    1235                 1240                 1245

atc ggc  tac cag ggc ttc tac  gtg ccc gag ggc tac  aag gac agg     20521
Ile Gly  Tyr Gln Gly Phe Tyr  Val Pro Glu Gly Tyr  Lys Asp Arg
    1250                 1255                 1260

atg tac  tct ttc ttc cgc aac  ttc caa ccc atg agc  cgc cag gtg     20566
Met Tyr  Ser Phe Phe Arg Asn  Phe Gln Pro Met Ser  Arg Gln Val
    1265                 1270                 1275

gtc gac  acc acc acc tac acc  gac tac aaa aac gtc  acc ctc ccc     20611
Val Asp  Thr Thr Thr Tyr Thr  Asp Tyr Lys Asn Val  Thr Leu Pro
    1280                 1285                 1290

ttc cag  cac aac aac tcg ggg  ttc gtg gga tac atg  ggc ccc acc     20656
Phe Gln  His Asn Asn Ser Gly  Phe Val Gly Tyr Met  Gly Pro Thr
    1295                 1300                 1305
```

-continued

```
atg cgc  gag ggg cag gcc tac  ccc gcc aac tac ccc  tac ccc ctg     20701
Met Arg  Glu Gly Gln Ala Tyr  Pro Ala Asn Tyr Pro  Tyr Pro Leu
    1310                 1315                 1320

atc ggc  aag acc gcc gtg ccc  agc ctc acg cag aaa  aag ttc ctc     20746
Ile Gly  Lys Thr Ala Val Pro  Ser Leu Thr Gln Lys  Lys Phe Leu
    1325                 1330                 1335

tgc gac  cgc acc atg tgg cgc  atc ccc ttc tcc agt  aac ttc atg     20791
Cys Asp  Arg Thr Met Trp Arg  Ile Pro Phe Ser Ser  Asn Phe Met
    1340                 1345                 1350

tcc atg  ggg gcg ctc acc gac  ctg ggg cag aac atg  ctg tac gcc     20836
Ser Met  Gly Ala Leu Thr Asp  Leu Gly Gln Asn Met  Leu Tyr Ala
    1355                 1360                 1365

aac tcc  gcc cac gcc ctc gac  atg acc ttc gag gtg  gac ccc atg     20881
Asn Ser  Ala His Ala Leu Asp  Met Thr Phe Glu Val  Asp Pro Met
    1370                 1375                 1380

gat gag  ccc acg ctt ctc tat  gtt ctg ttc gaa gtg  ttc gac gtc     20926
Asp Glu  Pro Thr Leu Leu Tyr  Val Leu Phe Glu Val  Phe Asp Val
    1385                 1390                 1395

gtg cgc  atc cac cag ccg cac  cgc ggc gtc atc gag  gcc gtc tac     20971
Val Arg  Ile His Gln Pro His  Arg Gly Val Ile Glu  Ala Val Tyr
    1400                 1405                 1410

ctg cgc  acg ccg ttc tcg gcc  ggt aac gcc acc acc  taa ggagggggcc  21020
Leu Arg  Thr Pro Phe Ser Ala  Gly Asn Ala Thr Thr
    1415                 1420                 1425

gccgacggat gggctccagc gagccggagc tggtcgccat cgcgcgcgac ctgggctgcg  21080

ggccctactt cctgggcacc tttgacaaac gcttcccggg cttcgtggcg ccgcacaagc  21140

tggcctgcgc catcgtcaac accgccggac gcgagaccgg cggcgtccac tggctggccc  21200

tggcctggaa cccccgcagc cgaacctgct acctcttcga ccccttcggc ttctcggacg  21260

acaggctcag gcagatctac cagttcgagt acgaaggcct gctccggcgc agcgccctcg  21320

cctccacccc cgaccactgc gtcaccctcg tcaagtccac ccagaccgtc caggggcccc  21380

gctcggccgc ctgcggcctc ttctgctgca tgttcctgca cgccttcgtg cgctggcccg  21440

cctcccccat ggacggcaac cccaccatgg acctccttac gggcgttccc aacagcatgc  21500

ttcagagtcc ccaggtcgag cccaccctcc accgcaacca ggaggaactc tacgccttcc  21560

tggctcggca ctcccccctac tttcgccgcc accgcgagcg catagaaaag gccaccgcgt  21620

ttgacaaaat gaacgactag attttctgtg aaaaacactc aataaagcct ttattggttc  21680

accacacgtg cacgcatgca gactttttat ttaaaagggc tccgcctcct cgtcgccgtg  21740

gctggtgggg agggagacgt tgcgatactg caggcgggag ctccatctga actcgggaat  21800

cagcagcttg ggcagggggc cctcgacgtt ctcgctccac agcttgcgca ccagctgcag  21860

ggcgcccagc aggtcgggcg cggagatctt gaagtcgcag ttggggccct ggttgccgcg  21920

ggagttgcgg tacaccgggt tggcgcactg gaacaccagc acgctggggt gctcgatgct  21980

ggccagcgcc gtcttgtcgg tcacctcgtc gccgcgcagg gactccgcgt tgctcagcgc  22040

gaaggcggtc agcttgcaca gctgccgacc cagcacgggc accccgctcg gctggttcag  22100

gcagtcgcag cgcatagcca tcagcagccg cttctgcccg tgctgcatct tcggatagtc  22160

ggctcgcatg aaggcctcca tctgccggaa ggccgtctgc gccttgctgc cctccgagaa  22220

gaacagcccg caggacttgc cggagaacac gttgttgccg cagctcacgt cttccacgca  22280

gcagcgcgcg tcgtcgttct tcagctgcac cacgctgcgg ccccagcggt tctgcaccac  22340

cttggtcttg ccgggatgtt ccttcagggc ccgctggccg ttctcgctgg tcacgtccat  22400

ctccaccacc tgctccttct ggatcatctc cagcccgtgg tagcagcgca gcacgccctc  22460
```

-continued

```
ctgctcggtg cacccgtgca gccagacggc gcagccggtc ggctccagct gttgaggttt  22520
caccccggcg taggtctcca cgtacgcccg caggaagcgg cccatcatct ccacaaaggt  22580
cttctgaccg gtgaaggtca gctgcagccc gcgatgctcc tcgttgagcc acgtctgaca  22640
gatcttgcgg tacaccttgc cctgctcggg cagaaacttg aaagcggcct tctcctcggg  22700
ctccacgtgg tacttctcca tcagcgccga catcagctcc atgcccttct cccaggccga  22760
caccagcggc tccgcgcggg ggttcaccac cgccatgcct cgggaagtgc cggggcgctc  22820
atcttcctcc tcctcctcgt cttcttcttg aggcggcggt ggcggcagtt gtctcacgaa  22880
tctcttgccg ttggccttct ggacgatctc cacgccgggg tgggtgaacc cgtgggccac  22940
caccacttcg tcctcttcct cttcgctgtc gggcacgact tcgggagagg gaggcggcgg  23000
aggaaccggt gcggccactg cggccatcgc ggcgttcttg cgcgccttct tgggggggcag  23060
aggcggcgtc tcgcgctccg ggctggtctc ttgcaggtag ggcgtgatgg tgtgggaggt  23120
ggggcgctct ggctgacggc cggccatgct gatgcttgac tcctaggcga aaagatggag  23180
gaggatctta gacagccgca gcccgtctcc gaaaccttaa ccacccccgc ctctgaggtc  23240
ggcgccggcg agctagacat gcaacgggag gaggaggagg acgtgcgagt ggagcaagac  23300
ccgggctacg tgacgccgcc cgaggacggc gaggagccgc aggcaccggc gccaacgctc  23360
agcgaagccg actacctggg aggggaggac gacgtgctgc tgaagcacct ggcgcggcag  23420
agcaccatcg tgcaggaggc cctcaaggag cgcgaggagg tcccgctgac ggtggaggag  23480
ctcagccggg cctacgaagc caacctcttc tcgccgcggg tgccccccaa gaagcaggcc  23540
aacggcacct gcgagcccaa cccccgcctc aacttctacc ccgtctttgc ggtgcccgag  23600
gcgctggcca cctatcacat cttcttcaag aaccagcgca tcccccctctc gtgccgcgcc  23660
aaccgcaccc gcgccgaccg cctcctgcat ctccgagccg gcgccgccat acctgagatc  23720
gcctccctgg aggaagtccc caagatcttc gaaggtctcg gcaaggacga gaagcgcgcg  23780
gcaaacgctc tggaaaagaa cgagagcgag ggtcagaacg tgctggtcga gctggaaggc  23840
gacaacgcgc gtctggccgt gctcaaacgc accatcgaag tctcccactt cgcctacccc  23900
gcgctcaacc ttccccccaa ggtcatgcgc tcggtcatgg atcagctgct catcaagcgc  23960
gccgagcccc tcgagaacga ctccgaggtg gattccgagg acggaaaacc cgtggtctcg  24020
gacgaggagc tcgcgcgctg gctgggcacg caggaccccg ccgagttgca agagcggcgc  24080
aagatgatga tggcggccgt gctggtcacc gccgagctcg agtgcctgca gcgcttcttc  24140
gccgaccccc agaccctgcg caaggtcgag gagtccctgc actacgcctt ccgccacggc  24200
tacgtgcgcc aggcctgcaa gatctccaac gtggagctta gcaacctggt ctcctacatg  24260
ggcatcctgc acgagaaccg cctcgggcag aacgtcctcc actgcaccct gaccggggag  24320
gcccgccgcg actacgtccg cgactgcatc tacctctttc tcaccctcac ctggcagacc  24380
gccatggggg tctggcagca gtgtctggag gagcgcaacc ttcgcgagct cgacaagcta  24440
ctgagccgcg agcgccgcga gctctggacg gctttcagcg agcgcaccgc cgcctgccgt  24500
ctggccgacc tcatcttccc cgagcgactc aggcaaaccc tccagaacgg cctgcccgac  24560
tttgtcagcc agagcatgct gcaaaacttt cgctccttca tcctggagcg atccggcatc  24620
ttgcccgcca tgagctgcgc cctgccctcc gatttcgtcc ccctctatta tcgcgagtgc  24680
cccccgccgc tctggagcca ctgctacctg ctgcgtctgg ccaactacct cgcccaccac  24740
tccgacctca tggaagactc cagcggcgag ggctgctgg agtgccactg ccgctgcaac  24800
```

-continued

```
ctctgcaccc cccaccgctc gctggtctgc aacaccgagc tgctcagcga gacgcaagtg  24860
atcggtacct ttgagatcca gggaccagag gggccggagg gtgcttccaa cctcaagctc  24920
agcccggcgc tctggacttc cgcctacctg cgcaaattta tccccgagga ctatcacgcc  24980
caccagatcc aattctacga agaccaatcg cgaccccca aagcccccct cacggcctgt  25040
gtcatcaccc agagccagat tctggcccaa ttgcaagcca tccagcaggc ccgccaagag  25100
ttcctcctga aaaagggtca cggggtctat ctggaccccc agaccggcga ggaactcaac  25160
accccgtcac cctccgccgc cgcttcgtgc cgcccgcaga accatgccgc ccaaagggaa  25220
caagcaggcc atcgcccagc ggcgggccaa gaagcagcaa gagctccagg agcagtggga  25280
cgaggagtcc tgggacagcc aggcggagga agtctcagac gaggaggagg acatggagag  25340
ctgggacagc ctagacgagg aggaggaggc cgaggagcta gaggacgagc ctctcgagga  25400
ggaagagccc agcagcgccg cggcaccatc ggcttccaaa gaagcggctc ggagccggcc  25460
ggccccgaag cagcagaagc agcaacagcc gccaccgtcg cccccgacgc caccaccagg  25520
ctcactcaaa gccagccgta ggtgggacgc ggtgtccatc gcgggatcgc ccaaagcccc  25580
agtcggtaag ccacccgggc ggtcgcggcg ggggtactgt tcctggcgcc cccacaagag  25640
caagatcgtc gcctgcctcc agcactgccg gggcaacatc tccttcgcgc ggcgctactt  25700
gctcttccac gacggggtgg cggtgccgcg caacgtcctc tactattacc gtcatctcta  25760
cagcccctac gagacagaag gcccggcctc cgcgtaagac cagccgccag acggtctcct  25820
ccgccatcgc gacccgccag gactcggccg ccacgcagga gctcagaaaa cgcatctttc  25880
ccaccctgta tgctatcttc cagcagagcc gcggccagca gctggaactg aaagtaaaaa  25940
accgctccct gcgttcgctc acccgcagct gtctgtacca caggagggaa gaccaactgc  26000
agcgcacgct cgaggacgcc gaggcactgt tcaataaata ctgctcggtg tctcttaagg  26060
actgaaagcc cgcgcttttt cagaggctca ttacgtcatc atcatcatga gcaaggacat  26120
tcccacgcct tacatgtgga gctaccagcc gcagatggga ctggcggccg gcgcctccca  26180
ggattactcc agtcgcatga actggctgag tgccggcccc cacatgatcg ggcgggtcaa  26240
tgggattcgt gccacccgca atcagatact gctggaacag gccgccctca cctccacccc  26300
gcgacgtcag ctgaacccgc ccgcttggcc cgccgcccag gtgtaccagg aaaaccccgc  26360
cccgaccaca gtcctcctgc cacgcgacgc ggaggccgaa gtccagatga ctaactccgg  26420
ggcgcaatta gcgggcggcg cccgccacgt cgtcgctccc gggtacagag gtcggcccgc  26480
accctacccc tccggcccta taaagaggct gatcattcga ggccgaggta tccagctcaa  26540
cgacgaggtg gtgagctcct cgaccggtct tcggcccgac ggagtcttcc agcttggagg  26600
cgccggccgc tcttccttca ccactcgcca ggcctacctg acgctccaga gctcttcctc  26660
ccagcctcgc tccggcggca tcggcaccct ccagttcgtg gaggagttcg tgccctcggt  26720
ctacttcaac ccgttctccg gctctcccgg ccgctacccg gacagcttca tccccaacta  26780
cgacgcggtg agcgaatccg tggacggcta cgattgatga ccgatggtgc ggccgtaact  26840
gcgcggcggc aacatctgca tcactgccat cgtcctcggt gcttcgcccg ggaggcctgt  26900
gagttcatct acttccagct cgccccggac cagcttcagg gcccttcgca cggcgttaag  26960
ctcgtgatag aggaagagct cgagagtagc tgcctgcgct gttttacctc gcgccccatc  27020
ctagtcgaga gggaacgcgg taggaccacc ctcaccctct actgcatctg tgactccccg  27080
gaattacatg aagatctgtg ttgccttcta tgtgccgaac aataacccct cttgtaacta  27140
cctacatcca caataaacca gaatttggaa actcctttcg tttgtttgca g atg aaa   27197
```

-continued

```
                                                      Met Lys

cgc gcc cgc  ctc gac gac gac ttc  aac ccc gtc tac ccc  tat gac     27242
Arg Ala Arg  Leu Asp Asp Asp Phe  Asn Pro Val Tyr Pro  Tyr Asp
        1430                 1435                 1440

act ccc aac  gct ccc tct gtt ccc  ttc atc act cct ccc  ttc gtc     27287
Thr Pro Asn  Ala Pro Ser Val Pro  Phe Ile Thr Pro Pro  Phe Val
        1445                 1450                 1455

tcc tcg gac  ggc ttg caa gaa aaa  cca ccc gga atg ctc  agt ctc     27332
Ser Ser Asp  Gly Leu Gln Glu Lys  Pro Pro Gly Met Leu  Ser Leu
        1460                 1465                 1470

aac tac caa  gat cct att acc acc  caa aac ggg gca tta  act cta     27377
Asn Tyr Gln  Asp Pro Ile Thr Thr  Gln Asn Gly Ala Leu  Thr Leu
        1475                 1480                 1485

aag ctt ggc  agc gga ctg aac ata  aac caa gat ggg gaa  ctt acc     27422
Lys Leu Gly  Ser Gly Leu Asn Ile  Asn Gln Asp Gly Glu  Leu Thr
        1490                 1495                 1500

tca gac gcc  agc gtt ctc gtc act  ccc ccc att aca aaa  gcc aac     27467
Ser Asp Ala  Ser Val Leu Val Thr  Pro Pro Ile Thr Lys  Ala Asn
        1505                 1510                 1515

aac aca ata  ggc cta gcc ttc aat  gca cct ctt acc ttg  caa agc     27512
Asn Thr Ile  Gly Leu Ala Phe Asn  Ala Pro Leu Thr Leu  Gln Ser
        1520                 1525                 1530

gat act tta  aat ctt gct tgt aac  gcc cca ctt acc gtg  caa gac     27557
Asp Thr Leu  Asn Leu Ala Cys Asn  Ala Pro Leu Thr Val  Gln Asp
        1535                 1540                 1545

aat agg ttg  gga ata aca tac aac  tct ccc ctc acc ttg  caa aac     27602
Asn Arg Leu  Gly Ile Thr Tyr Asn  Ser Pro Leu Thr Leu  Gln Asn
        1550                 1555                 1560

agc gaa ctt  gcc cta gcg gtc acc  ccg cct ctt gac act  gcc aat     27647
Ser Glu Leu  Ala Leu Ala Val Thr  Pro Pro Leu Asp Thr  Ala Asn
        1565                 1570                 1575

aac aca ctt  gcg ctt aaa acc gcc  cgg cct ata att aca  aac tct     27692
Asn Thr Leu  Ala Leu Lys Thr Ala  Arg Pro Ile Ile Thr  Asn Ser
        1580                 1585                 1590

aat aac gag  ctt aca ctc tcc gct  gat gct ccc cta aac  acc agc     27737
Asn Asn Glu  Leu Thr Leu Ser Ala  Asp Ala Pro Leu Asn  Thr Ser
        1595                 1600                 1605

acg ggt acc  ctc cgc cta caa agc  gca gca cca ctg ggg  cta gtt     27782
Thr Gly Thr  Leu Arg Leu Gln Ser  Ala Ala Pro Leu Gly  Leu Val
        1610                 1615                 1620

gac caa acc  ctg cga gtg ctt ttt  tct aac cca ctc tac  ttg caa     27827
Asp Gln Thr  Leu Arg Val Leu Phe  Ser Asn Pro Leu Tyr  Leu Gln
        1625                 1630                 1635

aac aac ttt  ctc tca cta gcc att  gaa cgc cca ttg gct  tta act     27872
Asn Asn Phe  Leu Ser Leu Ala Ile  Glu Arg Pro Leu Ala  Leu Thr
        1640                 1645                 1650

acc act ggt  tct atg gct atg cag  att tcc caa cca tta  aaa gtg     27917
Thr Thr Gly  Ser Met Ala Met Gln  Ile Ser Gln Pro Leu  Lys Val
        1655                 1660                 1665

gaa gac gga  agc tta agc ttg agc  att gaa agc cct cta  aat cta     27962
Glu Asp Gly  Ser Leu Ser Leu Ser  Ile Glu Ser Pro Leu  Asn Leu
        1670                 1675                 1680

aaa aac gga  aat ctt act tta gga  acc caa agt ccc cta  act gtc     28007
Lys Asn Gly  Asn Leu Thr Leu Gly  Thr Gln Ser Pro Leu  Thr Val
        1685                 1690                 1695

act ggt aac  aac ctc agc ctt aca  aca aca gcc cca tta  acg gtt     28052
Thr Gly Asn  Asn Leu Ser Leu Thr  Thr Thr Ala Pro Leu  Thr Val
        1700                 1705                 1710

cag aac aac  gct cta gcc ctc tca  gtg tta ctg ccg ctt  aga cta     28097
```

```
Gln Asn Asn  Ala Leu Ala Leu Ser  Val Leu Leu Pro Leu  Arg Leu
        1715                1720                1725

ttt aat aac  acc tca ctg gga gtg  gca ttc aac cca ccc  att tct     28142
Phe Asn Asn  Thr Ser Leu Gly Val  Ala Phe Asn Pro Pro  Ile Ser
        1730                1735                1740

tca gca aac  aac ggg ctg tct ctt  gac att gga aat ggc  ctt aca     28187
Ser Ala Asn  Asn Gly Leu Ser Leu  Asp Ile Gly Asn Gly  Leu Thr
        1745                1750                1755

ctg caa tac  aac agg ctc gta gtg  aac att ggc ggc ggg  cta cag     28232
Leu Gln Tyr  Asn Arg Leu Val Val  Asn Ile Gly Gly Gly  Leu Gln
        1760                1765                1770

ttt aac aac  ggt gct att acc gct  tcc ata aat gca gct  ctg ccg     28277
Phe Asn Asn  Gly Ala Ile Thr Ala  Ser Ile Asn Ala Ala  Leu Pro
        1775                1780                1785

ttg cag tat  tcc aat aac cag ctt  tct ctt aat att gga  ggc ggg     28322
Leu Gln Tyr  Ser Asn Asn Gln Leu  Ser Leu Asn Ile Gly  Gly Gly
        1790                1795                1800

ctg cga tac  aac ggc act tac aaa  aat tta gcc gtc aaa  acc gac     28367
Leu Arg Tyr  Asn Gly Thr Tyr Lys  Asn Leu Ala Val Lys  Thr Asp
        1805                1810                1815

tct ttt agg  ggt ctt gaa att gac  agt aat cag ttc ctg  gtg cca     28412
Ser Phe Arg  Gly Leu Glu Ile Asp  Ser Asn Gln Phe Leu  Val Pro
        1820                1825                1830

aga ctg ggt  tct ggt cta aag ttt  gat caa tat ggg tac  att agc     28457
Arg Leu Gly  Ser Gly Leu Lys Phe  Asp Gln Tyr Gly Tyr  Ile Ser
        1835                1840                1845

gtc ata cct  cca act gtt acg cca  aca aca ctt tgg act  aca gca     28502
Val Ile Pro  Pro Thr Val Thr Pro  Thr Thr Leu Trp Thr  Thr Ala
        1850                1855                1860

gac cct tct  ccc aac gct act ttt  tac gac agc tta gat  gct aag     28547
Asp Pro Ser  Pro Asn Ala Thr Phe  Tyr Asp Ser Leu Asp  Ala Lys
        1865                1870                1875

gta tgg ctg  gcc tta gta aaa tgc  aac ggc atg gtt aat  gga acc     28592
Val Trp Leu  Ala Leu Val Lys Cys  Asn Gly Met Val Asn  Gly Thr
        1880                1885                1890

ata gcc ata  aag gct tta aaa ggt  act ctg ctc caa cct  acg gct     28637
Ile Ala Ile  Lys Ala Leu Lys Gly  Thr Leu Leu Gln Pro  Thr Ala
        1895                1900                1905

agt ttt att  tct ttt gtt atg tat  ttt tac agc aat ggc  acc aga     28682
Ser Phe Ile  Ser Phe Val Met Tyr  Phe Tyr Ser Asn Gly  Thr Arg
        1910                1915                1920

aga act aac  tac ccc acg ttt gaa  aat gaa ggc ata cta  gct agt     28727
Arg Thr Asn  Tyr Pro Thr Phe Glu  Asn Glu Gly Ile Leu  Ala Ser
        1925                1930                1935

agt gct aca  tgg ggt tat cgt caa  gga aac tcg gca aac  acc aac     28772
Ser Ala Thr  Trp Gly Tyr Arg Gln  Gly Asn Ser Ala Asn  Thr Asn
        1940                1945                1950

gtc acc agt  gcc gtt gaa ttt atg  cct agc tcc aca aga  tat cct     28817
Val Thr Ser  Ala Val Glu Phe Met  Pro Ser Ser Thr Arg  Tyr Pro
        1955                1960                1965

gtt aac aag  ggt act gag gtt cag  aac atg gaa ctc acc  tac act     28862
Val Asn Lys  Gly Thr Glu Val Gln  Asn Met Glu Leu Thr  Tyr Thr
        1970                1975                1980

ttc ttg cag  gga gac ccc act atg  gcc ata tca ttt caa  gct att     28907
Phe Leu Gln  Gly Asp Pro Thr Met  Ala Ile Ser Phe Gln  Ala Ile
        1985                1990                1995

tat aac cat  gct ttg gaa ggt tac  tct tta aaa ttt acc  tgg cga     28952
Tyr Asn His  Ala Leu Glu Gly Tyr  Ser Leu Lys Phe Thr  Trp Arg
        2000                2005                2010
```

-continued

```
gtt cgc aac  agg gaa cgc ttt gat  atc ccc tgc tgt tct  ttt tct     28997
Val Arg Asn  Arg Glu Arg Phe Asp  Ile Pro Cys Cys Ser  Phe Ser
        2015                 2020                 2025

tac ata acg  gaa gaa taa acactgtttt tcttttcaat gtttttattc          29045
Tyr Ile Thr  Glu Glu
        2030

tgctttttta cacagttcga accgtcagac tccctccccc cttccacttc acccggtaca  29105

cctcccgctc cccctggatc gctgcgtaca actgcagttt ggtgttcaga cacgggttct  29165

taggtgacag tatccacacg gcctctttgc cggccaggcg ctggtccgta atgctcacaa  29225

atccctccga cacgtcctcc agacacacgg tggaatccaa ggcgcccgtc tacaaaacaa  29285

acacagtcat gctctccacg ggttctctcc tcggtcgtac tgcgccagcg tgaacgggcg  29345

atggtgctcc atcagggctc gcagcaaccg ctgtcggcgc ggctcaccca ggctccggcg  29405

aaaagcgccc cgtctgggag tgctattcaa aaaacgcacc gcctttatca acagtctcct  29465

cgtgcggcgg gcgcagcagc gcacctggat ctctgtcagg tctttacaat aggtacagcc  29525

catcaccacc atgttgttta aaatcccaaa gctaaacacg ctccacccaa atgacatgaa  29585

ttccagcacc gccgcggcgt ggccatcata caatatgcgg aggtaaatca ggtgccgccc  29645

cctaatacaa acgctcccca tatacatcac ctccttaggc agttgataat taaccacctc  29705

ccggtaccag ggaaacctca cgtttactaa agccccaaac accaacattt taaaccagtt  29765

agccagcacc accctcccg ccttacactg cagcgacccc ggctgtttac aatgacagtg  29825

aatcacccac ctctcatacc ccctaatgac ctggcgtggc tccacatcta tagtagcaca  29885

gcacacgcac accctcatgt aatgcttcat cacaaatctt tcccaagggg ttagtatcat  29945

gtcccagggt acgggccact cctgcagcac ggtgaaaggt acgcaggcgg gaacagtcct  30005

cacctcggac acataatgca tattcagatg ttcacactct aaaaccccgg ggcttccctc  30065

caacgcagcc actggcaagt tctcagaggg tggtgtaagg cggtggtgct gatagggact  30125

caatctgtgt cgacaccgtc tgtcgcgttg catcgtagac caacgcttgg cgcaccgcct  30185

cgtacttcgc ccaaagaaaa cgggtgcgac gccaacacac ttccgcgtac cgtgggttcc  30245

gcactcgagc tcgctcagtt ctcaacgcat aatgcagcca ttcctgtaat ccacacaaca  30305

gtcgctcggc ttccaaagag atgtgcacct cgtatcttat aacgtcccga tatatatcca  30365

agcaggcagt cagggccact tgcaaccagt gcacgcaggc ggactgatcg cgacacactg  30425

gaggtggagg gagagacgga agaggcatgt tactccagac ggtcgaaaag cggatcaaag  30485

tgcagatcgc gaagatggca gcgatccccg ccgctacgct ggtgatagat cacagccagg  30545

tcaaacataa tgcggttttc caaatgacct attaccgcct ccaccagagc cgccacgcgc  30605

acttccagaa acaccagcac ggctacggca ttctcctcaa aatcttcaaa cattaagctg  30665

catgattgaa tcacccccaa ataattctcc tccttccatt ctcgcaaaat ttgagtaaaa  30725

acctctcgca gattagctcc gtggcgttca aaaaggtcac ttagagcgcc ctccaccgcc  30785

atgcgcaagc acaccctcat gattgaaaaa tgccagtctc ctgaaccacc tgcagttgat  30845

ttaaaagacc tatattagga tcaattccac tctcccgcag ctccacgcgt agcattagct  30905

gcaaaaagtc atttaaatct tcgcaaacta gcgcggtaag ctcgccgccg ggaattaggt  30965

ctgaagcagt caccacacac ataatttcca gtgaaggagt cagtctaagc agcaaaaagc  31025

cgcatgagca gtgttgaaaa ggaggggtca cgcaatgtaa catatgcagc caaaaatctc  31085

caaggtgtct gtgcataaac tccaccactg aaaagtccaa atcatgtaaa tatgccatca  31145

ccgcctcagg aaccaccacg gacacaaaaa cgggccgtag caaatacatg gtgtcctgca  31205
```

```
aagcaaaaac acatttatac catagaggcg cgaattactt ggggaaaaat cactcgctcc  31265

aaaactaaac aggccaccgt ctgaccgcgc cagccataaa aaaagcggtt cgaatgatta  31325

aaaagaataa tagacacctc ccaccaggta ctcggctgca actcgtgcgc ccctatcaaa  31385

accccgcgga cgttcatgtc ggccatagaa aaaatgcggc ccaaatatcc caccggaatc  31445

tccacggcca gctgcagtga tagcaaaaga acgccatgag gagcaatcac aaaattttca  31505

ggcgataaaa gcacataaag gttagaatag ccctgctgca caggtaataa agcccgcgag  31565

ctcagcaaat gcacataaac cgcttcagcc atcccgtctt accgcgaaca aaaggctcac  31625

agtacacagt tactcaaccc acacgccaca cagtatttat acactcctca atcgccacgt  31685

cacccgcccc gaacaaactc caaaagtcca aaaagtccaa aacgcccgcg taaaagcccg  31745

ccaaaacagc acttcctcat ttactctccc acagtacgtc acttccgccg cgcccgccgc  31805

cctcgccccg ccctcaccct cgcgctccac cccgcgcccc acgtcagact cccaccccgc  31865

cccgcgcccg cgtcatccgc accccaccct cactccaccc ctaaccccgc ctcctcatta  31925

tcatattggc accgttccca aataaggtat attatgatga tg                    31967
```

<210> SEQ ID NO 13
<211> LENGTH: 508
<212> TYPE: PRT
<213> ORGANISM: Simian adenovirus

<400> SEQUENCE: 13

```
Met Arg Arg Ala Val Gly Val Pro Pro Val Met Ala Tyr Ala Glu Gly
1               5                   10                  15

Pro Pro Pro Ser Tyr Glu Thr Val Met Gly Ala Ala Asp Ser Pro Ala
            20                  25                  30

Thr Leu Glu Ala Leu Tyr Val Pro Pro Arg Tyr Leu Gly Pro Thr Glu
        35                  40                  45

Gly Arg Asn Ser Ile Arg Tyr Ser Glu Leu Ala Pro Leu Tyr Asp Thr
    50                  55                  60

Thr Arg Val Tyr Leu Val Asp Asn Lys Ser Ala Asp Ile Ala Ser Leu
65                  70                  75                  80

Asn Tyr Gln Asn Asp His Ser Asn Phe Leu Thr Thr Val Val Gln Asn
                85                  90                  95

Asn Asp Phe Thr Pro Val Glu Ala Gly Thr Gln Thr Ile Asn Phe Asp
            100                 105                 110

Glu Arg Ser Arg Trp Gly Gly Asp Leu Lys Thr Ile Leu Arg Thr Asn
        115                 120                 125

Met Pro Asn Ile Asn Glu Phe Met Ser Thr Asn Lys Phe Arg Ala Arg
    130                 135                 140

Leu Met Val Glu Lys Val Asn Lys Glu Thr Asn Ala Pro Arg Tyr Glu
145                 150                 155                 160

Trp Phe Glu Phe Thr Leu Pro Glu Gly Asn Tyr Ser Glu Thr Met Thr
                165                 170                 175

Ile Asp Leu Met Asn Asn Ala Ile Val Asp Asn Tyr Leu Glu Val Gly
            180                 185                 190

Arg Gln Asn Gly Val Leu Glu Ser Asp Ile Gly Val Lys Phe Asp Thr
        195                 200                 205

Arg Asn Phe Arg Leu Gly Trp Asp Pro Val Thr Lys Leu Val Met Pro
    210                 215                 220

Gly Val Tyr Thr Asn Glu Ala Phe His Pro Asp Ile Val Leu Leu Pro
225                 230                 235                 240
```

```
Gly Cys Gly Val Asp Phe Thr Gln Ser Arg Leu Ser Asn Leu Leu Gly
                245                 250                 255

Ile Arg Lys Arg Met Pro Phe Gln Ala Gly Phe Gln Ile Met Tyr Glu
            260                 265                 270

Asp Leu Glu Gly Gly Asn Ile Pro Ala Leu Leu Asp Val Ala Lys Tyr
        275                 280                 285

Glu Ala Ser Ile Gln Lys Ala Arg Glu Gln Gly Gln Glu Ile Arg Gly
    290                 295                 300

Asp Asn Phe Thr Val Ile Pro Arg Asp Val Glu Ile Val Pro Val Glu
305                 310                 315                 320

Lys Asp Ser Lys Asp Arg Ser Tyr Asn Leu Leu Pro Gly Asp Gln Thr
                325                 330                 335

Asn Thr Ala Tyr Arg Ser Trp Phe Leu Ala Tyr Asn Tyr Gly Asp Pro
            340                 345                 350

Glu Lys Gly Val Arg Ser Trp Thr Leu Leu Thr Thr Thr Asp Val Thr
        355                 360                 365

Cys Gly Ser Gln Gln Val Tyr Trp Ser Leu Pro Asp Met Met Gln Asp
    370                 375                 380

Pro Val Thr Phe Arg Pro Ser Ser Gln Val Ser Asn Tyr Pro Val Val
385                 390                 395                 400

Gly Val Glu Leu Leu Pro Val His Ala Lys Ser Phe Tyr Asn Glu Gln
                405                 410                 415

Ala Val Tyr Ser Gln Leu Ile Arg Gln Ser Thr Ala Leu Thr His Val
            420                 425                 430

Phe Asn Arg Phe Pro Glu Asn Gln Ile Leu Val Arg Pro Pro Ala Pro
        435                 440                 445

Thr Ile Thr Thr Val Ser Glu Asn Val Pro Ala Leu Thr Asp His Gly
    450                 455                 460

Thr Leu Pro Leu Arg Ser Ser Ile Ser Gly Val Gln Arg Val Thr Ile
465                 470                 475                 480

Thr Asp Ala Arg Arg Arg Thr Cys Pro Tyr Val His Lys Ala Leu Gly
                485                 490                 495

Ile Val Ala Pro Lys Val Leu Ser Ser Arg Thr Phe
            500                 505


<210> SEQ ID NO 14
<211> LENGTH: 917
<212> TYPE: PRT
<213> ORGANISM: Simian adenovirus

<400> SEQUENCE: 14

Met Ala Thr Pro Ser Met Met Pro Gln Trp Ser Tyr Met His Ile Ala
1               5                   10                  15

Gly Gln Asp Ala Ser Glu Tyr Leu Ser Pro Gly Leu Val Gln Phe Ala
            20                  25                  30

Arg Ala Thr Asp Thr Tyr Phe Ser Leu Gly Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Val Pro Val Asp Arg Glu Asp Thr Ala Tyr Ser Tyr
65                  70                  75                  80

Lys Val Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Ser
```

-continued

```
            100                 105                 110

Phe Lys Pro Tyr Ser Gly Thr Ala Tyr Asn Ser Leu Ala Pro Lys Gly
        115                 120                 125

Ala Pro Asn Pro Ser Glu Trp Lys Gly Ser Asp Asn Lys Ile Ser Val
    130                 135                 140

Arg Gly Gln Ala Pro Phe Phe Ser Thr Ser Ile Thr Lys Asp Gly Ile
145                 150                 155                 160

Gln Val Ala Thr Asp Thr Ser Ser Gly Ala Val Tyr Ala Lys Lys Glu
                165                 170                 175

Tyr Gln Pro Glu Pro Gln Val Gly Gln Glu Gln Trp Asn Ser Glu Ala
            180                 185                 190

Ser Asp Ser Asp Lys Val Ala Gly Arg Ile Leu Lys Asp Thr Thr Pro
        195                 200                 205

Met Phe Pro Cys Tyr Gly Ser Tyr Ala Lys Pro Thr Asn Glu Gln Gly
    210                 215                 220

Gly Gln Gly Thr Asn Thr Val Asp Leu Gln Phe Phe Ala Ser Ser Ser
225                 230                 235                 240

Ala Thr Ser Thr Pro Lys Ala Val Leu Tyr Ala Glu Asp Val Ala Ile
                245                 250                 255

Glu Ala Pro Asp Thr His Leu Val Tyr Lys Pro Ala Val Thr Thr Thr
            260                 265                 270

Thr Thr Ser Ser Gln Asp Leu Leu Thr Gln Gln Ala Ala Pro Asn Arg
        275                 280                 285

Pro Asn Tyr Ile Gly Phe Arg Asp Asn Phe Ile Gly Leu Met Tyr Tyr
    290                 295                 300

Asn Ser Thr Gly Asn Met Gly Val Leu Ala Gly Gln Ala Ser Gln Leu
305                 310                 315                 320

Asn Ala Val Val Asp Leu Gln Asp Arg Asn Thr Glu Leu Ser Tyr Gln
                325                 330                 335

Leu Met Leu Asp Ala Leu Gly Asp Arg Ser Arg Tyr Phe Ser Met Trp
            340                 345                 350

Asn Gln Ala Val Asp Ser Tyr Asp Pro Asp Val Arg Ile Ile Glu Asn
        355                 360                 365

His Gly Val Glu Asp Glu Leu Pro Asn Tyr Cys Phe Pro Leu Gly Gly
    370                 375                 380

Ser Leu Val Thr Glu Thr Tyr Thr Gly Leu Ser Pro Gln Asn Gly Ser
385                 390                 395                 400

Asn Thr Trp Thr Thr Asp Ser Thr Thr Tyr Ala Thr Arg Gly Val Glu
                405                 410                 415

Ile Gly Ser Gly Asn Met Phe Ala Met Glu Ile Asn Leu Ala Ala Asn
            420                 425                 430

Leu Trp Arg Ser Phe Leu Tyr Ser Asn Val Ala Leu Tyr Leu Pro Asp
        435                 440                 445

Glu Tyr Lys Leu Thr Pro Asp Asn Ile Thr Leu Pro Asp Asn Lys Asn
    450                 455                 460

Thr Tyr Asp Tyr Met Asn Gly Arg Val Ala Ala Pro Ser Ser Leu Asp
465                 470                 475                 480

Thr Tyr Val Asn Ile Gly Ala Arg Trp Ser Pro Asp Pro Met Asp Asn
                485                 490                 495

Val Asn Pro Phe Asn His His Arg Asn Ala Gly Leu Arg Tyr Arg Ser
            500                 505                 510

Met Leu Leu Gly Asn Gly Arg Tyr Val Pro Phe His Ile Gln Val Pro
        515                 520                 525
```

```
Gln Lys Phe Phe Ala Ile Lys Asn Leu Leu Leu Leu Pro Gly Ser Tyr
    530                 535                 540

Thr Tyr Glu Trp Asn Phe Arg Lys Asp Val Asn Met Ile Leu Gln Ser
545                 550                 555                 560

Ser Leu Gly Asn Asp Leu Arg Val Asp Gly Ala Ser Val Arg Phe Asp
                565                 570                 575

Ser Ile Asn Leu Tyr Ala Asn Phe Phe Pro Met Ala His Asn Thr Ala
            580                 585                 590

Ser Thr Leu Glu Ala Met Leu Arg Asn Asp Thr Asn Asp Gln Ser Phe
        595                 600                 605

Asn Asp Tyr Leu Cys Ala Ala Asn Met Leu Tyr Pro Ile Pro Ala Asn
    610                 615                 620

Ala Thr Ser Val Pro Ile Ser Ile Pro Ser Arg Asn Trp Ala Ala Phe
625                 630                 635                 640

Arg Gly Trp Ser Phe Thr Arg Leu Lys Thr Lys Glu Thr Pro Ser Leu
                645                 650                 655

Gly Ser Gly Phe Asp Pro Tyr Phe Thr Tyr Ser Gly Ser Ile Pro Tyr
            660                 665                 670

Leu Asp Gly Thr Phe Tyr Leu Asn His Thr Phe Lys Lys Val Ser Ile
        675                 680                 685

Met Phe Asp Ser Ser Val Ser Trp Pro Gly Asn Asp Arg Leu Leu Thr
    690                 695                 700

Pro Asn Glu Phe Glu Ile Lys Arg Thr Val Asp Gly Glu Gly Tyr Asn
705                 710                 715                 720

Val Ala Gln Cys Asn Met Thr Lys Asp Trp Phe Leu Ile Gln Met Leu
                725                 730                 735

Ser His Tyr Asn Ile Gly Tyr Gln Gly Phe Tyr Val Pro Glu Gly Tyr
            740                 745                 750

Lys Asp Arg Met Tyr Ser Phe Phe Arg Asn Phe Gln Pro Met Ser Arg
        755                 760                 765

Gln Val Val Asp Thr Thr Thr Tyr Thr Asp Tyr Lys Asn Val Thr Leu
    770                 775                 780

Pro Phe Gln His Asn Asn Ser Gly Phe Val Gly Tyr Met Gly Pro Thr
785                 790                 795                 800

Met Arg Glu Gly Gln Ala Tyr Pro Ala Asn Tyr Pro Tyr Pro Leu Ile
                805                 810                 815

Gly Lys Thr Ala Val Pro Ser Leu Thr Gln Lys Lys Phe Leu Cys Asp
            820                 825                 830

Arg Thr Met Trp Arg Ile Pro Phe Ser Ser Asn Phe Met Ser Met Gly
        835                 840                 845

Ala Leu Thr Asp Leu Gly Gln Asn Met Leu Tyr Ala Asn Ser Ala His
    850                 855                 860

Ala Leu Asp Met Thr Phe Glu Val Asp Pro Met Asp Glu Pro Thr Leu
865                 870                 875                 880

Leu Tyr Val Leu Phe Glu Val Phe Asp Val Val Arg Ile His Gln Pro
                885                 890                 895

His Arg Gly Val Ile Glu Ala Val Tyr Leu Arg Thr Pro Phe Ser Ala
            900                 905                 910

Gly Asn Ala Thr Thr
        915

<210> SEQ ID NO 15
<211> LENGTH: 607
```

```
<212> TYPE: PRT
<213> ORGANISM: Simian adenovirus

<400> SEQUENCE: 15

Met Lys Arg Ala Arg Leu Asp Asp Asp Phe Asn Pro Val Tyr Pro Tyr
1               5                   10                  15

Asp Thr Pro Asn Ala Pro Ser Val Pro Phe Ile Thr Pro Pro Phe Val
            20                  25                  30

Ser Ser Asp Gly Leu Gln Glu Lys Pro Pro Gly Met Leu Ser Leu Asn
        35                  40                  45

Tyr Gln Asp Pro Ile Thr Thr Gln Asn Gly Ala Leu Thr Leu Lys Leu
    50                  55                  60

Gly Ser Gly Leu Asn Ile Asn Gln Asp Gly Glu Leu Thr Ser Asp Ala
65                  70                  75                  80

Ser Val Leu Val Thr Pro Pro Ile Thr Lys Ala Asn Asn Thr Ile Gly
                85                  90                  95

Leu Ala Phe Asn Ala Pro Leu Thr Leu Gln Ser Asp Thr Leu Asn Leu
            100                 105                 110

Ala Cys Asn Ala Pro Leu Thr Val Gln Asp Asn Arg Leu Gly Ile Thr
        115                 120                 125

Tyr Asn Ser Pro Leu Thr Leu Gln Asn Ser Glu Leu Ala Leu Ala Val
    130                 135                 140

Thr Pro Pro Leu Asp Thr Ala Asn Asn Thr Leu Ala Leu Lys Thr Ala
145                 150                 155                 160

Arg Pro Ile Ile Thr Asn Ser Asn Asn Glu Leu Thr Leu Ser Ala Asp
                165                 170                 175

Ala Pro Leu Asn Thr Ser Thr Gly Thr Leu Arg Leu Gln Ser Ala Ala
            180                 185                 190

Pro Leu Gly Leu Val Asp Gln Thr Leu Arg Val Leu Phe Ser Asn Pro
        195                 200                 205

Leu Tyr Leu Gln Asn Asn Phe Leu Ser Leu Ala Ile Glu Arg Pro Leu
    210                 215                 220

Ala Leu Thr Thr Thr Gly Ser Met Ala Met Gln Ile Ser Gln Pro Leu
225                 230                 235                 240

Lys Val Glu Asp Gly Ser Leu Ser Leu Ser Ile Glu Ser Pro Leu Asn
                245                 250                 255

Leu Lys Asn Gly Asn Leu Thr Leu Gly Thr Gln Ser Pro Leu Thr Val
            260                 265                 270

Thr Gly Asn Asn Leu Ser Leu Thr Thr Thr Ala Pro Leu Thr Val Gln
        275                 280                 285

Asn Asn Ala Leu Ala Leu Ser Val Leu Leu Pro Leu Arg Leu Phe Asn
    290                 295                 300

Asn Thr Ser Leu Gly Val Ala Phe Asn Pro Pro Ile Ser Ser Ala Asn
305                 310                 315                 320

Asn Gly Leu Ser Leu Asp Ile Gly Asn Gly Leu Thr Leu Gln Tyr Asn
                325                 330                 335

Arg Leu Val Val Asn Ile Gly Gly Gly Leu Gln Phe Asn Asn Gly Ala
            340                 345                 350

Ile Thr Ala Ser Ile Asn Ala Ala Leu Pro Leu Gln Tyr Ser Asn Asn
        355                 360                 365

Gln Leu Ser Leu Asn Ile Gly Gly Gly Leu Arg Tyr Asn Gly Thr Tyr
    370                 375                 380

Lys Asn Leu Ala Val Lys Thr Asp Ser Phe Arg Gly Leu Glu Ile Asp
385                 390                 395                 400
```

-continued

```
Ser Asn Gln Phe Leu Val Pro Arg Leu Gly Ser Gly Leu Lys Phe Asp
                405                 410                 415

Gln Tyr Gly Tyr Ile Ser Val Ile Pro Pro Thr Val Thr Pro Thr Thr
            420                 425                 430

Leu Trp Thr Thr Ala Asp Pro Ser Pro Asn Ala Thr Phe Tyr Asp Ser
        435                 440                 445

Leu Asp Ala Lys Val Trp Leu Ala Leu Val Lys Cys Asn Gly Met Val
    450                 455                 460

Asn Gly Thr Ile Ala Ile Lys Ala Leu Lys Gly Thr Leu Leu Gln Pro
465                 470                 475                 480

Thr Ala Ser Phe Ile Ser Phe Val Met Tyr Phe Tyr Ser Asn Gly Thr
                485                 490                 495

Arg Arg Thr Asn Tyr Pro Thr Phe Glu Asn Glu Gly Ile Leu Ala Ser
            500                 505                 510

Ser Ala Thr Trp Gly Tyr Arg Gln Gly Asn Ser Ala Asn Thr Asn Val
        515                 520                 525

Thr Ser Ala Val Glu Phe Met Pro Ser Ser Thr Arg Tyr Pro Val Asn
    530                 535                 540

Lys Gly Thr Glu Val Gln Asn Met Glu Leu Thr Tyr Thr Phe Leu Gln
545                 550                 555                 560

Gly Asp Pro Thr Met Ala Ile Ser Phe Gln Ala Ile Tyr Asn His Ala
                565                 570                 575

Leu Glu Gly Tyr Ser Leu Lys Phe Thr Trp Arg Val Arg Asn Arg Glu
            580                 585                 590

Arg Phe Asp Ile Pro Cys Cys Ser Phe Ser Tyr Ile Thr Glu Glu
        595                 600                 605
```

METHODS OF GENERATING CHIMERIC ADENOVIRUSES AND USES FOR SUCH CHIMERIC ADENOVIRUSES

BACKGROUND OF THE INVENTION

The presence of humoral immunity (circulating antibodies) to adenovirus capsid proteins is a barrier to the use of adenovirus vectors for gene therapy. The prototype adenovirus vectors that have been developed for gene therapy are based on subgroup C adenoviruses such as that of serotype 5. The prevalence of neutralizing antibodies against subgroup C adenoviruses is generally high in human populations as a result of frequent exposure to these pathogens. This fact is likely to greatly limit the effectiveness of gene therapy vectors based on serotypes such as Ad5.

Analysis of the nature of the protective antibodies against adenoviruses has indicated that the most important target is the major capsid protein, hexon [Wolfhart (1988) *J. Virol* 62, 2321; Gall et al. (1996) *J. Virol.* 70, 2116]. Several efforts have been made to engineer the hexon so as to evade the anti-hexon antibodies by making chimeric adenoviruses harboring hexons from other serotypes [Roy et al. (1998) *J. Virol.* 72, 6875; U.S. Pat. No. 5,922,315; Gall et al. (1998) *J. Virol.* 72, 10260; Youil et al. (2002) *Hum. Gene Ther.* 13, 311; Wu et al. (2002) *J. Virol.* 76, 12775]. However, this has been largely unsuccessful when exchanges among distant serotypes are attempted.

Alternatively, investigators have proposed using adenovirus vectors that rarely cause human infections or using adenoviruses from non-human sources. However, the lack of a practical manner in which to produce large numbers of such vectors has proved to be a hindrance to developing such vectors.

SUMMARY OF THE INVENTION

The present invention provides a method of modifying adenoviruses having capsids, and particularly, including hexons, from serotypes which are not well adapted for growth in cells useful for adenoviral virion production. The method is useful for production of scalable amounts of adenoviruses. The modified, or chimeric, adenoviruses are useful for a variety of purposes which are described herein.

The invention further provides novel, isolated, adenovirus SA18 nucleic acid and amino acid sequences, vectors containing same, cell lines containing such SA18 sequences and/or vectors, and uses thereof.

Other aspects and advantages of the present invention will be readily apparent from the following detailed description of the invention.

DETAILED DESCRIPTION OF THE INVENTION

The present invention provides chimeric adenoviruses composed of the left terminal end and right terminal end of an adenovirus which can be cultured in the selected host cell, and the internal regions encoding, at a minimum, the capsid proteins of another adenovirus serotype. This invention is particularly advantageous for generating adenoviruses having serotypes which are difficult to culture in a desired cell type. The invention thus permits generation of chimeric adenoviruses of varying serotypes.

In the embodiments illustrated herein, chimeric adenoviruses have been constructed where most structural proteins, and not merely the hexon or fiber, are derived from an adenovirus of an unrelated serotype, thereby preserving the majority of the protein-protein interactions that are involved in capsid assembly. Most of the early genes such as those encoded by the adenovirus E1 and E4 regions that are responsible for transcription regulation and regulation of the host cell cycle, are retained from a different serotype that is known to result in high titer virus generation in the commonly used cell types, such as HEK 293 which supplies the Ad5 E1 proteins in trans.

In another embodiment, the invention provides novel nucleic acid and amino acid sequences from Ad SA18, which was originally isolated from vervet monkey [ATCC VR-943]. The present invention further provides novel adenovirus vectors and packaging cell lines to produce those vectors for use in the in vitro production of recombinant proteins or fragments or other reagents. The invention further provides compositions for use in delivering a heterologous molecule for therapeutic or vaccine purposes. Such therapeutic or vaccine compositions contain the adenoviral vectors carrying an inserted heterologous molecule. In addition, novel sequences of the invention are useful in providing the essential helper functions required for production of recombinant adeno-associated viral (AAV) vectors. Thus, the invention provides helper constructs, methods and cell lines which use these sequences in such production methods.

The term "substantial homology" or "substantial similarity," when referring to a nucleic acid or fragment thereof, indicates that, when optimally aligned with appropriate nucleotide insertions or deletions with another nucleic acid (or its complementary strand), there is nucleotide sequence identity in at least about 95 to 99% of the aligned sequences.

The term "substantial homology" or "substantial similarity," when referring to amino acids or fragments thereof, indicates that, when optimally aligned with appropriate amino acid insertions or deletions with another amino acid (or its complementary strand), there is amino acid sequence identity in at least about 95 to 99% of the aligned sequences. Preferably, the homology is over full-length sequence, or a protein thereof, or a fragment thereof which is at least 8 amino acids, or more desirably, at least 15 amino acids in length. Examples of suitable fragments are described herein.

The term "percent sequence identity" or "identical" in the context of nucleic acid sequences refers to the residues in the two sequences that are the same when aligned for maximum correspondence. The length of sequence identity comparison may be over the full-length of the genome (e.g., about 36 kbp), the full-length of an open reading frame of a gene, protein, subunit, or enzyme [see, e.g., the tables providing the adenoviral coding regions], or a fragment of at least about 500 to 5000 nucleotides, is desired. However, identity among smaller fragments, e.g., of at least about nine nucleotides, usually at least about 20 to 24 nucleotides, at least about 28 to 32 nucleotides, at least about 36 or more nucleotides, may also be desired. Similarly, "percent sequence identity" may be readily determined for amino acid sequences, over the full-length of a protein, or a fragment thereof. Suitably, a fragment is at least about 8 amino acids in length, and may be up to about 700 amino acids. Examples of suitable fragments are described herein.

Identity is readily determined using such algorithms and computer programs as are defined herein at default settings. Preferably, such identity is over the full length of the protein, enzyme, subunit, or over a fragment of at least about 8 amino acids in length. However, identity may be based upon shorter regions, where suited to the use to which the identical gene product is being put.

As described herein, alignments are performed using any of a variety of publicly or commercially available Multiple Sequence Alignment Programs, such as "Clustal W", accessible through Web Servers on the internet. Alternatively, Vector NTI utilities are also used. There are also a number of algorithms known in the art that can be used to measure nucleotide sequence identity, including those contained in the programs described above. As another example, polynucleotide sequences can be compared using Fasta, a program in GCG Version 6.1. Fasta provides alignments and percent sequence identity of the regions of the best overlap between the query and search sequences. For instance, percent sequence identity between nucleic acid sequences can be determined using Fasta with its default parameters (a word size of 6 and the NOPAM factor for the scoring matrix) as provided in GCG Version 6.1, herein incorporated by reference. Similarly programs are available for performing amino acid alignments. Generally, these programs are used at default settings, although one of skill in the art can alter these settings as needed. Alternatively, one of skill in the art can utilize another algorithm or computer program that provides at least the level of identity or alignment as that provided by the referenced algorithms and programs.

As used throughout this specification and the claims, the term "comprise" and its variants including, "comprises", "comprising", among other variants, is inclusive of other components, elements, integers, steps and the like. The term "consists of" or "consisting of" are exclusive of other components, elements, integers, steps and the like.

Except where otherwise specified, the term "vector" includes any genetic element known in the art which will deliver a target molecule to a cell, including, naked DNA, a plasmid, phage, transposon, cosmids, episomes, viruses, etc.

By "minigene" is meant the combination of a selected heterologous gene and the other regulatory elements necessary to drive translation, transcription and/or expression of the gene product in a host cell.

As used herein, the term "transcomplement" refers to when a gene (gene product) of one adenovirus serotype supplies an adenovirus serotype lacking this gene (gene product) from another serotype with the missing function. For example, human adenovirus serotype 5 E1a and E1b functions are known to transcomplement E1-deleted chimpanzee adenovirus Pan 9. Similarly, the inventors have found that human Ad5 E1 transcomplements E1-deleted chimpanzee adenovirus serotypes Pan5, Pan6, Pan7, and simian adenovirus serotypes SV1, SV25 and SV39. Other examples of transcomplementing serotypes include human Ad5 and human Ad2, Ad3, Ad4, Ad5, Ad7, and Ad12.

The term "functionally deleted" or "functional deletion" means that a sufficient amount of the gene region is removed or otherwise damaged, e.g., by mutation or modification, so that the gene region is no longer capable of producing functional products of gene expression. If desired, the entire gene region may be removed. Other suitable sites for gene disruption or deletion are discussed elsewhere in the application.

The term "functional" refers to a product (e.g., a protein or peptide) which performs its native function, although not necessarily at the same level as the native product. The term "functional" may also refer to a gene which encodes and from which a desired product can be expressed.

I. Chimeric Adenoviral Vectors

The compositions of this invention include chimeric adenoviral vectors that deliver a heterologous molecule to cells. For delivery of such a heterologous molecule, the vector can be a plasmid or, preferably, a chimeric adenovirus. The chimeric adenoviruses of the invention include adenovirus DNA from at least two source serotypes, a "donating serotype" and a "parental adenovirus" as described in more detail herein, and a minigene.

Because the adenoviral genome contains open reading frames on both strands, in many instances reference is made herein to 5' and 3' ends of the various regions to avoid confusion between specific open reading frames and gene regions. Thus, when reference is made herein to the "left" and "right" end of the adenoviral genome, this reference is to the ends of the approximately 36 kb adenoviral genome when depicted in schematic form as is conventional in the art [see, e.g., Horwitz, "Adenoviridae and Their Replication", in VIROLOGY, 2d ed., pp. 1679-1721 (1990)]. Thus, as used herein, the "left terminal end" of the adenoviral genome refers to portion of the adenoviral genome which, when the genome is depicted schematically in linear form, is located at the extreme left end of the schematic. Typically, the left end refers to be portion of the genome beginning at map unit 0 and extending to the right to include at least the 5' inverted terminal repeats (ITRs), and excludes the internal regions of the genome encoding the structural genes. As used herein, the "right terminal end" of the adenoviral genome refers to portion of the adenoviral genome which, when the genome is depicted schematically in linear form, is located at the extreme right end of the schematic. Typically, the right end of the adenoviral genome refers to be portion of the genome ending at map unit 36 and extending to the left to include at least the 3' ITRs, and excludes the internal regions of the genome encoding the structural genes.

A. Adenovirus Regulatory Sequences

1. Serotype

The selection of the adenovirus serotype donating its left terminal end and right terminal end can be readily made by one of skill in the art from among serotypes which can readily be cultured in the desired cell line. Among other factors which may be considered in selecting the serotype of the donating serotype is compatibility with the adenovirus serotype which will be supplying the internal regions at the location at which their sequences are hybridized.

Suitable adenoviruses for donating their left and right termini are available from the American Type Culture Collection, Manassas, Va., US (ATCC), a variety of academic and commercial sources, or the desired regions of the donating adenoviruses may be synthesized using known techniques with reference to sequences published in the literature or available from databases (e.g., GenBank, etc.). Examples of suitable donating adenoviruses include, without limitation, human adenovirus serotypes 2, 3, 4, 5, 7, and 12, and further including any of the presently identified human types [see, e.g., Horwitz, "Adenoviridae and Their Replication", in VIROLOGY, 2d ed., pp. 1679-1721 (1990)] which can be cultured in the desired cell. Similarly adenoviruses known to infect non-human primates (e.g., chimpanzees, rhesus, macaque, and other simian species) or other non-human mammals and which grow in the desired cell can be employed in the vector constructs of this invention. Such serotypes include, without limitation, chimpanzee adenoviruses Pan 5 [VR-591], Pan6 [VR-592], Pan7 [VR-593], and C68 (Pan9), described in U.S. Pat. No. 6,083,716; and simian adenoviruses including, without limitation SV1 [VR-195]; SV25 [SV-201]; SV35; SV15; SV-34; SV-36; SV-37, and baboon adenovirus [VR-275], among others. In the following examples, the human 293 cells and adenovirus type 5 (Ad5), Pan9, and Ad40 are used for convenience.

However, one of skill in the art will understand that other cell lines and/or comparable regions derived from other adenoviral strains may be readily selected and used in the present invention in the place of (or in combination with) these serotypes.

2. Sequences

The minimum sequences which must be supplied by the adenovirus donating its left terminal end and its right terminal end include the 5' cis-elements and the 3' cis-elements necessary for replication and packaging. Typically, the 5' cis-elements necessary for packaging and replication include the 5' inverted terminal repeat (ITR) sequences (which functions as origins of replication) and the native 5' packaging enhancer domains (that contain sequences necessary for packaging linear Ad genomes and enhancer elements for the E1 promoter). The right end of the adenoviral genome includes the 3' cis-elements (including the ITRs) necessary for packaging and encapsidation. Desirably, the adenovirus serotype donating its left and right termini and/or an adenovirus serotype which transcomplements the serotype of the donating adenovirus, further provides the functions of the necessary adenovirus early genes, including E1 (E1a and E1b), E2 (E2a and E2b), and E4 (including at least the ORF6 region). E3 is not essential and may be deleted as desired, e.g., for insertion of a transgene in this region or to provide space for a transgene inserted in another region (typically for packaging it is desirable for the total adenoviral genome to be under 36 kb).

In certain embodiments, the necessary adenovirus early genes are contained in the chimeric construct of the invention. In other embodiment, one or more of the necessary adenovirus early genes can be provided by the packaging host cell or in trans.

In general, the chimeric adenovirus of the invention contains regulatory sequences from the donating adenovirus serotype, or a transcomplementing serotype, to provide the chimeric adenovirus with compatible regulatory proteins. Optionally, one or more of the necessary adenoviral structural genes is provided by the adenovirus donating its left terminal and its right terminal end.

In certain embodiments, the chimeric adenovirus further contains one or more functional adenovirus genes, including, the Endoprotease open reading frame, DNA binding protein, 100 kDa scaffolding protein, 33 kDa protein, protein VIII, pTP, 52/55 kDa protein, protein VII, Mu and/or protein VI from the adenovirus serotype donating its left and right termini. Where all of these genes are derived from the adenovirus serotype donating the 5' and 3' ITRs, a "pseudotyped" chimeric is formed. Optionally, one or more of the genes can be hybrids formed from the fusion of the donating adenovirus serotype and the parental adenovirus serotype providing the capsid proteins (e.g., without limitation, polymerase, terminal protein, IIIa protein). Suitably, these genes express functional proteins which permit packaging of the adenovirus genes into the capsid. Alternatively, one or more of these proteins (whether hybrid or non-hybrid) can be functionally deleted in the chimeric adenovirus. Where desired, any necessary proteins functionally deleted in the chimeric adenovirus can be expressed in trans in the packaging cell.

B. Parental Adenovirus Structural Proteins

1. Serotypes

This invention is particularly well adapted for use in generating chimeric adenoviruses in which the capsid proteins are from a parental adenovirus which does not efficiently grow in a desirable host cell. The selection of the parental adenovirus serotype providing the internal regions can be readily made by one of skill in the art based on the information provided herein.

A variety of suitable adenoviruses can serve as a parental adenovirus supplying the regions encoding the structural (i.e., capsid proteins). Many of such adenoviruses can be obtained from the same sources as described above for the donating adenovirus serotypes. Examples of suitable parental adenovirus serotypes includes, without limitation, human adenovirus serotype 40, among others [see, e.g., Horwitz, "Adenoviridae and Their Replication", in VIROLOGY, 2d ed., pp. 1679-1721 (1990)], and adenoviruses known to infect non-human primates (e.g., chimpanzees, rhesus, macaque, and other simian species) or other non-human mammals, including, without limitation, chimpanzee adenovirus C1, described in U.S. Pat. No. 6,083,716; simian adenoviruses, and baboon adenoviruses, among others. In addition, the parental adenovirus supplying the internal regions may be from a non-naturally occurring adenovirus serotype, such as may be generated using a variety of techniques known to those of skill in the art.

In one embodiment illustrated herein, a chimeric virus that was constructed was that between the chimpanzee adenoviruses Pan-5 and C1 exhibited a higher titer in human 293 cells than the wild-type parental virus. However, the invention is not limited to the use of these chimpanzee adenoviruses, or to the combination of simian-simian, human-human, or simian-human chimeric adenoviruses. For example, it may be desirable to utilize bovine or canine adenoviruses, or other non-human mammalian adenoviruses which do not naturally infect and/or replicate in human cells.

In the following examples, the human adenovirus type 40 (Ad40) and the chimpanzee adenovirus C1, simian Pan 5 and Ad40, and Pan 5 and simian adenovirus SA18, are used. However, one of skill in the art will understand that other adenoviral serotypes may be readily selected and used in the present invention in the place of (or in combination with) these serotypes.

2. Sequences

The parental adenovirus provides to the chimeric construct of the invention its internal regions which includes structural proteins necessary for generating a capsid having the desired characteristics of the parental adenovirus. These desired characteristics include, but are not limited to, the ability to infect target cells and delivery a heterologous transgene, the ability to elude neutralizing antibodies directed to another adenovirus serotype (i.e., avoiding clearance due to cross-reactivity), and/or the ability to infect cells in the absence of an immune response to the chimeric adenovirus. The advantages of such characteristics may be most readily apparent in a regimen which involves repeat delivery of adenoviral vectors. The left and right termini of the parent adenovirus, including at least the 5' ITRs, the E1 region, the E4 region and the 3' ITRs are non-functional and, preferably, completely absent. Optionally, all adenovirus regulatory proteins from this parental adenovirus are non-functional and only the structural proteins (or selected structural proteins) are retained.

At a minimum, the parental adenovirus provides the adenoviral late region encoding the hexon protein. Suitably, the parental adenovirus further provides the late regions encoding the penton and the fiber. In certain embodiments, all of the functional adenoviral late regions, including L1 (encoding 52/55 Da, IIIa proteins), L2 (encoding penton, VII, V, Mu proteins), L3 (encoding VI, hexon, Endoprotease), L4 (encoding 100 kD, 33 kD, VIII proteins) and L5 (encoding fiber protein) are supplied by the parental adenovirus. Optionally, one or more of these late gene functions, with the exception of those encoding the hexon, penton and fiber proteins, can be functionally deleted. Any necessary structural proteins may be supplied in trans.

Thus, in certain embodiments, the chimeric adenovirus further contains one or more functional adenovirus genes, including, the Endoprotease open reading frame, DNA binding protein, 100 kDa scaffolding protein, 33 kDa protein, protein VIII, pTP, 52/55 kDa protein, protein VII, Mu and/or protein VI from the parental adenovirus donating its internal regions. Optionally, one or more of the genes can be hybrids formed from the fusion of the donating adenovirus serotype and the parental adenovirus serotype providing the capsid proteins, as described above.

C. The "Minigene"

Typically, an adenoviral vector of the invention is designed to contain a minigene which may be inserted into the site of a partially deleted, fully deleted (absent), or disrupted adenoviral gene. For example, the minigene may be located in the site of such a functional E1 deletion or functional E3 deletion, or another suitable site.

The methods employed for the selection of the transgene, the cloning and construction of the "minigene" and its insertion into the viral vector are within the skill in the art given the teachings provided herein.

1. The Transgene

The transgene is a nucleic acid sequence, heterologous to the vector sequences flanking the transgene, which encodes a polypeptide, protein, or other product, of interest. The nucleic acid coding sequence is operatively linked to regulatory components in a manner which permits transgene transcription, translation, and/or expression in a host cell.

The composition of the transgene sequence will depend upon the use to which the adenoviral vector will be put. For example, the adenoviral vector may be used as a helper virus in production of recombinant adeno-associated viruses or in production of recombinant adenoviruses deleted of essential adenoviral gene functions which are supplied by the adenoviral vector, or for a variety of production uses. Alternatively, the adenoviral vector may be used for diagnostic purposes.

One type of transgene sequence includes a reporter sequence, which upon expression produces a detectable signal. Such reporter sequences include, without limitation, DNA sequences encoding β-lactamase, β-galactosidase (LacZ), alkaline phosphatase, thymidine kinase, green fluorescent protein (GFP), chloramphenicol acetyltransferase (CAT), luciferase, membrane bound proteins including, for example, CD2, CD4, CD8, the influenza hemagglutinin protein, and others well known in the art, to which high affinity antibodies directed thereto exist or can be produced by conventional means, and fusion proteins comprising a membrane bound protein appropriately fused to an antigen tag domain from, among others, hemagglutinin or Myc. These coding sequences, when associated with regulatory elements which drive their expression, provide signals detectable by conventional means, including enzymatic, radiographic, colorimetric, fluorescence or other spectrographic assays, fluorescent activating cell sorting assays and immunological assays, including enzyme linked immunosorbent assay (ELISA), radioimmunoassay (RIA) and immunohistochemistry. For example, where the marker sequence is the LacZ gene, the presence of the vector carrying the signal is detected by assays for beta-galactosidase activity. Where the transgene is GFP or luciferase, the vector carrying the signal may be measured visually by color or light production in a luminometer.

However, desirably, the transgene is a non-marker sequence encoding a product which is useful in biology and medicine, such as proteins, peptides, RNA, enzymes, or catalytic RNAs. Desirable RNA molecules include tRNA, dsRNA, ribosomal RNA, si RNAs, small hairpin RNAs, trans-splicing RNAs, catalytic RNAs, and antisense RNAs. One example of a useful RNA sequence is a sequence which extinguishes expression of a targeted nucleic acid sequence in the treated animal.

The transgene may be used for treatment, e.g., of genetic deficiencies, as a cancer therapeutic or vaccine, for induction of an immune response, and/or for prophylactic vaccine purposes. As used herein, induction of an immune response refers to the ability of a molecule (e.g., a gene product) to induce a T cell and/or a humoral immune response to the molecule. The invention further includes using multiple transgenes, e.g., to correct or ameliorate a condition caused by a multi-subunit protein. In certain situations, a different transgene may be used to encode each subunit of a protein, or to encode different peptides or proteins. This is desirable when the size of the DNA encoding the protein subunit is large, e.g., for an immunoglobulin, the platelet-derived growth factor, or a dystrophin protein. In order for the cell to produce the multi-subunit protein, a cell is infected with the recombinant virus containing each of the different subunits. Alternatively, different subunits of a protein may be encoded by the same transgene. In this case, a single transgene includes the DNA encoding each of the subunits, with the DNA for each subunit separated by an internal ribozyme entry site (IRES). This is desirable when the size of the DNA encoding each of the subunits is small, e.g., the total size of the DNA encoding the subunits and the IRES is less than five kilobases. As an alternative to an IRES, the DNA may be separated by sequences encoding a 2A peptide, which self-cleaves in a post-translational event. See, e.g., M. L. Donnelly, et al, *J. Gen. Virol.*, 78(Pt 1):13-21 (January 1997); Furler, S., et al, *Gene Ther.*, 8(11):864-873 (June 2001); Klump H., et al., *Gene Ther.*, 8(10):811-817 (May 2001). This 2A peptide is significantly smaller than an IRES, making it well suited for use when space is a limiting factor. However, the selected transgene may encode any biologically active product or other product, e.g., a product desirable for study.

Suitable transgenes may be readily selected by one of skill in the art. The selection of the transgene is not considered to be a limitation of this invention.

2. Vector and Transgene Regulatory Elements

In addition to the major elements identified above for the minigene, the adenoviral vector also includes conventional control elements which are operably linked to the transgene in a manner that permits its transcription, translation and/or expression in a cell transfected with the plasmid vector or infected with the virus produced by the invention. As used herein, "operably linked" sequences include both expression control sequences that are contiguous with the gene of interest and expression control sequences that act in trans or at a distance to control the gene of interest.

Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al, *Cell,* 41:521-530 (1985)], the SV40 promoter, the dihydrofolate reductase promoter, the β-actin promoter, the phosphoglycerol kinase (PGK) promoter, and the EF1α promoter [Invitrogen].

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. For example, inducible promoters include the zinc-inducible sheep metallothionine (MT) promoter and the dexamethasone (Dex)-inducible mouse mammary tumor virus (MMTV) promoter. Other inducible systems include the T7 polymerase promoter system [WO 98/10088]; the ecdysone insect promoter [No et al, *Proc. Natl. Acad. Sci. USA,* 93:3346-3351 (1996)], the tetracycline-repressible system [Gossen et al, *Proc. Natl. Acad. Sci. USA,* 89:5547-5551 (1992)], the tetracycline-inducible system [Gossen et al, *Science,* 268:1766-1769 (1995), see also Harvey et al, *Curr. Opin. Chem. Biol.,* 2:512-518 (1998)]. Other systems include the FK506 dimer, VP16 or p65 using castradiol, diphenol murislerone, the RU486-inducible system [Wang et al, *Nat. Biotech.,* 15:239-243 (1997) and Wang et al, *Gene Ther.,* 4:432-441 (1997)] and the rapamycin-inducible system [Magari et al, *J. Clin. Invest.,* 100:2865-2872 (1997)]. The effectiveness of some inducible promoters increases over time. In such cases one can enhance the effectiveness of such systems by inserting multiple repressors in tandem, e.g., TetR linked to a TetR by an IRES. Alternatively, one can wait at least 3 days before screening for the desired function. One can enhance expression of desired proteins by known means to enhance the effectiveness of this system. For example, using the Woodchuck Hepatitis Virus Posttranscriptional Regulatory Element (WPRE).

In another embodiment, the native promoter for the transgene will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

Another embodiment of the transgene includes a transgene operably linked to a tissue-specific promoter. For instance, if expression in skeletal muscle is desired, a promoter active in muscle should be used. These include the promoters from genes encoding skeletal β-actin, myosin light chain 2A, dystrophin, muscle creatine kinase, as well as synthetic muscle promoters with activities higher than naturally occurring promoters (see L1 et al., Nat. Biotech., 17:241-245 (1999)). Examples of promoters that are tissue-specific are known for liver (albumin, Miyatake et al., *J. Virol.,* 71:5124-32 (1997); hepatitis B virus core promoter, Sandig et al., *Gene Ther.,* 3:1002-9 (1996); alpha-fetoprotein (AFP), Arbuthnot et al., *Hum. Gene Ther.,* 7:1503-14 (1996)), bone osteocalcin (Stein et al., *Mol. Biol. Rep.,* 24:185-96 (1997)); bone sialoprotein (Chen et al., *J Bone Miner. Res.,* 11:654-64 (1996)), lymphocytes (CD2, Hansal et al., *J. Immunol.,* 161:1063-8 (1998); immunoglobulin heavy chain; T cell receptor chain), neuronal such as neuron-specific enolase (NSE) promoter (Andersen et al., *Cell. Mol. Neurobiol.,* 13:503-15 (1993)), neurofilament light-chain gene (Piccioli et al., *Proc. Natl. Acad. Sci. USA,* 88:5611-5 (1991)), and the neuron-specific vgfgene (Piccioli et al., *Neuron,* 15:373-84 (1995)), among others.

Optionally, vectors carrying transgenes encoding therapeutically useful or immunogenic products may also include selectable markers or reporter genes may include sequences encoding geneticin, hygromicin or purimycin resistance, among others. Such selectable reporters or marker genes (preferably located outside the viral genome to be packaged into a viral particle) can be used to signal the presence of the plasmids in bacterial cells, such as ampicillin resistance. Other components of the vector may include an origin of replication. Selection of these and other promoters and vector elements are conventional and many such sequences are available [see, e.g., Sambrook et al, and references cited therein].

These vectors are generated using the techniques and sequences provided herein, in conjunction with techniques known to those of skill in the art. Such techniques include conventional cloning techniques of cDNA such as those described in texts [Sambrook et al, Molecular Cloning: A Laboratory Manual, Cold Spring Harbor Press, Cold Spring Harbor, N.Y.], use of overlapping oligonucleotide sequences of the adenovirus genomes, polymerase chain reaction, and any suitable method which provides the desired nucleotide sequence.

II. Production of the Recombinant Viral Particle

In one embodiment, the invention provides a method of generating recombinant chimeric adenoviral particles in which the capsid of the chimeric adenovirus is of a serotype incapable of efficient growth in the selected host cell. A vector suitable for production of recombinant chimeric adenoviral particles can be generated homologous recombination between a first vector containing the left end of the chimeric adenoviral genome and a second vector containing the right end of the chimeric adenoviral genome. However, any suitable methodology known to those of skill in the art can be readily utilized to generate a vector suitable to generate a production vector, preferably which contains the entire chimeric adenoviral genome, including a minigene. This production vector is then introduced into a host cell in which the adenoviral capsid protein is assembled and the chimeric adenoviral particle assembled as described.

The chimeric adenoviruses of the invention include those in which one or more adenoviral genes are absent, or otherwise rendered non-functional. If any of the missing gene functions are essential to the replication and infectivity of the adenoviral particle, these functions are supplied by a complementation (or transcomplementing) cell line or a helper vector expressing these functions during production of the chimeric adenoviral particle.

Examples of chimeric adenoviruses containing such missing adenoviral gene functions include those which are partially or completely deleted in the E1a and/or E1b gene. In such a case, the E1 gene functions can be supplied by the packaging host cell, permitting the chimeric construct to be deleted of E1 gene functions and, if desired, for a transgene to be inserted in this region. Optionally, the E1 gene can be of a serotype which transcomplements the serotype providing the other adenovirus sequences in order to further reduce the possibility of recombination and improve safety. In other embodiments, it is desirable to retain an intact E1a and/or E1 b region in the recombinant adenoviruses. Such an intact E1 region may be located in its native location in the adenoviral genome or placed in the site of a deletion in the native adenoviral genome (e.g., in the E3 region).

In another example, all or a portion of the adenovirus delayed early gene E3 may be eliminated from the chimeric adenovirus. The function of adenovirus E3 is believed to be irrelevant to the function and production of the recombinant virus particle. Chimeric adenovirus vectors may also be constructed having a deletion of at least the ORF6 region of the E4 gene, and more desirably because of the redundancy in the function of this region, the entire E4 region. Still another vector of this invention contains a deletion in the delayed early gene E2a. Similarly, deletions in the intermediate genes IX and $IVa_2$ may be useful for some purposes. Optionally, deletions may also be made in selected portions of the late genes L1 through L5, as described above.

Other deletions may be made in the other structural or non-structural adenovirus genes. The above-discussed deletions may be used individually, i.e., an adenovirus sequence for use in the present invention may contain deletions in only a single region. Alternatively, deletions of entire genes or portions thereof effective to destroy their biological activity may be used in any combination. For example, in one exemplary vector, the adenovirus sequence may have deletions of the E1 genes and the E4 gene, or of the E1, E2a and E3 genes, or of the E1 and E3 genes, or of E1, E2a and E4 genes, with or without deletion of E3, and so on. As discussed above, such deletions may be used in combination with other mutations, such as temperature-sensitive mutations, to achieve a desired result.

Examples of suitable transcomplementing serotypes are provided above. The use of transcomplementing serotypes can be particularly advantageous where there is diversity between the Ad sequences in the vector of the invention and the human AdE1 sequences found in currently available packaging cells. In such cases, the use of the current human E1-containing cells prevents the generation of replication-competent adenoviruses during the replication and production process. However, in certain circumstances, it will be desirable to utilize a cell line which expresses the E1 gene products can be utilized for production of an E1-deleted simian adenovirus. Such cell lines have been described. See, e.g., U.S. Pat. No. 6,083,716.

A. Packaging Host Cells

Suitably, the packaging host cell is selected from among cells in which the adenovirus serotype donating the left and right terminal ends of the chimeric genome are capable of efficient growth. The host cells are preferably of mammalian origin, and most preferably are of non-human primate or human origin.

Particularly desirable host cells are selected from among any mammalian species, including, without limitation, cells such as A549 [ATCC Accession No. CCL 185], 911 cells, WEHI, 3T3, 10T1/2, HEK 293 cells or PERC6 (both of which express functional adenoviral E1) [Fallaux, F J et al, (1998), *Hum Gene Ther,* 9:1909-1917], Saos, C2C12, L cells, HT1080, HepG2, HeLa [ATCC Accession No. CCL 2], KB [CCL 17], Detroit [e.g., Detroit 510, CCL 72] and WI-38 [CCL 75] cells, and primary fibroblast, hepatocyte and myoblast cells derived from mammals including human, monkey, mouse, rat, rabbit, and hamster. These cell lines are all available from the American Type Culture Collection, 10801 University Boulevard, Manassas, Va. 20110-2209. Other suitable cell lines may be obtained from other sources. The selection of the mammalian species providing the cells is not a limitation of this invention; nor is the type of mammalian cell, i.e., fibroblast, hepatocyte, tumor cell, etc.

As described above, a chimeric adenovirus of the invention can lack one or more functional adenoviral regulatory and/or structural genes which are supplied either by the host cell or in trans to effect packaging of the chimeric adenovirus into the viral capsid to generate the viral particle. Thus, the ability of a selected host cell to supply transcomplementing adenoviral sequences may be taken into consideration in selecting a desired host cell.

In one example, the cells are from a stable cell line which expresses adenovirus E1a and E1b functions from a cell line which transcomplements the adenovirus serotype which donates the left and right termini to the chimera of the invention, permitting the chimera to be E1-deleted. Alternatively, where the cell line does not transcomplement the adenovirus donating the termini, E1 functions may be provided by the chimera, or in trans.

If desired, one may utilize the sequences provided herein to generate a packaging cell or cell line that expresses, at a minimum, the adenovirus E1 gene from the adenovirus serotype donating the 5' ITR under the transcriptional control of a promoter for expression, or a transcomplementing serotype, in a selected parent cell line. Inducible or constitutive promoters may be employed for this purpose. Examples of such promoters are described in detail elsewhere in this specification. A parent cell is selected for the generation of a novel cell line expressing any desired adenovirus or adenovirus gene, including, e.g., a human Ad5, AdPan5, Pan6, Pan7, SV1, SV25 or SV39 gene. Without limitation, such a parent cell line may be HeLa [ATCC Accession No. CCL 2], A549 [ATCC Accession No. CCL 185], HEK 293, KB [CCL 17], Detroit [e.g., Detroit 510, CCL 72] and WI-38 [CCL 75] cells, among others. Many of these cell lines are all available from the ATCC. Other suitable parent cell lines may be obtained from other sources.

Such E1-expressing cell lines are useful in the generation of chimeric adenovirus E1 deleted vectors. Additionally, or alternatively, the invention provides cell lines that express one or more simian adenoviral gene products, e.g., E1a, E1b, E2a, and/or E4 ORF6, can be constructed using essentially the same procedures for use in the generation of chimeric viral vectors. Such cell lines can be utilized to transcomplement adenovirus vectors deleted in the essential genes that encode those products, or to provide helper functions necessary for packaging of a helper-dependent virus (e.g., adeno-associated virus). The preparation of a host cell according to this invention involves techniques such as assembly of selected DNA sequences. This assembly may be accomplished utilizing conventional techniques. Such techniques include cDNA and genomic cloning, which are well known and are described in Sambrook et al., cited above, use of overlapping oligonucleotide sequences of the adenovirus genomes, combined with polymerase chain reaction, synthetic methods, and any other suitable methods which provide the desired nucleotide sequence.

In still another alternative, the essential adenoviral gene products are provided in trans by the adenoviral vector and/or helper virus. In such an instance, a suitable host cell can be selected from any biological organism, including prokaryotic (e.g., bacterial) cells, and eukaryotic cells, including, insect cells, yeast cells and mammalian cells.

Particularly desirable host cells are selected from among any mammalian species, including, without limitation, cells such as A549, WEHI, 3T3, 10T1/2, HEK 293 cells or PERC6 (both of which express functional adenoviral E1) [Fallaux, F J et al, (1998), Hum Gene Ther, 9:1909-1917], Saos, C2C12, L cells, HT1080, HepG2 and primary fibroblast, hepatocyte and myoblast cells derived from mammals including human, monkey, mouse, rat, rabbit, and hamster. The selection of the mammalian species providing the cells is not a limitation of this invention; nor is the type of mammalian cell, i.e., fibroblast, hepatocyte, tumor cell, etc.

B. Helper Vectors

Thus, depending upon the adenovirus gene content of the adenoviral vectors and any adenoviral gene functions expressed from the host cell, a helper vector may be necessary to provide sufficient adenovirus gene sequences necessary to produce an infective recombinant viral particle containing the minigene. See, for example, the techniques described for preparation of a "minimal" human Ad vector in International Patent Application WO96/13597, published May 9, 1996, and incorporated herein by reference. Suitably, these helper vectors may be non-replicating genetic elements, a plasmid, or a virus.

Useful helper vectors contain selected adenovirus gene sequences not present in the adenovirus vector construct and/or not expressed by the packaging cell line in which the vector is transfected. In one embodiment, the helper virus is replication-defective and contains a variety of adenovirus genes in addition to the sequences described above. Such a helper vector is desirably used in combination with an E1-expressing cell line.

Helper vectors may be formed into poly-cation conjugates as described in Wu et al, *J. Biol. Chem.*, 264:16985-16987 (1989); K. J. Fisher and J. M. Wilson, *Biochem. J.*, 299:49 (Apr. 1, 1994). A helper vector may optionally contain a second reporter minigene. A number of such reporter genes are known to the art. The presence of a reporter gene on the helper virus which is different from the transgene on the adenovirus vector allows both the Ad vector and the helper vector to be independently monitored. This second reporter is used to enable separation between the resulting recombinant virus and the helper virus upon purification.

C. Assembly of Viral Particle and Transfection of a Cell Line

Generally, when delivering the vector comprising the minigene by transfection, the vector is delivered in an amount from about 5 μg to about 100 μg DNA, and preferably about 10 to about 50 μg DNA to about $1\times10^4$ cells to about $1\times10^{13}$ cells, and preferably about $10^5$ cells. However, the relative amounts of vector DNA to host cells may be adjusted, taking into consideration such factors as the selected vector, the delivery method and the host cells selected.

Introduction into the host cell of the vector may be achieved by any means known in the art or as disclosed above, including transfection, and infection. One or more of the adenoviral genes may be stably integrated into the genome of the host cell, stably expressed as episomes, or expressed transiently. The gene products may all be expressed transiently, on an episome or stably integrated, or some of the gene products may be expressed stably while others are expressed transiently.

Furthermore, the promoters for each of the adenoviral genes may be selected independently from a constitutive promoter, an inducible promoter or a native adenoviral promoter. The promoters may be regulated by a specific physiological state of the organism or cell (i.e., by the differentiation state or in replicating or quiescent cells) or by exogenously added factors, for example.

Introduction of the molecules (as plasmids or viruses) into the host cell may also be accomplished using techniques known to the skilled artisan and as discussed throughout the specification. In preferred embodiment, standard transfection techniques are used, e.g., $CaPO_4$ transfection or electroporation.

Assembly of the selected DNA sequences of the adenovirus (as well as the transgene and other vector elements) into various intermediate plasmids, and the use of the plasmids and vectors to produce a recombinant viral particle are all achieved using conventional techniques. Such techniques include conventional cloning techniques of cDNA such as those described in texts [Sambrook et al, cited above], use of overlapping oligonucleotide sequences of the adenovirus genomes, polymerase chain reaction, and any suitable method which provides the desired nucleotide sequence. Standard transfection and co-transfection techniques are employed, e.g., $CaPO_4$ precipitation techniques. Other conventional methods employed include homologous recombination of the viral genomes, plaquing of viruses in agar overlay, methods of measuring signal generation, and the like.

For example, following the construction and assembly of the desired minigene-containing viral vector, the vector is transfected in vitro in the presence of an optional helper vector into the packaging cell line. The functions expressed from the plasmid, packaging cell line and helper virus, if any, permits the adenovirus-transgene sequences in the vector to be replicated and packaged into virion capsids, resulting in the chimeric viral particles. The current method for producing such virus particles is transfection-based. However, the invention is not limited to such methods. The resulting chimeric adenoviruses are useful in transferring a selected transgene to a selected cell.

III. Use of the Chimeric Adenovirus Vectors

The chimeric adenovirus vectors of the invention are useful for gene transfer to a human or veterinary subject (including, non-human primates, non-simian primates, and other mammals) in vitro, ex vivo, and in vivo.

The recombinant adenovirus vectors described herein can be used as expression vectors for the production of the products encoded by the heterologous genes in vitro. For example, the recombinant adenoviruses containing a gene inserted into the location of an E1 deletion may be transfected into an E1-expressing cell line as described above. Alternatively, replication-competent adenoviruses may be used in another selected cell line. The transfected cells are then cultured in the conventional manner, allowing the recombinant adenovirus to express the gene product from the promoter. The gene product may then be recovered from the culture medium by known conventional methods of protein isolation and recovery from culture.

A chimeric adenoviral vector of the invention provides an efficient gene transfer vehicle that can deliver a selected transgene to a selected host cell in vivo or ex vivo even where the organism has neutralizing antibodies to one or more AAV serotypes. In one embodiment, the rAAV and the cells are mixed ex vivo; the infected cells are cultured using conventional methodologies; and the transduced cells are re-infused into the patient. These compositions are particularly well suited to gene delivery for therapeutic purposes and for immunization, including inducing protective immunity.

More commonly, the chimeric adenoviral vectors of the invention will be utilized for delivery of therapeutic or immunogenic molecules, as described below. It will be readily understood for both applications that the recombinant adenoviral vectors of the invention are particularly well suited for use in regimens involving repeat delivery of recombinant adenoviral vectors. Such regimens typically involve delivery of a series of viral vectors in which the viral capsids are alternated. The viral capsids may be changed for each subsequent administration, or after a pre-selected number of administrations of a particular serotype capsid (e.g., one, two, three, four or more). Thus, a regimen may involve delivery of a rAd with a first capsid, delivery with a rAd with a second capsid, and delivery with a third capsid. A variety of other regimens which use the Ad capsids of the invention alone, in combination with one another, or in combination with other Ad serotypes will be apparent to those of skill in the art. Optionally, such a regimen may involve administration of rAd with capsids of non-human primate adenoviruses, human adenoviruses, or artificial (e.g., chimeric) serotypes such as are described herein. Each phase of the regimen may involve administration of a series of injections (or other delivery routes) with a single Ad serotype capsid followed by a series with another Ad serotype capsid. Alternatively, the recombinant Ad vectors of the invention may be utilized in regimens involving other non-adenoviral-mediated delivery systems, including other viral systems, non-viral delivery systems, protein, peptides, and other biologically active molecules.

The following sections will focus on exemplary molecules which may be delivered via the adenoviral vectors of the invention.

A. Ad-Mediated Delivery of Therapeutic Molecules

In one embodiment, the Ad vectors described herein are administered to humans according to published methods for gene therapy. A viral vector of the invention bearing the selected transgene may be administered to a patient, preferably suspended in a biologically compatible solution or pharmaceutically acceptable delivery vehicle. A suitable vehicle includes sterile saline. Other aqueous and non-aqueous isotonic sterile injection solutions and aqueous and non-aqueous sterile suspensions known to be pharmaceutically acceptable carriers and well known to those of skill in the art may be employed for this purpose.

The adenoviral vectors are administered in sufficient amounts to transduce the target cells and to provide sufficient levels of gene transfer and expression to provide a therapeutic benefit without undue adverse or with medically acceptable physiological effects, which can be determined by those skilled in the medical arts. Conventional and pharmaceutically acceptable routes of administration include, but are not limited to, direct delivery to the retina and other intraocular delivery methods, direct delivery to the liver, inhalation, intranasal, intravenous, intramuscular, intratracheal, subcutaneous, intradermal, rectal, oral and other parenteral routes of administration. Routes of administration may be combined, if desired, or adjusted depending upon the transgene or the condition. The route of administration primarily will depend on the nature of the condition being treated.

Dosages of the viral vector will depend primarily on factors such as the condition being treated, the age, weight and health of the patient, and may thus vary among patients. For example, a therapeutically effective adult human or veterinary dosage of the viral vector is generally in the range of from about 100 μL to about 100 mL of a carrier containing concentrations of from about $1\times10^6$ to about $1\times10^{15}$ particles, about $1\times10^{11}$ to $1\times10^{13}$ particles, or about $1\times10^9$ to $1\times10^{12}$ particles virus. Dosages will range depending upon the size of the animal and the route of administration. For example, a suitable human or veterinary dosage (for about an 80 kg animal) for intramuscular injection is in the range of about $1\times10^9$ to about $5\times10^{12}$ particles per mL, for a single site. Optionally, multiple sites of administration may be delivered. In another example, a suitable human or veterinary dosage may be in the range of about $1\times10^{11}$ to about $1\times10^{15}$ particles for an oral formulation. One of skill in the art may adjust these doses, depending the route of administration, and the therapeutic or vaccinal application for which the recombinant vector is employed. The levels of expression of the transgene, or for an immunogen, the level of circulating antibody, can be monitored to determine the frequency of dosage administration. Yet other methods for determining the timing of frequency of administration will be readily apparent to one of skill in the art.

An optional method step involves the co-administration to the patient, either concurrently with, or before or after administration of the viral vector, of a suitable amount of a short acting immune modulator. The selected immune modulator is defined herein as an agent capable of inhibiting the formation of neutralizing antibodies directed against the recombinant vector of this invention or capable of inhibiting cytolytic T lymphocyte (CTL) elimination of the vector. The immune modulator may interfere with the interactions between the T helper subsets ($T_{H1}$ or $T_{H2}$) and B cells to inhibit neutralizing antibody formation. Alternatively, the immune modulator may inhibit the interaction between $T_{H1}$, cells and CTLs to reduce the occurrence of CTL elimination of the vector. A variety of useful immune modulators and dosages for use of same are disclosed, for example, in Yang et al., *J. Virol.,* 70(9) (September 1996); International Patent Application No. WO96/12406, published May 2, 1996; and International Patent Application No. PCT/US96/03035, all incorporated herein by reference. Typically, such immune modulators would be selected when the transgene is a therapeutic which requires repeat delivery.

1. Therapeutic Transgenes

Useful therapeutic products encoded by the transgene include hormones and growth and differentiation factors including, without limitation, insulin, glucagon, growth hormone (GH), parathyroid hormone (PTH), growth hormone releasing factor (GRF), follicle stimulating hormone (FSH), luteinizing hormone (LH), human chorionic gonadotropin (hCG), vascular endothelial growth factor (VEGF), angiopoietins, angiostatin, granulocyte colony stimulating factor (GCSF), erythropoietin (EPO), connective tissue growth factor (CTGF), basic fibroblast growth factor (bFGF), acidic fibroblast growth factor (aFGF), epidermal growth factor (EGF), transforming growth factor α (TGF α), platelet-derived growth factor (PDGF), insulin growth factors I and II (IGF-I and IGF-II), any one of the transforming growth factor superfamily, including TGF, activins, inhibins, or any of the bone morphogenic proteins (BMP) BMPs 1-15, any one of the heregluin/neuregulin/ARIA/neu differentiation factor (NDF) family of growth factors, nerve growth factor (NGF), brain-derived neurotrophic factor (BDNF), neurotrophins NT-3 and NT-4/5, ciliary neurotrophic factor (CNTF), glial cell line derived neurotrophic factor (GDNF), neurturin, agrin, any one of the family of semaphorins/collapsins, netrin-1 and netrin-2, hepatocyte growth factor (HGF), ephrins, noggin, sonic hedgehog and tyrosine hydroxylase.

Other useful transgene products include proteins that regulate the immune system including, without limitation, cytokines and lymphokines such as thrombopoietin (TPO), interleukins (IL) IL-1 through IL-25 (including, e.g., IL-2, IL-4, IL-12 and IL-18), monocyte chemoattractant protein, leukemia inhibitory factor, granulocyte-macrophage colony stimulating factor, Fas ligand, tumor necrosis factors and, interferons, and, stem cell factor, flk-2/flt3 ligand. Gene products produced by the immune system are also useful in the invention. These include, without limitation, immunoglobulins IgG, IgM, IgA, IgD and IgE, chimeric immunoglobulins, humanized antibodies, single chain antibodies, T cell receptors, chimeric T cell receptors, single chain T cell receptors, class I and class II MHC molecules, as well as engineered immunoglobulins and MHC molecules. Useful gene products also include complement regulatory proteins such as complement regulatory proteins, membrane cofactor protein (MCP), decay accelerating factor (DAF), CR1, CF2 and CD59.

Still other useful gene products include any one of the receptors for the hormones, growth factors, cytokines, lymphokines, regulatory proteins and immune system proteins. The invention encompasses receptors for cholesterol regulation, including the low density lipoprotein (LDL) receptor, high density lipoprotein (HDL) receptor, the very low density lipoprotein (VLDL) receptor, proteins useful in the regulation of lipids, including, e.g., apolipoprotein (apo) A and its isoforms (e.g., ApoAI), apoE and its isoforms including E2, E3 and E4), SRB1, ABC1, and the scavenger receptor. The invention also encompasses gene products such as members of the steroid hormone receptor superfamily including glucocorticoid receptors and estrogen receptors, Vitamin D receptors and other nuclear receptors. In addition, useful gene products include transcription factors such as jun, fos, max, mad, serum response factor (SRF), AP-1, AP2, myb, MyoD and myogenin, ETS-box containing proteins, TFE3, E2F, ATF1, ATF2, ATF3, ATF4, ZF5, NFAT, CREB, HNF-4, C/EBP, SP1, CCAAT-box binding proteins, interferon regulation factor (IRF-1), Wilms tumor protein, ETS-binding protein, STAT, GATA-box binding proteins, e.g., GATA-3, and the forkhead family of winged helix proteins.

Other useful gene products include, carbamoyl synthetase I, ornithine transcarbamylase, arginosuccinate synthetase, arginosuccinate lyase, arginase, fumarylacetacetate hydrolase, phenylalanine hydroxylase, alpha-1 antitrypsin, glucose-6-phosphatase, porphobilinogen deaminase, cystathione beta-synthase, branched chain ketoacid decarboxylase, albumin, isovaleryl-coA dehydrogenase, propionyl CoA carboxylase, methyl malonyl CoA mutase, glutaryl CoA dehydrogenase, insulin, beta-glucosidase, pyruvate carboxylate, hepatic phosphorylase, phosphorylase kinase, glycine decarboxylase, H-protein, T-protein, a cystic fibrosis transmembrane regulator (CFTR) sequence, and a dystrophin cDNA sequence. Other useful gene products include those useful for treatment of hemophilia A (e.g., Factor VIII and its variants, including the light chain and heavy chain of the heterodimer, optionally operably linked by a junction), and the B-domain deleted Factor VIII, see U.S. Pat. Nos. 6,200,560 and 6,221,349], and useful for treatment of hemophilia B (e.g, Factor IX).

Still other useful gene products include non-naturally occurring polypeptides, such as chimeric or hybrid polypeptides having a non-naturally occurring amino acid sequence containing insertions, deletions or amino acid substitutions. For example, single-chain engineered immunoglobulins could be useful in certain immunocompromised patients. Other types of non-naturally occurring gene sequences include antisense molecules and catalytic nucleic acids, such as ribozymes, which could be used to reduce overexpression of a target.

Reduction and/or modulation of expression of a gene are particularly desirable for treatment of hyperproliferative conditions characterized by hyperproliferating cells, as are cancers and psoriasis. Target polypeptides include those polypeptides which are produced exclusively or at higher levels in hyperproliferative cells as compared to normal cells. Target antigens include polypeptides encoded by oncogenes such as myb, myc, fyn, and the translocation gene bcr/abl, ras, src, P53, neu, trk and EGRF. In addition to oncogene products as target antigens, target polypeptides for anti-cancer treatments and protective regimens include variable regions of antibodies made by B cell lymphomas and variable regions of T cell receptors of T cell lymphomas which, in some embodiments, are also used as target antigens for autoimmune disease. Other tumor-associated polypeptides can be used as target polypeptides such as polypeptides which are found at higher levels in tumor cells including the polypeptide recognized by monoclonal antibody 17-1A and folate binding polypeptides.

Other suitable therapeutic polypeptides and proteins include those which may be useful for treating individuals suffering from autoimmune diseases and disorders by conferring a broad based protective immune response against targets that are associated with autoimmunity including cell receptors and cells which produce self-directed antibodies. T-cell mediated autoimmune diseases include rheumatoid arthritis (RA), multiple sclerosis (MS), Sjögren's syndrome, sarcoidosis, insulin dependent diabetes mellitus (IDDM), autoimmune thyroiditis, reactive arthritis, ankylosing spondylitis, scleroderma, polymyositis, dermatomyositis, psoriasis, vasculitis, Wegener's granulomatosis, Crohn's disease and ulcerative colitis. Each of these diseases is characterized by T cell receptors (TCRs) that bind to endogenous antigens and initiate the inflammatory cascade associated with autoimmune diseases.

The chimeric adenoviral vectors of the invention are particularly well suited for therapeutic regimens in which multiple adenoviral-mediated deliveries of transgenes is desired, e.g., in regimens involving redelivery of the same transgene or in combination regimens involving delivery of other transgenes. Such regimens may involve administration of a chimeric adenoviral vector, followed by re-administration with a vector from the same serotype adenovirus. Particularly desirable regimens involve administration of a chimeric adenoviral vector of the invention, in which the serotype of the viral vector delivered in the first administration differs from the serotype of the viral vector utilized in one or more of the subsequent administrations. For example, a therapeutic regimen involves administration of a chimeric vector and repeat administration with one or more adenoviral vectors of the same or different serotypes. In another example, a therapeutic regimen involves administration of an adenoviral vector followed by repeat administration with a chimeric vector of the invention which differs from the serotype of the first delivered adenoviral vector, and optionally further administration with another vector which is the same or, preferably, differs from the serotype of the vector in the prior administration steps. These regimens are not limited to delivery of adenoviral vectors constructed using the chimeric serotypes of the invention. Rather, these regimens can readily utilize chimeric or non-chimeric vectors of other adenoviral serotypes, which may be of artificial, human or non-human primate, or other mammalian sources, in combination with one or more of the chimeric vectors of the invention. Examples of such serotypes are discussed elsewhere in this document. Further, these therapeutic regimens may involve either simultaneous or sequential delivery of chimeric adenoviral vectors of the invention in combination with non-adenoviral vectors, non-viral vectors, and/or a variety of other therapeutically useful compounds or molecules. The present invention is not limited to these therapeutic regimens, a variety of which will be readily apparent to one of skill in the art.

B. Ad-Mediated Delivery of Immunogenic Transgenes

The adenoviruses of the invention may also be employed as immunogenic compositions. As used herein, an immunogenic composition is a composition to which a humoral (e.g., antibody) or cellular (e.g., a cytotoxic T cell) response is mounted to a transgene product delivered by the immunogenic composition following delivery to a mammal, and preferably a primate. The present invention provides an Ad that can contain in any of its adenovirus sequence deletions a gene encoding a desired immunogen. Chimeric adenoviruses based on simian or other non-human mammalian primate serotypes are likely to be better suited for use as a live recombinant virus vaccine in different animal species compared to an adenovirus of human origin, but is not limited to such a use. The recombinant adenoviruses can be used as prophylactic or therapeutic vaccines against any pathogen for which the antigen(s) crucial for induction of an immune response and able to limit the spread of the pathogen has been identified and for which the cDNA is available.

Such vaccinal (or other immunogenic) compositions are formulated in a suitable delivery vehicle, as described above. Generally, doses for the immunogenic compositions are in the range defined above for therapeutic compositions. The levels of immunity of the selected gene can be monitored to determine the need, if any, for boosters. Following an assessment of antibody titers in the serum, optional booster immunizations may be desired.

Optionally, a vaccinal composition of the invention may be formulated to contain other components, including, e.g. adjuvants, stabilizers, pH adjusters, preservatives and the like. Such components are well known to those of skill in the vaccine art. Examples of suitable adjuvants include, without limitation, liposomes, alum, monophosphoryl lipid A, and any biologically active factor, such as cytokine, an interleukin, a chemokine, a ligands, and optimally combinations thereof. Certain of these biologically active factors can be expressed in vivo, e.g., via a plasmid or viral vector. For example, such an adjuvant can be administered with a priming DNA vaccine encoding an antigen to enhance the antigen-specific immune response compared with the immune response generated upon priming with a DNA vaccine encoding the antigen only.

The adenoviruses are administered in "an immunogenic amount", that is, an amount of adenovirus that is effective in a route of administration to transfect the desired cells and provide sufficient levels of expression of the selected gene to induce an immune response. Where protective immunity is provided, the recombinant adenoviruses are considered to be vaccine compositions useful in preventing infection and/or recurrent disease.

Alternatively, or in addition, the vectors of the invention may contain a transgene encoding a peptide, polypeptide or protein which induces an immune response to a selected immunogen. The recombinant adenoviruses of this invention are expected to be highly efficacious at inducing cytolytic T cells and antibodies to the inserted heterologous antigenic protein expressed by the vector.

For example, immunogens may be selected from a variety of viral families. Example of desirable viral families against which an immune response would be desirable include, the picornavirus family, which includes the genera rhinoviruses, which are responsible for about 50% of cases of the common cold; the genera enteroviruses, which include polioviruses, coxsackieviruses, echoviruses, and human enteroviruses such as hepatitis A virus; and the genera apthoviruses, which are responsible for foot and mouth diseases, primarily in non-human animals. Within the picornavirus family of viruses, target antigens include the VP1, VP2, VP3, VP4, and VPG. Another viral family includes the calcivirus family, which encompasses the Norwalk group of viruses, which are an important causative agent of epidemic gastroenteritis. Still another viral family desirable for use in targeting antigens for inducing immune responses in humans and non-human animals is the togavirus family, which includes the genera alphavirus, which include Sindbis viruses, Ross-River virus, and Venezuelan, Eastern & Western Equine encephalitis, and rubivirus, including Rubella virus. The flaviviridae family includes dengue, yellow fever, Japanese encephalitis, St. Louis encephalitis and tick borne encephalitis viruses. Other target antigens may be generated from the Hepatitis C or the coronavirus family, which includes a number of non-human viruses such as infectious bronchitis virus (poultry), porcine transmissible gastroenteric virus (pig), porcine hemagglutinatin encephalomyelitis virus (pig), feline infectious peritonitis virus (cats), feline enteric coronavirus (cat), canine coronavirus (dog), and human respiratory coronaviruses, which may cause the common cold and/or non-A, B or C hepatitis. In addition, the human coronaviruses include the putative causative agent of sudden acute respiratory syndrome (SARS). Within the coronavirus family, target antigens include the E1 (also called M or matrix protein), E2 (also called S or Spike protein), E3 (also called HE or hemagglutin-elterose) glycoprotein (not present in all coronaviruses), or N (nucleocapsid). Still other antigens may be targeted against the rhabdovirus family, which includes the genera vesiculovirus (e.g., Vesicular Stomatitis Virus), and the general lyssavirus (e.g., rabies). Within the rhabdovirus family, suitable antigens may be derived from the G protein or the N protein. The family filoviridae, which includes hemorrhagic fever viruses such as Marburg and Ebola virus, may be a suitable source of antigens. The paramyxovirus family includes parainfluenza Virus Type 1, parainfluenza Virus Type 3, bovine parainfluenza Virus Type 3, rubulavirus (mumps virus), parainfluenza Virus Type 2, parainfluenza virus Type 4, Newcastle disease virus (chickens), rinderpest, morbillivirus, which includes measles and canine distemper, and pneumovirus, which includes respiratory syncytial virus. The influenza virus is classified within the family orthomyxovirus and is a suitable source of antigen (e.g., the HA protein, the N1 protein). The bunyavirus family includes the genera bunyavirus (California encephalitis, La Crosse), phlebovirus (Rift Valley Fever), hantavirus (puremala is a hemahagin fever virus), nairovirus (Nairobi sheep disease) and various unassigned bungaviruses. The arenavirus family provides a source of antigens against LCM and Lassa fever virus. The reovirus family includes the genera reovirus, rotavirus (which causes acute gastroenteritis in children), orbiviruses, and cultivirus (Colorado Tick fever), Lebombo (humans), equine encephalosis, blue tongue.

The retrovirus family includes the sub-family oncorivirinal which encompasses such human and veterinary diseases as feline leukemia virus, HTLVI and HTLVII, lentivirinal (which includes human immunodeficiency virus (HIV), simian immunodeficiency virus (SIV), feline immunodeficiency virus (FIV), equine infectious anemia virus, and spumavirinal). Among the lentiviruses, many suitable antigens have been described and can readily be selected. Examples of suitable HIV and SIV antigens include, without limitation the gag, pol, Vif, Vpx, VPR, Env, Tat, Nef, and Rev proteins, as well as various fragments thereof. For example, suitable fragments of the Env protein may include any of its subunits such as the gp120, gp160, gp41, or smaller fragments thereof, e.g., of at least about 8 amino acids in length. Similarly, fragments of the tat protein may be selected. [See, U.S. Pat. No. 5,891,994 and U.S. Pat. No. 6,193,981.] See, also, the HIV and SIV proteins described in D. H. Barouch et al, *J. Virol.,* 75(5):2462-2467 (March 2001), and R. R. Amara, et al, *Science,* 292:69-74 (6 Apr. 2001). In another example, the HIV and/or SIV immunogenic proteins or peptides may be used to form fusion proteins or other immunogenic molecules. See, e.g., the HIV-1 Tat and/or Nef fusion proteins and immunization regimens described in WO 01/54719, published Aug. 2, 2001, and WO 99/16884, published Apr. 8, 1999. The invention is not limited to the HIV and/or SIV immunogenic proteins or peptides described herein. In addition, a variety of modifications to these proteins have been described or could readily be made by one of skill in the art. See, e.g., the modified gag protein that is described in U.S. Pat. No. 5,972,596. Further, any desired HIV and/or SIV immunogens may be delivered alone or in combination. Such combinations may include expression from a single vector or from multiple vectors. Optionally, another combination may involve delivery of one or more expressed immunogens with delivery of one or more of the immunogens in protein form. Such combinations are discussed in more detail below.

The papovavirus family includes the sub-family polyomaviruses (BKU and JCU viruses) and the sub-family papillomavirus (associated with cancers or malignant progression of papilloma). The adenovirus family includes viruses (EX, AD7, ARD, O.B.) which cause respiratory disease and/or enteritis. The parvovirus includes family feline parvovirus (feline enteritis), feline panteucopeniavirus, canine parvovirus, and porcine parvovirus. The herpesvirus family includes the sub-family alphaherpesvirinae, which encompasses the genera simplexvirus (HSVI, HSVII), varicellovirus (pseudorabies, varicella zoster) and the sub-family betaherpesvirinae, which includes the genera cytomegalovirus (HCMV, muromegalovirus) and the sub-family gammaherpesvirinae, which includes the genera lymphocryptovirus, EBV (Burkitts lymphoma), infectious rhinotracheitis, Marek's disease virus, and rhadinovirus. The poxvirus family includes the sub-family chordopoxyirinae, which encompasses the genera orthopoxvirus (Variola (Smallpox) and Vaccinia (Cowpox)), parapoxvirus, avipoxvirus, capripoxvirus, leporipoxvirus, suipoxvirus, and the sub-family entomopoxyirinae. The hepadnavirus family includes the Hepatitis B virus. One unclassified virus which may be suitable source of antigens is the Hepatitis delta virus. Still other viral sources may include avian infectious bursal disease virus and porcine respiratory and reproductive syndrome virus. The alphavirus family includes equine arteritis virus and various Encephalitis viruses.

The viruses of the present invention may also carry immunogens which are useful to immunize a human or non-human animal against other pathogens including bacteria, fungi, parasitic microorganisms or multicellular parasites which infect human and non-human vertebrates, or from a cancer cell or tumor cell. Examples of bacterial pathogens include pathogenic gram-positive cocci include pneumococci; staphylococci; and streptococci. Pathogenic gram-negative cocci include meningococcus; gonococcus. Pathogenic enteric gram-negative bacilli include enterobacteriaceae; *pseudomonas*, acinetobacteria and *eikenella*; melioidosis; *salmonella; shigella; haemophilus; moraxella; H. ducreyi* (which causes chancroid); *brucella; Franisella tularensis* (which causes tularemia); *yersinia* (*pasteurella*); streptobacillus moniliformis and *spirillum*; Gram-positive bacilli include listeria monocytogenes; *erysipelothrix rhusiopathiae; Corynebacterium diphtheria* (*diphtheria*); cholera; *B. anthracis* (anthrax); donovanosis (granuloma inguinale); and bartonellosis. Diseases caused by pathogenic anaerobic bacteria include tetanus; botulism; other clostridia; tuberculosis; leprosy; and other mycobacteria. Pathogenic spirochetal diseases include syphilis; treponematoses: yaws, pinta and endemic syphilis; and leptospirosis. Other infections caused by higher pathogen bacteria and pathogenic fungi include actinomycosis; nocardiosis; cryptococcosis, blastomycosis, histoplasmosis and coccidioidomycosis; candidiasis, aspergillosis, and mucormycosis; sporotrichosis; paracoccidiodomycosis, petriellidiosis, torulopsosis, mycetoma and chromomycosis; and dermatophytosis. Rickettsial infections include Typhus fever, Rocky Mountain spotted fever, Q fever, and Rickettsialpox. Examples of mycoplasma and chlamydial infections include: mycoplasma pneumoniae; lymphogranuloma venereum; psittacosis; and perinatal chlamydial infections. Pathogenic eukaryotes encompass pathogenic protozoans and helminths and infections produced thereby include: amebiasis; malaria; leishmaniasis; trypanosomiasis; toxoplasmosis; *Pneumocystis carinii*; Trichans; *Toxoplasma gondii*; babesiosis; giardiasis; trichinosis; filariasis; schistosomiasis; nematodes; trematodes or flukes; and cestode (tapeworm) infections.

Many of these organisms and/or toxins produced thereby have been identified by the Centers for Disease Control [(CDC), Department of Heath and Human Services, USA], as agents which have potential for use in biological attacks. For example, some of these biological agents, include, *Bacillus anthracis* (anthrax), *Clostridium botulinum* and its toxin (botulism), *Yersinia pestis* (plague), variola major (smallpox), *Francisella tularensis* (tularemia), and viral hemorrhagic fevers [filoviruses (e.g., Ebola, Marburg], and arenaviruses [e.g., Lassa, Machupo]), all of which are currently classified as Category A agents; *Coxiella burnetti* (Q fever); *Brucella* species (brucellosis), *Burkholderia mallei* (glanders), *Burkholderia pseudomallei* (meloidosis), *Ricinus communis* and its toxin (ricin toxin), *Clostridium perfringens* and its toxin (epsilon toxin), *Staphylococcus* species and their toxins (enterotoxin B), *Chlamydia psittaci* (psittacosis), water safety threats (e.g., *Vibrio cholerae, Crytosporidium parvum*), Typhus fever (*Richettsia powazekii*), and viral encephalitis (alphaviruses, e.g., Venezuelan equine encephalitis; eastern equine encephalitis; western equine encephalitis); all of which are currently classified as Category B agents; and Nipan virus and hantaviruses, which are currently classified as Category C agents. In addition, other organisms, which are so classified or differently classified, may be identified and/or used for such a purpose in the future. It will be readily understood that the viral vectors and other constructs described herein are useful to deliver antigens from these organisms, viruses, their toxins or other by-products, which will prevent and/or treat infection or other adverse reactions with these biological agents.

Administration of the vectors of the invention to deliver immunogens against the variable region of the T cells elicit an immune response including CTLs to eliminate those T cells. In RA, several specific variable regions of TCRs which are involved in the disease have been characterized. These TCRs include V-3, V-14, V-17 and Vα-17. Thus, delivery of a nucleic acid sequence that encodes at least one of these polypeptides will elicit an immune response that will target T cells involved in RA. In MS, several specific variable regions of TCRs which are involved in the disease have been characterized. These TCRs include V-7 and Vα-10. Thus, delivery of a nucleic acid sequence that encodes at least one of these polypeptides will elicit an immune response that will target T cells involved in MS. In scleroderma, several specific variable regions of TCRs which are involved in the disease have been characterized. These TCRs include V-6, V-8, V-14 and Vα-16, Vα-3C, Vα-7, Vα-14, Vα-15, Vα-16, Vα-28 and Vα-12. Thus, delivery of a chimeric adenovirus that encodes at least one of these polypeptides will elicit an immune response that will target T cells involved in scleroderma.

C. Ad-Mediated Delivery Methods

The therapeutic levels, or levels of immunity, of the selected gene can be monitored to determine the need, if any, for boosters. Following an assessment of CD8+ T cell response, or optionally, antibody titers, in the serum, optional booster immunizations may be desired. Optionally, the adenoviral vectors of the invention may be delivered in a single administration or in various combination regimens, e.g., in combination with a regimen or course of treatment involving other active ingredients or in a prime-boost regimen. A variety of such regimens have been described in the art and may be readily selected.

For example, prime-boost regimens may involve the administration of a DNA (e.g., plasmid) based vector to prime the immune system to a second or further, booster, administration with a traditional antigen, such as a protein or a recombinant virus carrying the sequences encoding such an antigen. See, e.g., WO 00/11140, published Mar. 2, 2000, incorporated by reference. Alternatively, an immunization regimen may involve the administration of a chimeric adenoviral vector of the invention to boost the immune response to a vector (either viral or DNA-based) carrying an antigen, or a protein. In still another alternative, an immunization regimen involves administration of a protein followed by booster with a vector encoding the antigen.

In one embodiment, the invention provides a method of priming and boosting an immune response to a selected antigen by delivering a plasmid DNA vector carrying said antigen, followed by boosting with an adenoviral vector of the invention. In one embodiment, the prime-boost regimen involves the expression of multiproteins from the prime and/or the boost vehicle. See, e.g., R. R. Amara, *Science,* 292:69-74 (6 Apr. 2001) which describes a multiprotein regimen for expression of protein subunits useful for generating an immune response against HIV and SIV. For example, a DNA prime may deliver the Gag, Pol, Vif, VPX and Vpr and Env, Tat, and Rev from a single transcript. Alternatively, the SIV Gag, Pol and HIV-1 Env is delivered in a recombinant adenovirus construct of the invention. Still other regimens are described in WO 99/16884 and WO 01/54719.

However, the prime-boost regimens are not limited to immunization for HIV or to delivery of these antigens. For example, priming may involve delivering with a first vector of the invention followed by boosting with a second vector, or with a composition containing the antigen itself in protein form. In one example, the prime-boost regimen can provide a protective immune response to the virus, bacteria or other organism from which the antigen is derived. In another desired embodiment, the prime-boost regimen provides a therapeutic effect that can be measured using convention assays for detection of the presence of the condition for which therapy is being administered.

The priming composition may be administered at various sites in the body in a dose dependent manner, which depends on the antigen to which the desired immune response is being targeted. The invention is not limited to the amount or situs of injection(s) or to the pharmaceutical carrier. Rather, the regimen may involve a priming and/or boosting step, each of which may include a single dose or dosage that is administered hourly, daily, weekly or monthly, or yearly. As an example, the mammals may receive one or two doses containing between about 10 μg to about 50 μg of plasmid in carrier. A desirable amount of a DNA composition ranges between about 1 μg to about 10,000 μg of the DNA vector. Dosages may vary from about 1 μg to 1000 μg DNA per kg of subject body weight. The amount or site of delivery is desirably selected based upon the identity and condition of the mammal.

The dosage unit of the vector suitable for delivery of the antigen to the mammal is described herein. The vector is prepared for administration by being suspended or dissolved in a pharmaceutically or physiologically acceptable carrier such as isotonic saline; isotonic salts solution or other formulations that will be apparent to those skilled in such administration. The appropriate carrier will be evident to those skilled in the art and will depend in large part upon the route of administration. The compositions of the invention may be administered to a mammal according to the routes described above, in a sustained release formulation using a biodegradable biocompatible polymer, or by on-site delivery using micelles, gels and liposomes. Optionally, the priming step of this invention also includes administering with the priming composition, a suitable amount of an adjuvant, such as are defined herein.

Preferably, a boosting composition is administered about 2 to about 27 weeks after administering the priming composition to the mammalian subject. The administration of the boosting composition is accomplished using an effective amount of a boosting composition containing or capable of delivering the same antigen as administered by the priming DNA vaccine. The boosting composition may be composed of a recombinant viral vector derived from the same viral source (e.g., adenoviral sequences of the invention) or from another source. Alternatively, the "boosting composition" can be a composition containing the same antigen as encoded in the priming DNA vaccine, but in the form of a protein or peptide, which composition induces an immune response in the host. In another embodiment, the boosting composition contains a DNA sequence encoding the antigen under the control of a regulatory sequence directing its expression in a mammalian cell, e.g., vectors such as well-known bacterial or viral vectors. The primary requirements of the boosting composition are that the antigen of the composition is the same antigen, or a cross-reactive antigen, as that encoded by the priming composition.

In another embodiment, the adenoviral vectors of the invention are also well suited for use in a variety of other immunization and therapeutic regimens. Such regimens may involve delivery of adenoviral vectors of the invention simultaneously or sequentially with Ad vectors of different serotype capsids, regimens in which adenoviral vectors of the invention are delivered simultaneously or sequentially with non-Ad vectors, regimens in which the adenoviral vectors of the invention are delivered simultaneously or sequentially with proteins, peptides, and/or other biologically useful therapeutic or immunogenic compounds. Such uses will be readily apparent to one of skill in the art.

IV. Simian Adenovirus 18 Sequences

The invention provides nucleic acid sequences and amino acid sequences of Ad SA18, which are isolated from the other viral material with which they are associated in nature. These sequences are useful in preparing heterologous molecules containing the nucleic acid sequences and amino acid sequences, and regions or fragments thereof as are described herein, viral vectors which are useful for a variety of purposes, including the constructs and compositions, and such methods as are described herein for the chimeric adenoviruses, including, e.g., in host cells for production of viruses requiring adenoviral helper functions, as delivery vehicles for heterologous molecules such as those described herein. These sequences are also useful in generating the chimeric adenoviruses of the invention.

A. Nucleic Acid Sequences

The SA18 nucleic acid sequences of the invention include nucleotides SEQ ID NO: 12, nt 1 to 31967. See, Sequence Listing, which is incorporated by reference herein. The nucleic acid sequences of the invention further encompass the strand which is complementary to the sequences of SEQ ID NO: 12, as well as the RNA and cDNA sequences corresponding to the sequences of these sequences figures and their complementary strands. Further included in this invention are nucleic acid sequences which are greater than 95 to 98%, and more preferably about 99 to 99.9% homologous or identical to the Sequence Listing. Also included in the nucleic acid sequences of the invention are natural variants and engineered modifications of the sequences provided in SEQ ID NO: 12 and their complementary strands. Such modifications include, for example, labels that are known in the art, methylation, and substitution of one or more of the naturally occurring nucleotides with a degenerate nucleotide.

The invention further encompasses fragments of the sequences of SA18, their complementary strand, cDNA and RNA complementary thereto. Suitable fragments are at least 15 nucleotides in length, and encompass functional fragments, i.e., fragments which are of biological interest. For example, a functional fragment can express a desired adenoviral product or may be useful in production of recombinant viral vectors. Such fragments include the gene sequences and fragments listed in the tables below.

The following tables provide the transcript regions and open reading frames in the simian adenovirus sequences of the invention. For certain genes, the transcripts and open reading frames (ORFs) are located on the strand complementary to that presented in SEQ ID NO: 12. See, e.g., E2b, E4 and E2a. The calculated molecular weights of the encoded proteins are also shown.

| Adenovirus Gene | | Ad SA18, SEQ ID NO: 12 | | |
|---|---|---|---|---|
| Region | Protein | start | End | M.W. |
| ITR | | 1 | 180 | |
| E1a | 13S | 916 | 1765 | 27264 |
| | 12S | 916 | 1765 | 24081 |
| E1b | Small T | 1874 | 2380 | 19423 |
| | Large T | 2179 | 3609 | 52741 |
| | IX | 3678 | 4079 | 13701 |
| E2b | IVa2 | 5478 | 4126 | 51295 |
| | Polymerase | 13745 | 5229 | 128392 |
| | PTP | 13745 | 8597 | 75358 |
| | Agnoprotein | 8007 | 8705 | 23610 |
| L1 | 52/55 kD | 10788 | 11945 | 43416 |
| | IIIa | 11966 | 13699 | 63999 |
| L2 | Penton | 13796 | 15322 | 57166 |
| | VII | 15328 | 15873 | 20352 |
| | V | 15920 | 17050 | 42020 |
| L3 | VI | 17348 | 18154 | 29222 |
| | Hexon | 18257 | 21010 | 102912 |
| | Endoprotease | 21029 | 21640 | 23015 |
| 2a | DBP | 23147 | 21711 | 53626 |
| L4 | 100kD | 23175 | 25541 | 87538 |
| | 22 kD homolog | 25204 | 25797 | 22206 |
| | 33 kD homolog | 25204 | 26025 | 24263 |
| | VIII | 26107 | 26817 | 25490 |
| E3 | Orf #1 | 26817 | 27125 | 11814 |
| L5 | Fiber | 27192 | 29015 | 65455 |
| E4 | Orf 6/7 | 30169 | 29067 | 13768 |
| | Orf 6 | 30169 | 29303 | 33832 |
| | Orf 4 | 30464 | 30099 | 14154 |
| | Orf 3 | 30816 | 30466 | 13493 |
| | Orf 2 | 31205 | 30813 | 14698 |
| | Orf 1 | 31608 | 31231 | 14054 |
| ITR | | 31788 | 31967 | |

The SA18 adenoviral nucleic acid sequences are useful as therapeutic and immunogenic agents and in construction of a variety of vector systems and host cells. Such vectors are useful for any of the purposes described above for the chimeric adenovirus. Additionally, these SA18 sequences and products may be used alone or in combination with other adenoviral sequences or fragments, or in combination with elements from other adenoviral or non-adenoviral sequences. The adenoviral sequences of the invention are also useful as antisense delivery vectors, gene therapy vectors, or vaccine vectors, and in methods of using same. Thus, the invention further provides nucleic acid molecules, gene delivery vectors, and host cells which contain the Ad sequences of the invention.

For example, the invention encompasses a nucleic acid molecule containing simian Ad ITR sequences of the invention. In another example, the invention provides a nucleic acid molecule containing simian Ad sequences of the invention encoding a desired Ad gene product. Still other nucleic acid molecule constructed using the sequences of the invention will be readily apparent to one of skill in the art, in view of the information provided herein.

In one embodiment, the simian Ad gene regions identified herein may be used in a variety of vectors for delivery of a heterologous molecule to a cell. Examples of such molecules and methods of delivery are provided in Section III herein. For example, vectors are generated for expression of an adenoviral capsid protein (or fragment thereof) for purposes of generating a viral vector in a packaging host cell. Such vectors may be designed for expression in trans. Alternatively, such vectors are designed to provide cells which stably contain sequences which express desired adenoviral functions, e.g., one or more of E1a, E1b, the terminal repeat sequences, E2a, E2b, E4, E40RF6 region.

In addition, the adenoviral gene sequences and fragments thereof are useful for providing the helper functions necessary for production of helper-dependent viruses (e.g., adenoviral vectors deleted of essential functions or adeno-associated viruses (AAV)). For such production methods, the simian adenoviral sequences of the invention are utilized in such a method in a manner similar to those described for the human Ad. However, due to the differences in sequences between the simian adenoviral sequences of the invention and those of human Ad, the use of the sequences of the invention essentially eliminate the possibility of homologous recombination with helper functions in a host cell carrying human Ad E1 functions, e.g., 293 cells, which may produce infectious adenoviral contaminants during rAAV production.

Methods of producing rAAV using adenoviral helper functions have been described at length in the literature with human adenoviral serotypes. See, e.g., U.S. Pat. No. 6,258,595 and the references cited therein. See, also, U.S. Pat. No. 5,871,982; WO 99/14354; WO 99/15685; WO 99/47691. These methods may also be used in production of non-human serotype AAV, including non-human primate AAV serotypes. The simian adenoviral gene sequences of the invention which provide the necessary helper functions (e.g., E1a, E1 b, E2a and/or E4 ORF6) can be particularly useful in providing the necessary adenoviral function while minimizing or eliminating the possibility of recombination with any other adenoviruses present in the rAAV-packaging cell which are typically of human origin. Thus, selected genes or open reading frames of the adenoviral sequences of the invention may be utilized in these rAAV production methods.

Alternatively, recombinant adenoviral simian vectors of the invention may be utilized in these methods. Such recombinant adenoviral simian vectors may include, e.g., a hybrid simian Ad/AAV in which simian Ad sequences flank a rAAV expression cassette composed of, e.g., AAV 3' and/or 5' ITRs and a transgene under the control of regulatory sequences which control its expression. One of skill in the art will recognize that still other simian adenoviral vectors and/or gene sequences of the invention will be useful for production of rAAV and other viruses dependent upon adenoviral helper.

In still another embodiment, nucleic acid molecules are designed for delivery and expression of selected adenoviral gene products in a host cell to achieve a desired physiologic effect. For example, a nucleic acid molecule containing sequences encoding an adenovirus E1a protein of the invention may be delivered to a subject for use as a cancer therapeutic. Optionally, such a molecule is formulated in a lipid-based carrier and preferentially targets cancer cells. Such a formulation may be combined with other cancer therapeutics (e.g., cisplatin, taxol, or the like). Still other uses for the adenoviral sequences provided herein will be readily apparent to one of skill in the art.

In addition, one of skill in the art will readily understand that the Ad sequences of the invention can be readily adapted for use for a variety of viral and non-viral vector systems for in vitro, ex vivo or in vivo delivery of therapeutic and immunogenic molecules, including any of those identified as being deliverable via the chimeric adenoviruses of the invention. For example, the simian Ad genome of the invention can be utilized in a variety of rAd and non-rAd vector systems. Such vectors systems may include, e.g., plasmids, lentiviruses, retroviruses, poxviruses, vaccinia viruses, and adeno-associated viral systems, among others. Selection of these vector systems is not a limitation of the present invention.

The invention further provides molecules useful for production of the simian and simian-derived proteins of the invention. Such molecules which carry polynucleotides including the simian Ad DNA sequences of the invention can be in the form of a vector.

B. Simian Adenoviral Proteins of the Invention

The invention further provides gene products of the above adenoviruses, such as proteins, enzymes, and fragments thereof, which are encoded by the adenoviral nucleic acids of the invention. The invention further encompasses SA18 proteins, enzymes, and fragments thereof, having the amino acid sequences encoded by these nucleic acid sequences which are generated by other methods. Such proteins include those encoded by the open reading frames identified in the tables above, and fragments thereof.

Thus, in one aspect, the invention provides unique simian adenoviral proteins which are substantially pure, i.e., are free of other viral and proteinaceous proteins. Preferably, these proteins are at least 10% homogeneous, more preferably 60% homogeneous, and most preferably 95% homogeneous.

In one embodiment, the invention provides unique simian-derived capsid proteins. As used herein, a simian-derived capsid protein includes any adenoviral capsid protein that contains a SA18 capsid protein or a fragment thereof, as defined above, including, without limitation, chimeric capsid proteins, fusion proteins, artificial capsid proteins, synthetic capsid proteins, and recombinantly capsid proteins, without limitation to means of generating these proteins.

Suitably, these simian-derived capsid proteins contain one or more SA18 regions or fragments thereof (e.g., a hexon, penton, fiber or fragment thereof) in combination with capsid regions or fragments thereof of different adenoviral serotypes, or modified simian capsid proteins or fragments, as described herein. A "modification of a capsid protein associated with altered tropism" as used herein includes an altered capsid protein, i.e, a penton, hexon or fiber protein region, or fragment thereof, such as the knob domain of the fiber region, or a polynucleotide encoding same, such that specificity is altered. The simian-derived capsid may be constructed with one or more of the simian Ad of the invention or another Ad serotypes which may be of human or non-human origin. Such Ad may be obtained from a variety of sources including the ATCC, commercial and academic sources, or the sequences of the Ad may be obtained from GenBank or other suitable sources.

The amino acid sequences of the simian adenoviruses penton proteins of the invention are provided herein. The AdSA18 penton protein is provided in SEQ ID NO: 13. Suitably, any of these penton proteins, or unique fragments thereof, may be utilized for a variety of purposes. Examples of suitable fragments include the penton having N-terminal and/or C-terminal truncations of about 50, 100, 150, or 200 amino acids, based upon the amino acid numbering provided above. Other suitable fragments include shorter internal, C-terminal, or N-terminal fragments. Further, the penton protein may be modified for a variety of purposes known to those of skill in the art.

The invention further provides the amino acid sequences of the hexon protein of SA18, SEQ ID NO:14. Suitably, this hexon protein, or unique fragments thereof, may be utilized for a variety of purposes. Examples of suitable fragments include the hexon having N-terminal and/or C-terminal truncations of about 50, 100, 150, 200, 300, 400, or 500 amino acids, based upon the amino acid numbering provided above and in SEQ ID NO: 14. Other suitable fragments include shorter internal, C-terminal, or N-terminal fragments. For example, one suitable fragment the loop region (domain) of the hexon protein, designated DE1 and FG1, or a hypervariable region thereof. Such fragments include the regions spanning amino acid residues about 125 to 443; about 138 to 441, or smaller fragments, such as those spanning about residue 138 to residue 163; about 170 to about 176; about 195 to about 203; about 233 to about 246; about 253 to about 264; about 287 to about 297; about 404 to about 430, about 430 to 550, about 545 to 650; of the simian hexon proteins, with reference to SEQ ID NO: 14. Other suitable fragments may be readily identified by one of skill in the art. Further, the hexon protein may be modified for a variety of purposes known to those of skill in the art. Because the hexon protein is the determinant for serotype of an adenovirus, such artificial hexon proteins would result in adenoviruses having artificial serotypes. Other artificial capsid proteins can also be constructed using the chimp Ad penton sequences and/or fiber sequences of the invention and/or fragments thereof.

In one example, it may be desirable to generate an adenovirus having an altered hexon protein utilizing the sequences of a hexon protein of the invention. One suitable method for altering hexon proteins is described in U.S. Pat. No. 5,922,315, which is incorporated by reference. In this method, at least one loop region of the adenovirus hexon is changed with at least one loop region of another adenovirus serotype. Thus, at least one loop region of such an altered adenovirus hexon protein is a simian Ad hexon loop region of the invention. In one embodiment, a loop region of the SA18 hexon protein is replaced by a loop region from another adenovirus serotype. In another embodiment, the loop region of the SA18 hexon is used to replace a loop region from another adenovirus serotype. Suitable adenovirus serotypes may be readily selected from among human and non-human serotypes, as described herein. SA18 is selected for purposes of illustration only; the other simian Ad hexon proteins of the invention may be similarly altered, or used to alter another Ad hexon. The selection of a suitable serotype is not a limitation of the present invention. Still other uses for the hexon protein sequences of the invention will be readily apparent to those of skill in the art.

The invention further encompasses the fiber proteins of the simian adenoviruses of the invention. The fiber protein of AdSA18 has the amino acid sequence of SEQ ID NO: 15. Suitably, this fiber protein, or unique fragments thereof, may be utilized for a variety of purposes. One suitable fragment is the fiber knob, which spans about amino acids 247 to 425 of SEQ ID NO: 15. Examples of other suitable fragments include the fiber having N-terminal and/or C-terminal truncations of about 50, 100, 150, or 200 amino acids, based upon the amino acid numbering provided above and in SEQ ID NO: 15. Still other suitable fragments include internal fragments. Further, the fiber protein may be modified using a variety of techniques known to those of skill in the art.

The invention further encompasses unique fragments of the proteins of the invention which are at least 8 amino acids in length. However, fragments of other desired lengths can be readily utilized. In addition, the invention encompasses such modifications as may be introduced to enhance yield and/or expression of an SA18 gene product, e.g., construction of a fusion molecule in which all or a fragment of the SA18 gene product is fused (either directly or via a linker) with a fusion partner to enhance. Other suitable modifications include, without limitation, truncation of a coding region (e.g., a protein or enzyme) to eliminate a pre- or pro-protein ordinarily cleaved and to provide the mature protein or enzyme and/or mutation of a coding region to provide a secretable gene product. Still other modifications will be readily apparent to one of skill in the art. The invention further encompasses proteins having at least about 95% to 99% identity to the SA18 proteins provided herein.

As described herein, vectors of the invention containing the adenoviral capsid proteins of the invention are particularly well suited for use in applications in which the neutralizing antibodies diminish the effectiveness of other Ad serotype based vectors, as well as other viral vectors. The rAd vectors of the invention are particularly advantageous in readministration for repeat gene therapy or for boosting immune response (vaccine titers). Examples of such regimens are provided herein.

Under certain circumstances, it may be desirable to use one or more of the SA18 gene products (e.g., a capsid protein or a fragment thereof) to generate an antibody. The term "an antibody," as used herein, refers to an immunoglobulin molecule which is able to specifically bind to an epitope. Thus, the antibodies of the invention bind, preferably specifically and without cross-reactivity, to a SA18 epitope. The antibodies in the present invention exist in a variety of forms including, for example, high affinity polyclonal antibodies, monoclonal antibodies, synthetic antibodies, chimeric antibodies, recombinant antibodies and humanized antibodies. Such antibodies originate from immunoglobulin classes IgG, IgM, IgA, IgD and IgE.

Such antibodies may be generated using any of a number of methods know in the art. Suitable antibodies may be generated by well-known conventional techniques, e.g. Kohler and Milstein and the many known modifications thereof. Similarly desirable high titer antibodies are generated by applying known recombinant techniques to the monoclonal or polyclonal antibodies developed to these antigens [see, e.g., PCT Patent Application No. PCT/GB85/00392; British Patent Application Publication No. GB2188638A; Amit et al., 1986 *Science,* 233:747-753; Queen et al., 1989 *Proc. Nat'l. Acad. Sci. USA,* 86:10029-10033; PCT Patent Application No. PCT/WO9007861; and Riechmann et al., *Nature,* 332:323-327 (1988); Huse et al, 1988a *Science,* 246:1275-1281]. Alternatively, antibodies can be produced by manipulating the complementarity determining regions of animal or human antibodies to the antigen of this invention. See, e.g., E. Mark and Padlin, "Humanization of Monoclonal Antibodies", Chapter 4, The Handbook of Experimental Pharmacology, Vol. 113, The Pharmacology of Monoclonal Antibodies, Springer-Verlag (June, 1994); Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, *Proc. Natl. Acad. Sci. USA* 85:5879-5883; and Bird et al., 1988, *Science* 242:423-426. Further provided by the present invention are anti-idiotype antibodies (Ab2) and anti-anti-idiotype antibodies (Ab3). See, e.g., M. Wettendorff et al., "Modulation of anti-tumor immunity by anti-idiotypic antibodies." In Idiotypic Network and Diseases, ed. by J. Cerny and J. Hiernaux, 1990 *J. Am. Soc. Microbiol*., Washington D.C.: pp. 203-229]. These anti-idiotype and anti-anti-idiotype antibodies are produced using techniques well known to those of skill in the art. These antibodies may be used for a variety of purposes, including diagnostic and clinical methods and kits.

Under certain circumstances, it may be desirable to introduce a detectable label or a tag onto a SA18 gene product, antibody or other construct of the invention. As used herein, a detectable label is a molecule which is capable, alone or upon interaction with another molecule, of providing a detectable signal. Most desirably, the label is detectable visually, e.g. by fluorescence, for ready use in immunohistochemical analyses or immunofluorescent microscopy. For example, suitable labels include fluorescein isothiocyanate (FITC), phycoerythrin (PE), allophycocyanin (APC), coriphosphine-O (CPO) or tandem dyes, PE-cyanin-5 (PC5), and PE-Texas Red (ECD). All of these fluorescent dyes are commercially available, and their uses known to the art. Other useful labels include a colloidal gold label. Still other useful labels include radioactive compounds or elements. Additionally, labels include a variety of enzyme systems that operate to reveal a calorimetric signal in an assay, e.g., glucose oxidase (which uses glucose as a substrate) releases peroxide as a product which in the presence of peroxidase and a hydrogen donor such as tetramethyl benzidine (TMB) produces an oxidized TMB that is seen as a blue color. Other examples include horseradish peroxidase (HRP) or alkaline phosphatase (AP), and hexokinase in conjunction with glucose-6-phosphate dehydrogenase which reacts with ATP, glucose, and NAD+ to yield, among other products, NADH that is detected as increased absorbance at 340 nm wavelength.

Other label systems that are utilized in the methods of this invention are detectable by other means, e.g., colored latex microparticles [Bangs Laboratories, Indiana] in which a dye is embedded are used in place of enzymes to form conjugates with the target sequences provide a visual signal indicative of the presence of the resulting complex in applicable assays.

Methods for coupling or associating the label with a desired molecule are similarly conventional and known to those of skill in the art. Known methods of label attachment are described [see, for example, Handbook of Fluorescent probes and Research Chemicals, 6th Ed., R. P. M. Haugland, Molecular Probes, Inc., Eugene, Oreg., 1996; Pierce Catalog and Handbook, Life Science and Analytical Research Products, Pierce Chemical Company, Rockford, Ill., 1994/1995]. Thus, selection of the label and coupling methods do not limit this invention.

The sequences, proteins, and fragments of the invention may be produced by any suitable means, including recombinant production, chemical synthesis, or other synthetic means. Suitable production techniques are well known to those of skill in the art. See, e.g., Sambrook et al, Molecular Cloning: A Laboratory Manual, Cold Spring Harbor Press (Cold Spring Harbor, N.Y.). Alternatively, peptides can also be synthesized by the well known solid phase peptide synthesis methods (Merrifield, *J. Am. Chem. Soc.,* 85:2149 (1962); Stewart and Young, Solid Phase Peptide Synthesis (Freeman, San Francisco, 1969) pp. 27-62). These and other suitable production methods are within the knowledge of those of skill in the art and are not a limitation of the present invention.

In addition, one of skill in the art will readily understand that the Ad sequences of the invention can be readily adapted for use for a variety of viral and non-viral vector systems for in vitro, ex vivo or in vivo delivery of therapeutic and immunogenic molecules. For example, in one embodiment, the simian Ad capsid proteins and other simian adenovirus proteins described herein are used for non-viral, protein-based delivery of genes, proteins, and other desirable diagnostic, therapeutic and immunogenic molecules. In one such embodiment, a protein of the invention is linked, directly or indirectly, to a molecule for targeting to cells with a receptor for adenoviruses. Preferably, a capsid protein such as a hexon, penton, fiber or a fragment thereof having a ligand for a cell surface receptor is selected for such targeting. Suitable molecules for delivery are selected from among the therapeutic molecules described herein and their gene products. A variety of linkers including, lipids, polyLys, and the like may be utilized as linkers. For example, the simian penton protein may be readily utilized for such a purpose by production of a fusion protein using the simian penton sequences in a manner analogous to that described in Medina-Kauwe L K, et al, *Gene Ther.* 2001 May; 8(10): 795-803 and Medina-Kauwe L K, et al, *Gene Ther.* 2001 December; 8(23): 1753-1761. Alternatively, the amino acid sequences of simian Ad protein IX may be utilized for targeting vectors to a cell surface receptor, as described in US Patent Appln 20010047081. Suitable ligands include a CD40 antigen, an RGD-containing or polylysine-containing sequence, and the like. Still other simian Ad proteins, including, e.g., the hexon protein and/or the fiber protein, may be used for used for these and similar purposes.

Still other adenoviral proteins of the invention may be used as alone, or in combination with other adenoviral protein, for a variety of purposes which will be readily apparent to one of skill in the art. In addition, still other uses for the adenoviral proteins of the invention will be readily apparent to one of skill in the art.

The compositions of this invention include vectors that deliver a heterologous molecule to cells, either for therapeutic or vaccine purposes. Such vectors, containing simian adenovirus DNA of SA18 and a minigene, can be constructed using techniques such as those described herein for the chimeric adenoviruses and such techniques as are known in the art. Alternatively, SA19 may be a source for sequences of the chimeric adenoviruses are described herein.

The following examples are illustrative, and are not intended to limit the invention to those illustrated embodiments.

EXAMPLE 1—CONSTRUCTION Of Pan5/C1 CHIMERIC SIMIAN VIRUSES

Five different adenoviruses initially isolated from the chimpanzee, AdC68 [U.S. Pat. No. 6,083,716], AdPan5, AdPan7, AdPan6 and AdC1 [U.S. Pat. No. 6,083,716] have been sequenced. See, International Application No. PCT/US02/33645, filed November 2002 for the sequences of Pan5 [SEQ ID NO:1], Pan7 [SEQ ID NO:3], and Pan6 [SEQ ID NO:2]. This application also provides sequences for SV1, SV25 and SV39 [SEQ ID No. 4, 5, 6, respectively]. Sequence comparison of the capsid protein sequences predicted that AdC1 clearly belonged to a different serological subgroup than the other four chimpanzee derived adenoviruses.

However, attempts to cultivate AdC1 in HEK293 cells revealed it to be fastidious in its growth characteristics (data not shown) and therefore possibly unsuitable for use as a vector using the currently available E1 complementing cell lines. However, because of the obvious sequence dissimilarity of AdC1 capsid protein sequence from the other chimpanzee derived adenoviruses (as well as the huAd5), chimeric adenovirus vectors were generated with the capsid characteristics of AdC1. In view of the above-mentioned drawbacks associated with only making hexon changes, more extensive replacements were made in the chimera described herein, i.e., construction of chimeras where the replacement went beyond just the hexon, to achieve two goals. The first was to determine whether making extended replacements would allow for the rescue of viruses containing hexons of unrelated serotypes that may not otherwise be amenable to rescue. The second goal was to test whether the growth characteristics of adenovirus vectors such as AdPan5, that have been found in our laboratory to be able to be grown to high titer for the purpose of manufacture, would also be present in the chimeric virus, particularly when the hexon (and other capsid proteins) are derived from a virus such as AdC1 that are difficult to grow to a high yield in cell lines such as HEK293. An added bonus of extending the replacement to include the fiber protein would be to further increase the antigenic dissimilarity to beyond that afforded by a hexon change alone.

A. Construction of Two Pan5/C1-Chimeric Plasmids

The overall approach towards constructing chimeric viruses was to first assemble the complete E1 deleted virus DNA into a single plasmid flanked by recognition sites for the restriction enzyme SwaI, digest the plasmid DNA with SwaI to release the virus DNA ends, and transfect the DNA into HEK293 cells to determine whether viable chimeric adenovirus could be rescued. Two chimeric virus plasmids were constructed, p5C1short and p5C1long.

The plasmid p5C1short harbors an E1 deleted Pan5 virus where an internal 15226 bp segment (18332-33557) has been replaced by a functionally analogous 14127 bp (18531-32657) from AdC1. This results in the replacement of the Pan5 proteins hexon, endoprotease, DNA binding protein, 100 kD scaffolding protein, 33 kD protein, protein VIII, and fiber, as well as the entire E3 region, with the homologous segment from AdC1. The ClaI site at the left end of the AdC1 fragment is at the beginning of the hexon gene and the resulting protein is identical to the C1 hexon. The EcoRI site which constitutes the right end of the AdC1 fragment is within the E4 orf 7 part of the AdC1. The right end was ligated to a PCR generated right end fragment from AdPan5 such that the regenerated orf 7-translation product is chimeric between AdPan5 and AdC1.

The plasmid p5C1long harbors an E1 deleted Pan5 virus where an internal 25603 bp segment (7955-33557) has been replaced by a functionally analogous 24712 bp (7946-32657) from AdC1. This results in the replacement of the AdPan5 pre-terminal protein, 52/55 kD protein, penton base protein, protein VII, Mu, and protein VI with those from AdC1 in addition to those replaced in p5C1short. The AscI site at the left end of the AdC1 fragment is at the beginning of the DNA polymerase gene and results in a chimeric protein where the first 165 amino acids of the AdPan5 DNA polymerase has been replaced by a 167 amino acid segment from AdC1 DNA polymerase. In this N-terminal region, the homology between the AdPan5 and AdC1 DNA polymerase proteins is 81% (72% identity).

The plasmid pDVP5Mlu which contains the left end of AdPan5 was used as the starting plasmid for the chimeric vector construction.

The plasmid pDVP5Mlu was made as follows. A synthetic DNA fragment harboring recognition sites for the restriction enzymes SmaI, MluI, EcoRI and EcoRV respectively was ligated into pBR322 digested with EcoRI and NdeI so as to retain the origin of replication and the beta-lactamase gene. The left end of Pan5 extending to the MluI site (15135 bp) was cloned into this plasmid between the SmaI and MluI sites. The E1 gene was functionally deleted and replaced by a DNA fragment harboring recognition sites for the extremely rare cutter restriction enzyme sites I-CeuI and PI-SceI). The 2904 base pairs of the right end of Pan-5 was PCR amplified using the primers P5L [GCG CAC GCG TCT CTA TCG ATG AAT TCC ATT GGT GAT GGA CAT GC, SEQ ID NO:7] and P51TR [GCG CAT TTA AAT CAT CAT CAA TAA TAT ACC TCA AAC, SEQ ID NO:8] using Tgo polymerase (Roche). The PCR product was cut with MluI and SwaI, and cloned between MluI and EcoRV of pDVP5Mlu to yield pPan5Mlu+RE. A 3193 bp fragment extending from the MluI site (15135) to the ClaI (18328) site of Pan5 was then inserted between the same sites of pPan5Mlu+RE to yield pPan5Cla+RE. The 3671 bp ClaI (18531) to EcoRI (22202) fragment of the adenovirus C1 was cloned into pPan5Cla+RE between ClaI (16111) and EcoRI (16116) to yield pPan5C1delRI. The 10452 bp internal EcoRI fragment of the adenovirus C1 (22202-32653) was cloned into the EcoRI site of pPan5C1delRI to yield p5C1short. To construct p5C1long, the AdC1 replacement was further extended by replacing the AscI-ClaI 10379 bp fragment of AdPan5 in p5C1short with the AdC1 AscI-ClaI 10591 bp fragment. Finally a green fluorescent protein (GFP) expression cassette was inserted into both p5C1short and p5C1long between the I-CeuI and PI-SceI sites to yield p5C1shortGFP and p5C1longGFP respectively.

B. Rescue of Chimeric Pan5/C1 Recombinant Vector Adenoviruses

The plasmids p5C1shortGFP and p5C1longGFP were digested with the restriction enzyme SwaI and transfected into HEK 293 cells. A typical adenovirus induced cytopathic effect was observed. The rescue of recombinant chimeric adenovirus from the p5C1longGFP transfection was confirmed by collecting the supernatant from the transfection and re-infecting fresh cells which were found to be transduced as determined by GFP expression. Viral DNA prepared from the chimeric recombinant virus was digested with several restriction enzymes and found to have the expected pattern on electrophoresis (data not shown).

The chimeric adenoviral construct with the shorter replacement p5C1short encodes the C1 proteins hexon and fiber as well as the intervening open reading frames for endoprotease, DNA binding protein, 100 kDa scaffolding protein, 33 kDa protein, and protein VIII. (The E3 region is also included within this region but is unlikely to impact on the viability of the chimeric virus). When the replacement was extended to include the additional AdC1 proteins pTP (pre-terminal protein), 52/55 kDa protein, penton base, protein VII, Mu, and protein VI, there was no difficulty in rescuing viable chimeric virus. In this experiment, the chimeric adenovirus construction strategy utilized the presence of AscI and ClaI restriction enzyme sites present on the genes for DNA polymerase and hexon respectively on both AdPan5 and AdC1.

The reasons for the relatively higher yield of the chimeric virus compared to the wild-type AdC1 virus are not clear. In the growth of the 5C1 chimeric virus in 293 cells, the adenoviral early region gene products of E1 and E4 are derived from Ad5 and AdPan5 respectively. The E1 and E4 gene products bind, regulate and de-repress several cellular transcription complexes and coordinate their activity towards viral multiplication. Thus it is possible that the E1 gene products supplied in trans from the 293 cells and the E4 gene products from AdPan5 are more optimal in the human 293 cell background than are the equivalent AdC1 gene products. This may also apply to the activity of the major late promoter whose activity is responsible for the transcription of the capsid protein genes. In the chimeric virus, the major late promoter, and the protein IVa2 which transactivates it, are derived from AdPan5. However the E2 gene products required for adenoviral DNA replication pTP and single-stranded DNA—binding protein are derived from AdC1. The adenoviral DNA polymerase, which complexes with pTP, is chimeric in Ad5C1 but mostly AdPan5 derived.

EXAMPLE 2—GENERATION OF SIMIAN Pan5/HUMAN Ad40 CHIMERIC

Adenovirus and Chimpanzee Pan5/Simian SA18 Chimeric Adenovirus

The construction of plasmids designed to rescue chimeric adenoviruses where the outside flanking regions are derived from the chimpanzee adenovirus AdPan5, and the internal region (containing the structural capsid protein genes) are derived from the human adenovirus Ad40 and the simian adenovirus SA18, are described below.

As described for the Pan5-C1 chimeric adenovirus, the overall approach towards constructing chimeric viruses was to first assemble the complete E1 deleted virus DNA into a single plasmid flanked by recognition sites for the restriction enzyme SwaI, digest the plasmid DNA with SwaI to release the virus DNA ends, and transfect the DNA into HEK293 cells to determine whether viable chimeric adenovirus could be rescued. Two chimeric virus plasmids were constructed, pPan5-40 and pPan5-SA18 corresponding to the two chimeric adenoviruses referred to above. The plasmid pPan5-40 harbors an E1 deleted Pan5 virus where an internal 22975 bp segment (10400-33374) has been replaced by a functionally analogous 21603 bp (10043-21603) from Ad40. This results in the replacement of the AdPan5 52/55 kD protein, penton base protein, protein VII, Mu, protein VI, hexon, endoprotease, DNA binding protein, 100 kD scaffolding protein, 33 kD protein, protein VIII, and fiber, as well as the entire E3 region, with the homologous segment from Ad40. Similarly, the plasmid pPan5-SA18 harbors an E1 deleted Pan5 virus where an internal 22975 bp segment (10400-33374) has been replaced by a functionally analogous 19015 bp (10573-29587) from SA18. This results in the replacement of the AdPan5 52/55 kD protein, penton base protein, protein VII, Mu, protein VI, hexon, endoprotease, DNA binding protein, 100 kD scaffolding protein, 33 kD protein, protein VIII, and fiber, as well as the entire E3 region, with the homologous segment from SA18.

The construction of plasmids designed to rescue chimeric adenoviruses where the outside flanking regions are derived from the chimpanzee adenovirus AdPan5, and the internal region (containing the structural capsid protein genes) are derived from the human adenovirus Ad40 and the simian adenovirus SA18, are described below.

A. Silent Mutagenesis of XbaI Site:

The plasmid pDVP5Mlu which contains the left end of AdPan5 was used as the starting plasmid for the chimeric vector construction. As a first step the XbaI site (3820) was mutagenized to destroy the recognition site without changing the coding sequence for polymerase. This was done by first sub-cloning the NdeI (812) to HindIII (4931) fragment into the plasmid pNEB193 (New England Biolabs) using the same restriction sites in pNEB193, to yield pNEBp5. A PCR reaction was performed on pNEBp5 using the primers P5XTOP (GATACCTAGGAACGAGGAGGATTTGATATTG, SEQ ID NO:9) and P5XBOT (ATGTACGCCTCCGCGCTCAC, SEQ ID NO:10) to yield a 591 bp product. The PCR product was cleaved with AvrII and BbvCI and ligated into pNEBp5 cut with XbaI and BbvCI to yield the desired mutation in the plasmid pNEBp5mut. The mutated NdeI-HindIII fragment from pNEBp5mut was ligated back into pDVP5Mlu to yield the desired mutated plasmid pDVP5Mlumut.

B. Insertion of the Pan5 Right End Comprising the Right ITR and the Complete E4 Region:

The right end of Pan-5 was PCR amplified (P5RE2PCR) using the primers P5E4 [GATCGAATTCCCACTCTGTACCCCATCTCTG, SEQ ID NO:11] and P51TR [GCG CAT TTA AAT CAT CAT CAA TAA TAT ACC TCA AAC, SEQ ID NO:8] using Tgo polymerase, cut with EcoRI and SwaI, and cloned between EcoRI and EcoRV of pDVP5Mlumut to yield pPan5Mlumut+RE.

C. Insertion of Ad40 or SA18 Structural Protein Sequences:

In order to construct p5-40, the Ad40 segment from XbaI (10038) to EcoRI (31642) was ligated into pDVP5Mlumut+RE2 between XbaI (8178) and EcoRI (12924) in two steps: first, the XbaI (30494) to EcoRI (31642) fragment was inserted, followed by the XbaI (10038)-XbaI (30494) fragment.

To construct pPan5-SA18 the XbaI (10568) to EcoRI (29584) fragment from the simian adenovirus SA18 was inserted into pDVP5Mlumut+RE2 between XbaI (8178) and EcoRI (12924).

The minigene encoding for green fluorescent protein was inserted in place of the E1 deletion between the I-CeuI and PI-SceI sites in pPan5-40 and pPan5-SA18 respectively. This plasmids were purified, digested with SwaI and transfected into 293 cells.

All publications cited in this specification are incorporated herein by reference. While the invention has been described with reference to a particularly preferred embodiment, it will be appreciated that modifications can be made without departing from the spirit of the invention. Such modifications are intended to fall within the scope of the appended claims.

What is claimed is:

1. A method of producing a chimeric adenovirus in a selected host cell type, said chimeric adenovirus derived from a parental adenovirus which is not useful for adenovirus virion production in the host cell type, said method comprising the steps of:

(a) generating a chimeric adenovirus comprising:

(i) adenovirus sequences of the left terminal end and right terminal end of a first adenovirus which grows in the selected host cell type, said left end region comprising the 5' inverted terminal repeat (ITRs), and said right end region comprising the 3' inverted terminal repeat (ITRs); and (ii) the internal regions from the parental adenovirus, said internal regions comprising the late genes encoding the penton, hexon, and fiber and lacking its native 5' and 3' terminal regions from the parental adenovirus;

wherein the resulting chimeric adenovirus comprises, from 5' to 3', a left terminal region of the first adenovirus, the internal region of the parental adenovirus, and the right terminal region of the first adenovirus; and b) producing said chimeric adenovirus in the presence of functional adenovirus E1a, E1b, and E4 ORF6 genes from the first adenovirus or from an adenovirus serotype which transcomplements the first adenovirus, and further in the presence of necessary adenoviral structural genes from the left end of the first adenovirus or from an adenovirus serotype which transcomplements the first adenovirus.

2. The method according to claim 1, wherein the internal region of the parental adenovirus further comprises one or more functional adenovirus genes selected from the group consisting of Endoprotease open reading frame, DNA binding protein, 100 kDa scaffolding protein, 33 kDa protein, protein VIII, pTP (pre-Terminal Protein), 52/55 kDa protein, protein VII, Mu and protein VI.

3. The method according to claim 1, wherein the polymerase, terminal protein and 52/55 kDa protein functions are provided in trans.

4. The method according to claim 1, wherein the first adenovirus further comprises the polymerase, terminal protein and 52/55 kDa protein functions.

5. The method according to claim 1, wherein the chimeric adenovirus comprises the adenoviral late genes 1, 2, 3, 4, and 5 of the parental adenovirus.

6. The method according to claim 1, wherein the selected host cell stably contains one or more functional adenovirus E1a, E1b or E4 ORF6 genes.

7. The method according to claim 1, wherein the chimeric adenovirus comprises one or more functional adenovirus E1a, E1b or E4 ORF6 genes from the first adenovirus.

8. The method according to claim 1, wherein the first adenovirus is of human origin.

9. The method according to claim 1, wherein the first adenovirus is of simian origin.

10. The method according to claim 1, further comprising the step of isolating the chimeric adenovirus.

11. A chimeric adenovirus produced according to the method of claim 1.

12. The method according to claim 1, wherein the parental adenovirus is selected from the group consisting of adenovirus C1, adenovirus Ad40 and adenovirus SA18.

13. The method according to claim 1, wherein the first adenovirus is Pan5.

14. A host cell in vitro comprising a chimeric adenovirus according to claim 11.

15. The chimeric adenovirus according to claim 11, wherein said chimeric adenovirus is functionally deleted in E1a and/or E1b.

16. The chimeric adenovirus according to claim 11, wherein said chimeric adenovirus is functionally deleted in E40RF6.

17. A method for generating a chimeric adenovirus for production in a selected host cell, said chimeric adenovirus derived from a parental adenovirus which is not useful for adenovirus virion production in the host cell type, said method comprising the step of generating a chimeric adenovirus comprising:

5' and 3' terminal regions of a first adenovirus which grows in a selected host cell type, said 5' terminal regions comprising the 5' inverted terminal repeat (ITRs) and necessary E1 gene functions, and said 3' terminal regions comprising inverted terminal repeat (ITRs) and necessary E4 gene functions; and internal regions from the parental adenovirus, said internal regions comprising the hexon, penton base and fiber and lacking at least its native 5' and 3' terminal regions;

wherein the resulting chimeric adenovirus comprises, from 5' to 3', the 5' terminal region of the first adenovirus, the internal region of the parental adenovirus, and the 3' terminal regions of the first adenovirus.

18. A chimeric adenovirus comprising a hexon protein of a selected adenovirus serotype, said chimeric adenovirus derived from a parental adenovirus which is not useful for adenovirus virion production in a selected host cell type, said chimeric adenovirus comprising:

(a) adenovirus sequences of the left terminal end of a first adenovirus which grows in the selected host cell type, said left end region comprising the E1a, E1b and 5' inverted terminal repeat (ITRs);

(b) adenovirus sequences of the internal region of the selected parental adenovirus, said internal region comprising the genes encoding the penton, hexon and fiber of the selected adenovirus;

(c) adenovirus sequences of the right terminal end of the first adenovirus, said right end region comprising the necessary E4 gene functions and the 3' inverted terminal repeat (ITRs), wherein the resulting chimeric adenovirus comprises adenoviral structural and regulatory proteins necessary for infection and replication.

19. The chimeric adenovirus according to claim 18, wherein the chimeric adenovirus further comprises the IIIa, 52/55 kDa and pTP of the selected adenovirus serotype.

20. The chimeric adenovirus according to claim 18, wherein chimeric adenovirus comprises the polymerase of the first adenovirus.

21. The chimeric adenovirus according to claim 18, wherein the chimeric adenovirus expresses a functional chimeric protein formed from the first adenovirus and the selected adenovirus, said chimeric protein is selected from the group consisting of polymerase, terminal protein, 52/55 kDa protein, and IIIa.

22. The chimeric adenovirus according to claim 18, wherein the chimeric adenovirus comprises the terminal protein, 52/55 kDa, and/or IIIa of the selected adenovirus.

23. The host cell according to claim 14, wherein said host cell is a human cell.

* * * * *